US009175082B2

(12) United States Patent
Zhou et al.

(10) Patent No.: US 9,175,082 B2
(45) Date of Patent: Nov. 3, 2015

(54) ANTIGEN BINDING PROTEINS THAT BIND PD-L1

(71) Applicants: Heyue Zhou, San Diego, CA (US); Randy Gastwirt, San Diego, CA (US); Barbara A. Swanson, Encinitas, CA (US); John Dixon Gray, San Diego, CA (US); Gunnar F. Kaufmann, San Diego, CA (US)

(72) Inventors: Heyue Zhou, San Diego, CA (US); Randy Gastwirt, San Diego, CA (US); Barbara A. Swanson, Encinitas, CA (US); John Dixon Gray, San Diego, CA (US); Gunnar F. Kaufmann, San Diego, CA (US)

(73) Assignee: Sorrento Therapeutics, Inc., San Diego, CA (US)

( * ) Notice: Subject to any disclaimer, the term of this patent is extended or adjusted under 35 U.S.C. 154(b) by 153 days.

(21) Appl. No.: 13/907,685

(22) Filed: May 31, 2013

(65) Prior Publication Data

US 2013/0323249 A1    Dec. 5, 2013

Related U.S. Application Data

(60) Provisional application No. 61/654,022, filed on May 31, 2012, provisional application No. 61/739,982, filed on Dec. 20, 2012.

(51) Int. Cl.
*C07K 16/28* (2006.01)
*A61K 39/395* (2006.01)
*A61K 39/00* (2006.01)

(52) U.S. Cl.
CPC ......... *C07K 16/2818* (2013.01); *C07K 16/2827* (2013.01); *A61K 2039/505* (2013.01); *C07K 2317/21* (2013.01); *C07K 2317/73* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 6,632,927 | B2* | 10/2003 | Adair et al. ............... 530/387.3 |
| 2009/0055944 | A1 | 2/2009 | Korman et al. |
| 2009/0117095 | A1 | 5/2009 | Messmer et al. |
| 2011/0020325 | A1 | 1/2011 | Kwon et al. |
| 2011/0200615 | A1 | 8/2011 | Marks et al. |
| 2013/0108641 | A1* | 5/2013 | Baurin et al. ............. 424/139.1 |

FOREIGN PATENT DOCUMENTS

WO    2007005874    1/2007

OTHER PUBLICATIONS

Rudikoff et al. 1982, Proc. Natl. Acad. Sci. USA, , 79: 1979-1983.*
Panka et al., 1988, Proc. Natl. Acad. Sci. USA, 85: 3080-3084.*
Rentero et al., Chimia 2011, 65: 843-845.*
Homology Table, 2015, 4 pages.*
Near et al., Mol. Immunol. (1993) 30: 369-377.*
Brahmer et al. "Safety and Activity of Anti-PD-L1 Antibody in Patients with Advanced Cancer" New Engl. J. Med. 366:2455-2465, Jun. 28, 2012.
McDermott and Atkins "PD-1 as a potential target in cancer therapy" Cancer Medicine, 2(5):662-673, 2013.
Quezada and Peggs, "Exploiting CTLA-4, PD-1 and PD-L1 to reactivate the host immune response against cancer" Br. J. Cancer, 108:1560-1565, 2103.
Pilon-Thomas et al., "Blockade of PD-L1 Enhances the Therapeutic Efficacy of Combination Immunotherapy Against Melanoma" J. Immunol. 184(7):3442-3449, 2010.
Kasagi et al. "Anti-Programmed Cell Death 1 Antibody Reduces CD4+PD-1+ T Cells and Relieves the Lupus-Like Nephritis of NZB/W F1 Mice" J. Immunol. 184:23337-2347, 2010.

* cited by examiner

*Primary Examiner* — Ilia Ouspenski
(74) *Attorney, Agent, or Firm* — Jeffrey B. Oster

(57) ABSTRACT

There is disclosed compositions and methods relating to or derived from anti-PD-L1 antibodies. More specifically, there is disclosed fully human antibodies that bind PD-L1, PD-L1-binding fragments and derivatives of such antibodies, and PD-L1-binding polypeptides comprising such fragments. Further still, there is disclosed nucleic acids encoding such antibodies, antibody fragments and derivatives and polypeptides, cells comprising such polynucleotides, methods of making such antibodies, antibody fragments and derivatives and polypeptides, and methods of using such antibodies, antibody fragments and derivatives and polypeptides, including methods of treating or diagnosing subjects having PD-L1 related disorders or conditions, including various inflammatory disorders and various cancers.

5 Claims, 16 Drawing Sheets

Gated on CD56+

Gated on CD3+

Values on ordinate are %CD25+

Ordinate is IL-2 pg/ml

Ordinate is IFNγ pg/ml

SEQUENCE LISTING

<160> NUMBER OF SEQ ID NOS: 242

<210> SEQ ID NO 1
<211> LENGTH: 126
<212> TYPE: PRT
<213> ORGANISM: Artificial Sequence
<220> FEATURE:
<223> OTHER INFORMATION: E6-VH

<400> SEQUENCE: 1

```
Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Thr Tyr
            20                  25                  30

Ala Ile Ser Trp Val Arg Gln Ala Pro Gly Gln Gly Leu Glu Trp Met
        35                  40                  45

Gly Gly Ile Ile Pro Leu Phe Gly Lys Ala Asp Tyr Ala Gln Lys Phe
    50                  55                  60

Gln Asp Arg Val Thr Ile Thr Ala Asp Glu Ser Thr Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Lys Gly Arg Glu Glu Leu Gly Gly Asn Tyr Tyr Tyr Ala
            100                 105                 110

Val Asp Val Trp Gly Pro Gly Thr Thr Val Thr Val Ser Ser
        115                 120                 125
```

<210> SEQ ID NO 2
<211> LENGTH: 107
<212> TYPE: PRT
<213> ORGANISM: Artificial Sequence
<220> FEATURE:
<223> OTHER INFORMATION: E6-VL

<400> SEQUENCE: 2

```
Asp Ile Val Met Thr Gln Thr Pro Tyr Ser Val Ser Ala Ser Val Gly
1               5                   10                  15

Asp Arg Val Thr Ile Thr Cys Arg Ala Ser Gln Glu Val Ser Arg Trp
            20                  25                  30
```

```
Val Ala Trp Tyr Gln Gln Lys Pro Gly Gln Ala Pro Lys Ser Leu Ile
        35                  40                  45

Tyr Ala Ser Ser Arg Leu Gln Ser Gly Val Pro Ser Arg Phe Thr Ala
50                  55                  60

Ser Gly Ser Gly Thr Asp Phe Thr Leu Val Ile Ser Ser Leu Gln Pro
65                  70                  75                  80

Glu Asp Phe Ala Thr Tyr Tyr Cys Gln Gln Tyr Ser Arg Phe Pro Leu
                85                  90                  95

Thr Phe Gly Gly Gly Thr Lys Val Glu Ile Lys
            100                 105
```

<210> SEQ ID NO 3
<211> LENGTH: 121
<212> TYPE: PRT
<213> ORGANISM: Artificial Sequence
<220> FEATURE:
<223> OTHER INFORMATION: E7-VH

<400> SEQUENCE: 3

```
Gln Val Gln Leu Gln Gln Gly Pro Gly Leu Val Lys Pro Ser Gln
1               5                   10                  15

Thr Leu Ser Leu Thr Cys Ala Ile Ser Gly Asp Ser Val Ser Ser Asn
                20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Thr Asn Tyr Ala
50                  55                  60

Val Ser Met Arg Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Phe Cys Ala Gly Gly Asn Ser Ser Ser His Asp Asp Tyr Trp Gly
            100                 105                 110

Gln Gly Thr Leu Val Thr Val Ser Ser
        115                 120
```

<210> SEQ ID NO 4
<211> LENGTH: 110
<212> TYPE: PRT
<213> ORGANISM: Artificial Sequence
<220> FEATURE:
<223> OTHER INFORMATION: E7-VL

<400> SEQUENCE: 4

```
Gln Pro Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
        35                  40                  45

Met Val Tyr Asp Val Ser Lys Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Thr Glu Asp Glu Ala Asp Tyr Tyr Cys Ser Ser Tyr Thr Ser Ser
                85                  90                  95

Asn Thr Arg Val Phe Gly Thr Gly Thr Lys Leu Thr Val Leu
```

-continued

```
                100                 105                 110
```

<210> SEQ ID NO 5
<211> LENGTH: 124
<212> TYPE: PRT
<213> ORGANISM: Artificial Sequence
<220> FEATURE:
<223> OTHER INFORMATION: E9-VH

<400> SEQUENCE: 5

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Phe Pro Thr Ile Phe Trp Glu Gly Gly Ala Phe Asp
            100                 105                 110

Ile Trp Gly Gln Gly Thr Met Val Thr Val Ser Ser
        115                 120
```

<210> SEQ ID NO 6
<211> LENGTH: 107
<212> TYPE: PRT
<213> ORGANISM: Artificial Sequence
<220> FEATURE:
<223> OTHER INFORMATION: E9-VL

<400> SEQUENCE: 6

```
Asp Ile Val Met Thr Gln Ser Pro Ser Thr Leu Ser Ala Ser Val Gly
1               5                   10                  15

Asp Arg Val Thr Ile Thr Cys Arg Ala Ser Gln Ser Phe Thr Thr Tyr
            20                  25                  30

Leu Ala Trp Tyr Gln Gln Lys Pro Gly Lys Ala Pro Lys Leu Leu Ile
        35                  40                  45

Tyr Gln Thr Ser Asn Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ser Arg Tyr Trp Trp
                85                  90                  95

Ser Phe Gly Gln Gly Thr Arg Leu Glu Ile Lys
            100                 105
```

<210> SEQ ID NO 7
<211> LENGTH: 124
<212> TYPE: PRT
<213> ORGANISM: Artificial Sequence
<220> FEATURE:
<223> OTHER INFORMATION: E11-VH

<400> SEQUENCE: 7

```
Glu Val Gln Leu Val Gln Ser Gly Ala Glu Val Lys Lys Pro Gly Ala
1               5                   10                  15
```

```
Ser Leu Lys Val Ser Cys Lys Ala Ser Gly Tyr Thr Phe Asn Ser Tyr
            20                  25                  30

Asp Ile Asn Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
50                  55                  60

Gln Gly Arg Val Thr Met Thr Arg Asp Thr Ser Thr Ser Thr Val Tyr
65                  70                  75                  80

Met Glu Leu Ser Ser Leu Thr Ser Glu Asp Thr Ala Val Tyr Tyr Cys
                85                  90                  95

Ala Arg Asp Leu Phe Pro His Ile Tyr Gly Asn Tyr Tyr Gly Met Asp
            100                 105                 110

Ile Trp Gly Gln Gly Thr Thr Val Thr Val Ser Ser
            115                 120

<210> SEQ ID NO 8
<211> LENGTH: 107
<212> TYPE: PRT
<213> ORGANISM: Artificial Sequence
<220> FEATURE:
<223> OTHER INFORMATION: E11-VL

<400> SEQUENCE: 8

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ser Ser Thr Pro Leu
                85                  90                  95

Thr Phe Gly Gln Gly Thr Lys Val Glu Ile Lys
            100                 105

<210> SEQ ID NO 9
<211> LENGTH: 118
<212> TYPE: PRT
<213> ORGANISM: Artificial Sequence
<220> FEATURE:
<223> OTHER INFORMATION: F1-VH

<400> SEQUENCE: 9

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Phe Asp Gly Ser Asn Lys Tyr Tyr Ala Asp Ser Val
50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Thr Glu Asp Thr Ala Val Tyr Tyr Cys
```

```
                    85                  90                  95

Ala Arg Gly Trp Leu Asp Arg Asp Ile Asp Tyr Trp Gly Gln Gly Thr
                100                 105                 110

Leu Val Thr Val Ser Ser
        115

<210> SEQ ID NO 10
<211> LENGTH: 110
<212> TYPE: PRT
<213> ORGANISM: Artificial Sequence
<220> FEATURE:
<223> OTHER INFORMATION: F1-VL

<400> SEQUENCE: 10

Gln Ala Val Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Arg Thr Arg Pro Ser Gly Val Ser Asp Arg Phe
    50                  55                  60

Ser Gly Ser Lys Ser Gly Asn Thr Ala Ser Leu Ser Ile Ser Gly Leu
65              70                  75                  80

Gln Ala Glu Asp Glu Ala Asp Tyr Tyr Cys Ser Ser His Ser Ser Ser
                85                  90                  95

Thr Thr Val Ile Phe Gly Gly Gly Thr Lys Leu Thr Val Leu
                100                 105                 110

<210> SEQ ID NO 11
<211> LENGTH: 118
<212> TYPE: PRT
<213> ORGANISM: Artificial Sequence
<220> FEATURE:
<223> OTHER INFORMATION: F4-VH

<400> SEQUENCE: 11

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Asp Asn Thr Gly Ser Ala Gln Lys Phe
    50                  55                  60

Gln Gly Arg Val Phe Met Thr Lys Thr Thr Ser Leu Asn Thr Ala Tyr
65              70                  75                  80

Met Glu Leu Ser Gly Leu Arg Ser Glu Asp Thr Ala Ile Tyr Tyr Cys
                85                  90                  95

Ala Arg Glu Arg Ser Ser Gly Tyr Phe Asp Phe Trp Gly Gln Gly Thr
                100                 105                 110

Leu Val Thr Val Ser Ser
        115

<210> SEQ ID NO 12
<211> LENGTH: 107
<212> TYPE: PRT
<213> ORGANISM: Artificial Sequence
<220> FEATURE:
```

<223> OTHER INFORMATION: F4-VL

<400> SEQUENCE: 12

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ile
                85                  90                  95

Thr Phe Gly Gln Gly Thr Arg Leu Glu Ile Lys
            100                 105

<210> SEQ ID NO 13
<211> LENGTH: 118
<212> TYPE: PRT
<213> ORGANISM: Artificial Sequence
<220> FEATURE:
<223> OTHER INFORMATION: F7-VH

<400> SEQUENCE: 13

Glu Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Glu His Asp Ala Phe Asp Ile Trp Gly Gln Gly Thr
            100                 105                 110

Met Val Thr Val Ser Ser
        115

<210> SEQ ID NO 14
<211> LENGTH: 109
<212> TYPE: PRT
<213> ORGANISM: Artificial Sequence
<220> FEATURE:
<223> OTHER INFORMATION: F7-VL

<400> SEQUENCE: 14

Gln Ala Val Leu Thr Gln Pro Pro Ser Val Ser Ala Ala Pro Gly Gln
1               5                   10                  15

Arg Val Thr Ile Ser Cys Ser Gly Ser Asn Ser Asn Ile Ala Asp Thr
            20                  25                  30

Tyr Val Ser Trp Tyr Gln Gln Leu Pro Gly Thr Ala Pro Arg Leu Leu
        35                  40                  45

Ile Tyr Asp Asn Asp Gln Arg Pro Ser Gly Ile Pro Asp Arg Phe Ser

```
                    50                  55                  60
Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Ser Ser Leu
                    85                  90                  95

Ser Gly Val Phe Gly Thr Gly Thr Lys Val Thr Val Leu
                100                 105

<210> SEQ ID NO 15
<211> LENGTH: 121
<212> TYPE: PRT
<213> ORGANISM: Artificial Sequence
<220> FEATURE:
<223> OTHER INFORMATION: F8-VH

<400> SEQUENCE: 15

Gln Val Gln Leu Val Gln Ser Gly Gly Gly Val Val Gln Pro Gly Arg
  1               5                  10                  15

Ser Pro Arg Leu Ser Cys Ala Ala Ser Gly Phe Thr Phe Asn Thr Tyr
                 20                  25                  30

Gly Met His Trp Val Arg Gln Ala Pro Gly Lys Gly Leu Glu Trp Val
             35                  40                  45

Ala Val Ile Ser Asp Gly Gly Asn Asn Lys Lys Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Lys Asp Ile Gly Glu Ser Tyr Tyr Tyr Tyr Met Asp Val Trp Gly
                100                 105                 110

Lys Gly Thr Thr Val Thr Val Ser Ser
            115                 120

<210> SEQ ID NO 16
<211> LENGTH: 110
<212> TYPE: PRT
<213> ORGANISM: Artificial Sequence
<220> FEATURE:
<223> OTHER INFORMATION: F8-VL

<400> SEQUENCE: 16

Gln Ser Val Leu Thr Gln Pro Ala Ser Val Ser Gly Ser Pro Gly Gln
  1               5                  10                  15

Ser Val Thr Ile Ser Cys Thr Gly Thr Ser Ser Asp Val Gly Gly Phe
                 20                  25                  30

Asn Ser Val Ser Trp Tyr Gln Gln His Pro Gly Lys Ala Pro Lys Leu
             35                  40                  45

Met Ile Tyr Asp Val Ser Lys Arg Pro Ser Glu Ile Ser Asp Arg Phe
 50                  55                  60

Ser Gly Ser Lys Ser Gly Asn Thr Ala Ser Leu Thr Ile Ser Gly Leu
 65                  70                  75                  80

Gln Pro Glu Asp Glu Ala Asp Tyr Tyr Cys Ser Ser Tyr Thr Ser Ser
                 85                  90                  95

Ser Thr Leu Val Phe Gly Gly Gly Thr Lys Leu Thr Val Leu
                100                 105                 110

<210> SEQ ID NO 17
<211> LENGTH: 121
```

```
<212> TYPE: PRT
<213> ORGANISM: Artificial Sequence
<220> FEATURE:
<223> OTHER INFORMATION: F11-VH

<400> SEQUENCE: 17
```

Gln Val Gln Leu Gln Gln Ser Gly Pro Gly Leu Val Lys Pro Ser Gln
1               5                   10                  15

Ser Leu Ser Leu Thr Cys Ala Ile Ser Gly Asp Ser Leu Ser Ser Asn
            20                  25                  30

Ser Ala Ala Trp Asn Trp Ile Arg Gln Ser Pro Ser Gly Gly Leu Glu
        35                  40                  45

Trp Leu Gly Arg Thr Tyr Tyr Arg Ser Lys Trp Tyr Asn Glu Tyr Val
    50                  55                  60

Glu Ser Leu Lys Ser Arg Ile Thr Ile Asn Ser Asp Ile Ser Arg Asn
65                  70                  75                  80

Gln Phe Ser Leu His Leu Asn Ser Val Thr Pro Glu Asp Thr Ala Val
                85                  90                  95

Tyr Tyr Cys Ala Ser Gly Thr Gly Ala Arg Gly Met Asp Val Trp Gly
            100                 105                 110

Gln Gly Thr Thr Val Thr Val Ser Ser
        115                 120

```
<210> SEQ ID NO 18
<211> LENGTH: 108
<212> TYPE: PRT
<213> ORGANISM: Artificial Sequence
<220> FEATURE:
<223> OTHER INFORMATION: F11-VL

<400> SEQUENCE: 18
```

Ser Tyr Val Leu Thr Gln Pro Pro Ser Val Ser Val Ser Pro Gly Gln
1               5                   10                  15

Thr Ala Ser Ile Ser Cys Ser Gly Tyr Lys Leu Glu Asn Lys Tyr Val
            20                  25                  30

Ser Trp Tyr Gln Gln Arg Ala Gly Gln Ser Pro Val Leu Val Ile Tyr
        35                  40                  45

Gln Asp Asn Lys Arg Pro Ser Gly Ile Pro Glu Arg Phe Ser Gly Ser
    50                  55                  60

Asn Ser Gly Asn Thr Ala Ser Leu Thr Ile Thr Gly Leu Gln Pro Glu
65                  70                  75                  80

Asp Glu Ala Asp Tyr Tyr Cys Ser Ala Trp Asp Ser Ser Leu Arg Ala
                85                  90                  95

Trp Val Phe Gly Gly Gly Thr Gln Leu Thr Val Leu
            100                 105

```
<210> SEQ ID NO 19
<211> LENGTH: 121
<212> TYPE: PRT
<213> ORGANISM: Artificial Sequence
<220> FEATURE:
<223> OTHER INFORMATION: G4-VH

<400> SEQUENCE: 19
```

Gln Val Gln Leu Gln Gln Ser Gly Pro Gly Leu Val Lys Pro Ser Glu
1               5                   10                  15

Thr Leu Ser Leu Thr Cys Ala Ile Ser Gly Asp Ser Val Ser Glu Asn
            20                  25                  30

Ser Ala Ala Trp Asn Trp Ile Arg Gln Ser Pro Ser Gly Gly Leu Glu

```
                35                  40                  45

Trp Leu Gly Arg Thr Tyr Tyr Arg Ser Lys Trp Tyr Asn Glu Tyr Val
        50                  55                  60

Glu Ser Leu Lys Ser Arg Ile Thr Ile Asn Ser Asp Ile Ser Arg Asn
 65                  70                  75                  80

Gln Phe Ser Leu His Leu Asn Ser Val Thr Pro Glu Asp Thr Ala Val
                 85                  90                  95

Tyr Tyr Cys Ala Ser Gly Thr Gly Ala Arg Gly Met Asp Val Trp Gly
            100                 105                 110

Gln Gly Thr Thr Val Thr Val Ser Ser
        115                 120

<210> SEQ ID NO 20
<211> LENGTH: 107
<212> TYPE: PRT
<213> ORGANISM: Artificial Sequence
<220> FEATURE:
<223> OTHER INFORMATION: G4-VL

<400> SEQUENCE: 20

Gln Pro Val Leu Thr Gln Pro Pro Ser Val Ser Val Ser Pro Gly Gln
 1               5                  10                  15

Thr Ala Ser Ile Thr Cys Ser Gly Asp Glu Leu Gly Asn Lys Tyr Val
                20                  25                  30

Tyr Trp Tyr Gln Gln Lys Pro Gly Arg Ser Pro Val Leu Val Ile Tyr
            35                  40                  45

Gln Asp Ser Lys Arg Pro Ser Gly Phe Pro Ala Arg Phe Ser Gly Ala
        50                  55                  60

Asn Ser Gly Asn Thr Ala Thr Leu Thr Ile Ser Gly Thr Gln Ala Met
 65                  70                  75                  80

Asp Glu Ala Asp Tyr Phe Cys Gln Ala Trp Asp Ser Ser Thr Ala Trp
                 85                  90                  95

Val Phe Gly Gly Gly Thr Lys Leu Thr Val Leu
            100                 105

<210> SEQ ID NO 21
<211> LENGTH: 118
<212> TYPE: PRT
<213> ORGANISM: Artificial Sequence
<220> FEATURE:
<223> OTHER INFORMATION: G9-VH

<400> SEQUENCE: 21

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Asp Asn Thr Gly Ser Ala Gln Lys Phe
        50                  55                  60

Gln Gly Arg Val Phe Met Thr Lys Thr Thr Ser Leu Asn Thr Ala Tyr
 65                  70                  75                  80

Met Glu Leu Ser Gly Leu Arg Ser Glu Asp Thr Ala Ile Tyr Tyr Cys
                 85                  90                  95

Ala Arg Glu Arg Ser Ser Gly Tyr Phe Asp Phe Trp Gly Gln Gly Thr
            100                 105                 110
```

```
Leu Val Thr Val Ser Ser
        115

<210> SEQ ID NO 22
<211> LENGTH: 107
<212> TYPE: PRT
<213> ORGANISM: Artificial Sequence
<220> FEATURE:
<223> OTHER INFORMATION: G9-VL

<400> SEQUENCE: 22

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ile
                85                  90                  95

Thr Phe Gly Gln Gly Thr Arg Leu Glu Ile Lys
            100                 105

<210> SEQ ID NO 23
<211> LENGTH: 120
<212> TYPE: PRT
<213> ORGANISM: Artificial Sequence
<220> FEATURE:
<223> OTHER INFORMATION: G11-VH

<400> SEQUENCE: 23

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Arg Tyr
            20                  25                  30

Gly Val His Trp Val Arg Gln Ala Pro Gly Gln Gly Leu Glu Trp Met
        35                  40                  45

Gly Arg Leu Ile Pro Ile Val Ser Met Thr Asn Tyr Ala Gln Lys Phe
    50                  55                  60

Gln Asp Arg Val Ser Ile Thr Thr Asp Lys Ser Thr Gly Thr Ala Tyr
65                  70                  75                  80

Met Glu Leu Arg Ser Leu Thr Ser Glu Asp Thr Ala Leu Tyr Tyr Cys
                85                  90                  95

Ala Ser Val Gly Gln Gln Leu Pro Trp Val Phe Phe Ala Trp Gly Gln
            100                 105                 110

Gly Thr Leu Val Thr Val Ser Ser
        115                 120

<210> SEQ ID NO 24
<211> LENGTH: 111
<212> TYPE: PRT
<213> ORGANISM: Artificial Sequence
<220> FEATURE:
<223> OTHER INFORMATION: G11-VL

<400> SEQUENCE: 24

Leu Pro Val Leu Thr Gln Pro Ala Ser Val Ser Gly Ser Pro Gly Gln
```

```
  1               5                  10                 15
Ser Val Thr Ile Ser Cys Thr Gly Thr Ser Ser Asp Val Gly Gly His
                20                 25                 30

Asn Tyr Val Ser Trp Tyr Gln Gln His Pro Gly Lys Ala Pro Lys Leu
                35                 40                 45

Met Ile Tyr Glu Val Asn Lys Arg Pro Ser Gly Val Pro Asp Arg Phe
 50                 55                 60

Ser Gly Ser Lys Ser Asp Tyr Thr Ala Ser Leu Thr Ile Ser Gly Leu
 65                 70                 75                 80

Gln Pro Asp Asp Glu Ala Asp Tyr Phe Cys Ser Ser Tyr Thr Ala Thr
                85                 90                 95

Thr Thr Gly Val Val Phe Gly Thr Gly Thr Lys Val Thr Val Leu
                100                105                110

<210> SEQ ID NO 25
<211> LENGTH: 118
<212> TYPE: PRT
<213> ORGANISM: Artificial Sequence
<220> FEATURE:
<223> OTHER INFORMATION: G12-VH

<400> SEQUENCE: 25

Glu Val Gln Leu Val Gln Ser Gly Ala Glu Val Lys Lys Pro Gly Ala
1               5                  10                 15

Ser Val Lys Val Ser Cys Lys Ala Ser Gly Tyr Thr Phe Thr Gly Tyr
                20                 25                 30

Tyr Met His Trp Val Arg Gln Ala Pro Gly Gln Gly Leu Glu Trp Met
                35                 40                 45

Gly Trp Ile Asn Pro Asn Ser Asp Asn Thr Gly Ser Ala Gln Lys Phe
 50                 55                 60

Gln Gly Arg Val Phe Met Thr Lys Thr Thr Ser Leu Asn Thr Ala Tyr
 65                 70                 75                 80

Met Glu Leu Ser Gly Leu Arg Ser Glu Asp Thr Ala Ile Tyr Tyr Cys
                85                 90                 95

Ala Arg Glu Arg Ser Ser Gly Tyr Phe Asp Phe Trp Gly Gln Gly Thr
                100                105                110

Leu Val Thr Val Ser Ser
        115

<210> SEQ ID NO 26
<211> LENGTH: 107
<212> TYPE: PRT
<213> ORGANISM: Artificial Sequence
<220> FEATURE:
<223> OTHER INFORMATION: G12-VL

<400> SEQUENCE: 26

Asp Ile Val Met Thr Gln Ser Pro Ser Ser Leu Ser Ala Ser Val Gly
1               5                  10                 15

Asp Arg Val Thr Ile Thr Cys Arg Ala Ser Gln Ser Ile Ser Ser Tyr
                20                 25                 30

Leu Asn Trp Tyr Gln Gln Lys Pro Gly Lys Ala Pro Lys Leu Leu Ile
                35                 40                 45

Tyr Ala Ala Ser Ser Leu Gln Ser Gly Val Pro Ser Arg Phe Ser Gly
        50                 55                 60

Ser Gly Ser Gly Thr Asp Phe Thr Leu Thr Ile Ser Ser Leu Gln Pro
 65                 70                 75                 80
```

Glu Asp Phe Ala Thr Tyr Tyr Cys Gln Gln Ser Tyr Ser Thr Pro Ile
                85                  90                  95

Thr Phe Gly Gln Gly Thr Arg Leu Glu Ile Lys
            100                 105

<210> SEQ ID NO 27
<211> LENGTH: 124
<212> TYPE: PRT
<213> ORGANISM: Artificial Sequence
<220> FEATURE:
<223> OTHER INFORMATION: H1-VH

<400> SEQUENCE: 27

Gln Val Gln Leu Val Gln Ser Gly Ala Glu Val Lys Lys Pro Gly Ala
1               5                   10                  15

Ser Val Lys Val Ser Cys Lys Thr Ser Gly Asn Thr Phe Thr Asn Tyr
            20                  25                  30

Tyr Met His Trp Val Arg Gln Ala Pro Gly Gln Gly Leu Glu Trp Met
        35                  40                  45

Gly Ile Met Asn Pro Ser Gly Gly Ser Thr Ser Tyr Ala Gln Lys Phe
    50                  55                  60

Gln Gly Arg Val Thr Met Thr Arg Asp Lys Ser Thr Ser Thr Val Tyr
65                  70                  75                  80

Met Glu Leu Ser Ser Leu Thr Ser Glu Asp Thr Ala Val Tyr Tyr Cys
                85                  90                  95

Ala Arg Asp Leu Phe Pro His Ile Tyr Gly Asn Tyr Tyr Gly Met Asp
            100                 105                 110

Ile Trp Gly Gln Gly Thr Thr Val Thr Val Ser Ser
        115                 120

<210> SEQ ID NO 28
<211> LENGTH: 107
<212> TYPE: PRT
<213> ORGANISM: Artificial Sequence
<220> FEATURE:
<223> OTHER INFORMATION: H1-VL

<400> SEQUENCE: 28

Asp Ile Val Met Thr Gln Ser Pro Pro Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Val Glu Ile Lys
            100                 105

<210> SEQ ID NO 29
<211> LENGTH: 128
<212> TYPE: PRT
<213> ORGANISM: Artificial Sequence
<220> FEATURE:
<223> OTHER INFORMATION: H3-VH

```
<400> SEQUENCE: 29

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Ser Tyr Ala Gln Lys Phe
50                  55                  60

Gln Gly Arg Val Thr Ile Thr Ala Asp Glu Ser Thr Thr Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Pro Glu Tyr Cys Ser Gly Gly Thr Cys Tyr Ser Ala
            100                 105                 110

Asp Ala Phe Asp Ile Trp Gly Gln Gly Thr Met Val Thr Val Ser Ser
        115                 120                 125

<210> SEQ ID NO 30
<211> LENGTH: 110
<212> TYPE: PRT
<213> ORGANISM: Artificial Sequence
<220> FEATURE:
<223> OTHER INFORMATION: H3-VL

<400> SEQUENCE: 30

Gln Ser Val Val Thr Gln Pro Pro Ser Val Ser Ala Ala Pro Gly Gln
1               5                   10                  15

Lys Val Thr Ile Ser Cys Ser Gly Ser Thr Ser Asn Ile Glu Asn Tyr
                20                  25                  30

Ser Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Asn Arg Leu
                85                  90                  95

Ser Ser Val Val Phe Gly Gly Gly Thr Lys Val Thr Val Leu
            100                 105                 110

<210> SEQ ID NO 31
<211> LENGTH: 119
<212> TYPE: PRT
<213> ORGANISM: Artificial Sequence
<220> FEATURE:
<223> OTHER INFORMATION: H4-VH

<400> SEQUENCE: 31

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Arg Ile Ile Pro Ile Leu Gly Ile Ala Asn Tyr Ala Gln Lys Phe
50                  55                  60
```

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Ser Glu Ser Gly Ser Tyr Ser His Asp Tyr Trp Gly Gln Gly
        100                 105                 110

Thr Thr Val Thr Val Ser Ser
        115

<210> SEQ ID NO 32
<211> LENGTH: 110
<212> TYPE: PRT
<213> ORGANISM: Artificial Sequence
<220> FEATURE:
<223> OTHER INFORMATION: H4-VL

<400> SEQUENCE: 32

Gln Pro Val Leu Thr Gln Pro Pro Ser Val Ser Ala Ala Pro Gly Gln
1               5                   10                  15

Lys Val Thr Ile Ser Cys Ser Gly Ser Ser Asn Ile Gly Asn Ser
            20                  25                  30

His Val Ser Trp Phe Gln Gln Leu Pro Gly Thr Ala Pro Lys Leu Val
        35                  40                  45

Ile Tyr Asp Asn Asp Lys Arg Pro Ser Gly Ile Ala Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
            85                  90                  95

Ser Ala Gly Val Phe Gly Gly Gly Thr Lys Leu Thr Val Leu
        100                 105                 110

<210> SEQ ID NO 33
<211> LENGTH: 121
<212> TYPE: PRT
<213> ORGANISM: Artificial Sequence
<220> FEATURE:
<223> OTHER INFORMATION: H5-VH

<400> SEQUENCE: 33

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Ile Ile Asn Pro Ser Gly Gly Ser Thr Thr Tyr Ala Gln Lys Phe
    50                  55                  60

Gln Gly Arg Val Ser Met Thr Arg Asp Thr Ser Thr Arg Thr Val Tyr
65                  70                  75                  80

Met Glu Leu Ser Gly Leu Ile Ser Asp Asp Thr Ala Ile Tyr Tyr Cys
            85                  90                  95

Ala Arg Asp Asp Asp Phe Tyr Ser Gly Tyr Pro Gly Asp Tyr Trp Gly
        100                 105                 110

Gln Gly Thr Leu Val Thr Val Ser Ser
        115                 120

<210> SEQ ID NO 34

```
<211> LENGTH: 109
<212> TYPE: PRT
<213> ORGANISM: Artificial Sequence
<220> FEATURE:
<223> OTHER INFORMATION: H5-VL

<400> SEQUENCE: 34

Gln Ala Val Val Thr Gln Pro Pro Ser Ala Ser Gly Thr Pro Gly Gln
1               5                   10                  15

Arg Val Thr Ile Ser Cys Ser Gly Ser Ser Asn Val Gly Val Asn
            20                  25                  30

His Val Phe Trp Tyr Gln His Leu Pro Gly Met Ala Pro Lys Leu Leu
        35                  40                  45

Ile His Arg Thr Asn Gln Trp Pro Ser Gly Val Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Val Phe Gly Gly Gly Thr Lys Leu Thr Val Leu
            100                 105

<210> SEQ ID NO 35
<211> LENGTH: 121
<212> TYPE: PRT
<213> ORGANISM: Artificial Sequence
<220> FEATURE:
<223> OTHER INFORMATION: H6-VH

<400> SEQUENCE: 35

Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asn Ile Val Ala Thr Ile Thr Pro Leu Asp Tyr Trp Gly
            100                 105                 110

Gln Gly Thr Leu Val Thr Val Ser Ser
        115                 120

<210> SEQ ID NO 36
<211> LENGTH: 108
<212> TYPE: PRT
<213> ORGANISM: Artificial Sequence
<220> FEATURE:
<223> OTHER INFORMATION: H6-VL

<400> SEQUENCE: 36

Ser Tyr Glu Leu Met Gln Pro Pro Ser Val Ser Val Ala Pro Gly Lys
1               5                   10                  15

Thr Ala Thr Ile Ala Cys Gly Gly Glu Asn Ile Gly Arg Lys Thr Val
            20                  25                  30
```

His Trp Tyr Gln Gln Lys Pro Gly Gln Ala Pro Val Leu Val Ile Tyr
            35                  40                  45

Tyr Asp Ser Asp Arg Pro Ser Gly Ile Pro Glu Arg Phe Ser Gly Ser
     50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Asp His
                 85                  90                  95

Arg Ile Phe Gly Gly Gly Thr Lys Leu Thr Val Leu
             100                 105

<210> SEQ ID NO 37
<211> LENGTH: 118
<212> TYPE: PRT
<213> ORGANISM: Artificial Sequence
<220> FEATURE:
<223> OTHER INFORMATION: H10-VH

<400> SEQUENCE: 37

Glu Val Gln Leu Val Gln Ser Gly Gly Gly Leu Val Gln Pro Gly Gly
 1               5                   10                  15

Ser Leu Arg Leu Ser Cys Ala Ala Ser Gly Phe Thr Phe Ser Ser Tyr
             20                  25                  30

Ser Met Asn Trp Val Arg Gln Ala Pro Gly Lys Gly Leu Glu Trp Val
             35                  40                  45

Ser Tyr Ile Ser Ser Ser Ser Thr Ile Tyr Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Asp Glu Asp Thr Ala Val Tyr Tyr Cys
                 85                  90                  95

Ala Arg Gly Asp Tyr Tyr Tyr Gly Met Asp Val Trp Gly Gln Gly Thr
             100                 105                 110

Thr Val Thr Val Ser Ser
            115

<210> SEQ ID NO 38
<211> LENGTH: 108
<212> TYPE: PRT
<213> ORGANISM: Artificial Sequence
<220> FEATURE:
<223> OTHER INFORMATION: H10-VL

<400> SEQUENCE: 38

Glu Ile Val Leu Thr Gln Ser Pro Ser Ser Leu Ser Ala Ser Ile Gly
 1               5                   10                  15

Asp Arg Val Thr Leu Thr Cys Arg Ala Ser Gln Ser Ile Arg Arg Phe
             20                  25                  30

Leu Asn Trp Tyr Gln Gln Lys Pro Gly Lys Ala Pro Glu Leu Leu Ile
             35                  40                  45

Tyr Thr Ala Ser Ser Leu Gln Ser Gly Val Pro Ser Arg Phe Ser Gly
     50                  55                  60

Ser Gly Ser Gly Thr Asp Phe Thr Leu Thr Ile Asn Ser Leu Gln Pro
 65                  70                  75                  80

Glu Asp Phe Ala Thr Tyr Tyr Cys Gln Gln Ser Tyr Ala Val Ser Pro
                 85                  90                  95

Tyr Thr Phe Gly Gln Gly Thr Lys Val Glu Ile Arg
             100                 105

<210> SEQ ID NO 39
<211> LENGTH: 127
<212> TYPE: PRT
<213> ORGANISM: Artificial Sequence
<220> FEATURE:
<223> OTHER INFORMATION: H12-VH

<400> SEQUENCE: 39

```
Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Phe Trp Ser Gly Tyr Arg Thr Tyr Tyr Tyr Tyr
            100                 105                 110

Gly Met Asp Val Trp Gly Gln Gly Thr Met Val Thr Val Ser Ser
        115                 120                 125
```

<210> SEQ ID NO 40
<211> LENGTH: 110
<212> TYPE: PRT
<213> ORGANISM: Artificial Sequence
<220> FEATURE:
<223> OTHER INFORMATION: H12-VL

<400> SEQUENCE: 40

```
Gln Ser Val Val Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Val Val Phe Gly Gly Gly Thr Lys Leu Thr Val Leu
            100                 105                 110
```

<210> SEQ ID NO 41
<211> LENGTH: 118
<212> TYPE: PRT
<213> ORGANISM: Artificial Sequence
<220> FEATURE:
<223> OTHER INFORMATION: PDL-D2-VH

<400> SEQUENCE: 41

```
Gln Val Gln Leu Val Gln Ser Gly Ala Glu Val Lys Lys Pro Gly Ala
1               5                   10                  15
```

```
Ser Val Lys Val Ser Cys Lys Thr Ser Gly Tyr Thr Phe Thr Ser Asn
             20                  25                  30

Ala Ile Gly Trp Val Arg Gln Ala Pro Gly Gln Gly Leu Glu Trp Met
         35                  40                  45

Gly Trp Ile Ser Ala Tyr Asn Gly Asn Thr Asn Tyr Ala Gln Asn Leu
     50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Phe Tyr Cys
                 85                  90                  95

Ala Arg Lys Gly Thr Gly Leu His Phe Asp Tyr Trp Gly Gln Gly Thr
            100                 105                 110

Leu Val Thr Val Ser Ser
            115

<210> SEQ ID NO 42
<211> LENGTH: 108
<212> TYPE: PRT
<213> ORGANISM: Artificial Sequence
<220> FEATURE:
<223> OTHER INFORMATION: PDL-D2-VL

<400> SEQUENCE: 42

Ala Leu Thr Gln Pro Ala Ser Val Ser Gly Ser Leu Gly Gln Ser Ile
1               5                   10                  15

Thr Ile Ser Cys Thr Gly Ser Ser Ser Asp Val Gly Gly Tyr Lys Tyr
             20                  25                  30

Val Ser Trp Tyr Gln Gln His Pro Gly Lys Ala Pro Lys Leu Met Ile
         35                  40                  45

Tyr Asp Val Ile Asn Arg Pro Ser Gly Val Ser Ser Arg Phe Ser Gly
     50                  55                  60

Ser Lys Ser Ala Asn Thr Ala Ser Leu Thr Ile Ser Gly Leu Gln Ala
 65                  70                  75                  80

Glu Asp Glu Ala Asp Tyr Tyr Cys Phe Ser Tyr Ser Arg Ser Thr
                 85                  90                  95

Arg Ile Phe Gly Ser Gly Thr Lys Val Thr Val Leu
            100                 105

<210> SEQ ID NO 43
<211> LENGTH: 121
<212> TYPE: PRT
<213> ORGANISM: Artificial Sequence
<220> FEATURE:
<223> OTHER INFORMATION: PDL-D11-VH

<400> SEQUENCE: 43

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
             20                  25                  30

Ser Ala Ala Trp Asn Trp Ile Arg Gln Ser Pro Ser Arg Gly Leu Glu
         35                  40                  45

Trp Leu Gly Arg Thr Tyr Tyr Arg Ser Lys Trp Tyr Asn Asp Tyr Ala
     50                  55                  60

Val Ser Val Lys Ser Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
                 85                  90                  95
```

```
Tyr Tyr Cys Ala Arg Gly Ala Ala Gly Arg Ala Phe Asp Ile Trp Gly
            100                 105                 110

Gln Gly Thr Met Val Thr Val Ser Ser
        115                 120

<210> SEQ ID NO 44
<211> LENGTH: 110
<212> TYPE: PRT
<213> ORGANISM: Artificial Sequence
<220> FEATURE:
<223> OTHER INFORMATION: PDL-D11-VL

<400> SEQUENCE: 44

Gln Thr Val Val Thr Gln Pro Pro Ser Val Ser Lys Asp Leu Gly Gln
1               5                   10                  15

Thr Ala Thr Leu Thr Cys Thr Gly Asn Asn Asn Val Gly Asn His
            20                  25                  30

Gly Ala Ala Trp Leu Gln Gln His Gln Gly His Pro Pro Lys Leu Leu
        35                  40                  45

Ser Tyr Arg Asn Asn Asn Arg Pro Ser Gly Ile Ser Glu Arg Leu Ser
    50                  55                  60

Ala Ser Arg Ser Gly Asn Thr Ala Ser Leu Thr Ile Thr Gly Leu Gln
65                  70                  75                  80

Pro Glu Asp Glu Ala Asp Tyr Tyr Cys Ser Ala Trp Asp Arg Ser Leu
                85                  90                  95

Ser Ala Trp Val Phe Gly Gly Gly Thr Lys Leu Thr Val Leu
            100                 105                 110

<210> SEQ ID NO 45
<211> LENGTH: 118
<212> TYPE: PRT
<213> ORGANISM: Artificial Sequence
<220> FEATURE:
<223> OTHER INFORMATION: PDL-H1-VH

<400> SEQUENCE: 45

Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Gly Asp Tyr Tyr Gly Met Asp Val Trp Gly Gln Gly Thr
            100                 105                 110

Thr Val Thr Val Ser Ser
        115

<210> SEQ ID NO 46
<211> LENGTH: 108
<212> TYPE: PRT
<213> ORGANISM: Artificial Sequence
<220> FEATURE:
<223> OTHER INFORMATION: PDL-H1-VL
```

<400> SEQUENCE: 46

Glu Ile Val Leu Thr Gln Ser Pro Ser Ser Leu Ser Ala Ser Ile Gly
1               5                   10                  15

Asp Arg Val Thr Leu Thr Cys Arg Ala Ser Gln Ser Ile Arg Arg Phe
            20                  25                  30

Leu Asn Trp Tyr Gln Gln Lys Pro Gly Lys Ala Pro Glu Leu Leu Ile
        35                  40                  45

Tyr Thr Ala Ser Ser Leu Gln Ser Gly Val Pro Ser Arg Phe Ser Gly
50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Gln Gln Ser Tyr Ala Val Ser Pro
                85                  90                  95

Tyr Thr Phe Gly Gln Gly Thr Lys Val Glu Ile Lys
            100                 105

<210> SEQ ID NO 47
<211> LENGTH: 117
<212> TYPE: PRT
<213> ORGANISM: Artificial Sequence
<220> FEATURE:
<223> OTHER INFORMATION: RB4-VH

<400> SEQUENCE: 47

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Tyr Leu Gly Ser Tyr
            20                  25                  30

Trp Met Ala Trp Val Arg Gln Ala Pro Gly Lys Gly Leu Glu Trp Val
        35                  40                  45

Ala Ala Ile Arg Gln Asp Gly Ser Glu Thr Ile Tyr Val Asp Ser Val
50                  55                  60

Lys Gly Arg Phe Ile Ile Ser Arg Asp Asn Gly Asn Ser Val Thr
65                  70                  75                  80

Leu Gln Met Thr Thr Leu Arg Ala Gly Asp Thr Ala Val Tyr Tyr Cys
                85                  90                  95

Ala Arg Ala His Tyr Phe Gly Phe Asp Asn Trp Gly Gln Gly Thr Leu
            100                 105                 110

Val Thr Val Ser Ser
        115

<210> SEQ ID NO 48
<211> LENGTH: 110
<212> TYPE: PRT
<213> ORGANISM: Artificial Sequence
<220> FEATURE:
<223> OTHER INFORMATION: RB4-VL

<400> SEQUENCE: 48

Gln Ser Val Leu Thr Gln Pro Ala Ser Val Ser Gly Ser Pro Gly Gln
1               5                   10                  15

Ser Ile Ser Val Ser Cys Thr Gly Thr Ser Ser Asp Val Gly Arg Tyr
            20                  25                  30

Asn Phe Val Ser Trp Tyr Gln Gln His Pro Gly Lys Ala Pro Lys Leu
        35                  40                  45

Met Val Phe Asp Val Ser Asn Arg Pro Ser Gly Ile Ser Asn Arg Phe
50                  55                  60

```
Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Thr Asn
                 85                  90                  95

Ser Thr Tyr Val Phe Gly Ser Gly Thr Lys Val Thr Val Leu
            100                 105                 110

<210> SEQ ID NO 49
<211> LENGTH: 124
<212> TYPE: PRT
<213> ORGANISM: Artificial Sequence
<220> FEATURE:
<223> OTHER INFORMATION: RB11-VH

<400> SEQUENCE: 49

Gln Met Gln Leu Val Gln Ser Gly Ala Glu Val Lys Lys Pro Gly Ala
  1               5                  10                  15

Ser Val Lys Ile Ser Cys Lys Ala Ser Gly Tyr Pro Phe Arg Asn Tyr
                 20                  25                  30

Tyr Ile His Trp Val Arg Gln Ala Pro Gly Gln Gly Leu Glu Trp Val
             35                  40                  45

Gly Ile Ile Asn Pro Asp Gly Gly Thr Ile Thr Tyr Ala Gly Lys Phe
 50                  55                  60

Gln Gly Arg Val Ser Met Thr Arg Asp Thr Ser Thr Ser Thr Val Tyr
 65                  70                  75                  80

Met Glu Leu Ser Ser Leu Thr Ser Glu Asp Thr Ala Val Tyr Tyr Cys
                 85                  90                  95

Ala Arg Asp Leu Phe Pro His Ile Tyr Gly Asn Tyr Tyr Gly Met Asp
            100                 105                 110

Ile Trp Gly Gln Gly Thr Thr Val Thr Val Ser Ser
            115                 120

<210> SEQ ID NO 50
<211> LENGTH: 110
<212> TYPE: PRT
<213> ORGANISM: Artificial Sequence
<220> FEATURE:
<223> OTHER INFORMATION: RB11-VL

<400> SEQUENCE: 50

Gln Pro Val Leu Thr Gln Pro Pro Ser Val Ser Ala Ala Pro Gly Gln
  1               5                  10                  15

Lys Val Thr Ile Ser Cys Ser Gly Ser Ser Ser Asn Ile Ala Asn Asn
                 20                  25                  30

Tyr Val Ser Trp Tyr Gln Gln Leu Pro Gly Thr Ala Pro Lys Leu Leu
             35                  40                  45

Ile Phe Ala Asn Asn Lys Arg Pro Ser Gly Ile Pro Asp Arg Phe Ser
 50                  55                  60

Gly Ser Lys Ser Gly Thr Ser Ala Ala Leu Asp Ile Thr Gly Leu Gln
 65                  70                  75                  80

Thr Gly Asp Glu Ala Asp Tyr Tyr Cys Gly Thr Trp Asp Ser Asp Leu
                 85                  90                  95

Arg Ala Gly Val Phe Gly Gly Gly Thr Lys Leu Thr Val Leu
            100                 105                 110

<210> SEQ ID NO 51
<211> LENGTH: 121
<212> TYPE: PRT
```

<213> ORGANISM: Artificial Sequence
<220> FEATURE:
<223> OTHER INFORMATION: RC5-VH

<400> SEQUENCE: 51

Glu Val Gln Leu Leu Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ser Lys Asn Thr Val Ser
65                  70                  75                  80

Leu Gln Met Asn Ser Leu Arg Ala Glu Asp Thr Ala Val Tyr Tyr Cys
                85                  90                  95

Ala Lys Asp Arg Tyr Tyr Asn Phe Pro Leu Gly Met Asp Val Trp Gly
            100                 105                 110

Gln Gly Thr Thr Val Thr Val Ser Ser
        115                 120

<210> SEQ ID NO 52
<211> LENGTH: 107
<212> TYPE: PRT
<213> ORGANISM: Artificial Sequence
<220> FEATURE:
<223> OTHER INFORMATION: RC5-VL

<400> SEQUENCE: 52

Ala Ile Arg Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Thr Thr Ser Ser Leu Lys Ser Gly Val Pro Ser Arg Phe Ser Gly
    50                  55                  60

Ser Gly Ser Gly Thr Asp Phe Thr Leu Thr Ile Ser Arg Leu Gln Pro
65                  70                  75                  80

Glu Asp Phe Ala Thr Tyr Tyr Cys Gln Gln Ser Tyr Ser Ser Thr Trp
                85                  90                  95

Thr Phe Gly Arg Gly Thr Lys Val Glu Ile Lys
            100                 105

<210> SEQ ID NO 53
<211> LENGTH: 123
<212> TYPE: PRT
<213> ORGANISM: Artificial Sequence
<220> FEATURE:
<223> OTHER INFORMATION: RF5-VH

<400> SEQUENCE: 53

Glu Val Gln Leu Leu Glu Ser Gly Ala Glu Val Lys Lys Pro Gly Ser
1               5                   10                  15

Ser Val Lys Val Ser Cys Lys Ser Ser Gly Asp Thr Phe Thr Asn Phe
            20                  25                  30

Ala Ile Asn Trp Ile Arg Gln Ala Pro Gly Gln Gly Leu Glu Trp Met
        35                  40                  45

Gly Arg Ile Ile Pro Leu Phe Gly Thr Thr Asn Tyr Ala Gln Lys Phe
        50                  55                  60

Gln Gly Arg Val Thr Ile Thr Ala Asp Glu Ser Thr Ser Thr Ala Phe
65                  70                  75                  80

Met Asp Leu Asn Ser Leu Thr Ser Glu Asp Thr Ala Val Tyr Tyr Cys
                85                  90                  95

Ala Arg Thr Leu Gly Gly Asp Tyr Tyr Asp Ser Arg Gly Tyr Tyr Asn
                100                 105                 110

Trp Gly Gln Gly Thr Leu Val Thr Val Ser Ser
            115                 120

<210> SEQ ID NO 54
<211> LENGTH: 111
<212> TYPE: PRT
<213> ORGANISM: Artificial Sequence
<220> FEATURE:
<223> OTHER INFORMATION: RF5-VL

<400> SEQUENCE: 54

Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
                20                  25                  30

Asn Leu Val Ser Trp Tyr Gln Gln Tyr Pro Gly Lys Ala Pro Lys Leu
            35                  40                  45

Met Ile Tyr Glu Val Ser Glu Arg Pro Ser Gly Val Pro Asp Arg Phe
        50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Thr Asp Ser
                85                  90                  95

Asn Asn Phe Arg Val Phe Gly Gly Gly Thr Lys Leu Thr Val Leu
                100                 105                 110

<210> SEQ ID NO 55
<211> LENGTH: 116
<212> TYPE: PRT
<213> ORGANISM: Artificial Sequence
<220> FEATURE:
<223> OTHER INFORMATION: RG9-VH

<400> SEQUENCE: 55

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
                20                  25                  30

Ser Val Val Trp Asn Trp Phe Arg Gln Ser Pro Ser Arg Gly Leu Glu
            35                  40                  45

Trp Leu Gly Arg Ala Tyr Tyr Arg Ser Lys Trp Tyr Asn Asp Tyr Ala
        50                  55                  60

Val Ser Val Lys Ser Arg Ile Thr Ile Asn Pro Asp Thr Ser Lys Asn
65                  70                  75                  80

Gln Leu Ser Leu Gln Leu Asn Ser Val Thr Pro Glu Asp Thr Ala Val
                85                  90                  95

Tyr Tyr Cys Ala Lys Gly Leu Asp Val Trp Gly Gln Gly Thr Thr Val
                100                 105                 110

Thr Val Ser Ser

<210> SEQ ID NO 56
<211> LENGTH: 107
<212> TYPE: PRT
<213> ORGANISM: Artificial Sequence
<220> FEATURE:
<223> OTHER INFORMATION: RG9-VL

<400> SEQUENCE: 56

Glu Ile Val Met Thr Gln Ser Pro Ser Ser Leu Tyr Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Val Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Gly Leu Gln Pro
65                  70                  75                  80

Glu Asp Phe Ala Thr Tyr Tyr Cys Gln Gln Ser Tyr Thr Pro Ala Trp
                85                  90                  95

Thr Phe Gly Gln Gly Thr Lys Leu Glu Ile Lys
            100                 105

<210> SEQ ID NO 57
<211> LENGTH: 118
<212> TYPE: PRT
<213> ORGANISM: Artificial Sequence
<220> FEATURE:
<223> OTHER INFORMATION: RD1-VH

<400> SEQUENCE: 57

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Ile Val Ala Asp Phe Gln His Trp Gly Gln Gly Thr
            100                 105                 110

Leu Val Thr Val Ser Ser
        115

<210> SEQ ID NO 58
<211> LENGTH: 110
<212> TYPE: PRT
<213> ORGANISM: Artificial Sequence
<220> FEATURE:
<223> OTHER INFORMATION: RD1-VL

<400> SEQUENCE: 58

Gln Ser Val Val Thr Gln Pro Pro Ser Val Ser Ala Ala Pro Gly Gln
1               5                   10                  15

-continued

Lys Val Thr Ile Ser Cys Ser Gly Ser Ser Asn Ile Gly Asn Asn
            20                  25                  30

Tyr Val Ser Trp Tyr Gln Gln Val Pro Gly Thr Ala Pro Lys Leu Leu
        35                  40                  45

Ile Tyr Asp Asn Asp Lys Arg Pro Ser Gly Ile Pro Asp Arg Phe Ser
    50                  55                  60

Gly Ser Lys Ser Gly Thr Ser Ala Thr Leu Ala Ile Thr Gly Leu Gln
65                  70                  75                  80

Thr Gly Asp Glu Ala Asp Tyr Tyr Cys Gly Thr Trp Asp Ser Ser Leu
                85                  90                  95

Asn Ala Trp Val Phe Gly Gly Gly Thr Lys Leu Thr Val Leu
            100                 105                 110

<210> SEQ ID NO 59
<211> LENGTH: 118
<212> TYPE: PRT
<213> ORGANISM: Artificial Sequence
<220> FEATURE:
<223> OTHER INFORMATION: RF11-VH

<400> SEQUENCE: 59

Gln Val Gln Leu Val Gln Ser Gly Ala Glu Val Lys Lys Pro Gly Ala
1               5                   10                  15

Ser Val Arg Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Ile Val Ala Asp Phe Gln His Trp Gly Gln Gly Thr
            100                 105                 110

Leu Val Thr Val Ser Ser
        115

<210> SEQ ID NO 60
<211> LENGTH: 110
<212> TYPE: PRT
<213> ORGANISM: Artificial Sequence
<220> FEATURE:
<223> OTHER INFORMATION: RF11-VL

<400> SEQUENCE: 60

Gln Ser Val Leu Thr Gln Pro Pro Ser Val Ser Ala Ala Pro Gly Gln
1               5                   10                  15

Lys Val Thr Ile Ser Cys Ser Gly Ser Ser Asn Ile Glu Asn Asn
            20                  25                  30

Tyr Val Ser Trp Tyr Gln His Leu Pro Gly Thr Ala Pro Lys Leu Leu
        35                  40                  45

Ile Tyr Asp Asp Phe Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu

```
                     85                  90                  95

Ser Ala Val Val Phe Gly Gly Gly Thr Lys Leu Thr Val Leu
            100                 105                 110

<210> SEQ ID NO 61
<211> LENGTH: 118
<212> TYPE: PRT
<213> ORGANISM: Artificial Sequence
<220> FEATURE:
<223> OTHER INFORMATION: RH11-VH

<400> SEQUENCE: 61

Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Ser Tyr
            20                  25                  30

Pro Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Met Tyr Tyr Cys
                85                  90                  95

Ala Lys Asn His Pro Thr Ala Thr Leu Asp Tyr Trp Gly Gln Gly Thr
            100                 105                 110

Leu Val Thr Val Ser Ser
        115

<210> SEQ ID NO 62
<211> LENGTH: 111
<212> TYPE: PRT
<213> ORGANISM: Artificial Sequence
<220> FEATURE:
<223> OTHER INFORMATION: RH11-VL

<400> SEQUENCE: 62

Gln Ser Val Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Ser
                85                  90                  95

Asn Asn Leu Gly Val Phe Gly Gly Gly Thr Lys Leu Thr Val Leu
            100                 105                 110

<210> SEQ ID NO 63
<211> LENGTH: 121
<212> TYPE: PRT
<213> ORGANISM: Artificial Sequence
<220> FEATURE:
<223> OTHER INFORMATION: RD9-VH

<400> SEQUENCE: 63
```

Gln Val Gln Leu Val Gln Ser Gly Gly Asn Leu Val Lys Pro Gly Gly
1               5                   10                  15

Ser Leu Arg Leu Ser Cys Ala Ala Ser Gly Phe Ser Phe Ser Ser Tyr
            20                  25                  30

Asp Met Asn Trp Val Arg Gln Ala Pro Gly Arg Gly Leu Glu Trp Val
            35                  40                  45

Ser Ser Ile Ser Gly Thr Gly Arg Tyr Glu Tyr Tyr Ser Pro Ser Val
50                  55                  60

Lys Gly Arg Phe Thr Ile Ser Arg Asp Asn Ala Asn Thr Ser Leu Tyr
65                  70                  75                  80

Leu Gln Met Asn Ser Leu Thr Ala Asp Asp Thr Ala Val Tyr Phe Cys
            85                  90                  95

Thr Arg Gly Asp Ile Leu Thr Gly Ala Ser Ala Met Asp Val Trp Gly
            100                 105                 110

Gln Gly Thr Thr Val Thr Val Ser Ser
            115                 120

<210> SEQ ID NO 64
<211> LENGTH: 107
<212> TYPE: PRT
<213> ORGANISM: Artificial Sequence
<220> FEATURE:
<223> OTHER INFORMATION: RD9-VL

<400> SEQUENCE: 64

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
            85                  90                  95

Thr Phe Gly Gly Gly Thr Lys Val Glu Ile Lys
            100                 105

<210> SEQ ID NO 65
<211> LENGTH: 121
<212> TYPE: PRT
<213> ORGANISM: Artificial Sequence
<220> FEATURE:
<223> OTHER INFORMATION: RE10-VH

<400> SEQUENCE: 65

Glu Val Gln Leu Leu Glu Ser Gly Gly Asn Leu Val Lys Pro Gly Gly
1               5                   10                  15

Ser Leu Arg Leu Ser Cys Ala Ala Ser Gly Phe Ser Phe Ser Ser Tyr
            20                  25                  30

Asp Met Asn Trp Val Arg Gln Ala Pro Gly Arg Gly Leu Glu Trp Val
            35                  40                  45

Ser Ser Ile Ser Gly Thr Gly Arg Tyr Glu Tyr Tyr Ser Pro Ser Val
50                  55                  60

Lys Gly Arg Phe Thr Ile Ser Arg Asp Asn Ala Asn Thr Ser Leu Tyr

```
                65                  70                  75                  80
Leu Gln Met Asn Ser Leu Thr Ala Asp Asp Thr Ala Val Tyr Phe Cys
                    85                  90                  95

Thr Arg Gly Asp Ile Leu Thr Gly Ala Ser Ala Met Asp Val Trp Gly
                100                 105                 110

Gln Gly Thr Thr Val Thr Val Ser Ser
        115                 120

<210> SEQ ID NO 66
<211> LENGTH: 107
<212> TYPE: PRT
<213> ORGANISM: Artificial Sequence
<220> FEATURE:
<223> OTHER INFORMATION: RE10-VL

<400> SEQUENCE: 66

Asp Val Val Met Thr Gln Ser Pro Ser Thr Leu Ser Ala Ser Val Gly
1               5                   10                  15

Asp Arg Val Thr Ile Thr Cys Arg Ala Ser Gln Ser Ile Gly Thr Trp
                20                  25                  30

Leu Ala Trp Tyr Gln Gln Lys Pro Gly Lys Ala Pro Asn Leu Leu Ile
            35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Ala Asn Ser Phe Pro Leu
                85                  90                  95

Thr Phe Gly Gly Gly Thr Lys Val Glu Ile Lys
                100                 105

<210> SEQ ID NO 67
<211> LENGTH: 120
<212> TYPE: PRT
<213> ORGANISM: Artificial Sequence
<220> FEATURE:
<223> OTHER INFORMATION: RA3-VH

<400> SEQUENCE: 67

Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Arg Tyr
                20                  25                  30

Gly Val His Trp Val Arg Gln Ala Pro Gly Gln Gly Leu Glu Trp Met
            35                  40                  45

Gly Arg Leu Ile Pro Ile Val Ser Met Thr Asn Tyr Ala Gln Lys Phe
    50                  55                  60

Gln Asp Arg Val Ser Ile Thr Thr Asp Lys Ser Thr Gly Thr Ala Tyr
65                  70                  75                  80

Met Glu Leu Arg Ser Leu Thr Ser Glu Asp Thr Ala Leu Tyr Tyr Cys
                85                  90                  95

Ala Ser Val Gly Gln Gln Leu Pro Trp Val Phe Phe Ala Trp Gly Gln
                100                 105                 110

Gly Thr Leu Val Thr Val Ser Ser
        115                 120

<210> SEQ ID NO 68
<211> LENGTH: 107
```

<212> TYPE: PRT
<213> ORGANISM: Artificial Sequence
<220> FEATURE:
<223> OTHER INFORMATION: RA3-VL

<400> SEQUENCE: 68

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ser His Trp
                85                  90                  95

Thr Phe Gly Gln Gly Thr Lys Val Glu Ile Lys
            100                 105

<210> SEQ ID NO 69
<211> LENGTH: 120
<212> TYPE: PRT
<213> ORGANISM: Artificial Sequence
<220> FEATURE:
<223> OTHER INFORMATION: RG1-VH

<400> SEQUENCE: 69

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Arg Tyr
            20                  25                  30

Gly Val His Trp Val Arg Gln Ala Pro Gly Gln Gly Leu Glu Trp Met
        35                  40                  45

Gly Arg Leu Ile Pro Ile Val Ser Met Thr Asn Tyr Ala Gln Lys Phe
50                  55                  60

Gln Asp Arg Val Ser Ile Thr Thr Asp Lys Ser Thr Gly Thr Ala Tyr
65                  70                  75                  80

Met Glu Leu Arg Ser Leu Thr Ser Glu Asp Thr Ala Leu Tyr Tyr Cys
                85                  90                  95

Ala Ser Val Gly Gln Gln Leu Pro Trp Val Phe Phe Ala Trp Gly Gln
            100                 105                 110

Gly Thr Leu Val Thr Val Ser Ser
        115                 120

<210> SEQ ID NO 70
<211> LENGTH: 112
<212> TYPE: PRT
<213> ORGANISM: Artificial Sequence
<220> FEATURE:
<223> OTHER INFORMATION: RG1-VL

<400> SEQUENCE: 70

Gln Ser Val Val Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Gly Val His Trp Tyr Gln His Leu Pro Gly Ser Ala Pro Lys Leu

```
                35                  40                  45
Leu Ile Tyr Gly Asn Ser Asn Arg Pro Ser Gly Val Thr Asp Arg Ile
 50                  55                  60

Ser Gly Ser Lys Ser Gly Thr Ser Ala Ser Leu Ala Ile Thr Gly Leu
65                  70                  75                  80

Gln Ala Glu Asp Glu Ala Val Tyr Tyr Cys Gln Ser Tyr Asp Ser Ser
                85                  90                  95

Leu Ser Thr Ser Val Val Phe Gly Gly Gly Thr Lys Leu Thr Val Leu
            100                 105                 110

<210> SEQ ID NO 71
<211> LENGTH: 118
<212> TYPE: PRT
<213> ORGANISM: Artificial Sequence
<220> FEATURE:
<223> OTHER INFORMATION: RB1-VH

<400> SEQUENCE: 71

Gln Met Gln Leu Val Gln Ser Gly Gly Gly Leu Ile Gln Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Phe Asp Gly Ser Asn Lys Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Thr Glu Asp Thr Ala Val Tyr Tyr Cys
                85                  90                  95

Ala Arg Gly Trp Leu Asp Arg Asp Ile Asp Tyr Trp Gly Gln Gly Thr
            100                 105                 110

Leu Val Thr Val Ser Ser
        115

<210> SEQ ID NO 72
<211> LENGTH: 111
<212> TYPE: PRT
<213> ORGANISM: Artificial Sequence
<220> FEATURE:
<223> OTHER INFORMATION: RB1-VL

<400> SEQUENCE: 72

Gln Ala Gly Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Thr Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asn Tyr Tyr Cys Ser Ser Tyr Thr Ser Arg
                85                  90                  95

Ser Thr Ser Val Leu Phe Gly Gly Gly Thr Lys Leu Thr Val Leu
            100                 105                 110
```

<210> SEQ ID NO 73
<211> LENGTH: 118
<212> TYPE: PRT
<213> ORGANISM: Artificial Sequence
<220> FEATURE:
<223> OTHER INFORMATION: RG7-VH

<400> SEQUENCE: 73

```
Glu Val Gln Leu Val Glu Ser Gly Gly Gly Val Val Leu Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Phe Asp Gly Ser Asn Lys Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Thr Glu Asp Thr Ala Val Tyr Tyr Cys
                85                  90                  95

Ala Arg Gly Trp Leu Asp Arg Asp Ile Asp Tyr Trp Gly Gln Gly Thr
            100                 105                 110

Leu Val Thr Val Ser Ser
        115
```

<210> SEQ ID NO 74
<211> LENGTH: 110
<212> TYPE: PRT
<213> ORGANISM: Artificial Sequence
<220> FEATURE:
<223> OTHER INFORMATION: RG7-VL

<400> SEQUENCE: 74

```
Gln Pro Val Leu Thr Gln Pro Pro Ser Val Ser Glu Ala Pro Arg Gln
1               5                   10                  15

Arg Val Thr Ile Ser Cys Ser Gly Ser Ser Ser Asn Ile Gly His Asn
            20                  25                  30

Ala Val Thr Trp Tyr Gln Gln Val Pro Gly Lys Ala Pro Lys Leu Leu
        35                  40                  45

Ile Tyr Tyr Asp Asp Leu Leu Pro Ser Gly Val Ser Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Trp Val Phe Gly Gly Gly Thr Lys Leu Thr Val Leu
            100                 105                 110
```

<210> SEQ ID NO 75
<211> LENGTH: 118
<212> TYPE: PRT
<213> ORGANISM: Artificial Sequence
<220> FEATURE:
<223> OTHER INFORMATION: RA6-VH

<400> SEQUENCE: 75

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
```

```
            20                  25                  30
Ala Met His Trp Val Arg Gln Ala Pro Gly Lys Gly Leu Glu Trp Val
            35                  40                  45

Ala Val Ile Ser Phe Asp Gly Ser Asn Lys Tyr Tyr Ala Asp Ser Val
        50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Thr Glu Asp Thr Ala Val Tyr Tyr Cys
                85                  90                  95

Ala Arg Gly Trp Leu Asp Arg Asp Ile Asp Tyr Trp Gly Gln Gly Thr
            100                 105                 110

Leu Val Thr Val Ser Ser
            115

<210> SEQ ID NO 76
<211> LENGTH: 112
<212> TYPE: PRT
<213> ORGANISM: Artificial Sequence
<220> FEATURE:
<223> OTHER INFORMATION: RA6-VH

<400> SEQUENCE: 76

Gln Ala Gly Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
            35                  40                  45

Met Ile Tyr Asp Val Ser Asn Arg Pro Ser Gly Val Pro Asp Arg Phe
        50                  55                  60

Ser Gly Ser Lys Ser Gly Asn Thr Ala Ser Leu Thr Ile Ser Gly Leu
65                  70                  75                  80

Gln Ala Glu Asp Asp Ala Asp Tyr Tyr Cys Ala Ser Tyr Thr Ser Thr
                85                  90                  95

Ser Thr Leu Gly Val Val Phe Gly Gly Gly Thr Lys Leu Thr Val Leu
            100                 105                 110

<210> SEQ ID NO 77
<211> LENGTH: 118
<212> TYPE: PRT
<213> ORGANISM: Artificial Sequence
<220> FEATURE:
<223> OTHER INFORMATION: RA8-VH

<400> SEQUENCE: 77

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
            35                  40                  45

Ala Val Ile Ser Phe Asp Gly Ser Asn Lys Tyr Tyr Ala Asp Ser Val
        50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Thr Glu Asp Thr Ala Val Tyr Tyr Cys
                85                  90                  95
```

Ala Arg Gly Trp Leu Asp Arg Asp Ile Asp Tyr Trp Gly Gln Gly Thr
            100                 105                 110

Leu Val Thr Val Ser Ser
        115

<210> SEQ ID NO 78
<211> LENGTH: 111
<212> TYPE: PRT
<213> ORGANISM: Artificial Sequence
<220> FEATURE:
<223> OTHER INFORMATION: RA8-VL

<400> SEQUENCE: 78

Gln Pro Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln His Pro Gly Lys Ala Pro Lys Leu
        35                  40                  45

Met Ile Phe Asp Val Asn Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Asn Ser Tyr Thr Thr Ser
                85                  90                  95

Ser Thr Tyr Val Val Phe Gly Gly Gly Thr Lys Leu Thr Val Leu
            100                 105                 110

<210> SEQ ID NO 79
<211> LENGTH: 118
<212> TYPE: PRT
<213> ORGANISM: Artificial Sequence
<220> FEATURE:
<223> OTHER INFORMATION: RA9-VH

<400> SEQUENCE: 79

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Phe Asp Gly Ser Asn Lys Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Thr Glu Asp Thr Ala Val Tyr Tyr Cys
                85                  90                  95

Ala Arg Gly Trp Leu Asp Arg Asp Ile Asp Tyr Trp Gly Gln Gly Thr
            100                 105                 110

Leu Val Thr Val Ser Ser
        115

<210> SEQ ID NO 80
<211> LENGTH: 110
<212> TYPE: PRT
<213> ORGANISM: Artificial Sequence
<220> FEATURE:
<223> OTHER INFORMATION: RA9-VL

```
<400> SEQUENCE: 80

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
                20                  25                  30

Thr Val His Trp Tyr Gln Gln Leu Pro Gly Thr Ala Pro Lys Val Leu
            35                  40                  45

Ile Tyr Thr Asn Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Gln
65              70                  75                  80

Ser Glu Asp Glu Ala Asp Tyr Tyr Cys Ala Ala Trp Asp Gly Arg Leu
                85                  90                  95

Gln Gly Trp Val Phe Gly Gly Gly Thr Lys Leu Thr Val Leu
            100                 105                 110

<210> SEQ ID NO 81
<211> LENGTH: 118
<212> TYPE: PRT
<213> ORGANISM: Artificial Sequence
<220> FEATURE:
<223> OTHER INFORMATION: RB5-VH

<400> SEQUENCE: 81

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Val
            35                  40                  45

Ala Val Ile Ser Phe Asp Gly Ser Asn Lys Tyr Tyr Ala Asp Ser Val
50                  55                  60

Arg Gly Arg Phe Thr Ile Ser Arg Asp Asn Ser Lys Asn Thr Leu Tyr
65              70                  75                  80

Leu Gln Met Asn Ser Leu Arg Thr Glu Asp Thr Ala Val Tyr Tyr Cys
                85                  90                  95

Ala Arg Gly Trp Leu Asp Arg Asp Ile Asp Tyr Trp Gly Gln Gly Thr
            100                 105                 110

Leu Val Thr Val Ser Ser
        115

<210> SEQ ID NO 82
<211> LENGTH: 110
<212> TYPE: PRT
<213> ORGANISM: Artificial Sequence
<220> FEATURE:
<223> OTHER INFORMATION: RB5-VL

<400> SEQUENCE: 82

Gln Ser Val Val Thr Gln Pro Pro Ser Val Ser Ala Ala Pro Gly Gln
1               5                   10                  15

Lys Val Thr Ile Ser Cys Ser Gly Ser Asn Ser Asn Ile Ala Asn Asn
                20                  25                  30

Tyr Val Ser Trp Tyr Gln Gln Leu Pro Gly Thr Ala Pro Lys Leu Leu
            35                  40                  45

Ile Tyr Asp Ser Asn Lys Arg Pro Ser Gly Ile Pro Asp Arg Phe Ser
50                  55                  60
```

```
Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Ser Trp Asp Ser Ser Leu
                85                  90                  95

Ser Val Trp Met Phe Gly Gly Gly Thr Lys Leu Thr Val Leu
            100                 105                 110

<210> SEQ ID NO 83
<211> LENGTH: 118
<212> TYPE: PRT
<213> ORGANISM: Artificial Sequence
<220> FEATURE:
<223> OTHER INFORMATION: RB8-VH

<400> SEQUENCE: 83

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Val
            35                  40                  45

Ala Val Ile Ser Phe Asp Gly Ser Asn Lys Tyr Tyr Ala Asp Ser Val
        50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Thr Glu Asp Thr Ala Val Tyr Tyr Cys
                85                  90                  95

Ala Arg Gly Trp Leu Asp Arg Asp Ile Asp Tyr Trp Gly Gln Gly Thr
            100                 105                 110

Leu Val Thr Val Ser Ser
        115

<210> SEQ ID NO 84
<211> LENGTH: 112
<212> TYPE: PRT
<213> ORGANISM: Artificial Sequence
<220> FEATURE:
<223> OTHER INFORMATION: RB8-VL

<400> SEQUENCE: 84

Leu Pro Val Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Thr Lys Arg Pro Ser Gly Val Pro Asp Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Gly Ser
                85                  90                  95

Ser Thr Leu Gly Pro Val Phe Gly Gly Thr Lys Leu Thr Val Leu
            100                 105                 110

<210> SEQ ID NO 85
<211> LENGTH: 118
<212> TYPE: PRT
<213> ORGANISM: Artificial Sequence
```

<220> FEATURE:
<223> OTHER INFORMATION: RC8-VH

<400> SEQUENCE: 85

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Phe Asp Gly Ser Asn Lys Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Thr Glu Asp Thr Ala Val Tyr Tyr Cys
                85                  90                  95

Ala Arg Gly Trp Leu Asp Arg Asp Ile Asp Tyr Trp Gly Gln Gly Thr
            100                 105                 110

Leu Val Thr Val Ser Ser
            115

<210> SEQ ID NO 86
<211> LENGTH: 110
<212> TYPE: PRT
<213> ORGANISM: Artificial Sequence
<220> FEATURE:
<223> OTHER INFORMATION: RC8-VL

<400> SEQUENCE: 86

Gln Ser Val Leu Thr Gln Pro Pro Ser Val Ser Ala Ala Pro Gly Gln
1               5                   10                  15

Lys Val Thr Ile Ser Cys Ser Gly Asn Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asp Lys Arg Pro Ser Gly Ile Pro Asp Arg Phe Ser
    50                  55                  60

Gly Ser Lys Ser Gly Thr Ser Ala Ser Leu Ala Ile Ser Glu Leu Arg
65                  70                  75                  80

Phe Glu Asp Glu Ala Asp Tyr Tyr Cys Ala Ala Trp Asp Asp Thr Leu
                85                  90                  95

Ser Gly His Val Phe Gly Pro Gly Thr Lys Leu Thr Val Leu
            100                 105                 110

<210> SEQ ID NO 87
<211> LENGTH: 118
<212> TYPE: PRT
<213> ORGANISM: Artificial Sequence
<220> FEATURE:
<223> OTHER INFORMATION: RC10-VH

<400> SEQUENCE: 87

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

```
Ala Val Ile Ser Phe Asp Gly Ser Asn Lys Tyr Tyr Ala Asp Ser Val
        50                  55                  60

Arg Gly Arg Phe Thr Ile Ser Arg Asp Asn Ser Lys Asn Thr Leu Tyr
 65                  70                  75                  80

Leu Gln Met Asn Ser Leu Arg Thr Glu Asp Thr Ala Val Tyr Tyr Cys
                85                  90                  95

Ala Arg Gly Trp Leu Asp Arg Asp Ile Asp Tyr Trp Gly Gln Gly Thr
                100                 105                 110

Leu Val Thr Val Ser Ser
                115

<210> SEQ ID NO 88
<211> LENGTH: 108
<212> TYPE: PRT
<213> ORGANISM: Artificial Sequence
<220> FEATURE:
<223> OTHER INFORMATION: RC10-VL

<400> SEQUENCE: 88

Ser Tyr Glu Leu Met Gln Pro Pro Ser Val Ser Val Pro Pro Gly Glu
 1                   5                  10                  15

Thr Ala Arg Ile Thr Cys Gly Gly Asn Asn Ile Gly Asn Lys Asn Val
                20                  25                  30

His Trp Tyr Gln Gln Lys Pro Gly Gln Ala Pro Val Leu Val Val Arg
            35                  40                  45

Glu Asp Ser Ala Arg Pro Ala Gly Ile Pro Glu Arg Phe Ser Gly Ser
        50                  55                  60

Asn Ser Gly Asn Ser Ala Thr Leu Thr Ile Ser Arg Val Glu Ala Gly
 65                  70                  75                  80

Asp Glu Ala Asp Tyr Tyr Cys Gln Val Trp Asp Asn Thr Ser Asp His
                85                  90                  95

Val Val Phe Gly Gly Gly Thr Lys Leu Thr Val Leu
                100                 105

<210> SEQ ID NO 89
<211> LENGTH: 118
<212> TYPE: PRT
<213> ORGANISM: Artificial Sequence
<220> FEATURE:
<223> OTHER INFORMATION: RD2-VH

<400> SEQUENCE: 89

Gln Val Gln Leu Val Glu Ser Gly Gly Val Val Gln Pro Gly Arg
 1                   5                  10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Val
            35                  40                  45

Ala Val Ile Ser Phe Asp Gly Ser Asn Lys Tyr Tyr Ala Asp Ser Val
        50                  55                  60

Arg Gly Arg Phe Thr Ile Ser Arg Asp Asn Ser Lys Asn Thr Leu Tyr
 65                  70                  75                  80

Leu Gln Met Asn Ser Leu Arg Thr Glu Asp Thr Ala Val Tyr Tyr Cys
                85                  90                  95

Ala Arg Gly Trp Leu Asp Arg Asp Ile Asp Tyr Trp Gly Gln Gly Thr
                100                 105                 110

Leu Val Thr Val Ser Ser
                115
```

<210> SEQ ID NO 90
<211> LENGTH: 110
<212> TYPE: PRT
<213> ORGANISM: Artificial Sequence
<220> FEATURE:
<223> OTHER INFORMATION: RD2-VL

<400> SEQUENCE: 90

Ser Tyr Glu Leu Met Gln Pro Pro Ser Val Ser Glu Val Pro Gly Gln
1               5                   10                  15

Arg Val Thr Ile Ser Cys Ser Gly Ser Ser Asn Ile Gly Asn Asn
            20                  25                  30

Ala Val Asn Trp Phe Gln Gln Leu Pro Gly Lys Ala Pro Lys Leu Leu
        35                  40                  45

Val Tyr Tyr Asp Asp Trp Val Pro Ser Gly Ile Ser Gly Arg Phe Ser
50                  55                  60

Ala Ser Lys Ser Gly Thr Ser Ala Ser Leu Ala Ile Ser Gly Leu Gln
65                  70                  75                  80

Ser Gly Asp Glu Gly Asp Tyr Tyr Cys Ala Val Trp Asp Asp Arg Leu
                85                  90                  95

Ser Gly Val Val Phe Gly Gly Gly Thr Lys Leu Thr Val Leu
            100                 105                 110

<210> SEQ ID NO 91
<211> LENGTH: 118
<212> TYPE: PRT
<213> ORGANISM: Artificial Sequence
<220> FEATURE:
<223> OTHER INFORMATION: RE8-VH

<400> SEQUENCE: 91

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Phe Asp Gly Ser Asn Lys Tyr Tyr Ala Asp Ser Val
50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Thr Glu Asp Thr Ala Val Tyr Tyr Cys
                85                  90                  95

Ala Arg Gly Trp Leu Asp Arg Asp Ile Asp Tyr Trp Gly Gln Gly Thr
            100                 105                 110

Leu Val Thr Val Ser Ser
        115

<210> SEQ ID NO 92
<211> LENGTH: 110
<212> TYPE: PRT
<213> ORGANISM: Artificial Sequence
<220> FEATURE:
<223> OTHER INFORMATION: RE8-VL

<400> SEQUENCE: 92

Gln Ser Val Val Thr Gln Pro Pro Ser Val Ser Ala Ala Pro Gly Gln
1               5                   10                  15

```
Lys Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Thr Leu Leu
        35                  40                  45

Ile Tyr Asp Ser Asn Lys Arg Pro Ser Val Ile Pro Asp Arg Phe Ser
50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Leu
                85                  90                  95

Asn Gly Trp Val Phe Gly Gly Gly Thr Lys Leu Thr Val Leu
            100                 105                 110

<210> SEQ ID NO 93
<211> LENGTH: 118
<212> TYPE: PRT
<213> ORGANISM: Artificial Sequence
<220> FEATURE:
<223> OTHER INFORMATION: RE9-VH

<400> SEQUENCE: 93

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Phe Asp Gly Ser Asn Lys Tyr Tyr Ala Asp Ser Val
50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Thr Glu Asp Thr Ala Val Tyr Tyr Cys
                85                  90                  95

Ala Arg Gly Trp Leu Asp Arg Asp Ile Asp Tyr Trp Gly Gln Gly Thr
            100                 105                 110

Met Val Thr Val Ser Ser
        115

<210> SEQ ID NO 94
<211> LENGTH: 111
<212> TYPE: PRT
<213> ORGANISM: Artificial Sequence
<220> FEATURE:
<223> OTHER INFORMATION: RE9-VL

<400> SEQUENCE: 94

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Arg Ser Ser
                85                  90                  95
```

Thr Leu Gly Pro Val Phe Gly Gly Gly Thr Lys Leu Thr Val Leu
        100                 105                 110

<210> SEQ ID NO 95
<211> LENGTH: 118
<212> TYPE: PRT
<213> ORGANISM: Artificial Sequence
<220> FEATURE:
<223> OTHER INFORMATION: RG12-VH

<400> SEQUENCE: 95

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Phe Asp Gly Ser Asn Lys Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Thr Glu Asp Thr Ala Val Tyr Tyr Cys
                85                  90                  95

Ala Arg Gly Trp Leu Asp Arg Asp Ile Asp Tyr Trp Gly Gln Gly Thr
            100                 105                 110

Leu Val Thr Val Ser Ser
        115

<210> SEQ ID NO 96
<211> LENGTH: 111
<212> TYPE: PRT
<213> ORGANISM: Artificial Sequence
<220> FEATURE:
<223> OTHER INFORMATION: RG12-VL

<400> SEQUENCE: 96

Gln Ala Gly Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu Val Val Phe Gly Gly Gly Thr Lys Leu Thr Val Leu
            100                 105                 110

<210> SEQ ID NO 97
<211> LENGTH: 118
<212> TYPE: PRT
<213> ORGANISM: Artificial Sequence
<220> FEATURE:
<223> OTHER INFORMATION: RSA1-VH

<400> SEQUENCE: 97

```
Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Gly Asp Tyr Tyr Tyr Gly Met Asp Val Trp Gly Gln Gly Thr
            100                 105                 110

Thr Val Thr Val Ser Ser
            115
```

```
<210> SEQ ID NO 98
<211> LENGTH: 108
<212> TYPE: PRT
<213> ORGANISM: Artificial Sequence
<220> FEATURE:
<223> OTHER INFORMATION: RSA1-VL

<400> SEQUENCE: 98

Asn Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ser Arg Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Ala Leu Thr Ile Ser Ser Leu Gln Pro
65                  70                  75                  80

Glu Asp Phe Ala Thr Tyr Tyr Cys Gln Gln Ala Asp Ser Phe Phe Ser
                85                  90                  95

Ile Thr Phe Gly Gln Gly Thr Arg Leu Glu Ile Lys
            100                 105
```

```
<210> SEQ ID NO 99
<211> LENGTH: 118
<212> TYPE: PRT
<213> ORGANISM: Artificial Sequence
<220> FEATURE:
<223> OTHER INFORMATION: R2A7-VH

<400> SEQUENCE: 99

Gln Val Gln Leu Val Gln Ser Gly Ser Glu Val Lys Lys Pro Gly Ala
1               5                   10                  15

Ser Val Lys Val Ser Cys Arg Ala Ser Gly Tyr Leu Phe Thr Asn Tyr
            20                  25                  30

Gly Ile Ser Trp Val Arg Gln Ala Pro Gly Gln Gly Leu Glu Trp Met
        35                  40                  45

Gly Trp Val Ser Ala His Gly Glu Phe Thr Lys Tyr Ala Pro Ser Leu
    50                  55                  60

Gln Asp Arg Val Thr Met Thr Ser Asp Ile Ser Thr Thr Thr Ala Tyr
65                  70                  75                  80
```

```
Met Glu Leu Arg Ser Leu Arg Ser Asp Asp Ala Gly Val Tyr Tyr Cys
                85                  90                  95

Ala Arg Asp Arg Gly Ala Asp His Phe Asp Thr Trp Gly Gln Gly Thr
            100                 105                 110

Leu Val Thr Val Ser Ser
        115

<210> SEQ ID NO 100
<211> LENGTH: 107
<212> TYPE: PRT
<213> ORGANISM: Artificial Sequence
<220> FEATURE:
<223> OTHER INFORMATION: R2A7-VL

<400> SEQUENCE: 100

Ala Ile Gln Leu Thr Gln Ser Pro Ala Thr Leu Ser Leu Ser Pro Gly
1               5                   10                  15

Glu Arg Ala Thr Leu Ser Cys Arg Ala Ser Gln Ser Val Gly Val Tyr
            20                  25                  30

Leu Ala Trp Tyr Gln Gln Lys Pro Gly Gln Ser Pro Arg Leu Leu Ile
        35                  40                  45

Tyr Asp Thr Ser Lys Arg Ala Thr Gly Ile Pro Asp Arg Phe Ser Ala
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys His Gln Arg His Ser Trp Pro Thr
                85                  90                  95

Thr Phe Gly Gln Gly Thr Arg Leu Glu Ile Lys
            100                 105

<210> SEQ ID NO 101
<211> LENGTH: 124
<212> TYPE: PRT
<213> ORGANISM: Artificial Sequence
<220> FEATURE:
<223> OTHER INFORMATION: R2B12-VH

<400> SEQUENCE: 101

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Met Ile Asn Pro Ser Ser Ala Thr Thr Tyr Thr Gln Lys Phe
    50                  55                  60

Gln Gly Arg Val Ser Met Thr Arg Asp Thr Ser Thr Ser Thr Val Tyr
65                  70                  75                  80

Met Glu Leu Ser Ser Leu Thr Ser Glu Asp Thr Ala Val Tyr Tyr Cys
                85                  90                  95

Ala Arg Asp Leu Phe Pro His Ile Tyr Gly Asn Tyr Tyr Gly Met Asp
            100                 105                 110

Ile Trp Gly Gln Gly Thr Thr Val Thr Val Ser Ser
        115                 120

<210> SEQ ID NO 102
<211> LENGTH: 106
<212> TYPE: PRT
```

```
<213> ORGANISM: Artificial Sequence
<220> FEATURE:
<223> OTHER INFORMATION: R2B12-VL

<400> SEQUENCE: 102

Asn Ile Gln Met Thr Gln Ser Pro Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Leu Thr
                85                  90                  95

Phe Gly Gly Gly Thr Lys Val Glu Ile Lys
            100                 105

<210> SEQ ID NO 103
<211> LENGTH: 120
<212> TYPE: PRT
<213> ORGANISM: Artificial Sequence
<220> FEATURE:
<223> OTHER INFORMATION: R2C9-VH

<400> SEQUENCE: 103

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser His
            20                  25                  30

Val Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Met Arg Ser Glu Asp Thr Ala Val Tyr Tyr Cys
                85                  90                  95

Ala Thr Ser Gly Val Val Ala Ala Thr His Phe Gly Tyr Trp Gly Gln
            100                 105                 110

Gly Thr Leu Val Thr Val Ser Ser
        115                 120

<210> SEQ ID NO 104
<211> LENGTH: 111
<212> TYPE: PRT
<213> ORGANISM: Artificial Sequence
<220> FEATURE:
<223> OTHER INFORMATION: R2C9-VL

<400> SEQUENCE: 104

Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Asp Tyr
            20                  25                  30

Asn Leu Val Ser Trp Tyr Gln Gln His Pro Gly Lys Ala Pro Lys Leu
        35                  40                  45
```

```
Ile Ile Tyr Glu Val Asn Lys Arg Pro Ser Gly Val Ser Asn Arg Phe
         50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Ala Gly Tyr
                 85                  90                  95

Asn Asn Leu Tyr Val Phe Gly Thr Gly Thr Lys Val Thr Val Leu
            100                 105                 110

<210> SEQ ID NO 105
<211> LENGTH: 123
<212> TYPE: PRT
<213> ORGANISM: Artificial Sequence
<220> FEATURE:
<223> OTHER INFORMATION: R2D5-VH

<400> SEQUENCE: 105

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
             35                  40                  45

Gly Gly Ile Ile Pro Ile Phe Gly Thr Ala Asn Tyr Ala Gln Lys Phe
         50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Ala Ser Gly Ser Tyr Phe Ile Thr Thr Tyr Val Asp Tyr
            100                 105                 110

Trp Gly Gln Gly Thr Leu Val Thr Val Ser Ser
        115                 120

<210> SEQ ID NO 106
<211> LENGTH: 110
<212> TYPE: PRT
<213> ORGANISM: Artificial Sequence
<220> FEATURE:
<223> OTHER INFORMATION: R2D5-VL

<400> SEQUENCE: 106

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
             35                  40                  45

Ile Ile Tyr Asp Val Asn Met Arg Pro Ser Gly Val Pro Asp Arg Phe
         50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Ala Gly Leu
                 85                  90                  95

Tyr Phe Pro Leu Phe Gly Gly Gly Thr Gln Leu Thr Val Leu
            100                 105                 110
```

```
<210> SEQ ID NO 107
<211> LENGTH: 121
<212> TYPE: PRT
<213> ORGANISM: Artificial Sequence
<220> FEATURE:
<223> OTHER INFORMATION: R2D7-VH

<400> SEQUENCE: 107

Glu Val Gln Leu Val Glu Ser Gly Gly Gly Leu Val Gln Pro Gly Gly
1               5                   10                  15

Pro Leu Arg Leu Ser Cys Ala Ala Ser Gly Phe Thr Leu Ser Ser Tyr
            20                  25                  30

Trp Met Ser Trp Val Arg Gln Ala Pro Gly Lys Gly Leu Glu Trp Val
        35                  40                  45

Ala Asn Ile Lys Tyr Asp Gly Ser Glu Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Arg Leu Arg Leu Glu Asp Thr Ala Val Tyr Tyr Cys
                85                  90                  95

Ala Arg Glu Val Ser Ser Ala Ala Thr Ser Pro Leu Asp Arg Trp Gly
            100                 105                 110

Arg Gly Thr Leu Val Thr Val Ser Ser
        115                 120

<210> SEQ ID NO 108
<211> LENGTH: 107
<212> TYPE: PRT
<213> ORGANISM: Artificial Sequence
<220> FEATURE:
<223> OTHER INFORMATION: R2D7-VL

<400> SEQUENCE: 108

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser His Ser Ser Arg Tyr
                85                  90                  95

Thr Phe Gly Gln Gly Thr Lys Leu Glu Ile Lys
            100                 105

<210> SEQ ID NO 109
<211> LENGTH: 120
<212> TYPE: PRT
<213> ORGANISM: Artificial Sequence
<220> FEATURE:
<223> OTHER INFORMATION: R2F4-VH

<400> SEQUENCE: 109

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Arg Tyr
            20                  25                  30
```

Gly Val His Trp Val Arg Gln Ala Pro Gly Gln Gly Leu Glu Trp Met
            35                  40                  45

Gly Arg Leu Ile Pro Ile Val Ser Met Thr Asn Tyr Ala Gln Lys Phe
    50                  55                  60

Gln Asp Arg Val Ser Ile Thr Thr Asp Lys Ser Thr Gly Thr Ala Tyr
65                  70                  75                  80

Met Glu Leu Arg Ser Leu Thr Ser Glu Asp Thr Ala Leu Tyr Tyr Cys
                85                  90                  95

Ala Ser Val Gly Gln Gln Leu Pro Trp Val Phe Phe Ala Trp Gly Gln
                100                 105                 110

Gly Thr Leu Val Thr Val Ser Ser
            115                 120

<210> SEQ ID NO 110
<211> LENGTH: 112
<212> TYPE: PRT
<213> ORGANISM: Artificial Sequence
<220> FEATURE:
<223> OTHER INFORMATION: R2F4-VL

<400> SEQUENCE: 110

Gln Ser Val Val Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Gly Val His Trp Tyr Gln His Leu Pro Gly Ser Ala Pro Lys Leu
            35                  40                  45

Leu Ile Tyr Gly Asn Ser Asn Arg Pro Ser Gly Val Thr Asp Arg Ile
    50                  55                  60

Ser Gly Ser Lys Ser Gly Thr Ser Ala Ser Leu Ala Ile Thr Gly Leu
65                  70                  75                  80

Gln Ala Glu Asp Glu Ala Val Tyr Tyr Cys Gln Ser Tyr Asp Ser Ser
                85                  90                  95

Leu Ser Thr Ser Val Val Phe Gly Gly Gly Thr Lys Leu Thr Val Leu
                100                 105                 110

<210> SEQ ID NO 111
<211> LENGTH: 118
<212> TYPE: PRT
<213> ORGANISM: Artificial Sequence
<220> FEATURE:
<223> OTHER INFORMATION: R2A10-VH

<400> SEQUENCE: 111

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
            35                  40                  45

Ala Val Ile Ser Phe Asp Gly Ser Asn Lys Tyr Tyr Ala Asp Ser Val
    50                  55                  60

Arg Gly Arg Phe Thr Ile Ser Arg Asp Asn Lys Asn Thr Leu Tyr
65                  70                  75                  80

Leu Gln Met Asn Ser Leu Arg Thr Glu Asp Thr Ala Val Tyr Tyr Cys
                85                  90                  95

Ala Arg Gly Trp Leu Asp Arg Asp Ile Asp Tyr Trp Gly Gln Gly Thr

```
                    100                 105                 110

Leu Val Thr Val Ser Ser
        115

<210> SEQ ID NO 112
<211> LENGTH: 110
<212> TYPE: PRT
<213> ORGANISM: Artificial Sequence
<220> FEATURE:
<223> OTHER INFORMATION: R2A10-VL

<400> SEQUENCE: 112

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val His Trp Tyr Gln Gln Leu Pro Gly Thr Ala Pro Lys Val Leu
        35                  40                  45

Ile Tyr Thr Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Gly Arg Leu
                85                  90                  95

Gln Gly Trp Val Phe Gly Gly Gly Thr Gln Leu Thr Val Leu
            100                 105                 110

<210> SEQ ID NO 113
<211> LENGTH: 118
<212> TYPE: PRT
<213> ORGANISM: Artificial Sequence
<220> FEATURE:
<223> OTHER INFORMATION: R2E2-VH

<400> SEQUENCE: 113

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Phe Asp Gly Ser Asn Lys Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Thr Glu Asp Thr Ala Val Tyr Tyr Cys
                85                  90                  95

Ala Arg Gly Trp Leu Asp Arg Asp Ile Asp Tyr Trp Gly Gln Gly Thr
            100                 105                 110

Leu Val Thr Val Ser Ser
        115

<210> SEQ ID NO 114
<211> LENGTH: 110
<212> TYPE: PRT
<213> ORGANISM: Artificial Sequence
<220> FEATURE:
<223> OTHER INFORMATION: R2E2-VL

<400> SEQUENCE: 114
```

-continued

Gln Ala Gly Leu Thr Gln Pro Pro Ser Ala Ser Gly Thr Pro Gly Gln
1               5                   10                  15

Arg Val Thr Ile Ser Cys Phe Gly Ser Ser Asp Ile Gly Ser Asn
            20                  25                  30

Thr Val Asn Trp Tyr Gln Gln Val Ser Gly Arg Ala Pro Lys Leu Leu
            35                  40                  45

Leu Tyr Thr Asn Gly Gln Arg Pro Ser Gly Val Pro Asp Arg Phe Ser
50                  55                  60

Gly Ser Lys Ser Gly Ser Ser Ala Ser Leu Ala Ile Ser Gly Leu Gln
65                  70                  75                  80

Ser Glu Asp Glu Ala Asp Tyr Tyr Cys Ala Ser Trp Asp Ser Leu
            85                  90                  95

Lys Gly Tyr Val Phe Gly Thr Gly Thr Lys Val Thr Val Leu
            100                 105                 110

<210> SEQ ID NO 115
<211> LENGTH: 120
<212> TYPE: PRT
<213> ORGANISM: Artificial Sequence
<220> FEATURE:
<223> OTHER INFORMATION: R3B8-VH

<400> SEQUENCE: 115

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Arg Ile Ile Pro Ile Leu Gly Ile Ala Asn Tyr Ala Gln Lys Phe
50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Val Gly Gly Ala Gln Thr Pro Phe Asp Tyr Trp Gly Gln
            100                 105                 110

Gly Thr Leu Val Thr Val Ser Ser
            115                 120

<210> SEQ ID NO 116
<211> LENGTH: 109
<212> TYPE: PRT
<213> ORGANISM: Artificial Sequence
<220> FEATURE:
<223> OTHER INFORMATION: R3B8-VL

<400> SEQUENCE: 116

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Ser
            20                  25                  30

Tyr Val Ser Trp Tyr Gln His Leu Pro Gly Thr Ala Pro Lys Leu Leu
            35                  40                  45

Ile Tyr Asp Asn Asn Lys Arg Pro Ser Gly Ile Pro Asp Arg Phe Ser
50                  55                  60

Gly Ser Lys Ser Ala Thr Ser Ala Thr Leu Gly Ile Thr Gly Leu Gln

```
                65                  70                  75                  80
Thr Ala Asp Glu Ala Asp Tyr Tyr Cys Gly Thr Trp Asp Ser Ser Leu
                    85                  90                  95

Gly Val Val Phe Gly Gly Gly Thr Lys Leu Thr Val Leu
                100                 105

<210> SEQ ID NO 117
<211> LENGTH: 124
<212> TYPE: PRT
<213> ORGANISM: Artificial Sequence
<220> FEATURE:
<223> OTHER INFORMATION: R3C3-VH

<400> SEQUENCE: 117

Gln Val Gln Leu Val Gln Ser Gly Ser Glu Val Lys Arg Pro Gly Ala
1               5                   10                  15

Ser Val Arg Val Ser Cys Lys Ala Ser Gly Tyr Ile Phe Ser Gln Tyr
                20                  25                  30

Thr Ile His Trp Val Arg Gln Ala Pro Gly Glu Arg Leu Glu Trp Leu
            35                  40                  45

Gly Trp Ile Asn Ala Val Thr Gly Asn Thr Lys Tyr Ala Gln Lys Phe
    50                  55                  60

Gln Gly Arg Val Thr Ile Thr Met Asp Ser Ser Ala Ser Thr Ala Phe
65                  70                  75                  80

Met Glu Met Ser Ser Leu Arg Ser Glu Asp Ala Gly Val Tyr Phe Cys
                85                  90                  95

Ala Arg Asp Met Val Pro Phe Gly Gly Glu Ile Lys Tyr Gly Phe Asp
                100                 105                 110

Phe Trp Gly Gln Gly Thr Met Ile Thr Val Ser Ser
        115                 120

<210> SEQ ID NO 118
<211> LENGTH: 110
<212> TYPE: PRT
<213> ORGANISM: Artificial Sequence
<220> FEATURE:
<223> OTHER INFORMATION: R3C3-VL

<400> SEQUENCE: 118

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asn Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Phe Val Phe Gly Thr Gly Thr Lys Val Thr Val Leu
                100                 105                 110

<210> SEQ ID NO 119
<211> LENGTH: 122
<212> TYPE: PRT
<213> ORGANISM: Artificial Sequence
<220> FEATURE:
```

<223> OTHER INFORMATION: R3E9-VH

<400> SEQUENCE: 119

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
                35                  40                  45

Ala Leu Ile Ser Tyr Asp Gly Ser Asn Lys Tyr Tyr Ala Asp Ser Met
        50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Lys Thr Leu Met Pro Ala Ser Ile Met Gly Tyr Phe Thr His Trp
            100                 105                 110

Gly Gln Gly Thr Leu Val Thr Val Ser Ser
        115                 120

<210> SEQ ID NO 120
<211> LENGTH: 108
<212> TYPE: PRT
<213> ORGANISM: Artificial Sequence
<220> FEATURE:
<223> OTHER INFORMATION: R3E9-VL

<400> SEQUENCE: 120

Ser Tyr Glu Leu Met Gln Pro Pro Ser Val Ser Val Ala Pro Gly Glu
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Ile Leu Val Ile Tyr
                35                  40                  45

Tyr Asp Ser Gly Arg Pro Ser Gly Ile Pro Glu Arg Phe Ser Gly Ser
        50                  55                  60

Asn Ser Gly Asn Thr Ala Thr Leu Thr Ile Ser Arg Ala Glu Ala Gly
65                  70                  75                  80

Asp Glu Ala Asp Tyr Tyr Cys His Val Trp Asp Ser Tyr Thr Asp His
                85                  90                  95

Val Val Phe Gly Gly Gly Thr Lys Leu Thr Val Leu
            100                 105

<210> SEQ ID NO 121
<211> LENGTH: 120
<212> TYPE: PRT
<213> ORGANISM: Artificial Sequence
<220> FEATURE:
<223> OTHER INFORMATION: R3E10-VH

<400> SEQUENCE: 121

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
                35                  40                  45

Gly Ile Ile Asn Pro Ser Asp Gly Ser Thr Ser Tyr Ala Gln Lys Phe

-continued

```
                50                  55                  60
Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Tyr Tyr Gly Ser Gly Ile Ala Met Asp Val Trp Gly Gln
            100                 105                 110

Gly Thr Thr Val Thr Val Ser Ser
        115                 120
```

<210> SEQ ID NO 122
<211> LENGTH: 108
<212> TYPE: PRT
<213> ORGANISM: Artificial Sequence
<220> FEATURE:
<223> OTHER INFORMATION: R3E10-VL

<400> SEQUENCE: 122

```
Gln Pro Val Leu Thr Gln Pro Pro Ser Leu Ser Val Ala Pro Gly Lys
1               5                   10                  15

Thr Ala Ser Ile Ala Cys Gly Gly Asn Asn Ile Gly Ser Lys Arg Val
            20                  25                  30

His Trp Tyr Gln Gln Lys Pro Gly Gln Ala Pro Val Leu Val Ile Tyr
        35                  40                  45

Tyr Glu Ser Asp Arg Pro Ser Gly Ile Pro Glu Arg Phe Ser Gly Thr
    50                  55                  60

Ile Ser Gln Asn Thr Ala Thr Leu Ser Ile Ser Arg Val Glu Ala Gly
65                  70                  75                  80

Asp Glu Ala Asp Tyr Tyr Cys Gln Val Trp Asp Arg Ser Ser Ala His
                85                  90                  95

Val Val Phe Gly Gly Gly Thr Lys Val Thr Val Leu
            100                 105
```

<210> SEQ ID NO 123
<211> LENGTH: 118
<212> TYPE: PRT
<213> ORGANISM: Artificial Sequence
<220> FEATURE:
<223> OTHER INFORMATION: R3F7-VH

<400> SEQUENCE: 123

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Pro Glu Asp Thr Ala Val Tyr Tyr Cys
                85                  90                  95

Ala Arg Asp Asn Gly Asp Leu Gly Phe Asp Tyr Trp Gly Gln Gly Thr
            100                 105                 110

Leu Val Thr Val Ser Ser
        115
```

```
<210> SEQ ID NO 124
<211> LENGTH: 107
<212> TYPE: PRT
<213> ORGANISM: Artificial Sequence
<220> FEATURE:
<223> OTHER INFORMATION: R3F7-VL

<400> SEQUENCE: 124

Ala Ile Gln Met Thr Gln Ser Pro Ser Leu Ser Ala Ser Val Gly
1               5                   10                  15

Asp Arg Val Thr Ile Thr Cys Arg Ala Ser Gln Ser Ile Ser Thr Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Asn Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Arg
                85                  90                  95

Thr Phe Gly Pro Gly Thr Lys Val Asp Ile Lys
            100                 105

<210> SEQ ID NO 125
<211> LENGTH: 118
<212> TYPE: PRT
<213> ORGANISM: Artificial Sequence
<220> FEATURE:
<223> OTHER INFORMATION: R3F10-VH

<400> SEQUENCE: 125

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Thr Ile Tyr Tyr Ala Asp Ser Val Lys
    50                  55                  60

Gly Arg Phe Thr Ile Ser Arg Asp Ser Ser Lys Asn Thr Leu Tyr Leu
65                  70                  75                  80

His Met Asn Ser Leu Arg Ala Glu Asp Thr Gly Val Tyr Tyr Cys Ala
                85                  90                  95

Lys Gly Val Gly Ser Trp Ser Ile Phe Asp Tyr Trp Gly Gln Gly Thr
            100                 105                 110

Leu Val Thr Val Ser Ser
        115

<210> SEQ ID NO 126
<211> LENGTH: 106
<212> TYPE: PRT
<213> ORGANISM: Artificial Sequence
<220> FEATURE:
<223> OTHER INFORMATION: R3F10-VL

<400> SEQUENCE: 126

Asp Ile Gln Met Thr Gln Ser Pro Ser Leu Ser Ala Ser Val Gly
1               5                   10                  15

Asp Arg Val Thr Ile Thr Cys Gln Ala Ser Gln Asp Ile Ser Asn Tyr
```

```
                    20                  25                  30
Leu Asn Trp Tyr Gln Gln Lys Pro Gly Lys Ala Pro Lys Leu Leu Ile
            35                  40                  45

Phe Ala Gly Ser Asn Leu Gln Ser Gly Val Pro Ser Arg Phe Ser Gly
 50                  55                  60

Ser Gly Ser Gly Thr Asp Phe Thr Leu Thr Ile Thr Ser Leu Gln Pro
 65                  70                  75                  80

Glu Asp Phe Ala Thr Tyr Tyr Cys Gln Gln Ser Tyr Thr Thr Pro Thr
                85                  90                  95

Phe Gly Gln Gly Thr Lys Val Glu Ile Lys
            100                 105

<210> SEQ ID NO 127
<211> LENGTH: 117
<212> TYPE: PRT
<213> ORGANISM: Artificial Sequence
<220> FEATURE:
<223> OTHER INFORMATION: R4B10-VH

<400> SEQUENCE: 127

Glu Val Gln Leu Val Glu Ser Gly Ala Glu Leu Lys Lys Pro Gly Ser
 1               5                  10                  15

Ser Met Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Tyr Ile
            35                  40                  45

Gly Arg Ile Ile Pro Ile Phe Gly Val Thr Tyr Tyr Ala Gln Lys Phe
 50                  55                  60

Gln Gly Arg Val Thr Ile Ser Ala Asp Lys Ser Thr Ser Thr Val Tyr
 65                  70                  75                  80

Leu Asp Leu Arg Ser Leu Arg Ser Glu Asp Thr Ala Val Tyr Tyr Cys
                85                  90                  95

Ala Arg Asp Leu Gly Gly Gly Asp Gly Asp Trp Gly Gln Gly Thr Leu
            100                 105                 110

Val Thr Val Ser Ser
        115

<210> SEQ ID NO 128
<211> LENGTH: 109
<212> TYPE: PRT
<213> ORGANISM: Artificial Sequence
<220> FEATURE:
<223> OTHER INFORMATION: R4B10-VL

<400> SEQUENCE: 128

Gln Ser Val Val Thr Gln Pro Ala Ser Val Ser Gly Ser Pro Gly Gln
 1               5                  10                  15

Ser Ile Thr Ile Ser Cys Thr Gly Thr Ser Ser Asp Val Gly Ser Tyr
                20                  25                  30

Asn Leu Val Ser Trp Tyr Gln Gln His Pro Gly Lys Ala Pro Lys Leu
            35                  40                  45

Met Ile Tyr Glu Gly Ser Lys Arg Pro Ser Gly Val Ser Thr Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ser Asp Tyr Tyr Cys Ser Ser Tyr Thr Gly Ser
                85                  90                  95
```

```
Ala Trp Val Phe Gly Gly Gly Thr Lys Leu Thr Val Leu
            100                 105
```

<210> SEQ ID NO 129
<211> LENGTH: 114
<212> TYPE: PRT
<213> ORGANISM: Artificial Sequence
<220> FEATURE:
<223> OTHER INFORMATION: R4H1-VH

<400> SEQUENCE: 129

```
Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Arg Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Phe Cys
                85                  90                  95

Val Thr Ser Ala Trp Ser Asp Trp Gly Gln Gly Thr Leu Val Thr Val
            100                 105                 110

Ser Ser
```

<210> SEQ ID NO 130
<211> LENGTH: 110
<212> TYPE: PRT
<213> ORGANISM: Artificial Sequence
<220> FEATURE:
<223> OTHER INFORMATION: R4H1-VL

<400> SEQUENCE: 130

```
Gln Ser Val Val Thr Gln Pro Pro Ser Val Ser Ala Thr Pro Gly Gln
1               5                   10                  15

Lys Val Thr Ile Ser Cys Ser Gly Ser Asp Ser Asn Ile Gly Asn Asn
            20                  25                  30

Tyr Val Ser Trp Phe Leu Gln Leu Pro Gly Thr Ala Pro Lys Leu Leu
        35                  40                  45

Ile His Asn Asn Asp Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Gln Ser Phe Asp Asp Ser Leu
                85                  90                  95

Arg Gly Tyr Leu Phe Gly Thr Gly Thr Lys Val Thr Val Leu
            100                 105                 110
```

<210> SEQ ID NO 131
<211> LENGTH: 116
<212> TYPE: PRT
<213> ORGANISM: Artificial Sequence
<220> FEATURE:
<223> OTHER INFORMATION: R4A11-VH

<400> SEQUENCE: 131

```
Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Val Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Gly Ala Glu Asp Thr Ala Val Tyr Tyr Cys
                85                  90                  95

Ala Lys Gly Phe Tyr Tyr Pro Asp His Trp Gly Gln Gly Thr Leu Val
            100                 105                 110

Thr Val Ser Ser
        115

<210> SEQ ID NO 132
<211> LENGTH: 108
<212> TYPE: PRT
<213> ORGANISM: Artificial Sequence
<220> FEATURE:
<223> OTHER INFORMATION: R4A11-VL

<400> SEQUENCE: 132

Gln Ala Val Leu Thr Gln Pro Pro Ser Val Ser Ala Ala Pro Gly Gln
 1               5                  10                  15

Lys Val Thr Ile Ser Cys Ser Gly Gly Ser Ser Asn Ile Ala Asn Asn
            20                  25                  30

Tyr Val Ser Trp Tyr Gln His Leu Pro Gly Thr Ala Pro Lys Leu Leu
        35                  40                  45

Ile Tyr Asp Asp Asn Lys Arg Pro Ser Gly Ile Pro Asp Arg Phe Ser
 50                  55                  60

Gly Ser Lys Ser Gly Thr Ser Ala Thr Leu Gly Ile Thr Gly Leu Gln
 65                  70                  75                  80

Thr Gly Asp Gly Ala Asp Tyr Tyr Cys Gly Thr Trp Asp Asn Ser Leu
                85                  90                  95

Asn Ser Asp Trp Val Phe Gly Gly Gly Thr Lys Leu
            100                 105

<210> SEQ ID NO 133
<211> LENGTH: 119
<212> TYPE: PRT
<213> ORGANISM: Artificial Sequence
<220> FEATURE:
<223> OTHER INFORMATION: R3D2-VH

<400> SEQUENCE: 133

Glu Val Gln Leu Val Glu Ser Gly Gly Gly Val Val Gln Pro Gly Gly
 1               5                  10                  15

Ser Leu Arg Leu Ser Cys Glu Val Ser Gly Phe Ile Phe Ser Asp Tyr
            20                  25                  30

Gly Met His Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Met Tyr Tyr Cys
```

```
                85                  90                  95
Ala Arg Ser Trp Asn Tyr Gly Arg Phe Phe Asp Tyr Trp Asp Gln Gly
                100                 105                 110

Thr Leu Val Thr Val Ser Ser
        115

<210> SEQ ID NO 134
<211> LENGTH: 108
<212> TYPE: PRT
<213> ORGANISM: Artificial Sequence
<220> FEATURE:
<223> OTHER INFORMATION: R3D2-VL

<400> SEQUENCE: 134

Gln Ser Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
                20                  25                  30

His Trp Tyr Gln Gln Lys Pro Gly Gln Ala Pro Val Leu Val Ile Tyr
            35                  40                  45

Tyr Asp Ser Asp Arg Pro Ser Gly Ile Pro Glu Arg Phe Ser Gly Ser
50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Tyr Val Phe Gly Thr Gly Thr Lys Leu Thr Val Leu
                100                 105

<210> SEQ ID NO 135
<211> LENGTH: 119
<212> TYPE: PRT
<213> ORGANISM: Artificial Sequence
<220> FEATURE:
<223> OTHER INFORMATION: R5B8-VH

<400> SEQUENCE: 135

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ser Ser Arg Asn
                20                  25                  30

Trp Met His Trp Val Arg Leu Ala Pro Gly Lys Gly Leu Val Trp Val
            35                  40                  45

Ser Leu Ile Ala Pro Asp Gly Ser Leu Thr Thr Tyr Ala Asp Ser Val
    50                  55                  60

Lys Gly Arg Phe Thr Ile Ser Arg Asp Thr Ala Lys Asn Ser Val Gln
65                  70                  75                  80

Leu Leu Leu Asn Ser Leu Arg Ala Glu Asp Thr Gly Leu Tyr Phe Cys
                85                  90                  95

Ala Arg Glu Ala Gly Val Ser Gly Gly Leu Asp Val Trp Gly Gln Gly
                100                 105                 110

Thr Leu Val Thr Val Ser Ser
        115

<210> SEQ ID NO 136
<211> LENGTH: 107
<212> TYPE: PRT
<213> ORGANISM: Artificial Sequence
<220> FEATURE:
```

<223> OTHER INFORMATION: R5B8-VL

<400> SEQUENCE: 136

Val Ile Trp Met Thr Gln Ser Pro Ser Ser Leu Ser Ala Ser Val Gly
1               5                   10                  15

Asp Arg Val Thr Ile Thr Cys Arg Ala Ser Gln Thr Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys
            100                 105

<210> SEQ ID NO 137
<211> LENGTH: 123
<212> TYPE: PRT
<213> ORGANISM: Artificial Sequence
<220> FEATURE:
<223> OTHER INFORMATION: SH1A1Q-VH

<400> SEQUENCE: 137

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Thr Ile Tyr Asp Ser Ser Gly Tyr Ser Phe Asp Tyr
            100                 105                 110

Trp Gly Gln Gly Thr Leu Val Thr Val Ser Ser
        115                 120

<210> SEQ ID NO 138
<211> LENGTH: 110
<212> TYPE: PRT
<213> ORGANISM: Artificial Sequence
<220> FEATURE:
<223> OTHER INFORMATION: SH1A1Q-VL

<400> SEQUENCE: 138

Gln Ser Val Leu Thr Gln Pro Pro Ser Val Ser Ala Ala Pro Gly Gln
1               5                   10                  15

Lys Val Thr Ile Ser Cys Ser Gly Asn Asn Ser Asn Ile Ala Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Tyr Arg Pro Ser Gly Ile Pro Asp Arg Phe Ser

```
                    50                  55                  60
Gly Ser Lys Ser Gly Thr Ser Ala Thr Leu Asp Ile Thr Gly Leu Gln
 65                  70                  75                  80

Thr Gly Asp Glu Ala Asp Tyr Tyr Cys Gly Val Trp Asp Gly Ser Leu
                 85                  90                  95

Thr Thr Gly Val Phe Gly Gly Gly Thr Lys Leu Thr Val Leu
            100                 105                 110

<210> SEQ ID NO 139
<211> LENGTH: 124
<212> TYPE: PRT
<213> ORGANISM: Artificial Sequence
<220> FEATURE:
<223> OTHER INFORMATION: SH1B7B(K)-VH

<400> SEQUENCE: 139

Glu Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
                 20                  25                  30

Ala Ile Ser Trp Val Arg Gln Ala Pro Gly Gln Gly Leu Glu Trp Met
             35                  40                  45

Gly Ile Ile Asn Pro Ser Gly Gly Ser Thr Ser Tyr Ala Gln Lys Phe
         50                  55                  60

Gln Gly Arg Val Ser Met Thr Arg Asp Thr Ser Thr Ser Thr Val Tyr
 65                  70                  75                  80

Met Glu Leu Ser Ser Leu Thr Ser Glu Asp Thr Ala Val Tyr Tyr Cys
                 85                  90                  95

Ala Arg Asp Leu Phe Pro His Ile Tyr Gly Asn Tyr Tyr Gly Met Asp
                100                 105                 110

Ile Trp Gly Gln Gly Thr Thr Val Thr Val Ser Ser
            115                 120

<210> SEQ ID NO 140
<211> LENGTH: 107
<212> TYPE: PRT
<213> ORGANISM: Artificial Sequence
<220> FEATURE:
<223> OTHER INFORMATION: SH1B7B(K)-VL

<400> SEQUENCE: 140

Ala Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Asn Tyr
                 20                  25                  30

Leu Ala Trp Tyr Gln Gln Lys Pro Gly Lys Val Pro Lys Leu Leu Ile
             35                  40                  45

Tyr Ala Ala Ser Thr Leu Glu Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Leu Ala Thr Tyr Tyr Cys Gln Gln Leu His Thr Phe Pro Leu
                 85                  90                  95

Thr Phe Gly Gly Gly Thr Lys Val Glu Ile Lys
            100                 105

<210> SEQ ID NO 141
<211> LENGTH: 118
```

```
<212> TYPE: PRT
<213> ORGANISM: Artificial Sequence
<220> FEATURE:
<223> OTHER INFORMATION: SH1C1-VH

<400> SEQUENCE: 141
```

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Leu Ala Val Pro Gly Ala Phe Asp Ile Trp Gly Gln Gly Thr
            100                 105                 110

Met Val Thr Val Ser Ser
            115

```
<210> SEQ ID NO 142
<211> LENGTH: 111
<212> TYPE: PRT
<213> ORGANISM: Artificial Sequence
<220> FEATURE:
<223> OTHER INFORMATION: SH1C1-VL

<400> SEQUENCE: 142
```

Gln Pro Val Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Ala Tyr
            20                  25                  30

Asn Phe Val Ser Trp Tyr Arg Gln His Pro Gly Lys Ala Pro Lys Leu
        35                  40                  45

Met Ile Tyr Glu Val Asn Lys Arg Pro Ser Gly Val Pro Asp Arg Phe
50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Thr
            85                  90                  95

Asn Ser Leu Gly Ile Phe Gly Thr Gly Thr Lys Leu Thr Val Leu
            100                 105                 110

```
<210> SEQ ID NO 143
<211> LENGTH: 119
<212> TYPE: PRT
<213> ORGANISM: Artificial Sequence
<220> FEATURE:
<223> OTHER INFORMATION: SH1C8-VH

<400> SEQUENCE: 143
```

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val

```
                35                  40                  45
Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gln Trp Leu Val Thr Glu Leu Asp Tyr Trp Gly Gln Gly
            100                 105                 110

Thr Leu Val Thr Val Ser Ser
            115

<210> SEQ ID NO 144
<211> LENGTH: 111
<212> TYPE: PRT
<213> ORGANISM: Artificial Sequence
<220> FEATURE:
<223> OTHER INFORMATION: SH1C8-VL

<400> SEQUENCE: 144

Gln Ser Val Val Thr Gln Pro Pro Ser Val Ser Ala Ala Pro Gly Gln
1               5                   10                  15

Lys Val Thr Ile Ser Cys Ser Gly Ser Ser Ser Asp Ile Gly Asn His
                20                  25                  30

Tyr Val Ser Trp Tyr Gln Gln Leu Pro Gly Thr Ala Pro Lys Leu Leu
            35                  40                  45

Ile Tyr Asp Asn Asn Gln Arg Pro Ser Gly Ile Pro Asp Arg Phe Ser
    50                  55                  60

Gly Ser Lys Ser Gly Thr Ser Ala Thr Leu Ala Ile Thr Gly Leu Gln
65                  70                  75                  80

Thr Gly Asp Glu Ala Asp Tyr Tyr Cys Gly Thr Trp Asp Asn Ser Leu
                85                  90                  95

Ser Pro His Leu Leu Phe Gly Gly Gly Thr Lys Leu Thr Val Leu
            100                 105                 110

<210> SEQ ID NO 145
<211> LENGTH: 122
<212> TYPE: PRT
<213> ORGANISM: Artificial Sequence
<220> FEATURE:
<223> OTHER INFORMATION: SH1E10-VH

<400> SEQUENCE: 145

Glu Val Gln Leu Val Glu Ser Gly Ser Glu Val Glu Lys Pro Gly Ser
1               5                   10                  15

Ser Val Lys Val Ser Cys Lys Ala Ser Gly Gly Thr Phe Ser Asp Ser
                20                  25                  30

Gly Ile Ser Trp Val Arg Gln Ala Pro Gly Gln Gly Leu Glu Trp Met
            35                  40                  45

Gly Gly Ile Ile Pro Met Phe Ala Thr Pro Tyr Tyr Ala Gln Lys Phe
    50                  55                  60

Gln Asp Arg Val Thr Ile Thr Ala Asp Glu Ser Thr Ser Thr Val Tyr
65                  70                  75                  80

Met Glu Leu Ser Gly Leu Arg Ser Asp Thr Ala Val Phe Tyr Cys
                85                  90                  95

Ala Arg Asp Arg Gly Arg Gly His Leu Pro Trp Tyr Phe Asp Leu Trp
            100                 105                 110
```

Gly Arg Gly Thr Leu Val Thr Val Ser Ser
        115                 120

<210> SEQ ID NO 146
<211> LENGTH: 110
<212> TYPE: PRT
<213> ORGANISM: Artificial Sequence
<220> FEATURE:
<223> OTHER INFORMATION: SH1E10-VL

<400> SEQUENCE: 146

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Met Gly Asn Asn
            20                  25                  30

Tyr Val Ser Trp Tyr Lys Gln Val Pro Gly Thr Ala Pro Lys Leu Leu
        35                  40                  45

Ile Tyr Glu Asn Asp Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Asn Ser Leu
                85                  90                  95

Ser Gly Phe Val Phe Ala Ser Gly Thr Lys Val Thr Val Leu
            100                 105                 110

<210> SEQ ID NO 147
<211> LENGTH: 119
<212> TYPE: PRT
<213> ORGANISM: Artificial Sequence
<220> FEATURE:
<223> OTHER INFORMATION: SH1E2-VH

<400> SEQUENCE: 147

Glu Val Gln Leu Val Glu Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Pro Tyr Tyr Tyr Tyr Met Asp Val Trp Gly Gln Gly
            100                 105                 110

Thr Thr Val Thr Val Ser Ser
        115

<210> SEQ ID NO 148
<211> LENGTH: 109
<212> TYPE: PRT
<213> ORGANISM: Artificial Sequence
<220> FEATURE:
<223> OTHER INFORMATION: SH1E2-VL

<400> SEQUENCE: 148

Gln Ser Ala Leu Thr Gln Pro Ala Ser Val Ser Gly Ser Leu Gly Gln

```
                1               5                   10                  15
            Ser Val Thr Ile Ser Cys Thr Gly Ser Ser Asp Val Gly Ser Tyr
                            20                  25                  30

Asn Leu Val Ser Trp Tyr Gln Gln His Pro Gly Lys Ala Pro Asn Leu
                            35                  40                  45

Met Ile Tyr Asp Val Ser Lys Arg Ser Gly Val Ser Asn Arg Phe Ser
             50                  55                  60

Gly Ser Lys Ser Gly Asn Thr Ala Ser Leu Thr Ile Ser Gly Leu Gln
             65                  70                  75                  80

Ala Glu Asp Glu Ala Asp Tyr Tyr Cys Ser Ser Tyr Thr Gly Ile Ser
                            85                  90                  95

Thr Val Val Phe Gly Gly Gly Thr Lys Leu Thr Val Leu
                            100                 105
```

<210> SEQ ID NO 149
<211> LENGTH: 124
<212> TYPE: PRT
<213> ORGANISM: Artificial Sequence
<220> FEATURE:
<223> OTHER INFORMATION: SH1A9-VH

<400> SEQUENCE: 149

```
            Glu Val Gln Leu Leu Glu Ser Gly Ala Glu Val Lys Lys Pro Gly Ser
            1               5                   10                  15

Ser Val Lys Val Ser Cys Lys Ala Ser Gly Gly Thr Leu Ser Arg Tyr
                            20                  25                  30

Ala Leu Ser Trp Val Arg Gln Ala Pro Gly Gln Gly Pro Glu Trp Val
                            35                  40                  45

Gly Ala Ile Ile Pro Ile Phe Gly Thr Pro His Tyr Ser Lys Lys Phe
             50                  55                  60

Gln Asp Arg Val Ile Ile Thr Val Asp Thr Ser Thr Asn Thr Ala Phe
             65                  70                  75                  80

Met Glu Leu Ser Ser Leu Arg Phe Glu Asp Thr Ala Leu Tyr Phe Cys
                            85                  90                  95

Ala Arg Gly His Asp Glu Tyr Asp Ile Ser Gly Tyr His Arg Leu Asp
                            100                 105                 110

Tyr Trp Gly Gln Gly Thr Leu Val Thr Val Ser Ser
                            115                 120
```

<210> SEQ ID NO 150
<211> LENGTH: 110
<212> TYPE: PRT
<213> ORGANISM: Artificial Sequence
<220> FEATURE:
<223> OTHER INFORMATION: SH1A9-VL

<400> SEQUENCE: 150

```
            Gln Ser Val Leu Thr Gln Pro Ala Ser Val Ser Gly Ser Pro Gly Gln
            1               5                   10                  15

Ser Ile Thr Ile Ser Cys Thr Gly Thr Ser Ser Asp Val Gly Ser Tyr
                            20                  25                  30

Asn Leu Val Ser Trp Tyr Gln Gln His Pro Gly Lys Ala Pro Lys Leu
                            35                  40                  45

Met Ile Tyr Glu Val Ser Lys Arg Pro Ser Gly Val Ser Asn Arg Phe
             50                  55                  60

Ser Gly Ser Lys Ser Gly Asn Thr Ala Ser Leu Thr Ile Ser Gly Leu
             65                  70                  75                  80
```

Gln Ala Glu Asp Glu Ala Asp Tyr Tyr Cys Ser Ser Tyr Gly Gly Phe
                85                  90                  95

Asn Asn Leu Leu Phe Gly Gly Gly Thr Lys Leu Thr Val Leu
            100                 105                 110

<210> SEQ ID NO 151
<211> LENGTH: 121
<212> TYPE: PRT
<213> ORGANISM: Artificial Sequence
<220> FEATURE:
<223> OTHER INFORMATION: SH1B11-VH

<400> SEQUENCE: 151

Gln Val Gln Leu Val Gln Ser Gly Ser Glu Leu Lys Lys Pro Gly Ser
1               5                   10                  15

Ser Val Lys Val Ser Cys Lys Ala Ser Gly Tyr Ser Phe Ser Gly Tyr
            20                  25                  30

Tyr Ile His Trp Val Arg Gln Ala Pro Gly Gln Gly Leu Glu Trp Met
        35                  40                  45

Gly Trp Ile Asp Pro Asn Ser Gly Val Thr Asn Tyr Val Arg Arg Phe
    50                  55                  60

Gln Gly Arg Val Thr Met Thr Arg Asp Thr Ser Leu Ser Thr Ala Tyr
65                  70                  75                  80

Met Glu Leu Ser Gly Leu Thr Ala Asp Thr Ala Val Tyr Tyr Cys
                85                  90                  95

Ala Arg Asp Glu Asn Leu Trp Gln Phe Gly Tyr Leu Asp Tyr Trp Gly
            100                 105                 110

Gln Gly Thr Leu Val Thr Val Ser Ser
        115                 120

<210> SEQ ID NO 152
<211> LENGTH: 107
<212> TYPE: PRT
<213> ORGANISM: Artificial Sequence
<220> FEATURE:
<223> OTHER INFORMATION: SH1B11-VL

<400> SEQUENCE: 152

Asp Ile Val Met Thr Gln Ser Pro Ser Ser Leu Ser Ala Ser Ile Gly
1               5                   10                  15

Asp Arg Val Thr Ile Thr Cys Arg Ala Ser Gln Arg Ile Ser Ala Tyr
            20                  25                  30

Val Asn Trp Tyr Gln Gln Lys Pro Gly Lys Ala Pro Lys Val Leu Ile
        35                  40                  45

Tyr Ala Ala Ser Ser Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Ser Ser Pro Trp
                85                  90                  95

Thr Phe Gly Gln Gly Thr Lys Val Glu Ile Lys
            100                 105

<210> SEQ ID NO 153
<211> LENGTH: 120
<212> TYPE: PRT
<213> ORGANISM: Artificial Sequence
<220> FEATURE:
<223> OTHER INFORMATION: SH1E4-VH -continued

<400> SEQUENCE: 153

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Arg Tyr
            20                  25                  30

Gly Val His Trp Val Arg Gln Ala Pro Gly Gln Gly Leu Glu Trp Met
        35                  40                  45

Gly Arg Leu Ile Pro Ile Val Ser Met Thr Asn Tyr Ala Gln Lys Phe
    50                  55                  60

Gln Asp Arg Val Ser Ile Thr Thr Asp Lys Ser Thr Gly Thr Ala Tyr
65                  70                  75                  80

Met Glu Leu Arg Ser Leu Thr Ser Glu Asp Thr Ala Leu Tyr Tyr Cys
                85                  90                  95

Ala Ser Val Gly Gln Gln Leu Pro Trp Val Phe Phe Ala Trp Gly Gln
            100                 105                 110

Gly Thr Leu Val Thr Val Ser Ser
        115                 120

<210> SEQ ID NO 154
<211> LENGTH: 112
<212> TYPE: PRT
<213> ORGANISM: Artificial Sequence
<220> FEATURE:
<223> OTHER INFORMATION: SH1E4-VL

<400> SEQUENCE: 154

Gln Ser Val Leu Thr Gln Pro Pro Ser Ala Ser Gly Ser Pro Gly Gln
1               5                   10                  15

Ser Val Thr Ile Ser Cys Thr Gly Thr Ser Ser Asp Ile Gly Gly Tyr
            20                  25                  30

Asp Ser Val Ser Trp Tyr Gln Gln His Pro Gly Lys Ala Pro Lys Leu
        35                  40                  45

Met Ile Tyr Asp Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Ile Phe Phe Tyr Val Phe Gly Thr Gly Thr Lys Val Thr Val Leu
            100                 105                 110

<210> SEQ ID NO 155
<211> LENGTH: 118
<212> TYPE: PRT
<213> ORGANISM: Artificial Sequence
<220> FEATURE:
<223> OTHER INFORMATION: SH1B3-VH

<400> SEQUENCE: 155

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Phe Asp Gly Ser Asn Lys Tyr Tyr Ala Asp Ser Val
    50                  55                  60

```
Arg Gly Arg Phe Thr Ile Ser Arg Asp Asn Ser Lys Asn Thr Leu Tyr
 65                  70                  75                  80

Leu Gln Met Asn Ser Leu Arg Thr Glu Asp Thr Ala Val Tyr Tyr Cys
                 85                  90                  95

Ala Arg Gly Trp Leu Asp Arg Asp Ile Asp Tyr Trp Gly Gln Gly Thr
            100                 105                 110

Leu Val Thr Val Ser Ser
        115

<210> SEQ ID NO 156
<211> LENGTH: 110
<212> TYPE: PRT
<213> ORGANISM: Artificial Sequence
<220> FEATURE:
<223> OTHER INFORMATION: SH1B3-VL

<400> SEQUENCE: 156

Leu Pro Val Leu Thr Gln Pro Ala Ser Val Ser Gly Ser Pro Gly Gln
1               5                   10                  15

Ser Ile Thr Ile Ser Cys Thr Gly Thr Ser Asp Ile Gly Gly Tyr
            20                  25                  30

Asp Tyr Val Ser Trp Tyr Gln Gln His Pro Gly Lys Ala Pro Lys Leu
        35                  40                  45

Met Ile Tyr Asp Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ser
                 85                  90                  95

Ser Thr His Val Phe Gly Thr Gly Thr Lys Leu Thr Val Leu
            100                 105                 110

<210> SEQ ID NO 157
<211> LENGTH: 118
<212> TYPE: PRT
<213> ORGANISM: Artificial Sequence
<220> FEATURE:
<223> OTHER INFORMATION: SH1D1-VH

<400> SEQUENCE: 157

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Phe Asp Gly Ser Asn Lys Tyr Tyr Ala Asp Ser Val
    50                  55                  60

Arg Gly Arg Phe Thr Ile Ser Arg Asp Asn Ser Lys Asn Thr Leu Tyr
 65                  70                  75                  80

Leu Gln Met Asn Ser Leu Arg Thr Glu Asp Thr Ala Val Tyr Tyr Cys
                 85                  90                  95

Ala Arg Gly Trp Leu Asp Arg Asp Ile Asp Tyr Trp Gly Gln Gly Thr
            100                 105                 110

Leu Val Thr Val Ser Ser
        115

<210> SEQ ID NO 158
```

<211> LENGTH: 111
<212> TYPE: PRT
<213> ORGANISM: Artificial Sequence
<220> FEATURE:
<223> OTHER INFORMATION: SH1D1-VL

<400> SEQUENCE: 158

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Arg Ser Ser
                85                  90                  95

Thr Leu Gly Pro Val Phe Gly Gly Gly Thr Lys Leu Thr Val Leu
            100                 105                 110

<210> SEQ ID NO 159
<211> LENGTH: 118
<212> TYPE: PRT
<213> ORGANISM: Artificial Sequence
<220> FEATURE:
<223> OTHER INFORMATION: SH1D2-VH

<400> SEQUENCE: 159

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Phe Asp Gly Ser Asn Lys Tyr Tyr Ala Asp Ser Val
50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Thr Glu Asp Thr Ala Val Tyr Tyr Cys
                85                  90                  95

Ala Arg Gly Trp Leu Asp Arg Asp Ile Asp Tyr Trp Gly Gln Gly Thr
            100                 105                 110

Leu Val Thr Val Ser Ser
        115

<210> SEQ ID NO 160
<211> LENGTH: 110
<212> TYPE: PRT
<213> ORGANISM: Artificial Sequence
<220> FEATURE:
<223> OTHER INFORMATION: SH1D2-VL

<400> SEQUENCE: 160

Gln Ala Gly Leu Thr Gln Pro Pro Ser Val Ser Glu Ala Pro Arg Gln
1               5                   10                  15

Arg Val Thr Ile Ser Cys Ser Gly Ser Ser Ser Asn Ile Gly Asn Asn
            20                  25                  30

Ala Val Asn Trp Tyr Gln Gln Leu Pro Gly Lys Ala Pro Lys Leu Leu
            35                  40                  45

Ile Tyr Tyr Asp Asp Leu Leu Pro Ser Gly Val Ser Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Asn Gly Tyr Val Phe Gly Thr Gly Thr Lys Leu Thr Val Leu
                100                 105                 110

<210> SEQ ID NO 161
<211> LENGTH: 118
<212> TYPE: PRT
<213> ORGANISM: Artificial Sequence
<220> FEATURE:
<223> OTHER INFORMATION: SH1D12-VH

<400> SEQUENCE: 161

Glu Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Val
            35                  40                  45

Ala Val Ile Ser Phe Asp Gly Ser Asn Lys Tyr Tyr Ala Asp Ser Val
 50                  55                  60

Arg Gly Arg Phe Thr Ile Ser Arg Asp Asn Ser Lys Asn Thr Leu Tyr
 65                  70                  75                  80

Leu Gln Met Asn Ser Leu Arg Thr Glu Asp Thr Ala Val Tyr Tyr Cys
                 85                  90                  95

Ala Arg Gly Trp Leu Asp Arg Asp Ile Asp Tyr Trp Gly Gln Gly Thr
                100                 105                 110

Leu Val Thr Val Ser Ser
            115

<210> SEQ ID NO 162
<211> LENGTH: 110
<212> TYPE: PRT
<213> ORGANISM: Artificial Sequence
<220> FEATURE:
<223> OTHER INFORMATION: SH1D12-VL

<400> SEQUENCE: 162

Gln Ser Ala Leu Thr Gln Pro Arg Ser Val Ser Gly Ser Pro Gly Gln
 1               5                  10                  15

Ser Val Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Ser Lys Arg Pro Ser Gly Val Pro Asp Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ser
                 85                  90                  95

Thr Thr His Val Phe Gly Thr Gly Thr Lys Val Thr Val Leu
                100                 105                 110

<210> SEQ ID NO 163
<211> LENGTH: 118
<212> TYPE: PRT
<213> ORGANISM: Artificial Sequence
<220> FEATURE:
<223> OTHER INFORMATION: SH1E1-VH

<400> SEQUENCE: 163

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Phe Asp Gly Ser Asn Lys Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Thr Glu Asp Thr Ala Val Tyr Tyr Cys
                85                  90                  95

Ala Arg Gly Trp Leu Asp Arg Asp Ile Asp Tyr Trp Gly Gln Gly Thr
            100                 105                 110

Leu Val Thr Val Ser Ser
        115
```

<210> SEQ ID NO 164
<211> LENGTH: 110
<212> TYPE: PRT
<213> ORGANISM: Artificial Sequence
<220> FEATURE:
<223> OTHER INFORMATION: SH1E1-VL

<400> SEQUENCE: 164

```
Gln Ser Val Val Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Val Trp Val Phe Gly Gly Gly Thr Gln Leu Thr Val Leu
            100                 105                 110
```

<210> SEQ ID NO 165
<211> LENGTH: 118
<212> TYPE: PRT
<213> ORGANISM: Artificial Sequence
<220> FEATURE:
<223> OTHER INFORMATION: SH1G9-VH

<400> SEQUENCE: 165

```
Gln Val Gln Leu Val Glu Ser Gly Gly Gly Val Val Gln Pro Gly Arg
1               5                   10                  15
```

```
Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Val
        35                  40                  45

Ala Val Ile Ser Phe Asp Gly Ser Asn Lys Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Thr Glu Asp Thr Ala Val Tyr Tyr Cys
                85                  90                  95

Ala Arg Gly Trp Leu Asp Arg Asp Ile Asp Tyr Trp Gly Gln Gly Thr
            100                 105                 110

Leu Val Thr Val Ser Ser
            115
```

<210> SEQ ID NO 166
<211> LENGTH: 112
<212> TYPE: PRT
<213> ORGANISM: Artificial Sequence
<220> FEATURE:
<223> OTHER INFORMATION: SH1G9-VL

<400> SEQUENCE: 166

```
Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Arg Ala Pro Arg Leu
            35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Gly Asp Tyr Tyr Cys Ser Ser Tyr Thr Ser Gly
                85                  90                  95

Gly Thr Leu Gly Pro Val Phe Gly Gly Gly Thr Lys Leu Thr Val Leu
            100                 105                 110
```

<210> SEQ ID NO 167
<211> LENGTH: 121
<212> TYPE: PRT
<213> ORGANISM: Artificial Sequence
<220> FEATURE:
<223> OTHER INFORMATION: SH1A11-VH

<400> SEQUENCE: 167

```
Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
                20                  25                  30

Gly Met His Trp Val Arg Gln Pro Pro Gly Lys Gly Leu Glu Trp Leu
            35                  40                  45

Ala Val Ile Ser Tyr Asp Gly Ser Tyr Lys Ile His Ala Asp Ser Val
    50                  55                  60

Gln Gly Arg Phe Thr Ile Ser Arg Asp Asn Ala Lys Asn Ser Val Phe
65                  70                  75                  80

Leu Gln Met Asn Ser Leu Lys Thr Glu Asp Thr Ala Val Tyr Tyr Cys
                85                  90                  95
```

```
Thr Thr Asp Arg Lys Trp Leu Ala Trp His Gly Met Asp Val Trp Gly
            100                 105                 110
Gln Gly Thr Thr Val Thr Val Ser Ser
        115                 120
```

<210> SEQ ID NO 168
<211> LENGTH: 110
<212> TYPE: PRT
<213> ORGANISM: Artificial Sequence
<220> FEATURE:
<223> OTHER INFORMATION: SH1A11-VL

<400> SEQUENCE: 168

```
Gln Ala Gly Leu Thr Gln Pro Pro Ser Ala Ser Gly Thr Pro Gly Gln
1               5                   10                  15
Arg Val Thr Ile Ser Cys Ser Gly Ser Ser Asn Ile Gly Ser Asn
            20                  25                  30
Thr Val Asn Trp Tyr Gln Gln Leu Pro Gly Thr Ala Pro Lys Leu Leu
        35                  40                  45
Ile Tyr Ser Asn Asn Gln Arg Pro Ser Gly Val Pro Asp Arg Phe Ser
    50                  55                  60
Gly Ser Lys Ser Gly Thr Ser Ala Ser Leu Ala Ile Ser Gly Leu Gln
65                  70                  75                  80
Ser Glu Asp Glu Ala Asp Tyr Tyr Cys Ala Ala Trp Asp Asp Ser Leu
                85                  90                  95
Asn Gly Trp Val Phe Gly Gly Gly Thr Lys Leu Thr Val Leu
            100                 105                 110
```

<210> SEQ ID NO 169
<211> LENGTH: 118
<212> TYPE: PRT
<213> ORGANISM: Artificial Sequence
<220> FEATURE:
<223> OTHER INFORMATION: SH1C2-VH

<400> SEQUENCE: 169

```
Glu Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Tyr
            20                  25                  30
Ala Ile Ser Trp Val Arg Gln Ala Pro Gly Gln Gly Leu Glu Trp Met
        35                  40                  45
Gly Gly Ile Ile Pro Ile Phe Gly Thr Ala Asn Tyr Ala Gln Lys Phe
    50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Asp Gly Ile Val Ala Asp Phe Gln His Trp Gly Gln Gly Thr
            100                 105                 110
Leu Val Thr Val Ser Ser
        115
```

<210> SEQ ID NO 170
<211> LENGTH: 107
<212> TYPE: PRT
<213> ORGANISM: Artificial Sequence
<220> FEATURE:
<223> OTHER INFORMATION: SH1C2-VL

<400> SEQUENCE: 170

Ala Ile Arg Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Asn Trp Tyr Gln Gln Arg Pro Gly Lys Ala Pro Asn Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Ser Thr Pro Tyr
                85                  90                  95

Thr Phe Gly Gln Gly Thr Lys Leu Glu Ile Lys
            100                 105

<210> SEQ ID NO 171
<211> LENGTH: 121
<212> TYPE: PRT
<213> ORGANISM: Artificial Sequence
<220> FEATURE:
<223> OTHER INFORMATION: SH1G8-VH

<400> SEQUENCE: 171

Glu Val Gln Leu Val Glu Ser Gly Ala Glu Val Lys Lys Pro Gly Ala
1               5                   10                  15

Ser Val Lys Val Ser Cys Lys Ala Ser Gly Asp Thr Phe Ser Arg Tyr
            20                  25                  30

Gly Ile Thr Trp Val Arg Gln Ala Pro Gly Arg Gly Leu Glu Trp Met
        35                  40                  45

Gly Asn Ile Val Pro Phe Phe Gly Ala Thr Asn Tyr Ala Gln Lys Phe
    50                  55                  60

Gln Gly Arg Leu Thr Ile Thr Ala Asp Lys Ser Ser Tyr Thr Ser Tyr
65                  70                  75                  80

Met Asp Leu Ser Ser Leu Arg Ser Asp Asp Thr Ala Val Tyr Tyr Cys
                85                  90                  95

Ala Arg Asp His Phe Tyr Gly Ser Gly Gly Tyr Phe Asp Tyr Trp Gly
            100                 105                 110

Gln Gly Thr Leu Val Thr Val Ser Ser
        115                 120

<210> SEQ ID NO 172
<211> LENGTH: 111
<212> TYPE: PRT
<213> ORGANISM: Artificial Sequence
<220> FEATURE:
<223> OTHER INFORMATION: SH1G8-VL

<400> SEQUENCE: 172

Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Arg Gln His Pro Gly Lys Ala Pro Lys Leu
        35                  40                  45

Met Ile Tyr Asp Val Ser Tyr Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Asp Ser
                85                  90                  95

Ser Thr Arg Tyr Val Phe Gly Thr Gly Thr Lys Leu Thr Val Leu
            100                 105                 110

<210> SEQ ID NO 173
<211> LENGTH: 121
<212> TYPE: PRT
<213> ORGANISM: Artificial Sequence
<220> FEATURE:
<223> OTHER INFORMATION: SH1H2-VH

<400> SEQUENCE: 173

Glu Val Gln Leu Leu Glu Ser Gly Ala Glu Val Lys Lys Pro Gly Ala
1               5                   10                  15

Ser Val Lys Val Ser Cys Lys Ala Ser Gly Tyr Thr Phe Asn Ser Tyr
                20                  25                  30

Asp Ile Asn Trp Val Arg Gln Ala Pro Gly Gln Gly Leu Glu Trp Met
            35                  40                  45

Gly Gly Ile Ile Pro Val Phe Gly Thr Ala Asn Tyr Ala Glu Ser Phe
        50                  55                  60

Gln Gly Arg Val Thr Met Thr Ala Asp His Ser Thr Ser Thr Ala Tyr
65                  70                  75                  80

Met Glu Leu Asn Asn Leu Arg Ser Glu Asp Thr Ala Val Tyr Tyr Cys
                85                  90                  95

Ala Arg Asp Arg Trp His Tyr Glu Ser Arg Pro Met Asp Val Trp Gly
            100                 105                 110

Gln Gly Thr Thr Val Thr Val Ser Ser
        115                 120

<210> SEQ ID NO 174
<211> LENGTH: 110
<212> TYPE: PRT
<213> ORGANISM: Artificial Sequence
<220> FEATURE:
<223> OTHER INFORMATION: SH1H2-VL

<400> SEQUENCE: 174

Gln Pro Val Leu Thr Gln Pro Pro Ser Ala Ser Gly Thr Pro Gly Gln
1               5                   10                  15

Arg Val Ala Ile Ser Cys Ser Gly Ser Arg Ser Asn Ile Glu Ile Asn
                20                  25                  30

Ser Val Asn Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
        50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Ser Trp Asp Ser Ser Leu
                85                  90                  95

Ser Ala Asp Val Phe Gly Thr Gly Thr Lys Leu Thr Val Leu
            100                 105                 110

<210> SEQ ID NO 175
<211> LENGTH: 119
<212> TYPE: PRT

```
<213> ORGANISM: Artificial Sequence
<220> FEATURE:
<223> OTHER INFORMATION: SH1B10-VH

<400> SEQUENCE: 175

Glu Val Gln Leu Val Glu Ser Gly Gly Gly Leu Val Arg Pro Gly Gly
1               5                   10                  15

Ser Leu Arg Leu Ala Cys Ala Ala Ser Gly Phe Ser Phe Ser Asp Tyr
            20                  25                  30

Tyr Met Thr Trp Ile Arg Gln Ala Pro Gly Arg Gly Leu Glu Trp Ile
        35                  40                  45

Ala Tyr Ile Ser Asp Ser Gly Gln Thr Val His Tyr Ala Asp Ser Val
    50                  55                  60

Lys Gly Arg Phe Thr Ile Ser Arg Asp Asn Thr Lys Asn Ser Leu Phe
65                  70                  75                  80

Leu Gln Val Asn Thr Leu Arg Ala Glu Asp Thr Ala Val Tyr Tyr Cys
                85                  90                  95

Ala Arg Glu Asp Leu Leu Gly Tyr Tyr Leu Gln Ser Trp Gly Gln Gly
            100                 105                 110

Thr Leu Val Thr Val Ser Ser
        115

<210> SEQ ID NO 176
<211> LENGTH: 110
<212> TYPE: PRT
<213> ORGANISM: Artificial Sequence
<220> FEATURE:
<223> OTHER INFORMATION: SH1B10-VL

<400> SEQUENCE: 176

Gln Ser Val Leu Thr Gln Pro Pro Ser Val Ser Ala Ala Pro Gly Lys
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Asp Ser Leu
                85                  90                  95

Asn Gly Trp Val Phe Gly Gly Gly Thr Lys Leu Thr Val Leu
            100                 105                 110

<210> SEQ ID NO 177
<211> LENGTH: 131
<212> TYPE: PRT
<213> ORGANISM: Artificial Sequence
<220> FEATURE:
<223> OTHER INFORMATION: SH1B7A(L)-VH

<400> SEQUENCE: 177

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45
```

Trp Leu Gly Arg Thr Tyr Tyr Arg Ser Lys Trp Tyr Asn Asp Tyr Ala
            50                  55                  60

Val Ser Val Lys Ser Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
                85                  90                  95

Tyr Tyr Cys Ala Arg Asp Glu Pro Arg Ala Val Ala Gly Ser Gln Ala
            100                 105                 110

Tyr Tyr Tyr Tyr Gly Met Asp Val Trp Gly Gln Gly Thr Thr Val Thr
            115                 120                 125

Val Ser Ser
    130

<210> SEQ ID NO 178
<211> LENGTH: 111
<212> TYPE: PRT
<213> ORGANISM: Artificial Sequence
<220> FEATURE:
<223> OTHER INFORMATION: SH1B7A(L)-VL

<400> SEQUENCE: 178

Gln Ser Val Val Thr Gln Pro Pro Ser Val Ser Gly Ala Pro Gly Gln
 1               5                  10                  15

Arg Val Thr Ile Ser Cys Thr Gly Ser Ser Ser Asn Ile Gly Ala Gly
                20                  25                  30

Tyr Asp Val His Trp Tyr Gln Gln Leu Pro Gly Thr Ala Pro Lys Leu
                35                  40                  45

Leu Ile Tyr Gly Asn Asn Asn Arg His Ser Gly Val Pro Asp Arg Phe
 50                  55                  60

Ser Gly Ser Lys Ser Gly Thr Ser Ala Ser Leu Ala Ile Thr Gly Leu
 65                  70                  75                  80

Gln Ala Glu Asp Glu Ala Glu Phe Phe Cys Gly Thr Trp Asp Ser Arg
                85                  90                  95

Leu Thr Thr Tyr Val Phe Gly Ser Gly Thr Lys Leu Thr Val Leu
                100                 105                 110

<210> SEQ ID NO 179
<211> LENGTH: 120
<212> TYPE: PRT
<213> ORGANISM: Artificial Sequence
<220> FEATURE:
<223> OTHER INFORMATION: SH1E6-VH

<400> SEQUENCE: 179

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Arg Tyr
                20                  25                  30

Gly Val His Trp Val Arg Gln Ala Pro Gly Gln Gly Leu Glu Trp Met
                35                  40                  45

Gly Arg Leu Ile Pro Ile Val Ser Met Thr Asn Tyr Ala Gln Lys Phe
 50                  55                  60

Gln Asp Arg Val Ser Ile Thr Thr Asp Lys Ser Thr Gly Thr Ala Tyr
 65                  70                  75                  80

Met Glu Leu Arg Ser Leu Thr Ser Glu Asp Thr Ala Leu Tyr Tyr Cys
                85                  90                  95

Ala Ser Val Gly Gln Gln Leu Pro Trp Val Phe Phe Ala Trp Gly Gln 100                 105                 110

Gly Thr Leu Val Thr Val Ser Ser
            115                 120

<210> SEQ ID NO 180
<211> LENGTH: 110
<212> TYPE: PRT
<213> ORGANISM: Artificial Sequence
<220> FEATURE:
<223> OTHER INFORMATION: SH1E6-VL

<400> SEQUENCE: 180

Gln Ser Val Val Thr Gln Pro Pro Ser Val Ser Ala Ala Pro Gly Gln
1               5                   10                  15

Lys Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
        50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Val Val Phe Gly Gly Gly Thr Lys Leu Thr Val Leu
            100                 105                 110

<210> SEQ ID NO 181
<211> LENGTH: 124
<212> TYPE: PRT
<213> ORGANISM: Artificial Sequence
<220> FEATURE:
<223> OTHER INFORMATION: SH1C11-VH

<400> SEQUENCE: 181

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
            35                  40                  45

Gly Ile Ile Asn Pro Ser Asp Gly Ser Thr Ser Tyr Ala Gln Lys Phe
        50                  55                  60

Gln Gly Arg Val Thr Met Thr Arg Asp Thr Ser Thr Ser Thr Val His
65                  70                  75                  80

Met Glu Leu Ser Ser Leu Arg Ser Glu Asp Thr Ala Val Tyr Tyr Cys
                85                  90                  95

Ala Arg Asp Leu Phe Pro His Ile Tyr Gly Asn Tyr Tyr Gly Met Asp
            100                 105                 110

Ile Trp Gly Gln Gly Thr Thr Val Thr Val Ser Ser
            115                 120

<210> SEQ ID NO 182
<211> LENGTH: 107
<212> TYPE: PRT
<213> ORGANISM: Artificial Sequence
<220> FEATURE:
<223> OTHER INFORMATION: SH1C11-VL

<400> SEQUENCE: 182

```
Val Ile Trp Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Glu Ala Ser Thr Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Leu Glu Ile Lys
            100                 105

<210> SEQ ID NO 183
<211> LENGTH: 118
<212> TYPE: PRT
<213> ORGANISM: Artificial Sequence
<220> FEATURE:
<223> OTHER INFORMATION: SH1A2-VH

<400> SEQUENCE: 183

Gln Met Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Phe Asp Gly Ser Asn Lys Tyr Tyr Ala Asp Ser Val
50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Thr Glu Asp Thr Ala Val Tyr Tyr Cys
                85                  90                  95

Ala Arg Gly Trp Leu Asp Arg Asp Ile Asp Tyr Trp Gly Gln Gly Thr
            100                 105                 110

Leu Val Thr Val Ser Ser
        115

<210> SEQ ID NO 184
<211> LENGTH: 110
<212> TYPE: PRT
<213> ORGANISM: Artificial Sequence
<220> FEATURE:
<223> OTHER INFORMATION: SH1A2-VL

<400> SEQUENCE: 184

Gln Ser Val Val Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Val Pro Gly Thr Ala Pro Lys Leu Leu
        35                  40                  45

Ile Tyr Asp Asn Asn Lys Arg Pro Ser Gly Ile Pro Asp Arg Phe Ser
50                  55                  60

Gly Ser Asn Ser Asp Thr Ser Ala Thr Leu Gly Ile Thr Gly Leu Gln
```

```
              65                  70                  75                  80
Thr Gly Asp Glu Ala Asp Tyr Tyr Cys Gly Thr Trp Asp Ser Ser Leu
                    85                  90                  95

Ser Ala Trp Val Phe Gly Gly Gly Thr Lys Leu Thr Val Leu
                100                 105                 110

<210> SEQ ID NO 185
<211> LENGTH: 118
<212> TYPE: PRT
<213> ORGANISM: Artificial Sequence
<220> FEATURE:
<223> OTHER INFORMATION: SH1B1-VH

<400> SEQUENCE: 185

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Val
            35                  40                  45

Ala Val Ile Ser Phe Asp Gly Ser Asn Lys Tyr Tyr Ala Asp Ser Val
        50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Thr Glu Asp Thr Ala Val Tyr Tyr Cys
                85                  90                  95

Ala Arg Gly Trp Leu Asp Arg Asp Ile Asp Tyr Trp Gly Gln Gly Thr
                100                 105                 110

Leu Val Thr Val Ser Ser
            115

<210> SEQ ID NO 186
<211> LENGTH: 112
<212> TYPE: PRT
<213> ORGANISM: Artificial Sequence
<220> FEATURE:
<223> OTHER INFORMATION: SH1B1-VL

<400> SEQUENCE: 186

Gln Ser Val Val Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
        50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Gly Ser Val Val Phe Gly Gly Gly Thr Lys Leu Thr Val Leu
                100                 105                 110

<210> SEQ ID NO 187
<211> LENGTH: 118
<212> TYPE: PRT
<213> ORGANISM: Artificial Sequence
<220> FEATURE:
```

<223> OTHER INFORMATION: R6B2-VH

<400> SEQUENCE: 187

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Ile Val Ala Asp Phe Gln His Trp Gly Gln Gly Thr
            100                 105                 110

Leu Val Thr Val Ser Ser
        115

<210> SEQ ID NO 188
<211> LENGTH: 110
<212> TYPE: PRT
<213> ORGANISM: Artificial Sequence
<220> FEATURE:
<223> OTHER INFORMATION: R6B2-VL

<400> SEQUENCE: 188

Gln Pro Val Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Phe Val Ser Trp Tyr Gln Gln Asn Pro Gly Lys Ala Pro Lys Leu
        35                  40                  45

Met Ile Tyr Asp Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Arg Ala Glu Asp Glu Ala Asp Tyr Tyr Cys Ala Ser Tyr Ala Gly Gly
                85                  90                  95

Arg Thr Phe Val Phe Gly Gly Gly Thr Lys Val Thr Val Leu
            100                 105                 110

<210> SEQ ID NO 189
<211> LENGTH: 118
<212> TYPE: PRT
<213> ORGANISM: Artificial Sequence
<220> FEATURE:
<223> OTHER INFORMATION: R6B7-VH

<400> SEQUENCE: 189

Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Ser Tyr
            20                  25                  30

Pro Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe

```
                    50                  55                  60
Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Met Tyr Tyr Cys
                     85                  90                  95

Ala Lys Asn His Pro Thr Ala Thr Leu Asp Tyr Trp Gly Gln Gly Thr
                100                 105                 110

Leu Val Thr Val Ser Ser
            115
```

<210> SEQ ID NO 190
<211> LENGTH: 107
<212> TYPE: PRT
<213> ORGANISM: Artificial Sequence
<220> FEATURE:
<223> OTHER INFORMATION: R6B7-VL

<400> SEQUENCE: 190

```
Gln Ser Val Leu Thr Gln Ser Pro Ser Ser Phe Ser Ala Ser Thr Gly
 1               5                  10                  15

Asp Arg Val Thr Ile Thr Cys Arg Ala Ser Gln Gly Ile Ser Ser Tyr
                20                  25                  30

Leu Ala Trp Tyr Gln Gln Lys Pro Gly Lys Ala Pro Lys Leu Leu Ile
             35                  40                  45

Tyr Ala Ala Ser Thr Leu Gln Ser Gly Val Pro Ser Arg Phe Ser Gly
         50                  55                  60

Ser Gly Ser Gly Thr Asp Phe Thr Leu Thr Ile Ser Cys Leu Gln Ser
 65                  70                  75                  80

Glu Asp Phe Ala Thr Tyr Tyr Cys Gln Gln Tyr Tyr Ser Tyr Pro Leu
                 85                  90                  95

Thr Phe Gly Gly Gly Thr Lys Val Thr Val Leu
                100                 105
```

<210> SEQ ID NO 191
<211> LENGTH: 128
<212> TYPE: PRT
<213> ORGANISM: Artificial Sequence
<220> FEATURE:
<223> OTHER INFORMATION: R6B11-VH

<400> SEQUENCE: 191

```
Gln Val Gln Leu Val Gln Ser Gly Gly Val Val Gln Pro Gly Arg
 1               5                  10                  15

Ser Leu Arg Leu Ser Cys Ala Ala Ser Gly Phe Pro Phe Arg Ser Tyr
                20                  25                  30

Asp Met His Trp Val Arg Gln Ala Pro Gly Glu Gly Leu Glu Trp Val
             35                  40                  45

Ala Leu Ile Ser Ser Asp Gly Ser Asn Lys Tyr Tyr Leu Asp Ser Val
         50                  55                  60

Lys Gly Arg Phe Thr Ile Ser Arg Asp Asn Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Leu Leu Pro Tyr Ser Ser Ser Trp Asp Tyr Tyr Tyr Tyr
                100                 105                 110

Tyr Gly Met Asp Val Trp Gly Gln Gly Thr Thr Val Thr Val Ser Ser
            115                 120                 125
```

```
<210> SEQ ID NO 192
<211> LENGTH: 110
<212> TYPE: PRT
<213> ORGANISM: Artificial Sequence
<220> FEATURE:
<223> OTHER INFORMATION: R6B11-VL

<400> SEQUENCE: 192

Leu Pro Val Leu Thr Gln Pro Ala Ser Val Ser Ala Ser Ala Gly Gln
1               5                   10                  15

Ser Ile Ala Ile Ser Cys Thr Gly Ile Ser Ser Asp Ile Gly Asp Tyr
            20                  25                  30

Asn Ser Val Ser Trp Tyr Gln Arg His Pro Gly Lys Ala Pro Lys Leu
        35                  40                  45

Ile Ile Tyr Asp Val Ser Ser Arg Pro Ser Gly Val Ala Asp Arg Phe
50                  55                  60

Ser Gly Ser Lys Ser Gly Ser Thr Ala Ser Leu Ser Ile Ser Gly Leu
65                  70                  75                  80

Gln Ala Glu Asp Glu Ala Asp Tyr Tyr Cys Ala Ser Tyr Thr Ala Ser
                85                  90                  95

Asp Asn Pro Val Phe Gly Gly Thr Lys Leu Thr Val Leu
            100                 105                 110

<210> SEQ ID NO 193
<211> LENGTH: 120
<212> TYPE: PRT
<213> ORGANISM: Artificial Sequence
<220> FEATURE:
<223> OTHER INFORMATION: R6D1-VH

<400> SEQUENCE: 193

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 194
<211> LENGTH: 108
<212> TYPE: PRT
<213> ORGANISM: Artificial Sequence
<220> FEATURE:
<223> OTHER INFORMATION: R6D1-VL

<400> SEQUENCE: 194

Ser Tyr Glu Leu Met Gln Pro Pro Ser Val Ser Val Ala Pro Gly Lys
1               5                   10                  15

Thr Ala Thr Ile Ala Cys Gly Gly Glu Asn Ile Gly Arg Lys Thr Val
```

```
                        20                  25                  30
His Trp Tyr Gln Gln Lys Pro Gly Gln Ala Pro Val Leu Val Ile Tyr
            35                  40                  45

Tyr Asp Ser Asp Arg Pro Ser Gly Ile Pro Glu Arg Phe Ser Gly Ser
50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                        85                  90                  95

Arg Ile Phe Gly Gly Gly Thr Lys Leu Thr Val Leu
                100                 105

<210> SEQ ID NO 195
<211> LENGTH: 116
<212> TYPE: PRT
<213> ORGANISM: Artificial Sequence
<220> FEATURE:
<223> OTHER INFORMATION: R6C8-VH

<400> SEQUENCE: 195

Glu Val Gln Leu Val Glu Ser Gly Gly Gly Leu Val Lys Pro Gly Gly
1               5                   10                  15

Ser Arg Lys Leu Ser Cys Ala Ala Ser Gly Phe Thr Phe Ser Asn Tyr
                20                  25                  30

Gly Met His Trp Val Arg Gln Ala Pro Glu Lys Gly Leu Glu Trp Val
            35                  40                  45

Ala Tyr Ile Ser Ser Gly Ser Ser Thr Ile Tyr Tyr Ala Asp Thr Val
50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Arg Gly Leu Leu Leu Asp Tyr Trp Gly Gln Gly Thr Thr Leu
                100                 105                 110

Thr Val Ser Ser
        115

<210> SEQ ID NO 196
<211> LENGTH: 110
<212> TYPE: PRT
<213> ORGANISM: Artificial Sequence
<220> FEATURE:
<223> OTHER INFORMATION: R6C8-VL

<400> SEQUENCE: 196

Gln Ser Val Leu Thr Gln Pro Pro Ser Val Ser Ala Ala Pro Gly Gln
1               5                   10                  15

Glu Val Thr Ile Ser Cys Ser Gly Ser Asn Ser Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Asp Asn Asn Glu Arg Pro Ser Gly Ile Pro Asp Arg Phe Ser
50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95
```

-continued

Ser Ala Gly Val Phe Gly Gly Gly Thr Lys Leu Thr Val Leu
            100                 105                 110

<210> SEQ ID NO 197
<211> LENGTH: 124
<212> TYPE: PRT
<213> ORGANISM: Artificial Sequence
<220> FEATURE:
<223> OTHER INFORMATION: R9G8-VH

<400> SEQUENCE: 197

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Phe Pro Thr Ile Phe Trp Glu Gly Ala Phe Asp
            100                 105                 110

Ile Trp Gly Gln Gly Thr Met Val Thr Val Ser Ser
        115                 120

<210> SEQ ID NO 198
<211> LENGTH: 110
<212> TYPE: PRT
<213> ORGANISM: Artificial Sequence
<220> FEATURE:
<223> OTHER INFORMATION: R9G8-VL

<400> SEQUENCE: 198

Gln Ser Val Leu Thr Gln Pro Pro Ser Val Ser Ala Ala Pro Gly Gln
1               5                   10                  15

Glu Val Thr Ile Ser Cys Ser Gly Ser Asn Ser Asn Ile Gly Asn Asn
            20                  25                  30

Tyr Val Ser Trp Tyr Gln Leu Pro Gly Thr Ala Pro Lys Leu Leu
        35                  40                  45

Ile Tyr Asp Asn Asn Glu Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Gly Val Phe Gly Gly Gly Thr Lys Leu Thr Val Leu
            100                 105                 110

<210> SEQ ID NO 199
<211> LENGTH: 122
<212> TYPE: PRT
<213> ORGANISM: Artificial Sequence
<220> FEATURE:
<223> OTHER INFORMATION: R7D1-VH

<400> SEQUENCE: 199

Gln Val Gln Leu Val Gln Ser Gly Ser Glu Val Glu Lys Pro Gly Ser

```
                1               5                  10                 15
            Ser Val Lys Val Ser Cys Lys Ala Ser Gly Gly Thr Phe Ser Asp Ser
                            20                  25                 30

Gly Ile Ser Trp Val Arg Gln Ala Pro Gly Gln Gly Leu Glu Trp Met
                        35                  40                  45

Gly Gly Ile Ile Pro Met Phe Ala Thr Pro Tyr Tyr Ala Gln Lys Phe
                    50                  55                  60

Gln Asp Arg Val Thr Ile Thr Ala Asp Glu Ser Thr Ser Thr Val Tyr
            65                  70                  75                  80

Met Glu Leu Ser Gly Leu Arg Ser Asp Thr Ala Val Phe Tyr Cys
                            85                  90                  95

Ala Arg Asp Arg Gly Arg Gly His Leu Pro Trp Tyr Phe Asp Leu Trp
                            100                 105                110

Gly Arg Gly Thr Leu Val Thr Val Ser Ser
                        115                 120

<210> SEQ ID NO 200
<211> LENGTH: 110
<212> TYPE: PRT
<213> ORGANISM: Artificial Sequence
<220> FEATURE:
<223> OTHER INFORMATION: R7D1-VL

<400> SEQUENCE: 200

Gln Ser Val Leu Thr Gln Pro Pro Ser Val Ser Ala Ala Pro Gly Gln
            1               5                   10                  15

Glu Val Thr Ile Ser Cys Ser Gly Ser Asn Ser Asn Ile Gly Asn Asn
                            20                  25                  30

Tyr Val Ser Trp Tyr Gln Gln Leu Pro Gly Thr Ala Pro Lys Leu Leu
                        35                  40                  45

Ile Tyr Asp Asn Asn Glu Arg Pro Ser Gly Ile Pro Asp Arg Phe Ser
                    50                  55                  60

Gly Ser Lys Ser Gly Thr Ser Ala Thr Leu Gly Ile Thr Gly Leu Gln
            65                  70                  75                  80

Thr Gly Asp Glu Ala Asp Tyr Tyr Cys Gly Thr Trp Asp Ser Ser Leu
                            85                  90                  95

Ser Ala Gly Val Phe Gly Gly Gly Thr Lys Leu Thr Val Leu
                        100                 105                 110

<210> SEQ ID NO 201
<211> LENGTH: 118
<212> TYPE: PRT
<213> ORGANISM: Artificial Sequence
<220> FEATURE:
<223> OTHER INFORMATION: R7D2-VH

<400> SEQUENCE: 201

Gln Val Gln Leu Val Gln Ser Gly Ala Glu Val Lys Lys Pro Gly Ser
            1               5                   10                  15

Ser Val Lys Val Ser Cys Lys Ala Ser Gly Gly Thr Phe Ser Ser Tyr
                            20                  25                  30

Ala Ile Ser Trp Val Arg Gln Ala Pro Gly Gln Gly Leu Glu Trp Met
                        35                  40                  45

Gly Gly Ile Ile Pro Ile Phe Gly Thr Ala Asn Tyr Ala Gln Lys Phe
                    50                  55                  60

Gln Gly Arg Val Thr Ile Thr Ala Asp Glu Ser Thr Ser Thr Ala Tyr
            65                  70                  75                  80
```

```
Met Glu Leu Ser Ser Leu Arg Ser Glu Asp Thr Ala Val Tyr Tyr Cys
                85                  90                  95

Ala Arg Asp Gly Ile Val Ala Asp Phe Gln His Trp Gly Gln Gly Thr
            100                 105                 110

Leu Val Thr Val Ser Ser
        115

<210> SEQ ID NO 202
<211> LENGTH: 107
<212> TYPE: PRT
<213> ORGANISM: Artificial Sequence
<220> FEATURE:
<223> OTHER INFORMATION: R7D2-VL

<400> SEQUENCE: 202

Ala Ile Arg Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Asn Trp Tyr Gln Gln Arg Pro Gly Lys Ala Pro Asn Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Ser Thr Pro Tyr
                85                  90                  95

Thr Phe Gly Gln Gly Thr Lys Leu Glu Ile Lys
            100                 105

<210> SEQ ID NO 203
<211> LENGTH: 121
<212> TYPE: PRT
<213> ORGANISM: Artificial Sequence
<220> FEATURE:
<223> OTHER INFORMATION: R7E7-VH

<400> SEQUENCE: 203

Glu Val Gln Leu Leu Glu Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asp Tyr Ala Gln Lys Phe
    50                  55                  60

Gln Gly Arg Val Thr Ile Thr Ala Asp Lys Phe Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Thr Val Glu Gly Trp Gly Ala Val Thr Thr Phe Asp Tyr Trp Gly
            100                 105                 110

Gln Gly Thr Leu Val Thr Val Ser Ser
        115                 120

<210> SEQ ID NO 204
<211> LENGTH: 110
<212> TYPE: PRT
<213> ORGANISM: Artificial Sequence
```

```
<220> FEATURE:
<223> OTHER INFORMATION: R7E7-VL

<400> SEQUENCE: 204

Gln Ser Val Leu Thr Gln Pro Pro Ser Val Ser Ala Ala Pro Gly Gln
1               5                   10                  15

Glu Val Thr Ile Ser Cys Ser Gly Ser Asn Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Glu Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Gly Val Phe Gly Gly Gly Thr Lys Leu Thr Val Leu
            100                 105                 110

<210> SEQ ID NO 205
<211> LENGTH: 122
<212> TYPE: PRT
<213> ORGANISM: Artificial Sequence
<220> FEATURE:
<223> OTHER INFORMATION: R7F2-VH

<400> SEQUENCE: 205

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Leu Ser Ser Tyr
            20                  25                  30

Ala Ile Ser Trp Val Arg Gln Val Pro Gly His Gly Leu Glu Trp Met
        35                  40                  45

Gly Arg Ile Ile Ser Met Leu Gly Val Ser Asn Tyr Ala Gln Asn Phe
    50                  55                  60

Gln Gly Arg Val Thr Ile Thr Ala Asp Lys Ser Thr Ser Thr Ala Tyr
65                  70                  75                  80

Met Glu Leu Arg Ser Leu Thr Ser Asp Asp Thr Ala Val Tyr Tyr Cys
                85                  90                  95

Ala Thr Val Thr Ile Phe Asp Gly Asp Tyr Tyr Ala Met Asp Val Trp
            100                 105                 110

Gly Gln Gly Thr Thr Val Thr Val Ser Ser
        115                 120

<210> SEQ ID NO 206
<211> LENGTH: 111
<212> TYPE: PRT
<213> ORGANISM: Artificial Sequence
<220> FEATURE:
<223> OTHER INFORMATION: R7F2-VL

<400> SEQUENCE: 206

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val Tyr Trp Tyr Gln His Leu Leu Gly Lys Ala Pro Lys Leu
        35                  40                  45
```

```
Leu Ile Tyr Gly Asn Ser Asn Arg Pro Ser Gly Val Ser Asp Arg Phe
        50                  55                  60

Ser Ala Ser Lys Ser Gly Thr Ser Val Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Tyr Val Phe Gly Thr Gly Thr Lys Leu Thr Val Leu
            100                 105                 110
```

<210> SEQ ID NO 207
<211> LENGTH: 118
<212> TYPE: PRT
<213> ORGANISM: Artificial Sequence
<220> FEATURE:
<223> OTHER INFORMATION: R7F7-VH

<400> SEQUENCE: 207

```
Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser His
                20                  25                  30

Val Ile Ser Trp Val Arg Gln Ala Pro Gly Gln Gly Leu Glu Trp Met
            35                  40                  45

Gly Ile Ile Leu Pro Ser Phe Gly Lys Thr Asn Tyr Ala Gln Lys Phe
        50                  55                  60

Gln Gly Arg Val Thr Met Thr Gly Asp Thr Ser Thr Ser Thr Val Tyr
65                  70                  75                  80

Met Glu Leu Ser Ser Leu Thr Ser Glu Asp Thr Ala Val Tyr Tyr Cys
                85                  90                  95

Val Arg Glu Phe Ser Gly Gly Tyr Phe Asp Tyr Trp Gly Gln Gly Thr
            100                 105                 110

Leu Val Thr Val Ser Ser
        115
```

<210> SEQ ID NO 208
<211> LENGTH: 110
<212> TYPE: PRT
<213> ORGANISM: Artificial Sequence
<220> FEATURE:
<223> OTHER INFORMATION: R7F7-VL

<400> SEQUENCE: 208

```
Gln Pro Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
                20                  25                  30

Asn Leu Val Ser Trp Tyr Gln Gln His Pro Gly Lys Ala Pro Lys Leu
            35                  40                  45

Met Ile Tyr Glu Val Ser Lys Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Asn Thr Tyr Thr Ser Ser
                85                  90                  95

Gly Thr Tyr Val Ile Gly Thr Gly Thr Lys Val Thr Val Leu
            100                 105                 110
```

<210> SEQ ID NO 209

```
<211> LENGTH: 120
<212> TYPE: PRT
<213> ORGANISM: Artificial Sequence
<220> FEATURE:
<223> OTHER INFORMATION: R9H2-VH

<400> SEQUENCE: 209

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Ile His Trp Val Arg Gln Ala Pro Gly Gln Arg Leu Glu Trp Met
        35                  40                  45

Gly Trp Ile His Ala Gly Asn Gly His Thr Lys Tyr Ala Gln Asn Phe
    50                  55                  60

Gln Gly Arg Val Thr Ile Thr Arg Asp Thr Ser Ala Thr Thr Ala Tyr
65                  70                  75                  80

Val Glu Val Ser Ser Leu Gly Ser Glu Asp Thr Ala Leu Tyr Tyr Cys
                85                  90                  95

Ala Arg Glu Gly Ser Asp Ile Gly Leu Asp Leu His Tyr Trp Gly Gln
            100                 105                 110

Gly Thr Leu Val Thr Val Ser Ser
        115                 120

<210> SEQ ID NO 210
<211> LENGTH: 110
<212> TYPE: PRT
<213> ORGANISM: Artificial Sequence
<220> FEATURE:
<223> OTHER INFORMATION: R9H2-VL

<400> SEQUENCE: 210

Gln Pro Val Leu Thr Gln Pro Ala Ser Val Ser Gly Ser Pro Gly Gln
1               5                   10                  15

Ser Ile Thr Ile Ser Cys Thr Gly Thr Ser Ser Asp Ile Gly Arg Tyr
            20                  25                  30

Asn Tyr Val Ser Trp Tyr Gln Gln His Pro Gly Lys Ala Pro Lys Val
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Trp Val Phe Gly Gly Gly Thr Lys Leu Thr Val Leu
            100                 105                 110

<210> SEQ ID NO 211
<211> LENGTH: 121
<212> TYPE: PRT
<213> ORGANISM: Artificial Sequence
<220> FEATURE:
<223> OTHER INFORMATION: R9H6-VH

<400> SEQUENCE: 211

Glu Val Gln Leu Val Gln Ser Gly Gly Gly Val Val Gln Pro Gly Arg
1               5                   10                  15

Ser Leu Arg Leu Ser Cys Glu Ala Ser Gly Phe Thr Phe Arg Asn Phe
            20                  25                  30
```

Ala Met His Trp Val Arg Gln Ala Pro Gly Lys Gly Leu Glu Trp Ala
             35                  40                  45

Ala Val Ile Ser Val Asp Gly Ser Arg Glu His Tyr Ala Asp Ser Val
 50                  55                  60

Lys Gly Arg Phe Thr Ile Ser Arg Asp Asn Ser Gln Asn Thr Val Tyr
 65                  70                  75                  80

Leu Gln Met Asn Gly Leu Arg Pro Glu Asp Thr Ala Glu Tyr Tyr Cys
                 85                  90                  95

Ala Arg Glu Gly Glu Gly Ser Thr Trp Ser Ser Phe Asp Tyr Trp Gly
                100                 105                 110

Gln Gly Thr Leu Val Thr Val Ser Ser
            115                 120

<210> SEQ ID NO 212
<211> LENGTH: 110
<212> TYPE: PRT
<213> ORGANISM: Artificial Sequence
<220> FEATURE:
<223> OTHER INFORMATION: R9H6-VL

<400> SEQUENCE: 212

Gln Ser Val Val Thr Gln Pro Pro Ser Val Ser Ala Ala Pro Gly Gln
 1               5                  10                  15

Lys Val Thr Ile Ser Cys Ser Gly Ser Ser Ser Asn Ile Gly Asn Asn
                20                  25                  30

Tyr Val Ser Trp Tyr Gln Gln Leu Pro Gly Thr Ala Pro Lys Ile Leu
             35                  40                  45

Ile Tyr Asp Asn Asp Lys Arg Pro Ser Gly Ile Pro Asp Arg Phe Ser
 50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Arg Ser Leu
                 85                  90                  95

Ser Gly Tyr Val Phe Gly Thr Gly Thr Lys Val Thr Val Leu
                100                 105                 110

<210> SEQ ID NO 213
<211> LENGTH: 121
<212> TYPE: PRT
<213> ORGANISM: Artificial Sequence
<220> FEATURE:
<223> OTHER INFORMATION: H6B1L-VH

<400> SEQUENCE: 213

Gln Met Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
                20                  25                  30

Ala Tyr Ser Trp Val Arg Gln Ala Pro Gly Gln Gly Leu Glu Trp Met
             35                  40                  45

Gly Gly Ile Ile Pro Ser Phe Gly Thr Ala Asn Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Pro Ile Val Ala Thr Ile Thr Pro Leu Asp Tyr Trp Gly
                100                 105                 110

```
Gln Gly Thr Leu Val Thr Val Ser Ser
        115                 120

<210> SEQ ID NO 214
<211> LENGTH: 108
<212> TYPE: PRT
<213> ORGANISM: Artificial Sequence
<220> FEATURE:
<223> OTHER INFORMATION: H6B1L-VL

<400> SEQUENCE: 214

Ser Tyr Glu Leu Met Gln Pro Pro Ser Val Ser Val Ala Pro Gly Lys
1               5                   10                  15

Thr Ala Thr Ile Ala Cys Gly Gly Glu Asn Ile Gly Arg Lys Thr Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Leu Val Trp Asp Ser Ser Asp His
                85                  90                  95

Arg Ile Phe Gly Gly Gly Thr Lys Leu Thr Val Leu
            100                 105

<210> SEQ ID NO 215
<211> LENGTH: 121
<212> TYPE: PRT
<213> ORGANISM: Artificial Sequence
<220> FEATURE:
<223> OTHER INFORMATION: H6A1-VH

<400> SEQUENCE: 215

Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Tyr Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Pro Ile Val Ala Thr Ile Thr Pro Leu Asp Tyr Trp Gly
            100                 105                 110

Gln Gly Thr Leu Val Thr Val Ser Ser
        115                 120

<210> SEQ ID NO 216
<211> LENGTH: 108
<212> TYPE: PRT
<213> ORGANISM: Artificial Sequence
<220> FEATURE:
<223> OTHER INFORMATION: H6A1-VL

<400> SEQUENCE: 216
```

```
Ser Tyr Glu Leu Met Gln Pro Pro Ser Val Ser Val Ala Pro Gly Lys
1               5                   10                  15

Thr Ala Thr Ile Ala Cys Gly Gly Glu Asn Ile Gly Arg Lys Thr Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Arg Ile Phe Gly Gly Gly Thr Lys Leu Thr Val Leu
            100                 105
```

<210> SEQ ID NO 217
<211> LENGTH: 121
<212> TYPE: PRT
<213> ORGANISM: Artificial Sequence
<220> FEATURE:
<223> OTHER INFORMATION: H6B1-VH

<400> SEQUENCE: 217

```
Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Tyr Ser Trp Val Arg Gln Ala Pro Gly Gln Gly Leu Glu Trp Met
        35                  40                  45

Gly Gly Ile Ile Pro Ser Phe Gly Thr Ala Asn Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Pro Ile Val Ala Thr Ile Thr Pro Leu Asp Tyr Trp Gly
            100                 105                 110

Gln Gly Thr Leu Val Thr Val Ser Ser
        115                 120
```

<210> SEQ ID NO 218
<211> LENGTH: 108
<212> TYPE: PRT
<213> ORGANISM: Artificial Sequence
<220> FEATURE:
<223> OTHER INFORMATION: H6B1-VL

<400> SEQUENCE: 218

```
Ser Tyr Glu Leu Met Gln Pro Pro Ser Val Ser Val Ala Pro Gly Lys
1               5                   10                  15

Thr Ala Thr Ile Ala Cys Gly Gly Glu Asn Ile Gly Arg Lys Thr Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
50                  55                  60

Asn Ser Gly Asn Thr Ala Thr Leu Thr Ile Ser Arg Val Glu Ala Gly
65                  70                  75                  80
```

Asp Glu Ala Asp Tyr Tyr Cys Gln Val Trp Asp Ser Ser Asp His
                85                  90                  95

Arg Ile Phe Gly Gly Gly Thr Lys Leu Thr Val Leu
            100                 105

<210> SEQ ID NO 219
<211> LENGTH: 121
<212> TYPE: PRT
<213> ORGANISM: Artificial Sequence
<220> FEATURE:
<223> OTHER INFORMATION: H6B2-VH

<400> SEQUENCE: 219

Gln Met Gln Leu Val Gln Ser Gly Ala Glu Val Lys Lys Pro Gly Ser
1               5                   10                  15

Ser Val Lys Val Ser Cys Lys Ala Ser Gly Thr Phe Ser Ser Tyr
            20                  25                  30

Ala Ile Ser Trp Val Arg Gln Ala Pro Gly Gln Gly Leu Glu Trp Met
            35                  40                  45

Gly Gly Ile Ile Pro Ala Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Pro Ile Val Ala Thr Ile Thr Pro Leu Asp Tyr Trp Gly
            100                 105                 110

Gln Gly Thr Leu Val Thr Val Ser Ser
            115                 120

<210> SEQ ID NO 220
<211> LENGTH: 108
<212> TYPE: PRT
<213> ORGANISM: Artificial Sequence
<220> FEATURE:
<223> OTHER INFORMATION: H6B2-VL

<400> SEQUENCE: 220

Ser Tyr Glu Leu Met Gln Pro Pro Ser Val Ser Val Ala Pro Gly Lys
1               5                   10                  15

Thr Ala Thr Ile Ala Cys Gly Gly Glu Asn Ile Gly Arg Lys Thr Val
            20                  25                  30

His Trp Tyr Gln Gln Lys Pro Gly Gln Ala Pro Val Leu Val Ile Tyr
            35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Arg Ile Phe Gly Gly Gly Thr Lys Leu Thr Val Leu
            100                 105

<210> SEQ ID NO 221
<211> LENGTH: 124
<212> TYPE: PRT
<213> ORGANISM: Artificial Sequence
<220> FEATURE:
<223> OTHER INFORMATION: H19C-VH

```
<400> SEQUENCE: 221

Gln Val Gln Leu Val Gln Ser Gly Ala Glu Val Lys Lys Pro Gly Ala
1               5                   10                  15

Ser Val Lys Val Ser Cys Lys Thr Ser Gly Asn Thr Phe Thr Asn Tyr
            20                  25                  30

Ala Leu His Trp Val Arg Gln Ala Pro Gly Gln Gly Leu Glu Trp Met
        35                  40                  45

Gly Gly Met Lys Pro Ser Gly Ser Thr Ser Ile Ala Gln Lys Phe
    50                  55                  60

Gln Gly Arg Val Thr Met Thr Arg Asp Lys Ser Thr Ser Thr Val Tyr
65                  70                  75                  80

Met Glu Leu Ser Ser Leu Thr Ser Glu Asp Thr Ala Val Tyr Tyr Cys
                85                  90                  95

Ala Arg Asp Leu Phe Pro His Ile Phe Gly Asn Tyr Tyr Gly Met Asp
                100                 105                 110

Ile Trp Gly Gln Gly Thr Thr Val Thr Val Ser Ser
            115                 120

<210> SEQ ID NO 222
<211> LENGTH: 107
<212> TYPE: PRT
<213> ORGANISM: Artificial Sequence
<220> FEATURE:
<223> OTHER INFORMATION: H19C-VL

<400> SEQUENCE: 222

Asp Ile Val Met Thr Gln Ser Pro Pro Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Thr Ser Ser Leu Gln Tyr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gly Ser Tyr Ser Thr Pro Tyr
                85                  90                  95

Thr Phe Gly Gln Gly Thr Lys Val Glu Ile Lys
                100                 105

<210> SEQ ID NO 223
<211> LENGTH: 124
<212> TYPE: PRT
<213> ORGANISM: Artificial Sequence
<220> FEATURE:
<223> OTHER INFORMATION: H110D-VH

<400> SEQUENCE: 223

Gln Val Gln Leu Val Gln Ser Gly Ala Glu Val Lys Lys Pro Gly Ala
1               5                   10                  15

Ser Val Lys Val Ser Cys Lys Thr Ser Gly Asn Thr Phe Thr Asn Tyr
            20                  25                  30

Tyr Met His Trp Val Arg Gln Ala Pro Gly Gln Gly Leu Glu Trp Met
        35                  40                  45

Gly Ser Met Gln Pro Ser Gly Gly Ser Thr Ser Leu Ala Gln Lys Phe
    50                  55                  60
```

```
Gln Gly Arg Val Thr Met Thr Arg Asp Lys Ser Thr Ser Thr Val Tyr
65                  70                  75                  80

Met Glu Leu Ser Ser Leu Thr Ser Glu Asp Thr Ala Val Tyr Tyr Cys
                85                  90                  95

Ala Arg Asp Leu Phe Pro His Ile Leu Gly Asn Tyr Tyr Gly Met Asp
            100                 105                 110

Ile Trp Gly Gln Gly Thr Thr Val Thr Val Ser Ser
        115                 120

<210> SEQ ID NO 224
<211> LENGTH: 107
<212> TYPE: PRT
<213> ORGANISM: Artificial Sequence
<220> FEATURE:
<223> OTHER INFORMATION: H110D-VL

<400> SEQUENCE: 224

Asp Ile Val Met Thr Gln Ser Pro Pro Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gly Ser Tyr Ser Thr Pro Tyr
                85                  90                  95

Thr Phe Gly Gln Gly Thr Lys Val Glu Ile Lys
            100                 105

<210> SEQ ID NO 225
<211> LENGTH: 124
<212> TYPE: PRT
<213> ORGANISM: Artificial Sequence
<220> FEATURE:
<223> OTHER INFORMATION: H11F-VH

<400> SEQUENCE: 225

Gln Val Gln Leu Val Gln Ser Gly Ala Glu Val Lys Lys Pro Gly Ala
1               5                   10                  15

Ser Val Lys Val Ser Cys Lys Thr Ser Gly Asn Thr Phe Thr Asn Tyr
            20                  25                  30

Pro Met His Trp Val Arg Gln Ala Pro Gly Gln Gly Leu Glu Trp Met
        35                  40                  45

Gly Ser Met Lys Pro Ser Gly Gly Ser Thr Ser Leu Ala Pro Lys Phe
50                  55                  60

Gln Gly Arg Val Thr Met Thr Arg Asp Lys Ser Thr Ser Thr Val Tyr
65                  70                  75                  80

Met Glu Leu Ser Ser Leu Thr Ser Glu Asp Thr Ala Val Tyr Tyr Cys
                85                  90                  95

Ala Arg Asp Leu Phe Pro His Ile Ile Gly Asn Tyr Tyr Gly Met Asp
            100                 105                 110

Ile Trp Gly Gln Gly Thr Thr Val Thr Val Ser Ser
        115                 120
```

```
<210> SEQ ID NO 226
<211> LENGTH: 107
<212> TYPE: PRT
<213> ORGANISM: Artificial Sequence
<220> FEATURE:
<223> OTHER INFORMATION: H11F-VL

<400> SEQUENCE: 226

Asp Ile Val Met Thr Gln Ser Pro Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Tyr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gly Ser Tyr Ser Thr Pro Tyr
                85                  90                  95

Thr Phe Gly Gln Gly Thr Lys Val Glu Ile Lys
            100                 105

<210> SEQ ID NO 227
<211> LENGTH: 124
<212> TYPE: PRT
<213> ORGANISM: Artificial Sequence
<220> FEATURE:
<223> OTHER INFORMATION: H1C1-VH

<400> SEQUENCE: 227

Gln Val Gln Leu Val Gln Ser Gly Ala Glu Val Lys Lys Pro Gly Ala
1               5                   10                  15

Ser Val Lys Val Ser Cys Lys Thr Ser Gly Asn Thr Phe Thr Asn Tyr
            20                  25                  30

Ser Met His Trp Val Arg Gln Ala Pro Gly Gln Gly Leu Glu Trp Met
        35                  40                  45

Gly Ile Met Asn Pro Ser Gly Gly Ser Thr Ser Tyr Ala Gln Lys Phe
    50                  55                  60

Gln Gly Arg Val Thr Met Thr Arg Asp Lys Ser Thr Ser Thr Val Tyr
65                  70                  75                  80

Met Glu Leu Ser Ser Leu Thr Ser Glu Asp Thr Ala Val Tyr Tyr Cys
                85                  90                  95

Ala Arg Asp Leu Phe Pro His Ile Tyr Gly Asn Tyr Tyr Gly Met Asp
            100                 105                 110

Ile Trp Gly Gln Gly Thr Thr Val Thr Val Ser Ser
        115                 120

<210> SEQ ID NO 228
<211> LENGTH: 107
<212> TYPE: PRT
<213> ORGANISM: Artificial Sequence
<220> FEATURE:
<223> OTHER INFORMATION: H1C1-VL

<400> SEQUENCE: 228

Asp Ile Val Met Thr Gln Ser Pro Ser Leu Ser Ala Ser Val Gly
1               5                   10                  15

Asp Arg Val Thr Ile Thr Cys Arg Ala Ser Gln Ser Ile Ser Ser Tyr
            20                  25                  30
```

```
Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Val Glu Ile Lys
            100                 105
```

```
<210> SEQ ID NO 229
<211> LENGTH: 118
<212> TYPE: PRT
<213> ORGANISM: Artificial Sequence
<220> FEATURE:
<223> OTHER INFORMATION: GPG1A2-VH

<400> SEQUENCE: 229

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Asp Asn Thr Gly Ser Ala Gln Lys Phe
    50                  55                  60

Gln Gly Arg Val Phe Met Thr Lys Thr Thr Ser Leu Asn Thr Ala Tyr
65                  70                  75                  80

Met Glu Leu Ser Gly Leu Arg Ser Glu Asp Thr Ala Ile Tyr Tyr Cys
                85                  90                  95

Ala Arg Glu Arg Ser Ser Gly Tyr Phe Asp Phe Trp Gly Gln Gly Thr
            100                 105                 110

Leu Val Thr Val Ser Ser
        115
```

```
<210> SEQ ID NO 230
<211> LENGTH: 107
<212> TYPE: PRT
<213> ORGANISM: Artificial Sequence
<220> FEATURE:
<223> OTHER INFORMATION: GPG1A2-VL

<400> SEQUENCE: 230

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Phe
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ile
                85                  90                  95

Thr Phe Gly Gln Gly Thr Lys Val Glu Ile Lys
```

<210> SEQ ID NO 231
<211> LENGTH: 118
<212> TYPE: PRT
<213> ORGANISM: Artificial Sequence
<220> FEATURE:
<223> OTHER INFORMATION: GPGG8-VH

<400> SEQUENCE: 231

Gln Val Gln Leu Val Gln Ser Gly Ala Glu Val Lys Lys Leu Gly Ala
1               5                   10                  15

Ser Val Lys Val Ser Cys Lys Ala Ser Gly Tyr Pro Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Gly Asp Asn Thr Gly Leu Ala Gln Lys Phe
    50                  55                  60

Gln Gly Arg Val Phe Met Thr Lys Thr Thr Ser Leu Asn Thr Ala Tyr
65                  70                  75                  80

Met Glu Leu Ser Gly Leu Arg Ser Glu Asp Thr Ala Ile Tyr Tyr Cys
                85                  90                  95

Ala Arg Glu Arg Ser Ser Gly Tyr Phe Asp Phe Trp Gly Gln Gly Thr
            100                 105                 110

Leu Val Thr Val Ser Ser
        115

<210> SEQ ID NO 232
<211> LENGTH: 107
<212> TYPE: PRT
<213> ORGANISM: Artificial Sequence
<220> FEATURE:
<223> OTHER INFORMATION: GPGG8-VL

<400> SEQUENCE: 232

Asp Ile Val Met Thr Gln Ser Pro Ser Ser Leu Ser Ala Ser Val Gly
1               5                   10                  15

Asp Arg Val Thr Ile Thr Cys Arg Ala Thr Pro Ser Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ile
                85                  90                  95

Thr Phe Gly Gln Gly Thr Lys Leu Glu Ile Lys
            100                 105

<210> SEQ ID NO 233
<211> LENGTH: 118
<212> TYPE: PRT
<213> ORGANISM: Artificial Sequence
<220> FEATURE:
<223> OTHER INFORMATION: GPGG10-VH

<400> SEQUENCE: 233

Gln Val Gln Leu Val Gln Ser Gly Ala Glu Val Lys Lys Pro Gly Ala
1               5                   10                  15

```
Ser Val Lys Val Ser Cys Lys Thr Ser Gly Tyr Pro Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Leu Ser Asp Thr Thr Gly Ser Ala Gln Lys Phe
 50                  55                  60

Gln Gly Arg Val Phe Met Thr Lys Thr Thr Ser Leu Asn Thr Ala Tyr
 65                  70                  75                  80

Met Glu Leu Ser Gly Leu Arg Ser Glu Asp Thr Ala Ile Tyr Tyr Cys
                85                  90                  95

Ala Arg Glu Arg Ser Ser Gly Tyr Phe Asp Phe Trp Gly Gln Gly Thr
                100                 105                 110

Leu Val Thr Val Ser Ser
        115
```

<210> SEQ ID NO 234
<211> LENGTH: 107
<212> TYPE: PRT
<213> ORGANISM: Artificial Sequence
<220> FEATURE:
<223> OTHER INFORMATION: GPGG10-VL

<400> SEQUENCE: 234

```
Asp Ile Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Ile
                85                  90                  95

Thr Phe Gly Gln Gly Thr Lys Leu Glu Ile Lys
                100                 105
```

<210> SEQ ID NO 235
<211> LENGTH: 118
<212> TYPE: PRT
<213> ORGANISM: Artificial Sequence
<220> FEATURE:
<223> OTHER INFORMATION: GPGH7-VH

<400> SEQUENCE: 235

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Leu Ser Asp Asn Thr Gly Ser Ala Gln Lys Phe
 50                  55                  60

Gln Gly Arg Val Phe Met Thr Lys Thr Thr Ser Leu Asn Thr Ala Tyr
 65                  70                  75                  80

Met Glu Leu Ser Gly Leu Arg Ser Glu Asp Thr Ala Ile Tyr Tyr Cys
```

```
                        85                  90                  95

Ala Arg Glu Arg Ser Ser Gly Tyr Phe Asp Phe Trp Gly Gln Gly Thr
                100                 105                 110

Leu Val Thr Val Ser Ser
        115
```

<210> SEQ ID NO 236
<211> LENGTH: 107
<212> TYPE: PRT
<213> ORGANISM: Artificial Sequence
<220> FEATURE:
<223> OTHER INFORMATION: GPGH7-VL

<400> SEQUENCE: 236

```
Asp Ile Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Phe
                20                  25                  30

Leu Asn Trp Tyr Gln Gln Lys Pro Gly Lys Ala Pro Lys Leu Leu Ile
            35                  40                  45

Tyr Leu Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ile
                85                  90                  95

Thr Phe Gly Gln Gly Thr Lys Val Glu Ile Lys
            100                 105
```

<210> SEQ ID NO 237
<211> LENGTH: 118
<212> TYPE: PRT
<213> ORGANISM: Artificial Sequence
<220> FEATURE:
<223> OTHER INFORMATION: GPGH10-VH

<400> SEQUENCE: 237

```
Gln Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Asp Asn Thr Gly Tyr Ala Gln Lys Phe
50                  55                  60

Gln Gly Arg Val Phe Met Thr Lys Thr Thr Ser Leu Asn Thr Ala Tyr
65                  70                  75                  80

Met Glu Leu Ser Gly Leu Arg Ser Glu Asp Thr Ala Ile Tyr Tyr Cys
                85                  90                  95

Ala Arg Glu Arg Ser Ser Gly Tyr Phe Asp Phe Trp Gly Gln Gly Thr
                100                 105                 110

Leu Val Thr Val Ser Ser
        115
```

<210> SEQ ID NO 238
<211> LENGTH: 107
<212> TYPE: PRT
<213> ORGANISM: Artificial Sequence
<220> FEATURE:

<223> OTHER INFORMATION: GPGH10-VL

<400> SEQUENCE: 238

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Phe
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Tyr Ser Thr Pro Ile
                85                  90                  95

Thr Phe Gly Gln Gly Thr Lys Val Glu Ile Lys
            100                 105

<210> SEQ ID NO 239
<211> LENGTH: 118
<212> TYPE: PRT
<213> ORGANISM: Artificial Sequence
<220> FEATURE:
<223> OTHER INFORMATION: GPGH11-VH

<400> SEQUENCE: 239

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Pro Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Leu Ser Asp Ser Thr Gly Ser Ala Gln Lys Phe
50                  55                  60

Gln Gly Arg Val Phe Met Thr Lys Thr Thr Ser Leu Asn Thr Ala Tyr
65                  70                  75                  80

Met Glu Leu Ser Gly Leu Arg Ser Glu Asp Thr Ala Ile Tyr Tyr Cys
                85                  90                  95

Ala Arg Glu Arg Ser Ser Gly Tyr Phe Asp Phe Asp Trp Gly Gln Gly Thr
            100                 105                 110

Leu Val Thr Val Ser Ser
        115

<210> SEQ ID NO 240
<211> LENGTH: 107
<212> TYPE: PRT
<213> ORGANISM: Artificial Sequence
<220> FEATURE:
<223> OTHER INFORMATION: GPGH11-VL

<400> SEQUENCE: 240

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly

```
                    50                  55                  60
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Ile
                     85                  90                  95

Thr Phe Gly Gln Gly Thr Lys Leu Glu Ile Lys
                100                 105

<210> SEQ ID NO 241
<211> LENGTH: 118
<212> TYPE: PRT
<213> ORGANISM: Artificial Sequence
<220> FEATURE:
<223> OTHER INFORMATION: GPGH10P-VH

<400> SEQUENCE: 241

Gln Val Gln Leu Val Gln Ser Gly Ala Glu Val Lys Lys Pro Gly Ala
 1               5                  10                  15

Ser Val Lys Val Ser Cys Lys Ser Gly Tyr Thr Phe Thr Gly Tyr
                20                  25                  30

Tyr Met His Trp Val Arg Gln Ala Pro Gly Gln Gly Leu Glu Trp Met
             35                  40                  45

Gly Trp Ile Asn Pro Asn Ser Asp Asn Thr Gly Tyr Ala Gln Lys Phe
         50                  55                  60

Gln Gly Arg Val Phe Met Thr Lys Thr Thr Ser Leu Asn Thr Ala Tyr
 65                  70                  75                  80

Met Glu Leu Ser Gly Leu Arg Ser Glu Asp Thr Ala Ile Tyr Tyr Cys
                 85                  90                  95

Ala Arg Glu Arg Ser Ser Gly Tyr Phe Asp Trp Gly Gln Gly Thr
                100                 105                 110

Leu Val Thr Val Ser Ser
        115

<210> SEQ ID NO 242
<211> LENGTH: 107
<212> TYPE: PRT
<213> ORGANISM: Artificial Sequence
<220> FEATURE:
<223> OTHER INFORMATION: GPGH10P-VL

<400> SEQUENCE: 242

Asp Ile Val Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Phe
                20                  25                  30

Leu Asn Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Pro Tyr Ser Thr Pro Ile
                 85                  90                  95

Thr Phe Gly Gln Gly Thr Lys Val Glu Ile Lys
                100                 105
```

ANTIGEN BINDING PROTEINS THAT BIND PD-L1

CROSS REFERENCE TO RELATED APPLICATIONS

This patent application claims priority to U.S. provisional patent applications 61/654,022 filed 31 May 2012 and 61/739,982 filed 20 Dec. 2012.

TECHNICAL FIELD

The present disclosure provides compositions and methods relating to or derived from anti-PD-L1 antibodies. More specifically, the present disclosure provides human antibodies that bind PD-L1, PD-L1-binding fragments and derivatives of such antibodies, and PD-L1-binding polypeptides comprising such fragments. Further still, the present disclosure provides nucleic acids encoding such antibodies, antibody fragments and derivatives and polypeptides, cells comprising such polynucleotides, methods of making such antibodies, antibody fragments and derivatives and polypeptides, and methods of using such antibodies, antibody fragments and derivatives and polypeptides, including methods of treating or diagnosing subjects having PD-L1 related disorders or conditions, including various inflammatory disorders and various cancers.

BACKGROUND

Programmed death ligand 1 (PD-L1) is a 40 kDa type 1 transmembrane protein. PD-L1 (human PD-L1 cDNA is composed of the base sequence shown by EMBL/GenBank Acc. No. NM_001267706 and mouse PD-L1 cDNA is composed of the base sequence shown by NM_021893) that is a ligand of PD-1 is expressed in so-called antigen-presenting cells such as activated monocytes and dendritic cells. These cells present interaction molecules that induce a variety of immuno-inductive signals to T lymphocytes, and PD-L1 is one of these molecules that induce the inhibitory signal by ligating PD-1. It has been revealed that PD-L1 ligation suppressed the activation (cellular proliferation and induction of various cytokine productions) of PD-1 expressing T lymphocytes. PD-L1 expression has been confirmed in not only immunocompetent cells but also a certain kind of tumor cell lines (cell lines derived from monocytic leukemia, cell lines derived from mast cells, cell lines derived from hepatic carcinomas, cell lines derived from neuroblasts, and cell lines derived from breast carcinomas) (*Nature Immunology* (2001), vol. 2, issue 3, p. 261-267.).

Programmed death 1 (PD-1) is a member of the CD28 family of receptors, which includes CD28, CTLA-4, ICOS, PD-L1, and BTLA. The initial member of the family, CD28, was discovered by functional effect on augmenting T cell proliferation following the addition of monoclonal antibodies (Hutloff et al. (1999) *Nature* 397:263-266; Hansen et al. (1980) *Immunogenics* 10:247-260). Two cell surface glycoprotein ligands for PD-1 have been identified, PD-L1 and PDL-2, and have been shown to down-regulate T cell activation and cytokine secretion occur upon binding to PD-1 (Freeman et al. (2000) *J. Exp. Med.* 192:1027-34; Latchman et al. (2001) *Nat. Immunol.* 2:261-8; Carter et al. (2002) *Eur. J. Immunol.* 32:634-43; Ohigashi et al. (2005) *Clin. Cancer Res.* 11:2947-53). Both PD-L1 (B7-H1) and PD-L2 (B7-DC) are B7 homologs that bind to PD-1. Expression of PD-L1 on the cell surface has also been shown to be upregulated through IFN-γ stimulation.

PD-L1 expression has been found in several murine and human cancers, including human lung, ovarian and colon carcinoma and various myelomas (Iwai et al. (2002) *Proc. Natl. Acad. Sci. USA* 99:12293-7; Ohigashi et al. (2005) *Clin. Cancer Res.* 11:2947-53). PD-L1 has been suggested to play a role in tumor immunity by increasing apoptosis of antigen-specific T-cell clones (Dong et al. (2002) *Nat. Med.* 8:793-800). It has also been suggested that PD-L1 might be involved in intestinal mucosal inflammation and inhibition of PD-L1 suppresses wasting disease associated with colitis (Kanai et al. (2003) *J. Immunol.* 171:4156-63).

SUMMARY

The present disclosure provides a fully human antibody of an IgG class that binds to a PD-L1 epitope with a binding affinity of at least $10^{-6}$M, which has a heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 113, SEQ ID NO. 115, SEQ ID NO. 117, SEQ ID NO. 119, SEQ ID NO. 121, SEQ ID NO. 123, SEQ ID NO. 125, SEQ ID NO. 127, SEQ ID NO. 129, SEQ ID NO. 131, SEQ ID NO. 133, SEQ ID NO. 135, SEQ ID NO. 137, SEQ ID NO. 139, SEQ ID NO. 141, SEQ ID NO. 143, SEQ ID NO. 145, SEQ ID NO. 147, SEQ ID NO. 149, SEQ ID NO. 151, SEQ ID NO. 153, SEQ ID NO. 155, SEQ ID NO. 157, SEQ ID NO. 159, SEQ ID NO. 161, SEQ ID NO. 163, SEQ ID NO. 165, SEQ ID NO. 167, SEQ ID NO. 169, SEQ ID NO. 171, SEQ ID NO. 173, SEQ ID NO. 175, SEQ ID NO. 177, SEQ ID NO. 179, SEQ ID NO. 181, SEQ ID NO. 183, SEQ ID NO. 185, SEQ ID NO. 187, SEQ ID NO. 189, SEQ ID NO. 191, SEQ ID NO. 193, SEQ ID NO. 195, SEQ ID NO. 197, SEQ ID NO. 199, SEQ ID NO. 201, SEQ ID NO. 203, SEQ ID NO. 205, SEQ ID NO. 207, SEQ ID NO. 209, SEQ ID NO. 211, SEQ ID NO. 213, SEQ ID NO. 215, SEQ ID NO. 217, SEQ ID NO. 219, SEQ ID NO. 221, SEQ ID NO. 223, SEQ ID NO. 225, SEQ ID NO. 227, SEQ ID NO. 229, SEQ ID NO. 231, SEQ ID NO. 233, SEQ ID NO. 235, SEQ ID NO. 237, SEQ ID NO. 239, SEQ ID NO. 241, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 114, SEQ ID NO. 116, SEQ ID NO. 118, SEQ ID NO. 120, SEQ ID NO. 122, SEQ ID NO. 124, SEQ ID NO. 126, SEQ ID NO. 128, SEQ ID NO. 130, SEQ ID NO. 132, SEQ ID NO. 134, SEQ ID NO. 136, SEQ ID NO. 138, SEQ ID NO. 140, SEQ ID NO. 142, SEQ ID NO. 144, SEQ ID NO. 146, SEQ ID NO. 148, SEQ ID NO. 150, SEQ ID NO. 152, SEQ ID NO. 154, SEQ ID NO. 156, SEQ ID NO. 158, SEQ ID NO. 160, SEQ ID NO. 162, SEQ ID NO. 164, SEQ ID NO. 166, SEQ ID NO. 168, SEQ ID NO. 170, SEQ ID NO. 172, SEQ ID NO. 174, SEQ ID NO. 176, SEQ ID NO. 178, SEQ ID NO. 180, SEQ ID NO. 182, SEQ ID NO. 184, SEQ ID NO. 186, SEQ ID NO. 188, SEQ ID NO. 190, SEQ ID NO. 192, SEQ ID NO. 194, SEQ ID NO. 196, SEQ ID NO. 198, SEQ ID NO. 200, SEQ ID NO. 202, SEQ ID NO. 204, SEQ ID NO. 206, SEQ ID NO. 208, SEQ ID NO. 210, SEQ ID NO. 212, SEQ ID NO. 214, SEQ ID NO. 216, SEQ ID NO. 218, SEQ ID NO. 220, SEQ ID NO. 222, SEQ ID NO. 224, SEQ ID NO. 226, SEQ ID NO. 228, SEQ ID NO. 230, SEQ ID NO. 232, SEQ ID NO. 234, SEQ ID NO. 236, SEQ ID NO. 238, SEQ ID NO. 240, SEQ ID NO. 242, and combinations thereof. Preferably, the fully human antibody has both a heavy chain and a light chain wherein the antibody has a heavy chain/light chain variable domain sequence selected from the group consisting of SEQ ID NO. 1/SEQ ID NO. 2 (called E6 herein), SEQ ID NO. 3/SEQ ID NO. 4 (called E7 herein), SEQ ID NO. 5/SEQ ID NO. 6 (called E9 herein), SEQ ID NO. 7/SEQ ID NO. 8 (called E11 herein), SEQ ID NO. 9/SEQ ID NO. 10 (called F1 herein), SEQ ID NO. 11/SEQ ID NO. 12 (called F4 herein), SEQ ID NO. 13/SEQ ID NO. 14 (called F7 herein), SEQ ID NO. 15/SEQ ID NO. 16 (called F8 herein), SEQ ID NO. 17/SEQ ID NO. 18 (called F11 herein), SEQ ID NO. 19/SEQ ID NO. 20 (called G4 herein), SEQ ID NO. 21/SEQ ID NO. 22 (called G9 herein), SEQ ID NO. 23/SEQ ID NO. 24 (called G11 herein), SEQ ID NO. 25/SEQ ID NO. 26 (called G12 herein), SEQ ID NO. 27/SEQ ID NO. 28 (called H1 herein), SEQ ID NO. 29/SEQ ID NO. 30 (called H3 herein), SEQ ID NO. 31/SEQ ID NO. 32 (called H4 herein), SEQ ID NO. 33/SEQ ID NO. 34 (called H5 herein), SEQ ID NO. 35/SEQ ID NO. 36 (called H6 herein), SEQ ID NO. 37/SEQ ID NO. 38 (called H10 herein), SEQ ID NO. 39/SEQ ID NO. 40 (called H12 herein), SEQ ID NO. 41/SEQ ID NO. 42 (called PDL-D2 herein), SEQ ID NO. 43/SEQ ID NO. 44 (called PDL-D11 herein), SEQ ID NO. 45/SEQ ID NO. 46 (called PDL-H1 herein), SEQ ID NO. 47/SEQ ID NO. 48 (called RB4 herein), SEQ ID NO. 49/SEQ ID NO. 50 (called RB11 herein), SEQ ID NO. 51/SEQ ID NO. 52 (called RC5 herein), SEQ ID NO. 53/SEQ ID NO. 54 (called RF5 herein), SEQ ID NO. 55/SEQ ID NO. 56 (called RG9 herein), SEQ ID NO. 57/SEQ ID NO. 58 (called RD1 herein), SEQ ID NO. 59/SEQ ID NO. 60 (called RF11 herein), SEQ ID NO. 61/SEQ ID NO. 62 (called RH11 herein), SEQ ID NO. 63/SEQ ID NO. 64 (called RD9 herein), SEQ ID NO. 65/SEQ ID NO. 66 (called RE10 herein), SEQ ID NO. 67/SEQ ID NO. 68 (called RA3 herein), SEQ ID NO. 69/SEQ ID NO. 70 (called RG1 herein), SEQ ID NO. 71/SEQ ID NO. 72 (called RB1 herein), SEQ ID NO. 73/SEQ ID NO. 74 (called RG7 herein), SEQ ID NO. 75/SEQ ID NO. 76 (called RA6 herein), SEQ ID NO. 77/SEQ ID NO. 78 (called RA8 herein), SEQ ID NO. 79/SEQ ID NO. 80 (called RA9 herein), SEQ ID NO. 81/SEQ ID NO. 82 (called RB5 herein), SEQ ID NO. 83/SEQ ID NO. 84 (called RB8 herein), SEQ ID NO. 85/SEQ ID NO. 86 (called RC8 herein), SEQ ID NO. 87/SEQ ID NO. 88 (called RC10 herein), SEQ ID NO. 89/SEQ ID NO. 90 (called RD2 herein), SEQ ID NO. 91/SEQ ID NO. 92 (called RE8 herein), SEQ ID NO. 93/SEQ ID NO. 94 (called RE9 herein), SEQ ID NO. 95/SEQ ID NO. 96 (called RG12 herein), SEQ ID NO. 97/SEQ ID NO. 98 (called RSA1 herein), SEQ ID NO. 99/SEQ ID NO. 100 (called R2A7 herein), SEQ ID NO. 101/SEQ ID NO. 102 (called R2B12 herein), SEQ ID NO. 103/SEQ ID NO. 104 (called R2C9 herein), SEQ ID NO. 105/SEQ ID NO. 106 (called R2D5 herein), SEQ ID NO. 107/SEQ ID NO. 108 (called R2D7 herein), SEQ ID NO. 109/SEQ ID NO. 110 (called R2F4 herein), SEQ ID NO. 111/SEQ ID NO. 112 (called R2A10 herein), SEQ ID NO. 113/SEQ ID NO. 114 (called R2E2 herein), SEQ ID NO. 115/SEQ ID NO. 116 (called R3B8 herein), SEQ ID NO. 117/SEQ ID NO. 118 (called R3C3 herein), SEQ ID NO. 119/SEQ ID NO. 120 (called R3E9 herein), SEQ ID NO. 121/SEQ ID NO. 122 (called R3E10 herein), SEQ ID NO. 123/SEQ ID NO. 124 (called R3F7 herein), SEQ ID NO. 125/SEQ ID NO. 126 (called R3F10 herein), SEQ ID NO. 127/SEQ ID NO. 128 (called R4B10 herein), SEQ ID NO. 129/SEQ ID NO. 130 (called R4H1 herein), SEQ ID NO. 131/SEQ ID NO. 132 (called R4A11 herein), SEQ ID NO. 133/SEQ ID NO. 134 (called R3D2 herein), SEQ ID NO. 135/SEQ ID NO. 136 (called R5B8 herein), SEQ ID NO. 137/SEQ ID NO. 138 (called SH1A1Q herein), SEQ ID NO. 139/SEQ ID NO. 140 (called SH1B7B(K) herein), SEQ ID NO. 141/SEQ ID NO. 142 (called SH1C1 herein), SEQ ID NO. 143/SEQ ID NO. 144 (called SH1C8 herein), SEQ ID NO. 145/SEQ ID NO. 146 (called SH1E10 herein), SEQ ID NO. 147/SEQ ID NO. 148 (called SH1E2 herein), SEQ ID NO. 149/SEQ ID NO. 150 (called SH1A9 herein), SEQ ID NO. 151/SEQ ID NO. 152 (called SH1B11 herein), SEQ ID NO. 153/SEQ ID NO. 154 (called SH1E4 herein), SEQ ID NO. 155/SEQ ID NO. 156 (called SH1B3 herein), SEQ ID NO. 157/SEQ ID NO. 158 (called SH1D1 herein), SEQ ID NO. 159/SEQ ID NO. 160 (called SH1D2 herein), SEQ ID NO. 161/SEQ ID NO. 162 (called SH1D12 herein), SEQ ID NO. 163/SEQ ID NO. 164 (called SH1E1 herein), SEQ ID NO. 165/SEQ ID NO. 166 (called SH1G9 herein), SEQ ID NO. 167/SEQ ID NO. 168 (called SH1A11 herein), SEQ ID NO. 169/SEQ ID NO. 170 (called SH1C2 herein), SEQ ID NO. 171/SEQ ID NO. 172 (called SH1G8 herein), SEQ ID NO. 173/SEQ ID NO. 174 (called SH1H2 herein), SEQ ID NO. 175/SEQ ID NO. 176 (called SH1B10 herein), SEQ ID NO. 177/SEQ ID NO. 178 (called SH1B7A(L) herein), SEQ ID NO. 179/SEQ ID NO. 180 (called SH1E6 herein), SEQ ID NO. 181/SEQ ID NO. 182 (called SH1C11 herein), SEQ ID NO. 183/SEQ ID NO. 184 (called SH1A2 herein), SEQ ID NO. 185/SEQ ID NO. 186 (called SH1B1 herein), SEQ ID NO. 187/SEQ ID NO. 188 (called R6B2 herein), SEQ ID NO. 189/SEQ ID NO. 190 (called R6B7 herein), SEQ ID NO. 191/SEQ ID NO. 192 (called R6B11 herein), SEQ ID NO. 193/SEQ ID NO. 194 (called R6D1 herein), SEQ ID NO. 195/SEQ ID NO. 196 (called R6C8 herein), SEQ ID NO. 197/SEQ ID NO. 198 (called R9G8 herein), SEQ ID NO. 199/SEQ ID NO. 200 (called R7D1 herein), SEQ ID NO. 201/SEQ ID NO. 202 (called R7D2 herein), SEQ ID NO. 203/SEQ ID NO. 204 (called R7E7 herein), SEQ ID NO. 205/SEQ ID NO. 206 (called R7F2 herein), SEQ ID NO. 207/SEQ ID NO. 208 (called R7F7 herein), SEQ ID NO. 209/SEQ ID NO. 210 (called R9H2 herein), SEQ ID NO. 211/SEQ ID NO. 212 (called R9H6 herein), SEQ ID NO. 213/SEQ ID NO. 214 (called H6B1L herein), SEQ ID NO. 215/SEQ ID NO. 216 (called H6A1 herein), SEQ ID NO. 217/SEQ ID NO. 218 (called H6B1 herein), SEQ ID NO. 219/SEQ ID NO. 220

(called H6B2 herein), SEQ ID NO. 221/SEQ ID NO. 222 (called H19C herein), SEQ ID NO. 223/SEQ ID NO. 224 (called H110D herein), SEQ ID NO. 225/SEQ ID NO. 226 (called H11F herein), SEQ ID NO. 227/SEQ ID NO. 228 (called H1C1 herein), SEQ ID NO. 229/SEQ ID NO. 230 (called GPG1A2 herein), SEQ ID NO. 231/SEQ ID NO. 232 (called GPGG8 herein), SEQ ID NO. 233/SEQ ID NO. 234 (called GPGG10 herein), SEQ ID NO. 235/SEQ ID NO. 236 (called GPGH7 herein), SEQ ID NO. 237/SEQ ID NO. 238 (called GPGH10 herein), SEQ ID NO. 239/SEQ ID NO. 240 (called GPGH11 herein), SEQ ID NO. 241/SEQ ID NO. 242 (called GPGH10P herein), and combinations thereof.

The present disclosure provides a Fab fully human antibody fragment, having a variable domain region from a heavy chain and a variable domain region from a light chain, wherein the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 113, SEQ ID NO. 115, SEQ ID NO. 117, SEQ ID NO. 119, SEQ ID NO. 121, SEQ ID NO. 123, SEQ ID NO. 125, SEQ ID NO. 127, SEQ ID NO. 129, SEQ ID NO. 131, SEQ ID NO. 133, SEQ ID NO. 135, SEQ ID NO. 137, SEQ ID NO. 139, SEQ ID NO. 141, SEQ ID NO. 143, SEQ ID NO. 145, SEQ ID NO. 147, SEQ ID NO. 149, SEQ ID NO. 151, SEQ ID NO. 153, SEQ ID NO. 155, SEQ ID NO. 157, SEQ ID NO. 159, SEQ ID NO. 161, SEQ ID NO. 163, SEQ ID NO. 165, SEQ ID NO. 167, SEQ ID NO. 169, SEQ ID NO. 171, SEQ ID NO. 173, SEQ ID NO. 175, SEQ ID NO. 177, SEQ ID NO. 179, SEQ ID NO. 181, SEQ ID NO. 183, SEQ ID NO. 185, SEQ ID NO. 187, SEQ ID NO. 189, SEQ ID NO. 191, SEQ ID NO. 193, SEQ ID NO. 195, SEQ ID NO. 197, SEQ ID NO. 199, SEQ ID NO. 201, SEQ ID NO. 203, SEQ ID NO. 205, SEQ ID NO. 207, SEQ ID NO. 209, SEQ ID NO. 211, SEQ ID NO. 213, SEQ ID NO. 215, SEQ ID NO. 217, SEQ ID NO. 219, SEQ ID NO. 221, SEQ ID NO. 223, SEQ ID NO. 225, SEQ ID NO. 227, SEQ ID NO. 229, SEQ ID NO. 231, SEQ ID NO. 233, SEQ ID NO. 235, SEQ ID NO. 237, SEQ ID NO. 239, SEQ ID NO. 241, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 114, SEQ ID NO. 116, SEQ ID NO. 118, SEQ ID NO. 120, SEQ ID NO. 122, SEQ ID NO. 124, SEQ ID NO. 126, SEQ ID NO. 128, SEQ ID NO. 130, SEQ ID NO. 132, SEQ ID NO. 134, SEQ ID NO. 136, SEQ ID NO. 138, SEQ ID NO. 140, SEQ ID NO. 142, SEQ ID NO. 144, SEQ ID NO. 146, SEQ ID NO. 148, SEQ ID NO. 150, SEQ ID NO. 152, SEQ ID NO. 154, SEQ ID NO. 156, SEQ ID NO. 158, SEQ ID NO. 160, SEQ ID NO. 162, SEQ ID NO. 164, SEQ ID NO. 166, SEQ ID NO. 168, SEQ ID NO. 170, SEQ ID NO. 172, SEQ ID NO. 174, SEQ ID NO. 176, SEQ ID NO. 178, SEQ ID NO. 180, SEQ ID NO. 182, SEQ ID NO. 184, SEQ ID NO. 186, SEQ ID NO. 188, SEQ ID NO. 190, SEQ ID NO. 192, SEQ ID NO. 194, SEQ ID NO. 196, SEQ ID NO. 198, SEQ ID NO. 200, SEQ ID NO. 202, SEQ ID NO. 204, SEQ ID NO. 206, SEQ ID NO. 208, SEQ ID NO. 210, SEQ ID NO. 212, SEQ ID NO. 214, SEQ ID NO. 216, SEQ ID NO. 218, SEQ ID NO. 220, SEQ ID NO. 222, SEQ ID NO. 224, SEQ ID NO. 226, SEQ ID NO. 228, SEQ ID NO. 230, SEQ ID NO. 232, SEQ ID NO. 234, SEQ ID NO. 236, SEQ ID NO. 238, SEQ ID NO. 240, SEQ ID NO. 242, and combinations thereof. Preferably, the fully human antibody Fab fragment has both a heavy chain variable domain region and a light chain variable domain region wherein the antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO. 54, SEQ ID NO. 55/SEQ ID NO. 56, SEQ ID NO. 57/SEQ ID NO. 58, SEQ ID NO. 59/SEQ ID NO. 60, SEQ ID NO. 61/SEQ ID NO. 62, SEQ ID NO. 63/SEQ ID NO. 64, SEQ ID NO. 65/SEQ ID NO. 66, SEQ ID NO. 67/SEQ ID NO. 68, SEQ ID NO. 69/SEQ ID NO. 70, SEQ ID NO. 71/SEQ ID NO. 72, SEQ ID NO. 73/SEQ ID NO. 74, SEQ ID NO. 75/SEQ ID NO. 76, SEQ ID NO. 77/SEQ ID NO. 78, SEQ ID NO. 79/SEQ ID NO. 80, SEQ ID NO. 81/SEQ ID NO. 82, SEQ ID NO. 83/SEQ ID NO. 84, SEQ ID NO. 85/SEQ ID NO. 86, SEQ ID NO. 87/SEQ ID NO. 88, SEQ ID NO. 89/SEQ ID NO. 90, SEQ ID NO. 91/SEQ ID NO. 92, SEQ ID NO. 93/SEQ ID NO. 94, SEQ ID NO. 95/SEQ ID NO. 96, SEQ ID NO. 97/SEQ ID NO. 98, SEQ ID NO. 99/SEQ ID NO. 100, SEQ ID NO. 101/SEQ ID NO. 102, SEQ ID NO. 103/SEQ ID NO. 104, SEQ ID NO. 105/SEQ ID NO. 106, SEQ ID NO. 107/SEQ ID NO. 108, SEQ ID NO. 109/SEQ ID NO. 110, SEQ ID NO. 111/SEQ ID NO. 112, SEQ ID NO. 113/SEQ ID NO. 114, SEQ ID NO. 115/SEQ ID NO. 116, SEQ ID NO. 117/SEQ ID NO. 118, SEQ ID NO. 119/SEQ ID NO. 120, SEQ ID NO. 121/SEQ ID NO. 122, SEQ ID NO. 123/SEQ ID NO. 124, SEQ ID NO. 125/SEQ ID NO. 126, SEQ ID NO. 127/SEQ ID NO. 128, SEQ ID NO. 129/SEQ ID NO. 130, SEQ ID NO. 131/SEQ ID NO. 132, SEQ ID NO. 133/SEQ ID NO. 134, SEQ ID NO. 135/SEQ ID NO. 136, SEQ ID NO. 137/SEQ ID NO. 138, SEQ ID NO. 139/SEQ ID NO. 140, SEQ ID NO. 141/SEQ ID NO. 142, SEQ ID NO. 143/SEQ ID NO. 144, SEQ ID NO. 145/SEQ ID NO. 146, SEQ ID NO. 147/SEQ ID NO. 148, SEQ ID NO. 149/SEQ ID NO. 150, SEQ ID NO. 151/SEQ ID NO. 152, SEQ ID NO. 153/SEQ ID NO. 154, SEQ ID NO. 155/SEQ ID NO. 156, SEQ ID NO. 157/SEQ ID NO. 158, SEQ ID NO. 159/SEQ ID NO. 160, SEQ ID NO. 161/SEQ ID NO. 162, SEQ ID NO. 163/SEQ ID NO. 164, SEQ ID NO. 165/SEQ ID NO. 166, SEQ ID NO. 167/SEQ ID NO. 168, SEQ ID NO. 169/SEQ ID NO. 170, SEQ ID NO. 171/SEQ ID NO. 172, SEQ ID NO. 173/SEQ ID NO. 174, SEQ ID NO. 175/SEQ ID NO. 176, SEQ ID NO. 177/SEQ ID NO. 178, SEQ ID NO. 179/SEQ ID NO. 180, SEQ ID NO. 181/SEQ ID NO. 182, SEQ ID NO. 183/SEQ ID NO. 184, SEQ ID NO. 185/SEQ ID NO. 186, SEQ ID NO. 187/SEQ ID NO. 188, SEQ ID NO. 189/SEQ ID NO. 190, SEQ ID NO. 191/SEQ ID NO. 192, SEQ ID NO. 193/SEQ ID NO. 194, SEQ ID NO. 195/SEQ ID NO. 196, SEQ ID NO. 197/SEQ ID NO. 198, SEQ ID NO. 199/SEQ ID NO. 200, SEQ ID NO. 201/SEQ ID NO. 202, SEQ ID NO. 203/SEQ ID NO. 204, SEQ ID NO. 205/SEQ ID NO. 206, SEQ ID NO. 207/SEQ ID NO. 208, SEQ ID NO. 209/SEQ ID NO. 210, SEQ ID NO. 211/SEQ ID NO. 212, SEQ ID NO. 213/SEQ ID NO. 214, SEQ ID NO. 215/SEQ ID NO. 216, SEQ ID NO. 217/SEQ ID NO. 218, SEQ ID NO. 219/SEQ ID NO. 220, SEQ ID NO. 221/SEQ ID NO. 222, SEQ ID NO. 223/SEQ ID NO. 224, SEQ ID NO. 225/SEQ ID NO. 226, SEQ ID NO. 227/SEQ ID NO. 228, SEQ ID NO. 229/SEQ ID NO. 230, SEQ ID NO. 231/SEQ ID NO. 232, SEQ ID NO. 233/SEQ ID NO. 234, SEQ ID NO. 235/SEQ ID NO. 236, SEQ ID NO. 237/SEQ ID NO. 238, SEQ ID NO. 239/SEQ ID NO. 240, SEQ ID NO. 241/SEQ ID NO. 242, and combinations thereof.

The present disclosure provides a single chain human antibody, having a variable domain region from a heavy chain and a variable domain region from a light chain and a peptide linker connection the heavy chain and light chain variable domain regions, wherein the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 113, SEQ ID NO. 115, SEQ ID NO. 117, SEQ ID NO. 119, SEQ ID NO. 121, SEQ ID NO. 123, SEQ ID NO. 125, SEQ ID NO. 127, SEQ ID NO. 129, SEQ ID NO. 131, SEQ ID NO. 133, SEQ ID NO. 135, SEQ ID NO. 137, SEQ ID NO. 139, SEQ ID NO. 141, SEQ ID NO. 143, SEQ ID NO. 145, SEQ ID NO. 147, SEQ ID NO. 149, SEQ ID NO. 151, SEQ ID NO. 153, SEQ ID NO. 155, SEQ ID NO. 157, SEQ ID NO. 159, SEQ ID NO. 161, SEQ ID NO. 163, SEQ ID NO. 165, SEQ ID NO. 167, SEQ ID NO. 169, SEQ ID NO. 171, SEQ ID NO. 173, SEQ ID NO. 175, SEQ ID NO. 177, SEQ ID NO. 179, SEQ ID NO. 181, SEQ ID NO. 183, SEQ ID NO. 185, SEQ ID NO. 187, SEQ ID NO. 189, SEQ ID NO. 191, SEQ ID NO. 193, SEQ ID NO. 195, SEQ ID NO. 197, SEQ ID NO. 199, SEQ ID NO. 201, SEQ ID NO. 203, SEQ ID NO. 205, SEQ ID NO. 207, SEQ ID NO. 209, SEQ ID NO. 211, SEQ ID NO. 213, SEQ ID NO. 215, SEQ ID NO. 217, SEQ ID NO. 219, SEQ ID NO. 221, SEQ ID NO. 223, SEQ ID NO. 225, SEQ ID NO. 227, SEQ ID NO. 229, SEQ ID NO. 231, SEQ ID NO. 233, SEQ ID NO. 235, SEQ ID NO. 237, SEQ ID NO. 239, SEQ ID NO. 241, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 114, SEQ ID NO. 116, SEQ ID NO. 118, SEQ ID NO. 120, SEQ ID NO. 122, SEQ ID NO. 124, SEQ ID NO. 126, SEQ ID NO. 128, SEQ ID NO. 130, SEQ ID NO. 132, SEQ ID NO. 134, SEQ ID NO. 136, SEQ ID NO. 138, SEQ ID NO. 140, SEQ ID NO. 142, SEQ ID NO. 144, SEQ ID NO. 146, SEQ ID NO. 148, SEQ ID NO. 150, SEQ ID NO. 152, SEQ ID NO. 154, SEQ ID NO. 156, SEQ ID NO. 158, SEQ ID NO. 160, SEQ ID NO. 162, SEQ ID NO. 164, SEQ ID NO. 166, SEQ ID NO. 168, SEQ ID NO. 170, SEQ ID NO. 172, SEQ ID NO. 174, SEQ ID NO. 176, SEQ ID NO. 178, SEQ ID NO. 180, SEQ ID NO. 182, SEQ ID NO. 184, SEQ ID NO. 186, SEQ ID NO. 188, SEQ ID NO. 190, SEQ ID NO. 192, SEQ ID NO. 194, SEQ ID NO. 196, SEQ ID NO. 198, SEQ ID NO. 200, SEQ ID NO. 202, SEQ ID NO. 204, SEQ ID NO. 206, SEQ ID NO. 208, SEQ ID NO. 210, SEQ ID NO. 212, SEQ ID NO. 214, SEQ ID NO. 216, SEQ ID NO. 218, SEQ ID NO. 220, SEQ ID NO. 222, SEQ ID NO. 224, SEQ ID NO. 226, SEQ ID NO. 228, SEQ ID NO. 230, SEQ ID NO. 232, SEQ ID NO. 234, SEQ ID NO. 236, SEQ ID NO. 238, SEQ ID NO. 240, SEQ ID NO. 242, and combinations thereof. Preferably, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 49/SEQ ID NO. 50, SEQ ID NO.

51/SEQ ID NO. 52, SEQ ID NO. 53/SEQ ID NO. 54, SEQ ID NO. 55/SEQ ID NO. 56, SEQ ID NO. 57/SEQ ID NO. 58, SEQ ID NO. 59/SEQ ID NO. 60, SEQ ID NO. 61/SEQ ID NO. 62, SEQ ID NO. 63/SEQ ID NO. 64, SEQ ID NO. 65/SEQ ID NO. 66, SEQ ID NO. 67/SEQ ID NO. 68, SEQ ID NO. 69/SEQ ID NO. 70, SEQ ID NO. 71/SEQ ID NO. 72, SEQ ID NO. 73/SEQ ID NO. 74, SEQ ID NO. 75/SEQ ID NO. 76, SEQ ID NO. 77/SEQ ID NO. 78, SEQ ID NO. 79/SEQ ID NO. 80, SEQ ID NO. 81/SEQ ID NO. 82, SEQ ID NO. 83/SEQ ID NO. 84, SEQ ID NO. 85/SEQ ID NO. 86, SEQ ID NO. 87/SEQ ID NO. 88, SEQ ID NO. 89/SEQ ID NO. 90, SEQ ID NO. 91/SEQ ID NO. 92, SEQ ID NO. 93/SEQ ID NO. 94, SEQ ID NO. 95/SEQ ID NO. 96, SEQ ID NO. 97/SEQ ID NO. 98, SEQ ID NO. 99/SEQ ID NO. 100, SEQ ID NO. 101/SEQ ID NO. 102, SEQ ID NO. 103/SEQ ID NO. 104, SEQ ID NO. 105/SEQ ID NO. 106, SEQ ID NO. 107/SEQ ID NO. 108, SEQ ID NO. 109/SEQ ID NO. 110, SEQ ID NO. 111/SEQ ID NO. 112, SEQ ID NO. 113/SEQ ID NO. 114, SEQ ID NO. 115/SEQ ID NO. 116, SEQ ID NO. 117/SEQ ID NO. 118, SEQ ID NO. 119/SEQ ID NO. 120, SEQ ID NO. 121/SEQ ID NO. 122, SEQ ID NO. 123/SEQ ID NO. 124, SEQ ID NO. 125/SEQ ID NO. 126, SEQ ID NO. 127/SEQ ID NO. 128, SEQ ID NO. 129/SEQ ID NO. 130, SEQ ID NO. 131/SEQ ID NO. 132, SEQ ID NO. 133/SEQ ID NO. 134, SEQ ID NO. 135/SEQ ID NO. 136, SEQ ID NO. 137/SEQ ID NO. 138, SEQ ID NO. 139/SEQ ID NO. 140, SEQ ID NO. 141/SEQ ID NO. 142, SEQ ID NO. 143/SEQ ID NO. 144, SEQ ID NO. 145/SEQ ID NO. 146, SEQ ID NO. 147/SEQ ID NO. 148, SEQ ID NO. 149/SEQ ID NO. 150, SEQ ID NO. 151/SEQ ID NO. 152, SEQ ID NO. 153/SEQ ID NO. 154, SEQ ID NO. 155/SEQ ID NO. 156, SEQ ID NO. 157/SEQ ID NO. 158, SEQ ID NO. 159/SEQ ID NO. 160, SEQ ID NO. 161/SEQ ID NO. 162, SEQ ID NO. 163/SEQ ID NO. 164, SEQ ID NO. 165/SEQ ID NO. 166, SEQ ID NO. 167/SEQ ID NO. 168, SEQ ID NO. 169/SEQ ID NO. 170, SEQ ID NO. 171/SEQ ID NO. 172, SEQ ID NO. 173/SEQ ID NO. 174, SEQ ID NO. 175/SEQ ID NO. 176, SEQ ID NO. 177/SEQ ID NO. 178, SEQ ID NO. 179/SEQ ID NO. 180, SEQ ID NO. 181/SEQ ID NO. 182, SEQ ID NO. 183/SEQ ID NO. 184, SEQ ID NO. 185/SEQ ID NO. 186, SEQ ID NO. 187/SEQ ID NO. 188, SEQ ID NO. 189/SEQ ID NO. 190, SEQ ID NO. 191/SEQ ID NO. 192, SEQ ID NO. 193/SEQ ID NO. 194, SEQ ID NO. 195/SEQ ID NO. 196, SEQ ID NO. 197/SEQ ID NO. 198, SEQ ID NO. 199/SEQ ID NO. 200, SEQ ID NO. 201/SEQ ID NO. 202, SEQ ID NO. 203/SEQ ID NO. 204, SEQ ID NO. 205/SEQ ID NO. 206, SEQ ID NO. 207/SEQ ID NO. 208, SEQ ID NO. 209/SEQ ID NO. 210, SEQ ID NO. 211/SEQ ID NO. 212, SEQ ID NO. 213/SEQ ID NO. 214, SEQ ID NO. 215/SEQ ID NO. 216, SEQ ID NO. 217/SEQ ID NO. 218, SEQ ID NO. 219/SEQ ID NO. 220, SEQ ID NO. 221/SEQ ID NO. 222, SEQ ID NO. 223/SEQ ID NO. 224, SEQ ID NO. 225/SEQ ID NO. 226, SEQ ID NO. 227/SEQ ID NO. 228, SEQ ID NO. 229/SEQ ID NO. 230, SEQ ID NO. 231/SEQ ID NO. 232, SEQ ID NO. 233/SEQ ID NO. 234, SEQ ID NO. 235/SEQ ID NO. 236, SEQ ID NO. 237/SEQ ID NO. 238, SEQ ID NO. 239/SEQ ID NO. 240, SEQ ID NO. 241/SEQ ID NO. 242, and combinations thereof.

The present disclosure further provides a method for treating a broad spectrum of mammalian cancers or a broad-spectrum of inflammatory diseases and autoimmune diseases, comprising administering an effective amount of an anti-PD-L1 polypeptide, wherein the anti-PD-L1 polypeptide is selected from the group consisting of a fully human antibody of an IgG class that binds to a PD-L1 epitope with a binding affinity of at least $10^{-6}$M, a Fab fully human antibody fragment, having a variable domain region from a heavy chain and a variable domain region from a light chain, a single chain human antibody, having a variable domain region from a heavy chain and a variable domain region from a light chain and a peptide linker connection the heavy chain and light chain variable domain regions, and combinations thereof;

wherein the fully human antibody has a heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 113, SEQ ID NO. 115, SEQ ID NO. 117, SEQ ID NO. 119, SEQ ID NO. 121, SEQ ID NO. 123, SEQ ID NO. 125, SEQ ID NO. 127, SEQ ID NO. 129, SEQ ID NO. 131, SEQ ID NO. 133, SEQ ID NO. 135, SEQ ID NO. 137, SEQ ID NO. 139, SEQ ID NO. 141, SEQ ID NO. 143, SEQ ID NO. 145, SEQ ID NO. 147, SEQ ID NO. 149, SEQ ID NO. 151, SEQ ID NO. 153, SEQ ID NO. 155, SEQ ID NO. 157, SEQ ID NO. 159, SEQ ID NO. 161, SEQ ID NO. 163, SEQ ID NO. 165, SEQ ID NO. 167, SEQ ID NO. 169, SEQ ID NO. 171, SEQ ID NO. 173, SEQ ID NO. 175, SEQ ID NO. 177, SEQ ID NO. 179, SEQ ID NO. 181, SEQ ID NO. 183, SEQ ID NO. 185, SEQ ID NO. 187, SEQ ID NO. 189, SEQ ID NO. 191, SEQ ID NO. 193, SEQ ID NO. 195, SEQ ID NO. 197, SEQ ID NO. 199, SEQ ID NO. 201, SEQ ID NO. 203, SEQ ID NO. 205, SEQ ID NO. 207, SEQ ID NO. 209, SEQ ID NO. 211, SEQ ID NO. 213, SEQ ID NO. 215, SEQ ID NO. 217, SEQ ID NO. 219, SEQ ID NO. 221, SEQ ID NO. 223, SEQ ID NO. 225, SEQ ID NO. 227, SEQ ID NO. 229, SEQ ID NO. 231, SEQ ID NO. 233, SEQ ID NO. 235, SEQ ID NO. 237, SEQ ID NO. 239, SEQ ID NO. 241, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 114, SEQ ID NO. 116, SEQ ID NO. 118, SEQ ID NO. 120, SEQ ID NO. 122, SEQ ID NO. 124, SEQ ID NO. 126, SEQ ID NO. 128, SEQ ID NO. 130, SEQ ID NO. 132, SEQ ID NO. 134, SEQ ID NO. 136, SEQ ID NO. 138, SEQ ID NO. 140, SEQ ID NO. 142, SEQ ID NO.

144, SEQ ID NO. 146, SEQ ID NO. 148, SEQ ID NO. 150, SEQ ID NO. 152, SEQ ID NO. 154, SEQ ID NO. 156, SEQ ID NO. 158, SEQ ID NO. 160, SEQ ID NO. 162, SEQ ID NO. 164, SEQ ID NO. 166, SEQ ID NO. 168, SEQ ID NO. 170, SEQ ID NO. 172, SEQ ID NO. 174, SEQ ID NO. 176, SEQ ID NO. 178, SEQ ID NO. 180, SEQ ID NO. 182, SEQ ID NO. 184, SEQ ID NO. 186, SEQ ID NO. 188, SEQ ID NO. 190, SEQ ID NO. 192, SEQ ID NO. 194, SEQ ID NO. 196, SEQ ID NO. 198, SEQ ID NO. 200, SEQ ID NO. 202, SEQ ID NO. 204, SEQ ID NO. 206, SEQ ID NO. 208, SEQ ID NO. 210, SEQ ID NO. 212, SEQ ID NO. 214, SEQ ID NO. 216, SEQ ID NO. 218, SEQ ID NO. 220, SEQ ID NO. 222, SEQ ID NO. 224, SEQ ID NO. 226, SEQ ID NO. 228, SEQ ID NO. 230, SEQ ID NO. 232, SEQ ID NO. 234, SEQ ID NO. 236, SEQ ID NO. 238, SEQ ID NO. 240, SEQ ID NO. 242, and combinations thereof;

wherein the Fab fully human antibody fragment has the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 113, SEQ ID NO. 115, SEQ ID NO. 117, SEQ ID NO. 119, SEQ ID NO. 121, SEQ ID NO. 123, SEQ ID NO. 125, SEQ ID NO. 127, SEQ ID NO. 129, SEQ ID NO. 131, SEQ ID NO. 133, SEQ ID NO. 135, SEQ ID NO. 137, SEQ ID NO. 139, SEQ ID NO. 141, SEQ ID NO. 143, SEQ ID NO. 145, SEQ ID NO. 147, SEQ ID NO. 149, SEQ ID NO. 151, SEQ ID NO. 153, SEQ ID NO. 155, SEQ ID NO. 157, SEQ ID NO. 159, SEQ ID NO. 161, SEQ ID NO. 163, SEQ ID NO. 165, SEQ ID NO. 167, SEQ ID NO. 169, SEQ ID NO. 171, SEQ ID NO. 173, SEQ ID NO. 175, SEQ ID NO. 177, SEQ ID NO. 179, SEQ ID NO. 181, SEQ ID NO. 183, SEQ ID NO. 185, SEQ ID NO. 187, SEQ ID NO. 189, SEQ ID NO. 191, SEQ ID NO. 193, SEQ ID NO. 195, SEQ ID NO. 197, SEQ ID NO. 199, SEQ ID NO. 201, SEQ ID NO. 203, SEQ ID NO. 205, SEQ ID NO. 207, SEQ ID NO. 209, SEQ ID NO. 211, SEQ ID NO. 213, SEQ ID NO. 215, SEQ ID NO. 217, SEQ ID NO. 219, SEQ ID NO. 221, SEQ ID NO. 223, SEQ ID NO. 225, SEQ ID NO. 227, SEQ ID NO. 229, SEQ ID NO. 231, SEQ ID NO. 233, SEQ ID NO. 235, SEQ ID NO. 237, SEQ ID NO. 239, SEQ ID NO. 241, and combinations thereof, and that has the light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 114, SEQ ID NO. 116, SEQ ID NO. 118, SEQ ID NO. 120, SEQ ID NO. 122, SEQ ID NO. 124, SEQ ID NO. 126, SEQ ID NO. 128, SEQ ID NO. 130, SEQ ID NO. 132, SEQ ID NO. 134, SEQ ID NO. 136, SEQ ID NO. 138, SEQ ID NO. 140, SEQ ID NO. 142, SEQ ID NO. 144, SEQ ID NO. 146, SEQ ID NO. 148, SEQ ID NO. 150, SEQ ID NO. 152, SEQ ID NO. 154, SEQ ID NO. 156, SEQ ID NO. 158, SEQ ID NO. 160, SEQ ID NO. 162, SEQ ID NO. 164, SEQ ID NO. 166, SEQ ID NO. 168, SEQ ID NO. 170, SEQ ID NO. 172, SEQ ID NO. 174, SEQ ID NO. 176, SEQ ID NO. 178, SEQ ID NO. 180, SEQ ID NO. 182, SEQ ID NO. 184, SEQ ID NO. 186, SEQ ID NO. 188, SEQ ID NO. 190, SEQ ID NO. 192, SEQ ID NO. 194, SEQ ID NO. 196, SEQ ID NO. 198, SEQ ID NO. 200, SEQ ID NO. 202, SEQ ID NO. 204, SEQ ID NO. 206, SEQ ID NO. 208, SEQ ID NO. 210, SEQ ID NO. 212, SEQ ID NO. 214, SEQ ID NO. 216, SEQ ID NO. 218, SEQ ID NO. 220, SEQ ID NO. 222, SEQ ID NO. 224, SEQ ID NO. 226, SEQ ID NO. 228, SEQ ID NO. 230, SEQ ID NO. 232, SEQ ID NO. 234, SEQ ID NO. 236, SEQ ID NO. 238, SEQ ID NO. 240, SEQ ID NO. 242, and combinations thereof; and wherein the single chain human antibody has the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 113, SEQ ID NO. 115, SEQ ID NO. 117, SEQ ID NO. 119, SEQ ID NO. 121, SEQ ID NO. 123, SEQ ID NO. 125, SEQ ID NO. 127, SEQ ID NO. 129, SEQ ID NO. 131, SEQ ID NO. 133, SEQ ID NO. 135, SEQ ID NO. 137, SEQ ID NO. 139, SEQ ID NO. 141, SEQ ID NO. 143, SEQ ID NO. 145, SEQ ID NO. 147, SEQ ID NO. 149, SEQ ID NO. 151, SEQ ID NO. 153, SEQ ID NO. 155, SEQ ID NO. 157, SEQ ID NO. 159, SEQ ID NO. 161, SEQ ID NO. 163, SEQ ID NO. 165, SEQ ID NO. 167, SEQ ID NO. 169, SEQ ID NO. 171, SEQ ID NO. 173, SEQ ID NO. 175, SEQ ID NO. 177, SEQ ID NO. 179, SEQ ID NO. 181, SEQ ID NO. 183, SEQ ID NO. 185, SEQ ID NO. 187, SEQ ID NO. 189, SEQ ID NO. 191, SEQ ID NO. 193, SEQ ID NO. 195, SEQ ID NO. 197, SEQ ID NO. 199, SEQ ID NO. 201, SEQ ID NO. 203, SEQ ID NO. 205, SEQ ID NO. 207, SEQ ID NO. 209, SEQ ID NO. 211, SEQ ID NO. 213, SEQ ID NO. 215, SEQ ID NO. 217, SEQ ID NO. 219, SEQ ID NO. 221, SEQ ID NO. 223, SEQ ID NO. 225, SEQ ID NO. 227, SEQ ID NO. 229, SEQ ID NO. 231, SEQ ID NO. 233, SEQ ID NO. 235, SEQ ID NO. 237, SEQ ID NO. 239, SEQ ID NO. 241, and combinations thereof, and that has the light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 114, SEQ ID NO. 116, SEQ ID NO. 118, SEQ ID NO. 120, SEQ ID NO. 122, SEQ ID NO. 124, SEQ ID NO. 126, SEQ ID NO. 128, SEQ ID NO. 130, SEQ ID NO. 132, SEQ ID NO. 134, SEQ ID NO. 136, SEQ ID NO. 138, SEQ ID NO. 140, SEQ ID NO. 142, SEQ ID NO. 144, SEQ ID NO. 146, SEQ ID NO. 148, SEQ ID NO. 150, SEQ ID NO. 152, SEQ ID NO. 154, SEQ ID NO. 156, SEQ ID NO. 158, SEQ ID NO. 160, SEQ ID NO. 162, SEQ ID NO. 164, SEQ ID NO. 166, SEQ ID NO. 168, SEQ ID NO. 170, SEQ ID NO. 172, SEQ ID NO. 174, SEQ ID NO. 176, SEQ ID NO. 178, SEQ ID NO. 180, SEQ ID NO. 182, SEQ ID NO. 184, SEQ ID NO. 186, SEQ ID NO. 188, SEQ ID NO. 190, SEQ ID NO. 192, SEQ ID NO. 194, SEQ ID NO. 196, SEQ ID NO. 198, SEQ ID NO. 200, SEQ ID NO. 202, SEQ ID NO. 204, SEQ ID NO. 206, SEQ ID NO. 208, SEQ ID NO. 210, SEQ ID NO. 212, SEQ ID NO. 214, SEQ ID NO. 216, SEQ ID NO. 218, SEQ ID NO. 220, SEQ ID NO. 222, SEQ ID NO. 224, SEQ ID NO. 226, SEQ ID NO. 228, SEQ ID NO. 230, SEQ ID NO. 232, SEQ ID NO. 234, SEQ ID NO. 236, SEQ ID NO. 238, SEQ ID NO. 240, SEQ ID NO. 242, and combinations thereof.

Preferably, the fully human antibody has both a heavy chain and a light chain wherein the antibody has a heavy chain/light chain variable domain sequence selected from the group consisting of SEQ ID NO. 1/SEQ ID NO. 2 (called E6 herein), SEQ ID NO. 3/SEQ ID NO. 4 (called E7 herein), SEQ ID NO. 5/SEQ ID NO. 6 (called E9 herein), SEQ ID NO. 7/SEQ ID NO. 8 (called E11 herein), SEQ ID NO. 9/SEQ ID NO. 10 (called F1 herein), SEQ ID NO. 11/SEQ ID NO. 12 (called F4 herein), SEQ ID NO. 13/SEQ ID NO. 14 (called F7 herein), SEQ ID NO. 15/SEQ ID NO. 16 (called F8 herein), SEQ ID NO. 17/SEQ ID NO. 18 (called F11 herein), SEQ ID NO. 19/SEQ ID NO. 20 (called G4 herein), SEQ ID NO. 21/SEQ ID NO. 22 (called G9 herein), SEQ ID NO. 23/SEQ ID NO. 24 (called G11 herein), SEQ ID NO. 25/SEQ ID NO. 26 (called G12 herein), SEQ ID NO. 27/SEQ ID NO. 28 (called H1 herein), SEQ ID NO. 29/SEQ ID NO. 30 (called H3 herein), SEQ ID NO. 31/SEQ ID NO. 32 (called H4 herein), SEQ ID NO. 33/SEQ ID NO. 34 (called H5 herein), SEQ ID NO. 35/SEQ ID NO. 36 (called H6 herein), SEQ ID NO. 37/SEQ ID NO. 38 (called H10 herein), SEQ ID NO. 39/SEQ ID NO. 40 (called H12 herein), SEQ ID NO. 41/SEQ ID NO. 42 (called PDL-D2 herein), SEQ ID NO. 43/SEQ ID NO. 44 (called PDL-D11 herein), SEQ ID NO. 45/SEQ ID NO. 46 (called PDL-H1 herein), SEQ ID NO. 47/SEQ ID NO. 48 (called RB4 herein), SEQ ID NO. 49/SEQ ID NO. 50 (called RB11 herein), SEQ ID NO. 51/SEQ ID NO. 52 (called RC5 herein), SEQ ID NO. 53/SEQ ID NO. 54 (called RF5 herein), SEQ ID NO. 55/SEQ ID NO. 56 (called RG9 herein), SEQ ID NO. 57/SEQ ID NO. 58 (called RD1 herein), SEQ ID NO. 59/SEQ ID NO. 60 (called RF11 herein), SEQ ID NO. 61/SEQ ID NO. 62 (called RH11 herein), SEQ ID NO. 63/SEQ ID NO. 64 (called RD9 herein), SEQ ID NO. 65/SEQ ID NO. 66 (called RE10 herein), SEQ ID NO. 67/SEQ ID NO. 68 (called RA3 herein), SEQ ID NO. 69/SEQ ID NO. 70 (called RG1 herein), SEQ ID NO. 71/SEQ ID NO. 72 (called RB1 herein), SEQ ID NO. 73/SEQ ID NO. 74 (called RG7 herein), SEQ ID NO. 75/SEQ ID NO. 76 (called RA6 herein), SEQ ID NO. 77/SEQ ID NO. 78 (called RA8 herein), SEQ ID NO. 79/SEQ ID NO. 80 (called RA9 herein), SEQ ID NO. 81/SEQ ID NO. 82 (called RB5 herein), SEQ ID NO. 83/SEQ ID NO. 84 (called RB8 herein), SEQ ID NO. 85/SEQ ID NO. 86 (called RC8 herein), SEQ ID NO. 87/SEQ ID NO. 88 (called RC10 herein), SEQ ID NO. 89/SEQ ID NO. 90 (called RD2 herein), SEQ ID NO. 91/SEQ ID NO. 92 (called RE8 herein), SEQ ID NO. 93/SEQ ID NO. 94 (called RE9 herein), SEQ ID NO. 95/SEQ ID NO. 96 (called RG12 herein), SEQ ID NO. 97/SEQ ID NO. 98 (called RSA1 herein), SEQ ID NO. 99/SEQ ID NO. 100 (called R2A7 herein), SEQ ID NO. 101/SEQ ID NO. 102 (called R2B12 herein), SEQ ID NO. 103/SEQ ID NO. 104 (called R2C9 herein), SEQ ID NO. 105/SEQ ID NO. 106 (called R2D5 herein), SEQ ID NO. 107/SEQ ID NO. 108 (called R2D7 herein), SEQ ID NO. 109/SEQ ID NO. 110 (called R2F4 herein), SEQ ID NO. 111/SEQ ID NO. 112 (called R2A10 herein), SEQ ID NO. 113/SEQ ID NO. 114 (called R2E2 herein), SEQ ID NO. 115/SEQ ID NO. 116 (called R3B8 herein), SEQ ID NO. 117/SEQ ID NO. 118 (called R3C3 herein), SEQ ID NO. 119/SEQ ID NO. 120 (called R3E9 herein), SEQ ID NO. 121/SEQ ID NO. 122 (called R3E10 herein), SEQ ID NO. 123/SEQ ID NO. 124 (called R3F7 herein), SEQ ID NO. 125/SEQ ID NO. 126 (called R3F10 herein), SEQ ID NO. 127/SEQ ID NO. 128 (called R4B10 herein), SEQ ID NO. 129/SEQ ID NO. 130 (called R4H1 herein), SEQ ID NO. 131/SEQ ID NO. 132 (called R4A11 herein), SEQ ID NO. 133/SEQ ID NO. 134 (called R3D2 herein), SEQ ID NO. 135/SEQ ID NO. 136 (called R5B8 herein), SEQ ID NO. 137/SEQ ID NO. 138 (called SH1A1Q herein), SEQ ID NO. 139/SEQ ID NO. 140 (called SH1B7B(K) herein), SEQ ID NO. 141/SEQ ID NO. 142 (called SH1C1 herein), SEQ ID NO. 143/SEQ ID NO. 144 (called SH1C8 herein), SEQ ID NO. 145/SEQ ID NO. 146 (called SH1E10 herein), SEQ ID NO. 147/SEQ ID NO. 148 (called SH1E2 herein), SEQ ID NO. 149/SEQ ID NO. 150 (called SH1A9 herein), SEQ ID NO. 151/SEQ ID NO. 152 (called SH1B11 herein), SEQ ID NO. 153/SEQ ID NO. 154 (called SH1E4 herein), SEQ ID NO. 155/SEQ ID NO. 156 (called SH1B3 herein), SEQ ID NO. 157/SEQ ID NO. 158 (called SH1D1 herein), SEQ ID NO. 159/SEQ ID NO. 160 (called SH1D2 herein), SEQ ID NO. 161/SEQ ID NO. 162 (called SH1D12 herein), SEQ ID NO. 163/SEQ ID NO. 164 (called SH1E1 herein), SEQ ID NO. 165/SEQ ID NO. 166 (called SH1G9 herein), SEQ ID NO. 167/SEQ ID NO. 168 (called SH1A11 herein), SEQ ID NO. 169/SEQ ID NO. 170 (called SH1C2 herein), SEQ ID NO. 171/SEQ ID NO. 172 (called SH1G8 herein), SEQ ID NO. 173/SEQ ID NO. 174 (called SH1H2 herein), SEQ ID NO. 175/SEQ ID NO. 176 (called SH1B10 herein), SEQ ID NO. 177/SEQ ID NO. 178 (called SH1B7A(L) herein), SEQ ID NO. 179/SEQ ID NO. 180 (called SH1E6 herein), SEQ ID NO. 181/SEQ ID NO. 182 (called SH1C11 herein), SEQ ID NO. 183/SEQ ID NO. 184 (called SH1A2 herein), SEQ ID NO. 185/SEQ ID NO. 186 (called SH1B1 herein), SEQ ID NO. 187/SEQ ID NO. 188 (called R6B2 herein), SEQ ID NO. 189/SEQ ID NO. 190 (called R6B7 herein), SEQ ID NO. 191/SEQ ID NO. 192 (called R6B11 herein), SEQ ID NO. 193/SEQ ID NO. 194 (called R6D1 herein), SEQ ID NO. 195/SEQ ID NO. 196 (called R6C8 herein), SEQ ID NO.

197/SEQ ID NO. 198 (called R9G8 herein), SEQ ID NO. 199/SEQ ID NO. 200 (called R7D1 herein), SEQ ID NO. 201/SEQ ID NO. 202 (called R7D2 herein), SEQ ID NO. 203/SEQ ID NO. 204 (called R7E7 herein), SEQ ID NO. 205/SEQ ID NO. 206 (called R7F2 herein), SEQ ID NO. 207/SEQ ID NO. 208 (called R7F7 herein), SEQ ID NO. 209/SEQ ID NO. 210 (called R9H2 herein), SEQ ID NO. 211/SEQ ID NO. 212 (called R9H6 herein), SEQ ID NO. 213/SEQ ID NO. 214 (called H6B1L herein), SEQ ID NO. 215/SEQ ID NO. 216 (called H6A1 herein), SEQ ID NO. 217/SEQ ID NO. 218 (called H6B1 herein), SEQ ID NO. 219/SEQ ID NO. 220 (called H6B2 herein), SEQ ID NO. 221/SEQ ID NO. 222 (called H19C herein), SEQ ID NO. 223/SEQ ID NO. 224 (called H110D herein), SEQ ID NO. 225/SEQ ID NO. 226 (called H11F herein), SEQ ID NO. 227/SEQ ID NO. 228 (called H1C1 herein), SEQ ID NO. 229/SEQ ID NO. 230 (called GPG1A2 herein), SEQ ID NO. 231/SEQ ID NO. 232 (called GPGG8 herein), SEQ ID NO. 233/SEQ ID NO. 234 (called GPGG10 herein), SEQ ID NO. 235/SEQ ID NO. 236 (called GPGH7 herein), SEQ ID NO. 237/SEQ ID NO. 238 (called GPGH10 herein), SEQ ID NO. 239/SEQ ID NO. 240 (called GPGH11 herein), SEQ ID NO. 241/SEQ ID NO. 242 (called GPGH10P herein), and combinations thereof. Preferably, the fully human antibody Fab fragment has both a heavy chain variable domain region and a light chain variable domain region wherein the antibody has a heavy chain/light chain variable domain sequence selected from the group consisting of SEQ ID NO. 1/SEQ ID NO. 2 (called E6 herein), SEQ ID NO. 3/SEQ ID NO. 4 (called E7 herein), SEQ ID NO. 5/SEQ ID NO. 6 (called E9 herein), SEQ ID NO. 7/SEQ ID NO. 8 (called E11 herein), SEQ ID NO. 9/SEQ ID NO. 10 (called F1 herein), SEQ ID NO. 11/SEQ ID NO. 12 (called F4 herein), SEQ ID NO. 13/SEQ ID NO. 14 (called F7 herein), SEQ ID NO. 15/SEQ ID NO. 16 (called F8 herein), SEQ ID NO. 17/SEQ ID NO. 18 (called F11 herein), SEQ ID NO. 19/SEQ ID NO. 20 (called G4 herein), SEQ ID NO. 21/SEQ ID NO. 22 (called G9 herein), SEQ ID NO. 23/SEQ ID NO. 24 (called G11 herein), SEQ ID NO. 25/SEQ ID NO. 26 (called G12 herein), SEQ ID NO. 27/SEQ ID NO. 28 (called H1 herein), SEQ ID NO. 29/SEQ ID NO. 30 (called H3 herein), SEQ ID NO. 31/SEQ ID NO. 32 (called H4 herein), SEQ ID NO. 33/SEQ ID NO. 34 (called H5 herein), SEQ ID NO. 35/SEQ ID NO. 36 (called H6 herein), SEQ ID NO. 37/SEQ ID NO. 38 (called H10 herein), SEQ ID NO. 39/SEQ ID NO. 40 (called H12 herein), SEQ ID NO. 41/SEQ ID NO. 42 (called PDL-D2 herein), SEQ ID NO. 43/SEQ ID NO. 44 (called PDL-D11 herein), SEQ ID NO. 45/SEQ ID NO. 46 (called PDL-H1 herein), SEQ ID NO. 47/SEQ ID NO. 48 (called RB4 herein), SEQ ID NO. 49/SEQ ID NO. 50 (called RB11 herein), SEQ ID NO. 51/SEQ ID NO. 52 (called RC5 herein), SEQ ID NO. 53/SEQ ID NO. 54 (called RF5 herein), SEQ ID NO. 55/SEQ ID NO. 56 (called RG9 herein), SEQ ID NO. 57/SEQ ID NO. 58 (called RD1 herein), SEQ ID NO. 59/SEQ ID NO. 60 (called RF11 herein), SEQ ID NO. 61/SEQ ID NO. 62 (called RH11 herein), SEQ ID NO. 63/SEQ ID NO. 64 (called RD9 herein), SEQ ID NO. 65/SEQ ID NO. 66 (called RE10 herein), SEQ ID NO. 67/SEQ ID NO. 68 (called RA3 herein), SEQ ID NO. 69/SEQ ID NO. 70 (called RG1 herein), SEQ ID NO. 71/SEQ ID NO. 72 (called RB1 herein), SEQ ID NO. 73/SEQ ID NO. 74 (called RG7 herein), SEQ ID NO. 75/SEQ ID NO. 76 (called RA6 herein), SEQ ID NO. 77/SEQ ID NO. 78 (called RA8 herein), SEQ ID NO. 79/SEQ ID NO. 80 (called RA9 herein), SEQ ID NO. 81/SEQ ID NO. 82 (called RB5 herein), SEQ ID NO. 83/SEQ ID NO. 84 (called RB8 herein), SEQ ID NO. 85/SEQ ID NO. 86 (called RC8 herein), SEQ ID NO. 87/SEQ ID NO. 88 (called RC10 herein), SEQ ID NO. 89/SEQ ID NO. 90 (called RD2 herein), SEQ ID NO. 91/SEQ ID NO. 92 (called RE8 herein), SEQ ID NO. 93/SEQ ID NO. 94 (called RE9 herein), SEQ ID NO. 95/SEQ ID NO. 96 (called RG12 herein), SEQ ID NO. 97/SEQ ID NO. 98 (called RSA1 herein), SEQ ID NO. 99/SEQ ID NO. 100 (called R2A7 herein), SEQ ID NO. 101/SEQ ID NO. 102 (called R2B12 herein), SEQ ID NO. 103/SEQ ID NO. 104 (called R2C9 herein), SEQ ID NO. 105/SEQ ID NO. 106 (called R2D5 herein), SEQ ID NO. 107/SEQ ID NO. 108 (called R2D7 herein), SEQ ID NO. 109/SEQ ID NO. 110 (called R2F4 herein), SEQ ID NO. 111/SEQ ID NO. 112 (called R2A10 herein), SEQ ID NO. 113/SEQ ID NO. 114 (called R2E2 herein), SEQ ID NO. 115/SEQ ID NO. 116 (called R3B8 herein), SEQ ID NO. 117/SEQ ID NO. 118 (called R3C3 herein), SEQ ID NO. 119/SEQ ID NO. 120 (called R3E9 herein), SEQ ID NO. 121/SEQ ID NO. 122 (called R3E10 herein), SEQ ID NO. 123/SEQ ID NO. 124 (called R3F7 herein), SEQ ID NO. 125/SEQ ID NO. 126 (called R3F10 herein), SEQ ID NO. 127/SEQ ID NO. 128 (called R4B10 herein), SEQ ID NO. 129/SEQ ID NO. 130 (called R4H1 herein), SEQ ID NO. 131/SEQ ID NO. 132 (called R4A11 herein), SEQ ID NO. 133/SEQ ID NO. 134 (called R3D2 herein), SEQ ID NO. 135/SEQ ID NO. 136 (called R5B8 herein), SEQ ID NO. 137/SEQ ID NO. 138 (called SH1A1Q herein), SEQ ID NO. 139/SEQ ID NO. 140 (called SH1B7B(K) herein), SEQ ID NO. 141/SEQ ID NO. 142 (called SH1C1 herein), SEQ ID NO. 143/SEQ ID NO. 144 (called SH1C8 herein), SEQ ID NO. 145/SEQ ID NO. 146 (called SH1E10 herein), SEQ ID NO. 147/SEQ ID NO. 148 (called SH1E2 herein), SEQ ID NO. 149/SEQ ID NO. 150 (called SH1A9 herein), SEQ ID NO. 151/SEQ ID NO. 152 (called SH1B11 herein), SEQ ID NO. 153/SEQ ID NO. 154 (called SH1E4 herein), SEQ ID NO. 155/SEQ ID NO. 156 (called SH1B3 herein), SEQ ID NO. 157/SEQ ID NO. 158 (called SH1D1 herein), SEQ ID NO. 159/SEQ ID NO. 160 (called SH1D2 herein), SEQ ID NO. 161/SEQ ID NO. 162 (called SH1D12 herein), SEQ ID NO. 163/SEQ ID NO. 164 (called SH1E1 herein), SEQ ID NO. 165/SEQ ID NO. 166 (called SH1G9 herein), SEQ ID NO. 167/SEQ ID NO. 168 (called SH1A11 herein), SEQ ID NO. 169/SEQ ID NO. 170 (called SH1C2 herein), SEQ ID NO. 171/SEQ ID NO. 172 (called SH1G8 herein), SEQ ID NO. 173/SEQ ID NO. 174 (called SH1H2 herein), SEQ ID NO. 175/SEQ ID NO. 176 (called SH1B10 herein), SEQ ID NO. 177/SEQ ID NO. 178 (called SH1B7A(L) herein), SEQ ID NO. 179/SEQ ID NO. 180 (called SH1E6 herein), SEQ ID NO. 181/SEQ ID NO. 182 (called SH1C11 herein), SEQ ID NO. 183/SEQ ID NO. 184 (called SH1A2 herein), SEQ ID NO. 185/SEQ ID NO. 186 (called SH1B1 herein), SEQ ID NO. 187/SEQ ID NO. 188 (called R6B2 herein), SEQ ID NO. 189/SEQ ID NO. 190 (called R6B7 herein), SEQ ID NO. 191/SEQ ID NO. 192 (called R6B11 herein), SEQ ID NO. 193/SEQ ID NO. 194 (called R6D1 herein), SEQ ID NO. 195/SEQ ID NO. 196 (called R6C8 herein), SEQ ID NO. 197/SEQ ID NO. 198 (called R9G8 herein), SEQ ID NO. 199/SEQ ID NO. 200 (called R7D1 herein), SEQ ID NO. 201/SEQ ID NO. 202 (called R7D2 herein), SEQ ID NO. 203/SEQ ID NO. 204 (called R7E7 herein), SEQ ID NO. 205/SEQ ID NO. 206 (called R7F2 herein), SEQ ID NO. 207/SEQ ID NO. 208 (called R7F7 herein), SEQ ID NO. 209/SEQ ID NO. 210 (called R9H2 herein), SEQ ID NO. 211/SEQ ID NO. 212 (called R9H6 herein), SEQ ID NO. 213/SEQ ID NO. 214 (called H6B1L herein), SEQ ID NO. 215/SEQ ID NO. 216 (called H6A1 herein), SEQ ID NO. 217/SEQ ID NO. 218 (called H6B1 herein), SEQ ID NO. 219/SEQ ID NO. 220 (called H6B2 herein), SEQ ID NO. 221/SEQ ID NO. 222 (called H19C herein), SEQ ID NO. 223/SEQ ID NO. 224

(called H110D herein), SEQ ID NO. 225/SEQ ID NO. 226 (called H11F herein), SEQ ID NO. 227/SEQ ID NO. 228 (called H1C1 herein), SEQ ID NO. 229/SEQ ID NO. 230 (called GPG1A2 herein), SEQ ID NO. 231/SEQ ID NO. 232 (called GPGG8 herein), SEQ ID NO. 233/SEQ ID NO. 234 (called GPGG10 herein), SEQ ID NO. 235/SEQ ID NO. 236 (called GPGH7 herein), SEQ ID NO. 237/SEQ ID NO. 238 (called GPGH10 herein), SEQ ID NO. 239/SEQ ID NO. 240 (called GPGH11 herein), SEQ ID NO. 241/SEQ ID NO. 242 (called GPGH10P herein), and combinations thereof. Preferably, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO. 54, SEQ ID NO. 55/SEQ ID NO. 56, SEQ ID NO. 57/SEQ ID NO. 58, SEQ ID NO. 59/SEQ ID NO. 60, SEQ ID NO. 61/SEQ ID NO. 62, SEQ ID NO. 63/SEQ ID NO. 64, SEQ ID NO. 65/SEQ ID NO. 66, SEQ ID NO. 67/SEQ ID NO. 68, SEQ ID NO. 69/SEQ ID NO. 70, SEQ ID NO. 71/SEQ ID NO. 72, SEQ ID NO. 73/SEQ ID NO. 74, SEQ ID NO. 75/SEQ ID NO. 76, SEQ ID NO. 77/SEQ ID NO. 78, SEQ ID NO. 79/SEQ ID NO. 80, SEQ ID NO. 81/SEQ ID NO. 82, SEQ ID NO. 83/SEQ ID NO. 84, SEQ ID NO. 85/SEQ ID NO. 86, SEQ ID NO. 87/SEQ ID NO. 88, SEQ ID NO. 89/SEQ ID NO. 90, SEQ ID NO. 91/SEQ ID NO. 92, SEQ ID NO. 93/SEQ ID NO. 94, SEQ ID NO. 95/SEQ ID NO. 96, SEQ ID NO. 97/SEQ ID NO. 98, SEQ ID NO. 99/SEQ ID NO. 100, SEQ ID NO. 101/SEQ ID NO. 102, SEQ ID NO. 103/SEQ ID NO. 104, SEQ ID NO. 105/SEQ ID NO. 106, SEQ ID NO. 107/SEQ ID NO. 108, SEQ ID NO. 109/SEQ ID NO. 110, SEQ ID NO. 111/SEQ ID NO. 112, SEQ ID NO. 113/SEQ ID NO. 114, SEQ ID NO. 115/SEQ ID NO. 116, SEQ ID NO. 117/SEQ ID NO. 118, SEQ ID NO. 119/SEQ ID NO. 120, SEQ ID NO. 121/SEQ ID NO. 122, SEQ ID NO. 123/SEQ ID NO. 124, SEQ ID NO. 125/SEQ ID NO. 126, SEQ ID NO. 127/ SEQ ID NO. 128, SEQ ID NO. 129/SEQ ID NO. 130, SEQ ID NO. 131/SEQ ID NO. 132, SEQ ID NO. 133/SEQ ID NO. 134, SEQ ID NO. 135/SEQ ID NO. 136, SEQ ID NO. 137/ SEQ ID NO. 138, SEQ ID NO. 139/SEQ ID NO. 140, SEQ ID NO. 141/SEQ ID NO. 142, SEQ ID NO. 143/SEQ ID NO. 144, SEQ ID NO. 145/SEQ ID NO. 146, SEQ ID NO. 147/ SEQ ID NO. 148, SEQ ID NO. 149/SEQ ID NO. 150, SEQ ID NO. 151/SEQ ID NO. 152, SEQ ID NO. 153/SEQ ID NO. 154, SEQ ID NO. 155/SEQ ID NO. 156, SEQ ID NO. 157/ SEQ ID NO. 158, SEQ ID NO. 159/SEQ ID NO. 160, SEQ ID NO. 161/SEQ ID NO. 162, SEQ ID NO. 163/SEQ ID NO. 164, SEQ ID NO. 165/SEQ ID NO. 166, SEQ ID NO. 167/ SEQ ID NO. 168, SEQ ID NO. 169/SEQ ID NO. 170, SEQ ID NO. 171/SEQ ID NO. 172, SEQ ID NO. 173/SEQ ID NO. 174, SEQ ID NO. 175/SEQ ID NO. 176, SEQ ID NO. 177/ SEQ ID NO. 178, SEQ ID NO. 179/SEQ ID NO. 180, SEQ ID NO. 181/SEQ ID NO. 182, SEQ ID NO. 183/SEQ ID NO. 184, SEQ ID NO. 185/SEQ ID NO. 186, SEQ ID NO. 187/ SEQ ID NO. 188, SEQ ID NO. 189/SEQ ID NO. 190, SEQ ID NO. 191/SEQ ID NO. 192, SEQ ID NO. 193/SEQ ID NO. 194, SEQ ID NO. 195/SEQ ID NO. 196, SEQ ID NO. 197/ SEQ ID NO. 198, SEQ ID NO. 199/SEQ ID NO. 200, SEQ ID NO. 201/SEQ ID NO. 202, SEQ ID NO. 203/SEQ ID NO. 204, SEQ ID NO. 205/SEQ ID NO. 206, SEQ ID NO. 207/ SEQ ID NO. 208, SEQ ID NO. 209/SEQ ID NO. 210, SEQ ID NO. 211/SEQ ID NO. 212, SEQ ID NO. 213/SEQ ID NO. 214, SEQ ID NO. 215/SEQ ID NO. 216, SEQ ID NO. 217/ SEQ ID NO. 218, SEQ ID NO. 219/SEQ ID NO. 220, SEQ ID NO. 221/SEQ ID NO. 222, SEQ ID NO. 223/SEQ ID NO. 224, SEQ ID NO. 225/SEQ ID NO. 226, SEQ ID NO. 227/ SEQ ID NO. 228, SEQ ID NO. 229/SEQ ID NO. 230, SEQ ID NO. 231/SEQ ID NO. 232, SEQ ID NO. 233/SEQ ID NO. 234, SEQ ID NO. 235/SEQ ID NO. 236, SEQ ID NO. 237/ SEQ ID NO. 238, SEQ ID NO. 239/SEQ ID NO. 240, SEQ ID NO. 241/SEQ ID NO. 242, and combinations thereof.

Preferably, the broad spectrum of mammalian cancers to be treated is selected from the group consisting of ovarian, colon, breast, lung cancers, myelomas, neuroblastic-derived CNS tumors, monocytic leukemias, B-cell derived leukemias, T-cell derived leukemias, B-cell derived lymphomas, T-cell derived lymphomas, mast cell derived tumors, and combinations thereof. Preferably, the autoimmune disease or inflammatory disease is selected from the group consisting of intestinal mucosal inflammation, wasting disease associated with colitis, multiple sclerosis, systemic lupus erythematosus, viral infections, rheumatoid arthritis, osteoarthritis, psoriasis, Cohn's disease, and inflammatory bowel disease.

DETAILED DESCRIPTION

Figure 1:
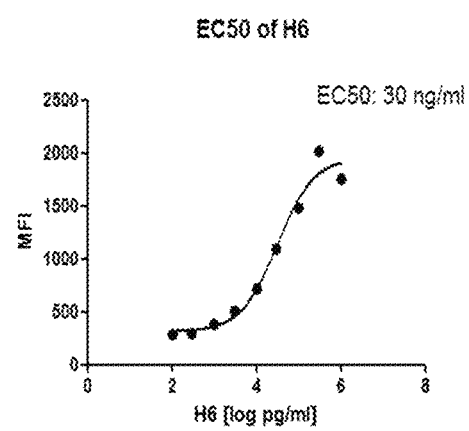
FIG. 1 shows anti-PD-L1 antibodies H6 and H10 binding to human PD-L1 expressed on human lymphocytes and the $EC_{50}$ determination in the 100 µM range
Figure 1:
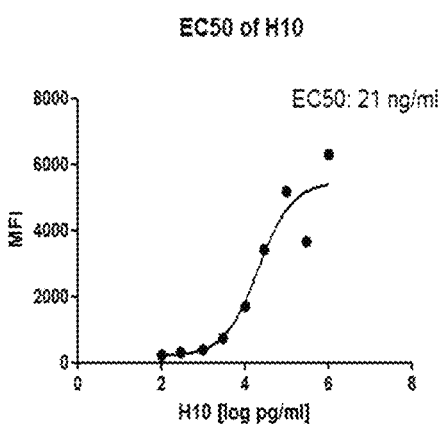

The present disclosure provides a fully human antibody of an IgG class that binds to a PD-L1 epitope with a binding affinity of $10^{-6}$M or less, that has a heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 113, SEQ ID NO. 115, SEQ ID NO. 117, SEQ ID NO. 119, SEQ ID NO. 121, SEQ ID NO. 123, SEQ ID NO. 125, SEQ ID NO. 127, SEQ ID NO. 129, SEQ ID NO. 131, SEQ ID NO. 133, SEQ ID NO. 135, SEQ ID NO. 137, SEQ ID NO. 139, SEQ ID NO. 141, SEQ ID NO. 143, SEQ ID NO. 145, SEQ ID NO. 147, SEQ ID NO. 149, SEQ ID NO. 151, SEQ ID NO. 153, SEQ ID NO. 155, SEQ ID NO. 157, SEQ ID NO. 159, SEQ ID NO. 161, SEQ ID NO. 163, SEQ ID NO. 165, SEQ ID NO. 167, SEQ ID NO. 169, SEQ ID NO. 171, SEQ ID NO. 173, SEQ ID NO. 175, SEQ ID NO. 177, SEQ ID NO. 179, SEQ ID NO. 181, SEQ ID NO. 183, SEQ ID NO. 185, SEQ ID NO. 187, SEQ ID NO. 189, SEQ ID NO. 191, SEQ ID NO. 193, SEQ ID NO. 195, SEQ ID NO. 197, SEQ ID NO. 199, SEQ ID NO. 201, SEQ ID NO. 203, SEQ ID NO. 205, SEQ ID NO. 207, SEQ ID NO. 209, SEQ ID NO. 211, SEQ ID NO. 213, SEQ ID NO. 215, SEQ ID NO. 217, SEQ ID NO. 219, SEQ ID NO. 221, SEQ ID NO. 223, SEQ ID NO. 225, SEQ ID NO. 227, SEQ ID NO. 229, SEQ ID NO. 231, SEQ ID NO. 233, SEQ ID NO. 235, SEQ ID NO. 237, SEQ ID NO. 239, SEQ ID NO. 241, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 114, SEQ ID NO. 116, SEQ ID NO. 118, SEQ ID NO. 120, SEQ ID NO. 122, SEQ ID NO. 124, SEQ ID NO. 126, SEQ ID NO. 128, SEQ ID NO. 130, SEQ ID NO. 132, SEQ ID NO. 134, SEQ ID NO. 136, SEQ ID NO. 138, SEQ ID NO. 140, SEQ ID NO. 142, SEQ ID NO. 144, SEQ ID NO. 146, SEQ ID NO. 148, SEQ ID NO. 150, SEQ ID NO. 152, SEQ ID NO. 154, SEQ ID NO. 156, SEQ ID NO. 158, SEQ ID NO. 160, SEQ ID NO. 162, SEQ ID NO. 164, SEQ ID NO. 166, SEQ ID NO. 168, SEQ ID NO. 170, SEQ ID NO. 172, SEQ ID NO. 174, SEQ ID NO. 176, SEQ ID NO. 178, SEQ ID NO. 180, SEQ ID NO. 182, SEQ ID NO. 184, SEQ ID NO. 186, SEQ ID NO. 188, SEQ ID NO. 190, SEQ ID NO. 192, SEQ ID NO. 194, SEQ ID NO. 196, SEQ ID NO. 198, SEQ ID NO. 200, SEQ ID NO. 202, SEQ ID NO. 204, SEQ ID NO. 206, SEQ ID NO. 208, SEQ ID NO. 210, SEQ ID NO. 212, SEQ ID NO. 214, SEQ ID NO. 216, SEQ ID NO. 218, SEQ ID NO. 220, SEQ ID NO. 222, SEQ ID NO. 224, SEQ ID NO. 226, SEQ ID NO. 228, SEQ ID NO. 230, SEQ ID NO. 232, SEQ ID NO. 234, SEQ ID NO. 236, SEQ ID NO. 238, SEQ ID NO. 240, SEQ ID NO. 242, and combinations thereof. Preferably, the fully human antibody has both a heavy chain and a light chain wherein the antibody has a heavy chain/light chain variable domain sequence selected from the group consisting of SEQ ID NO. 1/SEQ ID NO. 2 (called E6 herein), SEQ ID NO. 3/SEQ ID NO. 4 (called E7 herein), SEQ ID NO. 5/SEQ ID NO. 6 (called E9 herein), SEQ ID NO. 7/SEQ ID NO. 8 (called E11 herein), SEQ ID NO. 9/SEQ ID NO. 10 (called F1 herein), SEQ ID NO. 11/SEQ ID NO. 12 (called F4 herein), SEQ ID NO. 13/SEQ ID NO. 14 (called F7 herein), SEQ ID NO. 15/SEQ ID NO. 16 (called F8 herein), SEQ ID NO. 17/SEQ ID NO. 18 (called F11 herein), SEQ ID NO. 19/SEQ ID NO. 20 (called G4 herein), SEQ ID NO. 21/SEQ ID NO. 22 (called G9 herein), SEQ ID NO. 23/SEQ ID NO. 24 (called G11 herein), SEQ ID NO. 25/SEQ ID NO. 26 (called G12 herein), SEQ ID NO. 27/SEQ ID NO. 28 (called H1 herein), SEQ ID NO. 29/SEQ ID NO. 30 (called H3 herein), SEQ ID NO. 31/SEQ ID NO. 32 (called H4 herein), SEQ ID NO. 33/SEQ ID NO. 34 (called H5 herein), SEQ ID NO. 35/SEQ ID NO. 36 (called H6 herein), SEQ ID NO. 37/SEQ ID NO. 38 (called H10 herein), SEQ ID NO. 39/SEQ ID NO. 40 (called H12 herein), SEQ ID NO. 41/SEQ ID NO. 42 (called PDL-D2 herein), SEQ ID NO. 43/SEQ ID NO. 44 (called PDL-D11 herein), SEQ ID NO. 45/SEQ ID NO. 46 (called PDL-H1 herein), SEQ ID NO. 47/SEQ ID NO. 48 (called RB4 herein), SEQ ID NO. 49/SEQ ID NO. 50 (called RB11 herein), SEQ ID NO. 51/SEQ ID NO. 52 (called RC5 herein), SEQ ID NO. 53/SEQ ID NO. 54 (called RF5 herein), SEQ ID NO. 55/SEQ ID NO. 56 (called RG9 herein), SEQ ID NO. 57/SEQ ID NO. 58 (called RD1 herein), SEQ ID NO. 59/SEQ ID NO. 60 (called RF11 herein), SEQ ID NO. 61/SEQ ID NO. 62 (called RH11 herein), SEQ ID NO. 63/SEQ ID NO. 64 (called RD9 herein), SEQ ID NO. 65/SEQ ID NO. 66 (called RE10 herein), SEQ ID NO. 67/SEQ ID NO. 68 (called RA3 herein), SEQ ID NO. 69/SEQ ID NO. 70 (called RG1 herein), SEQ ID NO. 71/SEQ ID NO. 72 (called RB1 herein), SEQ ID NO. 73/SEQ ID NO. 74 (called RG7 herein), SEQ ID NO. 75/SEQ ID NO. 76 (called RA6 herein), SEQ ID NO. 77/SEQ ID NO. 78 (called RA8 herein), SEQ ID NO. 79/SEQ ID NO. 80 (called RA9 herein), SEQ ID NO. 81/SEQ ID NO. 82 (called RB5 herein), SEQ ID NO. 83/SEQ ID NO. 84 (called RB8 herein), SEQ ID NO. 85/SEQ ID NO. 86 (called RC8 herein), SEQ ID NO. 87/SEQ ID NO. 88 (called RC10 herein), SEQ ID NO. 89/SEQ ID NO. 90 (called RD2 herein), SEQ ID NO. 91/SEQ ID NO. 92 (called RE8 herein), SEQ ID NO. 93/SEQ ID NO. 94 (called RE9 herein), SEQ ID NO. 95/SEQ ID NO. 96 (called RG12 herein), SEQ ID NO. 97/SEQ ID NO. 98 (called RSA1 herein), SEQ ID NO. 99/SEQ ID NO. 100 (called R2A7 herein), SEQ ID NO. 101/SEQ ID NO. 102 (called R2B12 herein), SEQ ID NO. 103/SEQ ID NO. 104 (called R2C9 herein), SEQ ID NO. 105/SEQ ID NO. 106 (called R2D5 herein), SEQ ID NO. 107/SEQ ID NO. 108 (called R2D7 herein), SEQ ID NO. 109/SEQ ID NO. 110 (called R2F4 herein), SEQ ID NO. 111/SEQ ID NO. 112 (called R2A10 herein), SEQ ID NO. 113/SEQ ID NO. 114 (called R2E2 herein), SEQ ID NO. 115/SEQ ID NO. 116 (called R3B8 herein), SEQ ID NO. 117/SEQ ID NO. 118 (called R3C3 herein), SEQ ID NO. 119/SEQ ID NO. 120 (called R3E9 herein), SEQ ID NO. 121/SEQ ID NO. 122 (called R3E10 herein), SEQ ID NO. 123/SEQ ID NO. 124 (called R3F7 herein), SEQ ID NO. 125/SEQ ID NO. 126 (called R3F10 herein), SEQ ID NO. 127/SEQ ID NO. 128 (called R4B10 herein), SEQ ID NO. 129/SEQ ID NO. 130 (called R4H1 herein), SEQ ID NO. 131/SEQ ID NO. 132 (called R4A11 herein), SEQ ID NO. 133/SEQ ID NO. 134 (called R3D2 herein), SEQ ID NO. 135/SEQ ID NO. 136 (called R5B8 herein), SEQ ID NO. 137/SEQ ID NO. 138 (called SH1A1Q herein), SEQ ID NO. 139/SEQ ID NO. 140 (called SH1B7B(K) herein), SEQ ID NO. 141/SEQ ID NO. 142 (called SH1C1 herein), SEQ ID NO. 143/SEQ ID NO. 144 (called SH1C8 herein), SEQ ID NO. 145/SEQ ID NO. 146 (called SH1E10 herein), SEQ ID NO. 147/SEQ ID NO. 148 (called SH1E2 herein), SEQ ID NO. 149/SEQ ID NO. 150 (called SH1A9 herein), SEQ ID NO. 151/SEQ ID NO. 152 (called SH1B11 herein), SEQ ID NO. 153/SEQ ID NO. 154 (called SH1E4 herein), SEQ ID NO. 155/SEQ ID NO. 156 (called SH1B3 herein), SEQ ID NO. 157/SEQ ID NO. 158 (called SH1D1 herein), SEQ ID NO. 159/SEQ ID NO. 160 (called SH1D2 herein), SEQ ID NO. 161/SEQ ID NO. 162 (called SH1D12 herein), SEQ ID NO. 163/SEQ ID NO. 164 (called SH1E1 herein), SEQ ID NO. 165/SEQ ID NO. 166 (called SH1G9 herein), SEQ ID NO. 167/SEQ ID NO. 168 (called SH1A11 herein), SEQ ID NO. 169/SEQ ID NO. 170 (called SH1C2 herein), SEQ ID NO. 171/SEQ ID NO. 172 (called SH1G8 herein), SEQ ID NO. 173/SEQ ID NO. 174 (called SH1H2 herein), SEQ ID NO. 175/SEQ ID NO. 176 (called SH1B10 herein), SEQ ID NO. 177/SEQ ID NO. 178 (called SH1B7A(L) herein), SEQ ID NO. 179/SEQ ID NO. 180 (called SH1E6 herein), SEQ ID NO. 181/SEQ ID NO. 182 (called SH1C11 herein), SEQ ID NO. 183/SEQ ID NO. 184 (called SH1A2 herein), SEQ ID NO. 185/SEQ ID NO. 186 (called SH1B1 herein), SEQ ID NO. 187/SEQ ID NO. 188 (called R6B2 herein), SEQ ID NO. 189/SEQ ID NO. 190 (called R6B7 herein), SEQ ID NO. 191/SEQ ID NO. 192 (called R6B11 herein), SEQ ID NO. 193/SEQ ID NO. 194 (called R6D1 herein), SEQ ID NO. 195/SEQ ID NO. 196 (called R6C8 herein), SEQ ID NO. 197/SEQ ID NO. 198 (called R9G8 herein), SEQ ID NO. 199/SEQ ID NO. 200 (called R7D1 herein), SEQ ID NO. 201/SEQ ID NO. 202 (called R7D2 herein), SEQ ID NO. 203/SEQ ID NO. 204 (called R7E7 herein), SEQ ID NO. 205/SEQ ID NO. 206 (called R7F2 herein), SEQ ID NO. 207/SEQ ID NO. 208 (called R7F7 herein), SEQ ID NO. 209/SEQ ID NO. 210 (called R9H2 herein), SEQ ID NO. 211/SEQ ID NO. 212 (called R9H6 herein), SEQ ID NO. 213/SEQ ID NO. 214 (called H6B1L herein), SEQ ID NO. 215/SEQ ID NO. 216 (called H6A1 herein), SEQ ID NO. 217/SEQ ID NO. 218 (called H6B1 herein), SEQ ID NO. 219/SEQ ID NO. 220 (called H6B2 herein), SEQ ID NO. 221/SEQ ID NO. 222 (called H19C herein), SEQ ID NO. 223/SEQ ID NO. 224 (called H110D herein), SEQ ID NO. 225/SEQ ID NO. 226 (called H11F herein), SEQ ID NO. 227/SEQ ID NO. 228 (called H1C1 herein), SEQ ID NO. 229/SEQ ID NO. 230 (called GPG1A2 herein), SEQ ID NO. 231/SEQ ID NO. 232 (called GPGG8 herein), SEQ ID NO. 233/SEQ ID NO. 234 (called GPGG10 herein), SEQ ID NO. 235/SEQ ID NO. 236 (called GPGH7 herein), SEQ ID NO. 237/SEQ ID NO. 238 (called GPGH10 herein), SEQ ID NO. 239/SEQ ID NO. 240 (called GPGH11 herein), SEQ ID NO. 241/SEQ ID NO. 242 (called GPGH10P herein), and combinations thereof.

The present disclosure provides a Fab fully human antibody fragment, having a variable domain region from a heavy chain and a variable domain region from a light chain, wherein the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 113, SEQ ID NO. 115, SEQ ID NO. 117, SEQ ID NO. 119, SEQ ID NO. 121, SEQ ID NO. 123, SEQ ID NO. 125, SEQ ID NO. 127, SEQ ID NO. 129, SEQ ID NO. 131, SEQ ID NO. 133, SEQ ID NO. 135, SEQ ID NO. 137, SEQ ID NO. 139, SEQ ID NO. 141, SEQ ID NO. 143, SEQ ID NO. 145, SEQ ID NO. 147, SEQ ID NO. 149, SEQ ID NO. 151, SEQ ID NO. 153, SEQ ID NO. 155, SEQ ID NO. 157, SEQ ID NO. 159, SEQ ID NO. 161, SEQ ID NO. 163, SEQ ID NO. 165, SEQ ID NO. 167, SEQ ID NO. 169, SEQ ID NO. 171, SEQ ID NO. 173, SEQ ID NO. 175, SEQ ID NO. 177, SEQ ID NO. 179, SEQ ID NO. 181, SEQ ID NO. 183, SEQ ID NO. 185, SEQ ID NO. 187, SEQ ID NO. 189, SEQ ID NO. 191, SEQ ID NO. 193, SEQ ID NO. 195, SEQ ID NO. 197, SEQ ID NO. 199, SEQ ID NO. 201, SEQ ID NO. 203, SEQ ID NO. 205, SEQ ID NO. 207, SEQ ID NO. 209, SEQ ID NO. 211, SEQ ID NO. 213, SEQ ID NO. 215, SEQ ID NO. 217, SEQ ID NO. 219, SEQ ID NO. 221, SEQ ID NO. 223, SEQ ID NO. 225, SEQ ID NO. 227, SEQ ID NO. 229, SEQ ID NO. 231, SEQ ID NO. 233, SEQ ID NO. 235, SEQ ID NO. 237, SEQ ID NO. 239, SEQ ID NO. 241, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 114, SEQ ID NO. 116, SEQ ID NO. 118, SEQ ID NO. 120, SEQ ID NO. 122, SEQ ID NO. 124, SEQ ID NO. 126, SEQ ID NO. 128, SEQ ID NO. 130, SEQ ID NO. 132, SEQ ID NO. 134, SEQ ID NO. 136, SEQ ID NO. 138, SEQ ID NO. 140, SEQ ID NO. 142, SEQ ID NO. 144, SEQ ID NO. 146, SEQ ID NO. 148, SEQ ID NO. 150, SEQ ID NO. 152, SEQ ID NO. 154, SEQ ID NO. 156, SEQ ID NO. 158, SEQ ID NO. 160, SEQ ID NO. 162, SEQ ID NO. 164, SEQ ID NO. 166, SEQ ID NO. 168, SEQ ID NO. 170, SEQ ID NO. 172, SEQ ID NO. 174, SEQ ID NO. 176, SEQ ID NO. 178, SEQ ID NO. 180, SEQ ID NO. 182, SEQ ID NO. 184, SEQ ID NO. 186, SEQ ID NO. 188, SEQ ID NO. 190, SEQ ID NO. 192, SEQ ID NO. 194, SEQ ID NO. 196, SEQ ID NO. 198, SEQ ID NO. 200, SEQ ID NO. 202, SEQ ID NO. 204, SEQ ID NO. 206, SEQ ID NO. 208, SEQ ID NO. 210, SEQ ID NO. 212, SEQ ID NO. 214, SEQ ID NO. 216, SEQ ID NO. 218, SEQ ID NO. 220, SEQ ID NO. 222, SEQ ID NO. 224, SEQ ID NO. 226, SEQ ID NO. 228, SEQ ID NO. 230, SEQ ID NO. 232, SEQ ID NO. 234, SEQ ID NO. 236, SEQ ID NO. 238, SEQ ID NO. 240, SEQ ID NO. 242, and combinations thereof. Preferably, the fully human antibody Fab fragment has both a heavy chain variable domain region and a light chain variable domain region wherein the antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO. 54, SEQ ID NO. 55/SEQ ID NO. 56, SEQ ID NO. 57/SEQ ID NO. 58, SEQ ID NO. 59/SEQ ID NO. 60, SEQ ID NO. 61/SEQ ID NO. 62, SEQ ID NO. 63/SEQ ID NO. 64, SEQ ID NO. 65/SEQ ID NO. 66, SEQ ID NO. 67/SEQ ID NO. 68, SEQ ID NO. 69/SEQ ID NO. 70, SEQ ID NO. 71/SEQ ID NO. 72, SEQ ID NO. 73/SEQ ID NO. 74, SEQ ID NO. 75/SEQ ID NO. 76, SEQ ID NO. 77/SEQ ID NO. 78, SEQ ID NO. 79/SEQ ID NO. 80, SEQ ID NO. 81/SEQ ID NO. 82, SEQ ID NO. 83/SEQ ID NO. 84, SEQ ID NO. 85/SEQ ID NO. 86, SEQ ID NO. 87/SEQ ID NO. 88, SEQ ID NO. 89/SEQ ID NO. 90, SEQ ID NO. 91/SEQ ID NO. 92, SEQ ID NO. 93/SEQ ID NO. 94, SEQ ID NO. 95/SEQ ID NO. 96, SEQ ID NO. 97/SEQ ID NO. 98, SEQ ID NO. 99/SEQ ID NO. 100, SEQ ID NO. 101/SEQ ID NO. 102, SEQ ID NO. 103/SEQ ID NO. 104, SEQ ID NO. 105/SEQ ID NO. 106, SEQ ID NO. 107/SEQ ID NO. 108, SEQ ID NO. 109/SEQ ID NO. 110, SEQ ID NO. 111/SEQ ID NO. 112, SEQ ID NO. 113/SEQ ID NO. 114, SEQ ID NO. 115/SEQ ID NO. 116, SEQ ID NO. 117/SEQ ID NO. 118, SEQ ID NO. 119/SEQ ID NO. 120, SEQ ID NO. 121/SEQ ID NO. 122, SEQ ID NO. 123/SEQ ID NO. 124, SEQ ID NO. 125/SEQ ID NO. 126, SEQ ID NO. 127/SEQ ID NO. 128, SEQ ID NO. 129/SEQ ID NO. 130, SEQ ID NO. 131/SEQ ID NO. 132, SEQ ID NO. 133/SEQ ID NO. 134, SEQ ID NO. 135/SEQ ID NO. 136, SEQ ID NO. 137/SEQ ID NO. 138, SEQ ID NO. 139/SEQ ID NO. 140, SEQ ID NO. 141/SEQ ID NO. 142, SEQ ID NO. 143/SEQ ID NO. 144, SEQ ID NO. 145/SEQ ID NO. 146, SEQ ID NO. 147/SEQ ID NO. 148, SEQ ID NO. 149/SEQ ID NO. 150, SEQ ID NO. 151/SEQ ID NO. 152, SEQ ID NO. 153/SEQ ID NO. 154, SEQ ID NO. 155/SEQ ID NO. 156, SEQ ID NO. 157/SEQ ID NO. 158, SEQ ID NO. 159/SEQ ID NO. 160, SEQ ID NO. 161/SEQ ID NO. 162, SEQ ID NO. 163/SEQ ID NO. 164, SEQ ID NO. 165/SEQ ID NO. 166, SEQ ID NO. 167/SEQ ID NO. 168, SEQ ID NO. 169/SEQ ID NO. 170, SEQ ID NO. 171/SEQ ID NO. 172, SEQ ID NO. 173/SEQ ID NO. 174, SEQ ID NO. 175/SEQ ID NO. 176, SEQ ID NO. 177/SEQ ID NO. 178, SEQ ID NO. 179/SEQ ID NO. 180, SEQ ID NO. 181/SEQ ID NO. 182, SEQ ID NO. 183/SEQ ID NO. 184, SEQ ID NO. 185/SEQ ID NO. 186, SEQ ID NO. 187/SEQ ID NO. 188, SEQ ID NO. 189/SEQ ID NO. 190, SEQ ID NO. 191/SEQ ID NO. 192, SEQ ID NO. 193/SEQ ID NO. 194, SEQ ID NO. 195/SEQ ID NO. 196, SEQ ID NO. 197/SEQ ID NO. 198, SEQ ID NO. 199/SEQ ID NO. 200, SEQ ID NO. 201/SEQ ID NO. 202, SEQ ID NO. 203/SEQ ID NO. 204, SEQ ID NO. 205/SEQ ID NO. 206, SEQ ID NO. 207/SEQ ID NO. 208, SEQ ID NO. 209/SEQ ID NO. 210, SEQ ID NO. 211/SEQ ID NO. 212, SEQ ID NO. 213/SEQ ID NO. 214, SEQ ID NO. 215/SEQ ID NO. 216, SEQ ID NO. 217/SEQ ID NO. 218, SEQ ID NO. 219/SEQ ID NO. 220, SEQ ID NO. 221/SEQ ID NO. 222, SEQ ID NO. 223/SEQ ID NO. 224, SEQ ID NO. 225/SEQ ID NO. 226, SEQ ID NO. 227/SEQ ID NO. 228, SEQ ID NO. 229/SEQ ID NO. 230, SEQ ID NO. 231/SEQ ID NO. 232, SEQ ID NO. 233/SEQ ID NO. 234, SEQ ID NO. 235/SEQ ID NO. 236, SEQ ID NO. 237/SEQ ID NO. 238, SEQ ID NO. 239/SEQ ID NO. 240, SEQ ID NO. 241/SEQ ID NO. 242, and combinations thereof.

The present disclosure provides a single chain human antibody, having a variable domain region from a heavy chain and a variable domain region from a light chain and a peptide linker connection the heavy chain and light chain variable domain regions, wherein the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 113, SEQ ID NO. 115, SEQ ID NO. 117, SEQ ID NO. 119, SEQ ID NO. 121, SEQ ID NO. 123, SEQ ID NO. 125, SEQ ID NO. 127, SEQ ID NO. 129, SEQ ID NO. 131, SEQ ID NO. 133, SEQ ID NO. 135, SEQ ID NO. 137, SEQ ID NO. 139, SEQ ID NO. 141, SEQ ID NO. 143, SEQ ID NO. 145, SEQ ID NO. 147, SEQ ID NO. 149, SEQ ID NO. 151, SEQ ID NO. 153, SEQ ID NO. 155, SEQ ID NO. 157, SEQ ID NO. 159, SEQ ID NO. 161, SEQ ID NO. 163, SEQ ID NO. 165, SEQ ID NO. 167, SEQ ID NO. 169, SEQ ID NO. 171, SEQ ID NO. 173, SEQ ID NO. 175, SEQ ID NO. 177, SEQ ID NO. 179, SEQ ID NO. 181, SEQ ID NO. 183, SEQ ID NO. 185, SEQ ID NO. 187, SEQ ID NO. 189, SEQ ID NO. 191, SEQ ID NO. 193, SEQ ID NO. 195, SEQ ID NO. 197, SEQ ID NO. 199, SEQ ID NO. 201, SEQ ID NO. 203, SEQ ID NO. 205, SEQ ID NO. 207, SEQ ID NO. 209, SEQ ID NO. 211, SEQ ID NO. 213, SEQ ID NO. 215, SEQ ID NO. 217, SEQ ID NO. 219, SEQ ID NO. 221, SEQ ID NO. 223, SEQ ID NO. 225, SEQ ID NO. 227, SEQ ID NO. 229, SEQ ID NO. 231, SEQ ID NO. 233, SEQ ID NO. 235, SEQ ID NO. 237, SEQ ID NO. 239, SEQ ID NO. 241, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 114, SEQ ID NO. 116, SEQ ID NO. 118, SEQ ID NO. 120, SEQ ID NO. 122, SEQ ID NO. 124, SEQ ID NO. 126, SEQ ID NO. 128, SEQ ID NO. 130, SEQ ID NO. 132, SEQ ID NO. 134, SEQ ID NO. 136, SEQ ID NO. 138, SEQ ID NO. 140, SEQ ID NO. 142, SEQ ID NO. 144, SEQ ID NO. 146, SEQ ID NO. 148, SEQ ID NO. 150, SEQ ID NO. 152, SEQ ID NO. 154, SEQ ID NO. 156, SEQ ID NO. 158, SEQ ID NO. 160, SEQ ID NO. 162, SEQ ID NO. 164, SEQ ID NO. 166, SEQ ID NO. 168, SEQ ID NO. 170, SEQ ID NO. 172, SEQ ID NO. 174, SEQ ID NO. 176, SEQ ID NO. 178, SEQ ID NO. 180, SEQ ID NO. 182, SEQ ID NO. 184, SEQ ID NO. 186, SEQ ID NO. 188, SEQ ID NO. 190, SEQ ID NO. 192, SEQ ID NO. 194, SEQ ID NO. 196, SEQ ID NO. 198, SEQ ID NO. 200, SEQ ID NO. 202, SEQ ID NO. 204, SEQ ID NO. 206, SEQ ID NO. 208, SEQ ID NO. 210, SEQ ID NO. 212, SEQ ID NO. 214, SEQ ID NO. 216, SEQ ID NO. 218, SEQ ID NO. 220, SEQ ID NO. 222, SEQ ID NO. 224, SEQ ID NO. 226, SEQ ID NO. 228, SEQ ID NO. 230, SEQ ID NO. 232, SEQ ID NO. 234, SEQ ID NO. 236, SEQ ID NO. 238, SEQ ID NO. 240, SEQ ID NO. 242, and combinations thereof. Preferably, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO. 54, SEQ ID NO. 55/SEQ ID NO. 56, SEQ ID NO. 57/SEQ ID NO. 58, SEQ ID NO. 59/SEQ ID NO. 60, SEQ ID NO. 61/SEQ ID NO. 62, SEQ ID NO. 63/SEQ ID NO. 64, SEQ ID NO. 65/SEQ ID NO. 66, SEQ ID NO. 67/SEQ ID NO. 68, SEQ ID NO. 69/SEQ ID NO. 70, SEQ ID NO. 71/SEQ ID NO. 72, SEQ ID NO. 73/SEQ ID NO. 74, SEQ ID NO. 75/SEQ ID NO. 76, SEQ ID NO. 77/SEQ ID NO. 78, SEQ ID NO. 79/SEQ ID NO. 80, SEQ ID NO. 81/SEQ ID NO. 82, SEQ ID NO. 83/SEQ ID NO. 84, SEQ ID NO. 85/SEQ ID NO. 86, SEQ ID NO. 87/SEQ ID NO. 88, SEQ ID NO. 89/SEQ ID NO. 90, SEQ ID NO. 91/SEQ ID NO. 92, SEQ ID NO. 93/SEQ ID NO. 94, SEQ ID NO. 95/SEQ ID NO. 96, SEQ ID NO. 97/SEQ ID NO. 98, SEQ ID NO. 99/SEQ ID NO. 100, SEQ ID NO. 101/SEQ ID NO. 102, SEQ ID NO. 103/SEQ ID NO. 104, SEQ ID NO. 105/SEQ ID NO. 106, SEQ ID NO.

107/SEQ ID NO. 108, SEQ ID NO. 109/SEQ ID NO. 110, SEQ ID NO. 111/SEQ ID NO. 112, SEQ ID NO. 113/SEQ ID NO. 114, SEQ ID NO. 115/SEQ ID NO. 116, SEQ ID NO. 117/SEQ ID NO. 118, SEQ ID NO. 119/SEQ ID NO. 120, SEQ ID NO. 121/SEQ ID NO. 122, SEQ ID NO. 123/SEQ ID NO. 124, SEQ ID NO. 125/SEQ ID NO. 126, SEQ ID NO. 127/SEQ ID NO. 128, SEQ ID NO. 129/SEQ ID NO. 130, SEQ ID NO. 131/SEQ ID NO. 132, SEQ ID NO. 133/SEQ ID NO. 134, SEQ ID NO. 135/SEQ ID NO. 136, SEQ ID NO. 137/SEQ ID NO. 138, SEQ ID NO. 139/SEQ ID NO. 140, SEQ ID NO. 141/SEQ ID NO. 142, SEQ ID NO. 143/SEQ ID NO. 144, SEQ ID NO. 145/SEQ ID NO. 146, SEQ ID NO. 147/SEQ ID NO. 148, SEQ ID NO. 149/SEQ ID NO. 150, SEQ ID NO. 151/SEQ ID NO. 152, SEQ ID NO. 153/SEQ ID NO. 154, SEQ ID NO. 155/SEQ ID NO. 156, SEQ ID NO. 157/SEQ ID NO. 158, SEQ ID NO. 159/SEQ ID NO. 160, SEQ ID NO. 161/SEQ ID NO. 162, SEQ ID NO. 163/SEQ ID NO. 164, SEQ ID NO. 165/SEQ ID NO. 166, SEQ ID NO. 167/SEQ ID NO. 168, SEQ ID NO. 169/SEQ ID NO. 170, SEQ ID NO. 171/SEQ ID NO. 172, SEQ ID NO. 173/SEQ ID NO. 174, SEQ ID NO. 175/SEQ ID NO. 176, SEQ ID NO. 177/SEQ ID NO. 178, SEQ ID NO. 179/SEQ ID NO. 180, SEQ ID NO. 181/SEQ ID NO. 182, SEQ ID NO. 183/SEQ ID NO. 184, SEQ ID NO. 185/SEQ ID NO. 186, SEQ ID NO. 187/SEQ ID NO. 188, SEQ ID NO. 189/SEQ ID NO. 190, SEQ ID NO. 191/SEQ ID NO. 192, SEQ ID NO. 193/SEQ ID NO. 194, SEQ ID NO. 195/SEQ ID NO. 196, SEQ ID NO. 197/SEQ ID NO. 198, SEQ ID NO. 199/SEQ ID NO. 200, SEQ ID NO. 201/SEQ ID NO. 202, SEQ ID NO. 203/SEQ ID NO. 204, SEQ ID NO. 205/SEQ ID NO. 206, SEQ ID NO. 207/SEQ ID NO. 208, SEQ ID NO. 209/SEQ ID NO. 210, SEQ ID NO. 211/SEQ ID NO. 212, SEQ ID NO. 213/SEQ ID NO. 214, SEQ ID NO. 215/SEQ ID NO. 216, SEQ ID NO. 217/SEQ ID NO. 218, SEQ ID NO. 219/SEQ ID NO. 220, SEQ ID NO. 221/SEQ ID NO. 222, SEQ ID NO. 223/SEQ ID NO. 224, SEQ ID NO. 225/SEQ ID NO. 226, SEQ ID NO. 227/SEQ ID NO. 228, SEQ ID NO. 229/SEQ ID NO. 230, SEQ ID NO. 231/SEQ ID NO. 232, SEQ ID NO. 233/SEQ ID NO. 234, SEQ ID NO. 235/SEQ ID NO. 236, SEQ ID NO. 237/SEQ ID NO. 238, SEQ ID NO. 239/SEQ ID NO. 240, SEQ ID NO. 241/SEQ ID NO. 242, and combinations thereof.

The present disclosure further provides a method for treating a broad spectrum of mammalian cancers or inflammatory diseases or autoimmune diseases, comprising administering an effective amount of an anti-PD-L1 polypeptide, wherein the anti-PD-L1 polypeptide is selected from the group consisting of a fully human antibody of an IgG class that binds to a PD-L1 epitope with a binding affinity of at least $10^{-6}$M, a Fab fully human antibody fragment, having a variable domain region from a heavy chain and a variable domain region from a light chain, a single chain human antibody, having a variable domain region from a heavy chain and a variable domain region from a light chain and a peptide linker connection the heavy chain and light chain variable domain regions, and combinations thereof;

wherein the fully human antibody has a heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 113, SEQ ID NO. 115, SEQ ID NO. 117, SEQ ID NO. 119, SEQ ID NO. 121, SEQ ID NO. 123, SEQ ID NO. 125, SEQ ID NO. 127, SEQ ID NO. 129, SEQ ID NO. 131, SEQ ID NO. 133, SEQ ID NO. 135, SEQ ID NO. 137, SEQ ID NO. 139, SEQ ID NO. 141, SEQ ID NO. 143, SEQ ID NO. 145, SEQ ID NO. 147, SEQ ID NO. 149, SEQ ID NO. 151, SEQ ID NO. 153, SEQ ID NO. 155, SEQ ID NO. 157, SEQ ID NO. 159, SEQ ID NO. 161, SEQ ID NO. 163, SEQ ID NO. 165, SEQ ID NO. 167, SEQ ID NO. 169, SEQ ID NO. 171, SEQ ID NO. 173, SEQ ID NO. 175, SEQ ID NO. 177, SEQ ID NO. 179, SEQ ID NO. 181, SEQ ID NO. 183, SEQ ID NO. 185, SEQ ID NO. 187, SEQ ID NO. 189, SEQ ID NO. 191, SEQ ID NO. 193, SEQ ID NO. 195, SEQ ID NO. 197, SEQ ID NO. 199, SEQ ID NO. 201, SEQ ID NO. 203, SEQ ID NO. 205, SEQ ID NO. 207, SEQ ID NO. 209, SEQ ID NO. 211, SEQ ID NO. 213, SEQ ID NO. 215, SEQ ID NO. 217, SEQ ID NO. 219, SEQ ID NO. 221, SEQ ID NO. 223, SEQ ID NO. 225, SEQ ID NO. 227, SEQ ID NO. 229, SEQ ID NO. 231, SEQ ID NO. 233, SEQ ID NO. 235, SEQ ID NO. 237, SEQ ID NO. 239, SEQ ID NO. 241, and combinations thereof, and that has a light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 114, SEQ ID NO. 116, SEQ ID NO. 118, SEQ ID NO. 120, SEQ ID NO. 122, SEQ ID NO. 124, SEQ ID NO. 126, SEQ ID NO. 128, SEQ ID NO. 130, SEQ ID NO. 132, SEQ ID NO. 134, SEQ ID NO. 136, SEQ ID NO. 138, SEQ ID NO. 140, SEQ ID NO. 142, SEQ ID NO. 144, SEQ ID NO. 146, SEQ ID NO. 148, SEQ ID NO. 150, SEQ ID NO. 152, SEQ ID NO. 154, SEQ ID NO. 156, SEQ ID NO. 158, SEQ ID NO. 160, SEQ ID NO. 162, SEQ ID NO. 164, SEQ ID NO. 166, SEQ ID NO. 168, SEQ ID NO. 170, SEQ ID NO. 172, SEQ ID NO. 174, SEQ ID NO. 176, SEQ ID NO. 178, SEQ ID NO. 180, SEQ ID NO. 182, SEQ ID NO. 184, SEQ ID NO. 186, SEQ ID NO. 188, SEQ ID NO. 190, SEQ ID NO. 192, SEQ ID NO. 194, SEQ ID NO. 196, SEQ ID NO. 198, SEQ ID NO. 200, SEQ ID NO. 202, SEQ ID NO. 204, SEQ ID NO. 206, SEQ ID NO. 208, SEQ ID NO. 210, SEQ ID NO. 212, SEQ ID NO. 214, SEQ ID NO. 216, SEQ ID NO. 218, SEQ ID NO. 220, SEQ ID NO. 222, SEQ ID NO. 224, SEQ ID NO. 226, SEQ ID NO. 228, SEQ ID NO. 230, SEQ ID NO. 232, SEQ ID NO. 234, SEQ ID NO. 236, SEQ ID NO. 238, SEQ ID NO. 240, SEQ ID NO. 242, and combinations thereof;

wherein the Fab fully human antibody fragment has the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 113, SEQ ID NO. 115, SEQ ID NO. 117, SEQ ID NO. 119, SEQ ID NO. 121, SEQ ID NO. 123, SEQ ID NO. 125, SEQ ID NO. 127, SEQ ID NO. 129, SEQ ID NO. 131, SEQ ID NO. 133, SEQ ID NO. 135, SEQ ID NO. 137, SEQ ID NO. 139, SEQ ID NO. 141, SEQ ID NO. 143, SEQ ID NO. 145, SEQ ID NO. 147, SEQ ID NO. 149, SEQ ID NO. 151, SEQ ID NO. 153, SEQ ID NO. 155, SEQ ID NO. 157, SEQ ID NO. 159, SEQ ID NO. 161, SEQ ID NO. 163, SEQ ID NO. 165, SEQ ID NO. 167, SEQ ID NO. 169, SEQ ID NO. 171, SEQ ID NO. 173, SEQ ID NO. 175, SEQ ID NO. 177, SEQ ID NO. 179, SEQ ID NO. 181, SEQ ID NO. 183, SEQ ID NO. 185, SEQ ID NO. 187, SEQ ID NO. 189, SEQ ID NO. 191, SEQ ID NO. 193, SEQ ID NO. 195, SEQ ID NO. 197, SEQ ID NO. 199, SEQ ID NO. 201, SEQ ID NO. 203, SEQ ID NO. 205, SEQ ID NO. 207, SEQ ID NO. 209, SEQ ID NO. 211, SEQ ID NO. 213, SEQ ID NO. 215, SEQ ID NO. 217, SEQ ID NO. 219, SEQ ID NO. 221, SEQ ID NO. 223, SEQ ID NO. 225, SEQ ID NO. 227, SEQ ID NO. 229, SEQ ID NO. 231, SEQ ID NO. 233, SEQ ID NO. 235, SEQ ID NO. 237, SEQ ID NO. 239, SEQ ID NO. 241, and combinations thereof, and that has the light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 114, SEQ ID NO. 116, SEQ ID NO. 118, SEQ ID NO. 120, SEQ ID NO. 122, SEQ ID NO. 124, SEQ ID NO. 126, SEQ ID NO. 128, SEQ ID NO. 130, SEQ ID NO. 132, SEQ ID NO. 134, SEQ ID NO. 136, SEQ ID NO. 138, SEQ ID NO. 140, SEQ ID NO. 142, SEQ ID NO. 144, SEQ ID NO. 146, SEQ ID NO. 148, SEQ ID NO. 150, SEQ ID NO. 152, SEQ ID NO. 154, SEQ ID NO. 156, SEQ ID NO. 158, SEQ ID NO. 160, SEQ ID NO. 162, SEQ ID NO. 164, SEQ ID NO. 166, SEQ ID NO. 168, SEQ ID NO. 170, SEQ ID NO. 172, SEQ ID NO. 174, SEQ ID NO. 176, SEQ ID NO. 178, SEQ ID NO. 180, SEQ ID NO. 182, SEQ ID NO. 184, SEQ ID NO. 186, SEQ ID NO. 188, SEQ ID NO. 190, SEQ ID NO. 192, SEQ ID NO. 194, SEQ ID NO. 196, SEQ ID NO. 198, SEQ ID NO. 200, SEQ ID NO. 202, SEQ ID NO. 204, SEQ ID NO. 206, SEQ ID NO. 208, SEQ ID NO. 210, SEQ ID NO. 212, SEQ ID NO. 214, SEQ ID NO. 216, SEQ ID NO. 218, SEQ ID NO. 220, SEQ ID NO. 222, SEQ ID NO. 224, SEQ ID NO. 226, SEQ ID NO. 228, SEQ ID NO. 230, SEQ ID NO. 232, SEQ ID NO. 234, SEQ ID NO. 236, SEQ ID NO. 238, SEQ ID NO. 240, SEQ ID NO. 242, and combinations thereof; and wherein the single chain human antibody has the heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 113, SEQ ID NO. 115, SEQ ID NO. 117, SEQ ID NO. 119, SEQ ID NO. 121, SEQ ID NO. 123, SEQ ID NO. 125, SEQ ID NO. 127, SEQ ID NO. 129, SEQ ID NO. 131, SEQ ID NO. 133, SEQ ID NO. 135, SEQ ID NO. 137, SEQ ID NO. 139, SEQ ID NO. 141, SEQ ID NO. 143, SEQ ID NO. 145, SEQ ID NO. 147, SEQ ID NO. 149, SEQ ID NO. 151, SEQ ID NO. 153, SEQ ID NO. 155, SEQ ID NO. 157, SEQ ID NO. 159, SEQ ID NO. 161, SEQ ID NO. 163, SEQ ID NO. 165, SEQ ID NO. 167, SEQ ID NO. 169, SEQ ID NO. 171, SEQ ID NO. 173, SEQ ID NO. 175, SEQ ID NO. 177, SEQ ID NO. 179, SEQ ID NO. 181, SEQ ID NO. 183, SEQ ID NO. 185, SEQ ID NO. 187, SEQ ID NO. 189, SEQ ID NO. 191, SEQ ID NO. 193, SEQ ID NO. 195, SEQ ID NO. 197, SEQ ID NO. 199, SEQ ID NO. 201, SEQ ID NO. 203, SEQ ID NO. 205, SEQ ID NO. 207, SEQ ID NO. 209, SEQ ID NO. 211, SEQ ID NO. 213, SEQ ID NO. 215, SEQ ID NO. 217, SEQ ID NO. 219, SEQ ID NO. 221, SEQ ID NO. 223, SEQ ID NO. 225, SEQ ID NO. 227, SEQ ID NO. 229, SEQ ID NO. 231, SEQ ID NO. 233, SEQ ID NO. 235, SEQ ID NO. 237, SEQ ID NO. 239, SEQ ID NO. 241, and combinations thereof, and that has the light chain variable domain sequence that is at least 95% identical to the amino acid sequences selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 114, SEQ ID NO. 116, SEQ ID NO. 118, SEQ ID NO. 120, SEQ ID NO. 122, SEQ ID NO. 124, SEQ ID NO. 126, SEQ ID NO. 128, SEQ ID NO. 130, SEQ ID NO. 132, SEQ ID NO. 134, SEQ ID NO. 136, SEQ ID NO. 138, SEQ ID NO. 140, SEQ ID NO. 142, SEQ ID NO. 144, SEQ ID NO. 146, SEQ ID NO. 148, SEQ ID NO. 150, SEQ ID NO. 152, SEQ ID NO. 154, SEQ ID NO. 156, SEQ ID NO. 158, SEQ ID NO. 160, SEQ ID NO. 162, SEQ ID NO. 164, SEQ ID NO. 166, SEQ ID NO. 168, SEQ ID NO. 170, SEQ ID NO. 172, SEQ ID NO. 174, SEQ ID NO. 176, SEQ ID NO. 178, SEQ ID NO. 180, SEQ ID NO. 182, SEQ ID NO. 184, SEQ ID NO. 186, SEQ ID NO. 188, SEQ ID NO. 190, SEQ ID NO. 192, SEQ ID NO. 194, SEQ ID NO. 196, SEQ ID NO. 198, SEQ ID NO. 200, SEQ ID NO. 202, SEQ ID NO. 204, SEQ ID NO. 206, SEQ ID NO. 208, SEQ ID NO. 210, SEQ ID NO. 212, SEQ ID NO. 214, SEQ ID NO. 216, SEQ ID NO. 218, SEQ ID NO. 220, SEQ ID NO. 222, SEQ ID NO. 224, SEQ ID NO. 226, SEQ ID NO. 228, SEQ ID NO. 230, SEQ ID NO. 232, SEQ ID NO. 234, SEQ ID NO. 236, SEQ ID NO. 238, SEQ ID NO. 240, SEQ ID NO. 242, and combinations thereof.

Preferably, the fully human antibody has both a heavy chain and a light chain wherein the antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO. 54, SEQ ID NO. 55/SEQ ID NO. 56, SEQ ID NO. 57/SEQ ID NO. 58, SEQ ID NO. 59/SEQ ID NO. 60, SEQ ID NO. 61/SEQ ID NO. 62, SEQ ID NO. 63/SEQ ID NO. 64, SEQ ID NO. 65/SEQ ID NO. 66, SEQ ID NO. 67/SEQ ID NO. 68, SEQ ID NO. 69/SEQ ID NO. 70, SEQ ID NO. 71/SEQ ID NO. 72, SEQ ID NO. 73/SEQ ID NO. 74, SEQ ID NO. 75/SEQ ID NO. 76, SEQ ID NO. 77/SEQ ID NO. 78, SEQ ID NO. 79/SEQ ID NO. 80, SEQ ID NO. 81/SEQ ID NO. 82, SEQ ID NO. 83/SEQ ID NO. 84, SEQ ID NO. 85/SEQ ID NO. 86, SEQ ID NO. 87/SEQ ID NO. 88, SEQ ID NO. 89/SEQ ID NO. 90, SEQ ID NO. 91/SEQ ID NO. 92, SEQ ID NO. 93/SEQ ID NO. 94, SEQ ID NO. 95/SEQ ID NO. 96, SEQ ID NO. 97/SEQ ID NO. 98, SEQ ID NO. 99/SEQ ID NO. 100, SEQ ID NO. 101/SEQ ID NO. 102, SEQ ID NO. 103/SEQ ID NO. 104, SEQ ID NO. 105/SEQ ID NO. 106, SEQ ID NO. 107/SEQ ID NO. 108, SEQ ID NO. 109/SEQ ID NO. 110, SEQ ID NO. 111/SEQ ID NO. 112, SEQ ID NO. 113/SEQ ID NO. 114, SEQ ID NO. 115/SEQ ID NO. 116, SEQ ID NO. 117/SEQ ID NO. 118, SEQ ID NO. 119/SEQ ID NO. 120, SEQ ID NO. 121/SEQ ID NO. 122, SEQ ID NO. 123/SEQ ID NO. 124, SEQ ID NO. 125/SEQ ID NO. 126, SEQ ID NO. 127/SEQ ID NO. 128, SEQ ID NO. 129/SEQ ID NO. 130, SEQ ID NO. 131/SEQ ID NO. 132, SEQ ID NO. 133/SEQ ID NO. 134, SEQ ID NO. 135/SEQ ID NO. 136, SEQ ID NO. 137/SEQ ID NO. 138, SEQ ID NO. 139/SEQ ID NO. 140, SEQ ID NO. 141/SEQ ID NO. 142, SEQ ID NO. 143/SEQ ID NO. 144, SEQ ID NO. 145/SEQ ID NO. 146, SEQ ID NO. 147/SEQ ID NO. 148, SEQ ID NO. 149/SEQ ID NO. 150, SEQ ID NO. 151/SEQ ID NO. 152, SEQ ID NO. 153/SEQ ID NO. 154, SEQ ID NO. 155/SEQ ID NO. 156, SEQ ID NO. 157/SEQ ID NO. 158, SEQ ID NO. 159/SEQ ID NO. 160, SEQ ID NO. 161/SEQ ID NO. 162, SEQ ID NO. 163/SEQ ID NO. 164, SEQ ID NO. 165/SEQ ID NO. 166, SEQ ID NO. 167/SEQ ID NO. 168, SEQ ID NO. 169/SEQ ID NO. 170, SEQ ID NO. 171/SEQ ID NO. 172, SEQ ID NO. 173/SEQ ID NO. 174, SEQ ID NO. 175/SEQ ID NO. 176, SEQ ID NO. 177/SEQ ID NO. 178, SEQ ID NO. 179/SEQ ID NO. 180, SEQ ID NO. 181/SEQ ID NO. 182, SEQ ID NO. 183/SEQ ID NO. 184, SEQ ID NO. 185/SEQ ID NO. 186, SEQ ID NO. 187/SEQ ID NO. 188, SEQ ID NO. 189/SEQ ID NO. 190, SEQ ID NO. 191/SEQ ID NO. 192, SEQ ID NO. 193/SEQ ID NO. 194, SEQ ID NO. 195/SEQ ID NO. 196, SEQ ID NO. 197/SEQ ID NO. 198, SEQ ID NO. 199/SEQ ID NO. 200, SEQ ID NO. 201/SEQ ID NO. 202, SEQ ID NO. 203/SEQ ID NO. 204, SEQ ID NO. 205/SEQ ID NO. 206, SEQ ID NO. 207/SEQ ID NO. 208, SEQ ID NO. 209/SEQ ID NO. 210, SEQ ID NO. 211/SEQ ID NO. 212, SEQ ID NO. 213/SEQ ID NO. 214, SEQ ID NO. 215/SEQ ID NO. 216, SEQ ID NO. 217/SEQ ID NO. 218, SEQ ID NO. 219/SEQ ID NO. 220, SEQ ID NO. 221/SEQ ID NO. 222, SEQ ID NO. 223/SEQ ID NO. 224, SEQ ID NO. 225/SEQ ID NO. 226, SEQ ID NO. 227/SEQ ID NO. 228, SEQ ID NO. 229/SEQ ID NO. 230, SEQ ID NO. 231/SEQ ID NO. 232, SEQ ID NO. 233/SEQ ID NO. 234, SEQ ID NO. 235/SEQ ID NO. 236, SEQ ID NO. 237/SEQ ID NO. 238, SEQ ID NO. 239/SEQ ID NO. 240, SEQ ID NO. 241/SEQ ID NO. 242, and combinations thereof. Preferably, the fully human antibody Fab fragment has both a heavy chain variable domain region and a light chain variable domain region wherein the antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO. 54, SEQ ID NO. 55/SEQ ID NO. 56, SEQ ID NO. 57/SEQ ID NO. 58, SEQ ID NO. 59/SEQ ID NO. 60, SEQ ID NO. 61/SEQ ID NO. 62, SEQ ID NO. 63/SEQ ID NO. 64, SEQ ID NO. 65/SEQ ID NO. 66, SEQ ID NO. 67/SEQ ID NO. 68, SEQ ID NO. 69/SEQ ID NO. 70, SEQ ID NO. 71/SEQ ID NO. 72, SEQ ID NO. 73/SEQ ID NO. 74, SEQ ID NO. 75/SEQ ID NO. 76, SEQ ID NO. 77/SEQ ID NO. 78, SEQ ID NO. 79/SEQ ID NO. 80, SEQ ID NO. 81/SEQ ID NO. 82, SEQ ID NO. 83/SEQ ID NO. 84, SEQ ID NO. 85/SEQ ID NO. 86, SEQ ID NO. 87/SEQ ID NO. 88, SEQ ID NO. 89/SEQ ID NO. 90, SEQ ID NO. 91/SEQ ID NO. 92, SEQ ID NO. 93/SEQ ID NO. 94, SEQ ID NO. 95/SEQ ID NO. 96, SEQ ID NO. 97/SEQ ID NO. 98, SEQ ID NO. 99/SEQ ID NO. 100, SEQ ID NO. 101/SEQ ID NO. 102, SEQ ID NO. 103/SEQ ID NO. 104, SEQ ID NO. 105/SEQ ID NO. 106, SEQ ID NO. 107/SEQ ID NO. 108, SEQ ID NO. 109/SEQ ID NO. 110, SEQ ID NO. 111/SEQ ID NO. 112, SEQ ID NO. 113/SEQ ID NO. 114, SEQ ID NO. 115/SEQ ID NO. 116, SEQ ID NO. 117/SEQ ID NO. 118, SEQ ID NO. 119/SEQ ID NO. 120, SEQ ID NO. 121/SEQ ID NO. 122, SEQ ID NO. 123/SEQ ID NO. 124, SEQ ID NO. 125/SEQ ID NO. 126, SEQ ID NO. 127/SEQ ID NO. 128, SEQ ID NO. 129/SEQ ID NO. 130, SEQ ID NO. 131/SEQ ID NO. 132, SEQ ID NO. 133/SEQ ID NO. 134, SEQ ID NO. 135/SEQ ID NO. 136, SEQ ID NO. 137/SEQ ID NO. 138, SEQ ID NO. 139/SEQ ID NO. 140, SEQ ID NO. 141/SEQ ID NO. 142, SEQ ID NO. 143/SEQ ID NO. 144, SEQ ID NO. 145/SEQ ID NO. 146, SEQ ID NO. 147/SEQ ID NO. 148, SEQ ID NO. 149/SEQ ID NO. 150, SEQ ID NO. 151/SEQ ID NO. 152, SEQ ID NO. 153/SEQ ID NO. 154, SEQ ID NO. 155/SEQ ID NO. 156, SEQ ID NO. 157/SEQ ID NO. 158, SEQ ID NO. 159/SEQ ID NO. 160, SEQ ID NO. 161/SEQ ID NO. 162, SEQ ID NO. 163/SEQ ID NO. 164, SEQ ID NO. 165/SEQ ID NO. 166, SEQ ID NO. 167/SEQ ID NO. 168, SEQ ID NO. 169/SEQ ID NO. 170, SEQ ID NO. 171/SEQ ID NO. 172, SEQ ID NO. 173/SEQ ID NO. 174, SEQ ID NO. 175/SEQ ID NO. 176, SEQ ID NO. 177/SEQ ID NO. 178, SEQ ID NO. 179/SEQ ID NO. 180, SEQ ID NO. 181/SEQ ID NO. 182, SEQ ID NO. 183/SEQ ID NO. 184, SEQ ID NO. 185/SEQ ID NO. 186, SEQ ID NO. 187/SEQ ID NO. 188, SEQ ID NO. 189/SEQ ID NO. 190, SEQ ID NO. 191/SEQ ID NO. 192, SEQ ID NO. 193/SEQ ID NO. 194, SEQ ID NO. 195/SEQ ID NO. 196, SEQ ID NO. 197/SEQ ID NO. 198, SEQ ID NO. 199/SEQ ID NO. 200, SEQ ID NO. 201/SEQ ID NO. 202, SEQ ID NO. 203/SEQ ID NO. 204, SEQ ID NO. 205/SEQ ID NO. 206, SEQ ID NO. 207/SEQ ID NO. 208, SEQ ID NO. 209/SEQ ID NO. 210, SEQ ID NO. 211/SEQ ID NO. 212, SEQ ID NO. 213/SEQ ID NO. 214, SEQ ID NO. 215/SEQ ID NO. 216, SEQ ID NO. 217/SEQ ID NO. 218, SEQ ID NO. 219/SEQ ID NO. 220, SEQ ID NO. 221/SEQ ID NO. 222, SEQ ID NO. 223/SEQ ID NO. 224, SEQ ID NO. 225/SEQ ID NO. 226, SEQ ID NO. 227/SEQ ID NO. 228, SEQ ID NO. 229/SEQ ID NO. 230, SEQ ID NO. 231/SEQ ID NO. 232, SEQ ID NO. 233/SEQ ID NO. 234, SEQ ID NO. 235/SEQ ID NO. 236, SEQ ID NO. 237/SEQ ID NO. 238, SEQ ID NO. 239/SEQ ID NO. 240, SEQ ID NO. 241/SEQ ID NO. 242, and combinations thereof. Preferably, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO. 54, SEQ ID NO. 55/SEQ ID NO. 56, SEQ ID NO. 57/SEQ ID NO. 58, SEQ ID NO. 59/SEQ ID NO. 60, SEQ ID NO. 61/SEQ ID NO. 62, SEQ ID NO. 63/SEQ ID NO. 64, SEQ ID NO. 65/SEQ ID NO. 66, SEQ ID NO. 67/SEQ ID NO. 68, SEQ ID NO. 69/SEQ ID NO. 70, SEQ ID NO. 71/SEQ ID NO. 72, SEQ ID NO. 73/SEQ ID NO. 74, SEQ ID NO. 75/SEQ ID NO. 76, SEQ ID NO. 77/SEQ ID NO. 78, SEQ ID NO. 79/SEQ ID NO. 80, SEQ ID NO. 81/SEQ ID NO. 82, SEQ ID NO. 83/SEQ ID NO. 84, SEQ ID NO. 85/SEQ ID NO. 86, SEQ ID NO. 87/SEQ ID NO. 88, SEQ ID NO. 89/SEQ ID NO. 90, SEQ ID NO. 91/SEQ ID NO. 92, SEQ ID NO. 93/SEQ ID NO. 94, SEQ ID NO. 95/SEQ ID NO. 96, SEQ ID NO. 97/SEQ ID NO. 98, SEQ ID NO. 99/SEQ ID NO. 100, SEQ ID NO. 101/SEQ ID NO. 102, SEQ ID NO. 103/SEQ ID NO. 104, SEQ ID NO. 105/SEQ ID NO. 106, SEQ ID NO. 107/SEQ ID NO. 108, SEQ ID NO. 109/SEQ ID NO. 110, SEQ ID NO. 111/SEQ ID NO. 112, SEQ ID NO. 113/SEQ ID NO. 114, SEQ ID NO. 115/SEQ ID NO. 116, SEQ ID NO. 117/SEQ ID NO. 118, SEQ ID NO. 119/SEQ ID NO. 120, SEQ ID NO. 121/SEQ ID NO. 122, SEQ ID NO. 123/SEQ ID NO. 124, SEQ ID NO. 125/SEQ ID NO. 126, SEQ ID NO. 127/SEQ ID NO. 128, SEQ ID NO. 129/SEQ ID NO. 130, SEQ ID NO. 131/SEQ ID NO. 132, SEQ ID NO. 133/SEQ ID NO. 134, SEQ ID NO. 135/SEQ ID NO. 136, SEQ ID NO. 137/SEQ ID NO. 138, SEQ ID NO. 139/SEQ ID NO. 140, SEQ ID NO. 141/SEQ ID NO. 142, SEQ ID NO. 143/SEQ ID NO. 144, SEQ ID NO. 145/SEQ ID NO. 146, SEQ ID NO. 147/SEQ ID NO. 148, SEQ ID NO. 149/SEQ ID NO. 150, SEQ ID NO. 151/SEQ ID NO. 152, SEQ ID NO. 153/SEQ ID NO. 154, SEQ ID NO. 155/SEQ ID NO. 156, SEQ ID NO. 157/SEQ ID NO. 158, SEQ ID NO. 159/SEQ ID NO. 160, SEQ ID NO. 161/SEQ ID NO. 162, SEQ ID NO. 163/SEQ ID NO. 164, SEQ ID NO. 165/SEQ ID NO. 166, SEQ ID NO. 167/SEQ ID NO. 168, SEQ ID NO. 169/SEQ ID NO. 170, SEQ ID NO. 171/SEQ ID NO. 172, SEQ ID NO. 173/SEQ ID NO. 174, SEQ ID NO. 175/SEQ ID NO. 176, SEQ ID NO. 177/SEQ ID NO. 178, SEQ ID NO. 179/SEQ ID NO. 180, SEQ ID NO. 181/SEQ ID NO. 182, SEQ ID NO. 183/SEQ ID NO. 184, SEQ ID NO. 185/SEQ ID NO. 186, SEQ ID NO. 187/SEQ ID NO. 188, SEQ ID NO. 189/SEQ ID NO. 190, SEQ ID NO. 191/SEQ ID NO. 192, SEQ ID NO. 193/SEQ ID NO. 194, SEQ ID NO. 195/SEQ ID NO. 196, SEQ ID NO. 197/SEQ ID NO. 198, SEQ ID NO. 199/SEQ ID NO. 200, SEQ ID NO. 201/SEQ ID NO. 202, SEQ ID NO. 203/SEQ ID NO. 204, SEQ ID NO. 205/SEQ ID NO. 206, SEQ ID NO. 207/SEQ ID NO. 208, SEQ ID NO. 209/SEQ ID NO. 210, SEQ ID NO. 211/SEQ ID NO. 212, SEQ ID NO. 213/SEQ ID NO. 214, SEQ ID NO. 215/SEQ ID NO. 216, SEQ ID NO. 217/SEQ ID NO. 218, SEQ ID NO. 219/SEQ ID NO. 220, SEQ ID NO. 221/SEQ ID NO. 222, SEQ ID NO. 223/SEQ ID NO. 224, SEQ ID NO. 225/SEQ ID NO. 226, SEQ ID NO. 227/SEQ ID NO. 228, SEQ ID NO. 229/SEQ ID NO. 230, SEQ ID NO. 231/SEQ ID NO. 232, SEQ ID NO. 233/SEQ ID NO. 234, SEQ ID NO. 235/SEQ ID NO. 236, SEQ ID NO. 237/SEQ ID NO. 238, SEQ ID NO. 239/SEQ ID NO. 240, SEQ ID NO. 241/SEQ ID NO. 242, and combinations thereof.

Preferably, the broad spectrum of mammalian cancers to be treated is selected from the group consisting of ovarian, colon, breast, lung cancers, myelomas, neuroblastic-derived CNS tumors, monocytic leukemias, B-cell derived leukemias, T-cell derived leukemias, B-cell derived lymphomas, T-cell derived lymphomas, mast cell derived tumors, and combinations thereof. Preferably, the autoimmune disease or inflammatory disease is selected from the group consisting of intestinal mucosal inflammation, wasting disease associated with colitis, multiple sclerosis, systemic lupus erythematosus, viral infections, rheumatoid arthritis, osteoarthritis, psoriasis, Cohn's disease, and inflammatory bowel disease.

An "antigen binding protein" is a protein comprising a portion that binds to an antigen and, optionally, a scaffold or framework portion that allows the antigen binding portion to adopt a conformation that promotes binding of the antigen binding protein to the antigen. Examples of antigen binding proteins include antibodies, antibody fragments (e.g., an antigen binding portion of an antibody), antibody derivatives, and antibody analogs. The antigen binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the antigen binding protein as well as wholly synthetic scaffolds comprising, for example, a biocompatible polymer. See, for example, Korndorfer et al., 2003, *Proteins: Structure, Function, and Bioinformatics, Volume* 53, Issue 1:121-129; Roque et al., 2004, *Biotechnol. Prog.* 20:639-654. In addition, peptide antibody mimetics ("PAMs") can be used, as well as scaffolds based on antibody mimetics utilizing fibronection components as a scaffold.

An antigen binding protein can have, for example, the structure of a naturally occurring immunoglobulin. An "immunoglobulin" is a tetrameric molecule. In a naturally occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa or lambda light chains. Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)) (incorporated by reference in its entirety for all purposes). The variable regions of each light/heavy chain pair form the antibody binding site such that an intact immunoglobulin has two binding sites.

The variable regions of naturally occurring immunoglobulin chains exhibit the same general structure of relatively conserved framework regions (FR) joined by three hypervariable regions, also called complementarity determining regions or CDRs. From N-terminus to C-terminus, both light and heavy chains comprise the domains FR1, CDR1, FR2, CDR2, FR3, CDR3 and FR4. The assignment of amino acids to each domain is in accordance with the definitions of Kabat et al. in Sequences of Proteins of Immunological Interest, 5$^{th}$ Ed., US Dept. of Health and Human Services, PHS, NIH, NIH Publication no. 91-3242, 1991. Other numbering systems for the amino acids in immunoglobulin chains include IMGT®. (international ImMunoGeneTics information system; Lefranc et al, *Dev. Comp. Immunol.* 29:185-203; 2005) and AHo (Honegger and Pluckthun, *J. Mol. Biol.* 309(3):657-670; 2001).

Antibodies can be obtained from sources such as serum or plasma that contain immunoglobulins having varied antigenic specificity. If such antibodies are subjected to affinity purification, they can be enriched for a particular antigenic specificity. Such enriched preparations of antibodies usually are made of less than about 10% antibody having specific binding activity for the particular antigen. Subjecting these preparations to several rounds of affinity purification can increase the proportion of antibody having specific binding activity for the antigen. Antibodies prepared in this manner are often referred to as "monospecific." Monospecfic antibody preparations can be made up of about 10%, 20%, 30%, 40%, 50%, 60%, 70%, 75%, 80%, 85%, 90%, 95%, 97%, 99%, or 99.9% antibody having specific binding activity for the particular antigen.

An "antibody" refers to an intact immunoglobulin or to an antigen binding portion thereof that competes with the intact antibody for specific binding, unless otherwise specified. Antigen binding portions may be produced by recombinant DNA techniques or by enzymatic or chemical cleavage of intact antibodies. Antigen binding portions include, inter alia, Fab, Fab', F(ab')$_2$, Fv, domain antibodies (dAbs), and complementarity determining region (CDR) fragments, single-chain antibodies (scFv), chimeric antibodies, diabodies, triabodies, tetrabodies, and polypeptides that contain at least a portion of an immunoglobulin that is sufficient to confer specific antigen binding to the polypeptide.

A Fab fragment is a monovalent fragment having the $V_L$, $V_H$, $C_L$ and $C_{H1}$ domains; a F(ab')$_2$ fragment is a bivalent fragment having two Fab fragments linked by a disulfide bridge at the hinge region; a Fd fragment has the $V_H$ and $C_{H1}$ domains; an Fv fragment has the $V_L$ and $V_H$ domains of a single arm of an antibody; and a dAb fragment has a $V_H$ domain, a $V_L$ domain, or an antigen-binding fragment of a $V_H$ or VL domain (U.S. Pat. Nos. 6,846,634; 6,696,245, US App. Pub.20/0202512; 2004/0202995; 2004/0038291; 2004/0009507; 2003/0039958, and Ward et al., *Nature* 341:544-546, 1989).

A single-chain antibody (scFv) is an antibody in which a $V_L$ and a $V_H$ region are joined via a linker (e.g., a synthetic sequence of amino acid residues) to form a continuous protein chain wherein the linker is long enough to allow the protein chain to fold back on itself and form a monovalent antigen binding site (see, e.g., Bird et al., 1988, *Science* 242:423-26 and Huston et al., 1988, *Proc. Natl. Acad. Sci. USA* 85:5879-83). Diabodies are bivalent antibodies comprising two polypeptide chains, wherein each polypeptide chain comprises $V_H$ and $V_L$ domains joined by a linker that is too short to allow for pairing between two domains on the same chain, thus allowing each domain to pair with a complementary domain on another polypeptide chain (see, e.g., Holliger et al., 1993, *Proc. Natl. Acad. Sci. USA* 90:6444-48, and Poljak et al., 1994, *Structure* 2:1121-23). If the two polypeptide chains of a diabody are identical, then a diabody resulting from their pairing will have two identical antigen binding sites. Polypeptide chains having different sequences can be used to make a diabody with two different antigen binding sites. Similarly, tribodies and tetrabodies are antibodies comprising three and four polypeptide chains, respectively, and forming three and four antigen binding sites, respectively, which can be the same or different.

Complementarity determining regions (CDRs) and framework regions (FR) of a given antibody may be identified using the system described by Kabat et al. supra; Lefranc et al., supra and/or Honegger and Pluckthun, supra. One or more CDRs may be incorporated into a molecule either covalently or noncovalently to make it an antigen binding protein. An antigen binding protein may incorporate the CDR(s) as part of a larger polypeptide chain, may covalently link the CDR(s) to another polypeptide chain, or may incorporate the CDR(s) noncovalently. The CDRs permit the antigen binding protein to specifically bind to a particular antigen of interest.

An antigen binding protein may have one or more binding sites. If there is more than one binding site, the binding sites may be identical to one another or may be different. For example, a naturally occurring human immunoglobulin typically has two identical binding sites, while a "bispecific" or "bifunctional" antibody has two different binding sites.

The term "human antibody" includes all antibodies that have one or more variable and constant regions derived from human immunoglobulin sequences. In one embodiment, all of the variable and constant domains are derived from human immunoglobulin sequences (a fully human antibody). These antibodies may be prepared in a variety of ways, examples of which are described below, including through the immunization with an antigen of interest of a mouse that is genetically modified to express antibodies derived from human heavy and/or light chain-encoding genes.

A humanized antibody has a sequence that differs from the sequence of an antibody derived from a non-human species by one or more amino acid substitutions, deletions, and/or additions, such that the humanized antibody is less likely to induce an immune response, and/or induces a less severe immune response, as compared to the non-human species antibody, when it is administered to a human subject. In one embodiment, certain amino acids in the framework and constant domains of the heavy and/or light chains of the non-human species antibody are mutated to produce the humanized antibody. In another embodiment, the constant domain(s) from a human antibody are fused to the variable domain(s) of a non-human species. In another embodiment, one or more amino acid residues in one or more CDR sequences of a non-human antibody are changed to reduce the likely immunogenicity of the non-human antibody when it is administered to a human subject, wherein the changed amino acid residues either are not critical for immunospecific binding of the antibody to its antigen, or the changes to the amino acid sequence that are made are conservative changes, such that the binding of the humanized antibody to the antigen is not significantly worse than the binding of the non-human antibody to the antigen. Examples of how to make humanized antibodies may be found in U.S. Pat. Nos. 6,054,297, 5,886,152 and 5,877,293.

The term "chimeric antibody" refers to an antibody that contains one or more regions from one antibody and one or more regions from one or more other antibodies. In one embodiment, one or more of the CDRs are derived from a human anti-PD-L1 antibody. In another embodiment, all of the CDRs are derived from a human anti-PD-L1 antibody. In another embodiment, the CDRs from more than one human anti-PD-L1 antibodies are mixed and matched in a chimeric antibody. For instance, a chimeric antibody may comprise a CDR1 from the light chain of a first human anti-PAR-2 antibody, a CDR2 and a CDR3 from the light chain of a second human anti-PD-L1 antibody, and the CDRs from the heavy chain from a third anti-PD-L1 antibody. Other combinations are possible.

Further, the framework regions may be derived from one of the same anti-PD-L1 antibodies, from one or more different antibodies, such as a human antibody, or from a humanized antibody. In one example of a chimeric antibody, a portion of the heavy and/or light chain is identical with, homologous to, or derived from an antibody from a particular species or belonging to a particular antibody class or subclass, while the remainder of the chain(s) is/are identical with, homologous to, or derived from an antibody (-ies) from another species or belonging to another antibody class or subclass. Also included are fragments of such antibodies that exhibit the desired biological activity (i.e., the ability to specifically bind PD-L1).

A "neutralizing antibody" or an "inhibitory antibody" is an antibody that inhibits the proteolytic activation of PD-L1 when an excess of the anti-PD-L1 antibody reduces the amount of activation by at least about 20% using an assay such as those described herein in the Examples. In various embodiments, the antigen binding protein reduces the amount of amount of proteolytic activation of PD-L1 by at least 30%, 40%, 50%, 60%, 70%, 75%, 80%, 85%, 90%, 95%, 97%, 99%, and 99.9%.

Fragments or analogs of antibodies can be readily prepared by those of ordinary skill in the art following the teachings of this specification and using techniques known in the art. Preferred amino- and carboxy-termini of fragments or analogs occur near boundaries of functional domains. Structural and functional domains can be identified by comparison of the nucleotide and/or amino acid sequence data to public or proprietary sequence databases. Computerized comparison methods can be used to identify sequence motifs or predicted protein conformation domains that occur in other proteins of known structure and/or function. Methods to identify protein sequences that fold into a known three-dimensional structure are known. See, Bowie et al., 1991, *Science* 253:164.

A "CDR grafted antibody" is an antibody comprising one or more CDRs derived from an antibody of a particular species or isotype and the framework of another antibody of the same or different species or isotype.

A "multi-specific antibody" is an antibody that recognizes more than one epitope on one or more antigens. A subclass of this type of antibody is a "bi-specific antibody" which recognizes two distinct epitopes on the same or different antigens.

An antigen binding protein "specifically binds" to an antigen (e.g., human PD-L1) if it binds to the antigen with a dissociation constant of 1 nanomolar or less.

An "antigen binding domain," "antigen binding region," or "antigen binding site" is a portion of an antigen binding protein that contains amino acid residues (or other moieties) that interact with an antigen and contribute to the antigen binding protein's specificity and affinity for the antigen. For an antibody that specifically binds to its antigen, this will include at least part of at least one of its CDR domains.

An "epitope" is the portion of a molecule that is bound by an antigen binding protein (e.g., by an antibody). An epitope can comprise non-contiguous portions of the molecule (e.g., in a polypeptide, amino acid residues that are not contiguous in the polypeptide's primary sequence but that, in the context of the polypeptide's tertiary and quaternary structure, are near enough to each other to be bound by an antigen binding protein).

The "percent identity" of two polynucleotide or two polypeptide sequences is determined by comparing the sequences using the GAP computer program (a part of the GCG Wisconsin Package, version 10.3 (Accelrys, San Diego, Calif.)) using its default parameters.

The terms "polynucleotide," "oligonucleotide" and "nucleic acid" are used interchangeably throughout and include DNA molecules (e.g., cDNA or genomic DNA), RNA molecules (e.g., mRNA), analogs of the DNA or RNA generated using nucleotide analogs (e.g., peptide nucleic acids and non-naturally occurring nucleotide analogs), and hybrids thereof. The nucleic acid molecule can be single-stranded or double-stranded. In one embodiment, the nucleic acid molecules of the invention comprise a contiguous open reading frame encoding an antibody, or a fragment, derivative, mutein, or variant thereof.

Two single-stranded polynucleotides are "the complement" of each other if their sequences can be aligned in an anti-parallel orientation such that every nucleotide in one polynucleotide is opposite its complementary nucleotide in the other polynucleotide, without the introduction of gaps, and without unpaired nucleotides at the 5' or the 3' end of either sequence. A polynucleotide is "complementary" to another polynucleotide if the two polynucleotides can hybridize to one another under moderately stringent conditions. Thus, a polynucleotide can be complementary to another polynucleotide without being its complement.

A "vector" is a nucleic acid that can be used to introduce another nucleic acid linked to it into a cell. One type of vector is a "plasmid," which refers to a linear or circular double stranded DNA molecule into which additional nucleic acid segments can be ligated. Another type of vector is a viral vector (e.g., replication defective retroviruses, adenoviruses and adeno-associated viruses), wherein additional DNA segments can be introduced into the viral genome. Certain vectors are capable of autonomous replication in a host cell into which they are introduced (e.g., bacterial vectors comprising a bacterial origin of replication and episomal mammalian vectors). Other vectors (e.g., non-episomal mammalian vectors) are integrated into the genome of a host cell upon introduction into the host cell, and thereby are replicated along with the host genome. An "expression vector" is a type of vector that can direct the expression of a chosen polynucleotide.

A nucleotide sequence is "operably linked" to a regulatory sequence if the regulatory sequence affects the expression (e.g., the level, timing, or location of expression) of the nucleotide sequence. A "regulatory sequence" is a nucleic acid that affects the expression (e.g., the level, timing, or location of expression) of a nucleic acid to which it is operably linked. The regulatory sequence can, for example, exert its effects directly on the regulated nucleic acid, or through the action of one or more other molecules (e.g., polypeptides that bind to the regulatory sequence and/or the nucleic acid). Examples of regulatory sequences include promoters, enhancers and other expression control elements (e.g., polyadenylation signals). Further examples of regulatory sequences are described in, for example, Goeddel, 1990, *Gene Expression Technology: Methods in Enzymology* 185, Academic Press, San Diego, Calif. and Baron et al., 1995, *Nucleic Acids Res.* 23:3605-06.

A "host cell" is a cell that can be used to express a nucleic acid, e.g., a nucleic acid of the invention. A host cell can be a prokaryote, for example, *E. coli*, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Examples of host cells include the COS-7 line of monkey kidney cells (ATCC CRL 1651) (see Gluzman et al., 1981, *Cell* 23:175), L cells, C127 cells, 3T3 cells (ATCC CCL 163), Chinese hamster ovary (CHO) cells or their derivatives such as Veggie CHO and related cell lines which grow in serum-free media (see Rasmussen et al., 1998, *Cytotechnology* 28:31) or CHO strain DX-B11, which is deficient in DHFR (see Urlaub et al., 1980, *Proc. Natl. Acad. Sci. USA* 77:4216-20), HeLa cells, BHK (ATCC CRL 10) cell lines, the CV1/EBNA cell line derived from the African green monkey kidney cell line CV1 (ATCC CCL 70) (see McMahan et al., 1991, *EMBO J.* 10:2821), human embryonic kidney cells such as 293,293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Typically, a host cell is a cultured cell that can be transformed or transfected with a polypeptide-encoding nucleic acid, which can then be expressed in the host cell. The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but also to the progeny or potential progeny of such a cell. Because certain modifications may occur in succeeding generations due to, e.g., mutation or environmental influence, such progeny may not, in fact, be identical to the parent cell, but are still included within the scope of the term as used herein.

Preferably, the mammalian cancer to be treated is selected from the group consisting of ovarian, colon, breast or hepatic carcinoma cell lines, myelomas, neuroblastic-derived CNS tumors, monocytic leukemias, B-cell derived leukemia's, T-cell derived leukemias, B-cell derived lymphomas, T-cell derived lymphomas, mast cell derived tumors, and combinations thereof.

Polypeptides of the present disclosure can be produced using any standard methods known in the art. In one example, the polypeptides are produced by recombinant DNA methods by inserting a nucleic acid sequence (e.g., a cDNA) encoding the polypeptide into a recombinant expression vector and expressing the DNA sequence under conditions promoting expression.

Nucleic acids encoding any of the various polypeptides disclosed herein may be synthesized chemically. Codon usage may be selected so as to improve expression in a cell. Such codon usage will depend on the cell type selected. Specialized codon usage patterns have been developed for *E. coli* and other bacteria, as well as mammalian cells, plant cells, yeast cells and insect cells. See for example: Mayfield et al., *Proc. Natl. Acad. Sci. USA*. 2003 100(2):438-42; Sinclair et al. *Protein Expr. Purif.* 2002 (1):96-105; Connell N D. *Curr. Opin. Biotechnol.* 2001 12(5):446-9; Makrides et al. *Microbiol. Rev.* 1996 60(3):512-38; and Sharp et al. *Yeast.* 1991 7(7):657-78.

General techniques for nucleic acid manipulation are described for example in Sambrook et al., *Molecular Cloning: A Laboratory Manual*, Vols. 1-3, Cold Spring Harbor Laboratory Press, 2 ed., 1989, or F. Ausubel et al., *Current Protocols in Molecular Biology* (Green Publishing and Wiley-Interscience: New York, 1987) and periodic updates, herein incorporated by reference. The DNA encoding the polypeptide is operably linked to suitable transcriptional or translational regulatory elements derived from mammalian, viral, or insect genes. Such regulatory elements include a transcriptional promoter, an optional operator sequence to control transcription, a sequence encoding suitable mRNA ribosomal binding sites, and sequences that control the termination of transcription and translation. The ability to replicate in a host, usually conferred by an origin of replication, and a selection gene to facilitate recognition of transformants is additionally incorporated.

The recombinant DNA can also include any type of protein tag sequence that may be useful for purifying the protein. Examples of protein tags include but are not limited to a histidine tag, a FLAG tag, a myc tag, an HA tag, or a GST tag. Appropriate cloning and expression vectors for use with bacterial, fungal, yeast, and mammalian cellular hosts can be found in *Cloning Vectors: A Laboratory Manual*, (Elsevier, N.Y., 1985).

The expression construct is introduced into the host cell using a method appropriate to the host cell. A variety of methods for introducing nucleic acids into host cells are known in the art, including, but not limited to, electroporation; transfection employing calcium chloride, rubidium chloride, calcium phosphate, DEAE-dextran, or other substances; microprojectile bombardment; lipofection; and infection (where the vector is an infectious agent). Suitable host cells include prokaryotes, yeast, mammalian cells, or bacterial cells.

Suitable bacteria include gram negative or gram positive organisms, for example, *E. coli* or *Bacillus* spp. Yeast, preferably from the *Saccharomyces* species, such as *S. cerevisiae*, may also be used for production of polypeptides. Various mammalian or insect cell culture systems can also be employed to express recombinant proteins. Baculovirus systems for production of heterologous proteins in insect cells are reviewed by Luckow and Summers, (*Bio/Technology*, 6:47, 1988). Examples of suitable mammalian host cell lines include endothelial cells, COS-7 monkey kidney cells, CV-1, L cells, C127, 3T3, Chinese hamster ovary (CHO), human embryonic kidney cells, HeLa, 293, 293T, and BHK cell lines. Purified polypeptides are prepared by culturing suitable host/vector systems to express the recombinant proteins. For many applications, the small size of many of the polypeptides disclosed herein would make expression in *E. coli* as the preferred method for expression. The protein is then purified from culture media or cell extracts.

Proteins disclosed herein can also be produced using cell-translation systems. For such purposes the nucleic acids encoding the polypeptide must be modified to allow in vitro transcription to produce mRNA and to allow cell-free translation of the mRNA in the particular cell-free system being utilized (eukaryotic such as a mammalian or yeast cell-free translation system or prokaryotic such as a bacterial cell-free translation system.

PD-L1-binding polypeptides can also be produced by chemical synthesis (e.g., by the methods described in Solid Phase Peptide Synthesis, 2nd ed., 1984, The Pierce Chemical Co., Rockford, Ill.). Modifications to the protein can also be produced by chemical synthesis.

The polypeptides of the present disclosure can be purified by isolation/purification methods for proteins generally known in the field of protein chemistry. Non-limiting examples include extraction, recrystallization, salting out (e.g., with ammonium sulfate or sodium sulfate), centrifugation, dialysis, ultrafiltration, adsorption chromatography, ion exchange chromatography, hydrophobic chromatography, normal phase chromatography, reversed-phase chromatography, gel filtration, gel permeation chromatography, affinity chromatography, electrophoresis, countercurrent distribution or any combinations of these. After purification, polypeptides may be exchanged into different buffers and/or concentrated by any of a variety of methods known to the art, including, but not limited to, filtration and dialysis.

The purified polypeptide is preferably at least 85% pure, more preferably at least 95% pure, and most preferably at least 98% pure. Regardless of the exact numerical value of the purity, the polypeptide is sufficiently pure for use as a pharmaceutical product.

Post-Translational Modifications of Polypeptides

In certain embodiments, the binding polypeptides of the invention may further comprise post-translational modifications. Exemplary post-translational protein modifications include phosphorylation, acetylation, methylation, ADP-ribosylation, ubiquitination, glycosylation, carbonylation, sumoylation, biotinylation or addition of a polypeptide side chain or of a hydrophobic group. As a result, the modified soluble polypeptides may contain non-amino acid elements, such as lipids, poly- or mono-saccharide, and phosphates. A preferred form of glycosylation is sialylation, which conjugates one or more sialic acid moieties to the polypeptide. Sialic acid moieties improve solubility and serum half-life while also reducing the possible immunogeneticity of the protein. See Raju et al. *Biochemistry*. 2001 31; 40(30):8868-76. Effects of such non-amino acid elements on the functionality of a polypeptide may be tested for its antagonizing role in PD-L1 or PD-1 function, e.g., its inhibitory effect on angiogenesis or on tumor growth.

In one specific embodiment, modified forms of the subject soluble polypeptides comprise linking the subject soluble polypeptides to nonproteinaceous polymers. In one specific embodiment, the polymer is polyethylene glycol ("PEG"), polypropylene glycol, or polyoxyalkylenes, in the manner as set forth in U.S. Pat. Nos. 4,640,835; 4,496,689; 4,301,144; 4,670,417; 4,791,192 or 4,179,337.

PEG is a water soluble polymer that is commercially available or can be prepared by ring-opening polymerization of ethylene glycol according to methods well known in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented by the formula: $X\text{—}O(CH_2CH_2O)_n\text{-}1CH_2CH_2OH$ (1), where n is 20 to 2300 and X is H or a terminal modification, e.g., a $C_{1-4}$ alkyl. In one embodiment, the PEG of the invention terminates on one end with hydroxy or methoxy, i.e., X is H or $CH_3$ ("methoxy PEG"). A PEG can contain further chemical groups which are necessary for binding reactions; which results from the chemical synthesis of the molecule; or which is a spacer for optimal distance of parts of the molecule. In addition, such a PEG can consist of one or more PEG side-chains which are linked together. PEGs with more than one PEG chain are called multiarmed or branched PEGs. Branched PEGs can be prepared, for example, by the addition of polyethylene oxide to various polyols, including glycerol, pentaerythriol, and sorbitol. For example, a four-armed branched PEG can be prepared from pentaerythriol and ethylene oxide. Branched PEG are described in, for example, EP-A 0 473 084 and U.S. Pat. No. 5,932,462. One form of PEGs includes two PEG side-chains (PEG2) linked via the primary amino groups of a lysine (Monfardini et al., *Bioconjugate Chem.* 6 (1995) 62-69).

Although PEG is well-known, this is, to our knowledge, the first demonstration that a pegylated $^{10F}$n3 polypeptide can be pegylated and retain ligand binding activity. In a preferred embodiment, the pegylated $^{10F}$n3 polypeptide is produced by site-directed pegylation, particularly by conjugation of PEG to a cysteine moiety at the N- or C-terminus. Accordingly, the present disclosure provides a target-binding $^{10F}$n3 polypeptide with improved pharmacokinetic properties, the polypeptide comprising: a $^{10F}$n3 domain having from about 80 to about 150 amino acids, wherein at least one of the loops of said $^{10F}$n3 domain participate in target binding; and a covalently bound PEG moiety, wherein said $^{10F}$n3 polypeptide binds to the target with a $K_D$ of less than 100 nM and has a clearance rate of less than 30 mL/hr/kg in a mammal. The PEG moiety may be attached to the $^{10F}$n3 polypeptide by site directed pegylation, such as by attachment to a Cys residue, where the Cys residue may be positioned at the N-terminus of the $^{0F}$n3 polypeptide or between the N-terminus and the most N-terminal beta or beta-like strand or at the C-terminus of the $^{10F}$n3 polypeptide or between the C-terminus and the most C-terminal beta or beta-like strand. A Cys residue may be situated at other positions as well, particularly any of the loops that do not participate in target binding. A PEG moiety may also be attached by other chemistry, including by conjugation to amines.

PEG conjugation to peptides or proteins generally involves the activation of PEG and coupling of the activated PEG-intermediates directly to target proteins/peptides or to a linker, which is subsequently activated and coupled to target proteins/peptides (see Abuchowski et al., *J. Biol. Chem.*, 252, 3571 (1977) and *J. Biol. Chem.*, 252, 3582 (1977), Zalipsky, et al., and Harris et. al., in: *Poly(ethylene glycol) Chemistry: Biotechnical and Biomedical Applications*; (J. M. Harris ed.) Plenum Press: New York, 1992; Chap. 21 and 22). It is noted that a binding polypeptide containing a PEG molecule is also known as a conjugated protein, whereas the protein lacking an attached PEG molecule can be referred to as unconjugated.

A variety of molecular mass forms of PEG can be selected, e.g., from about 1,000 Daltons (Da) to 100,000 Da (n is 20 to 2300), for conjugating to PD-L1-binding polypeptides. The number of repeating units "n" in the PEG is approximated for the molecular mass described in Daltons. It is preferred that the combined molecular mass of PEG on an activated linker is suitable for pharmaceutical use. Thus, in one embodiment, the molecular mass of the PEG molecules does not exceed 100,000 Da. For example, if three PEG molecules are attached to a linker, where each PEG molecule has the same molecular mass of 12,000 Da (each n is about 270), then the total molecular mass of PEG on the linker is about 36,000 Da (total n is about 820). The molecular masses of the PEG attached to the linker can also be different, e.g., of three molecules on a linker two PEG molecules can be 5,000 Da each (each n is about 110) and one PEG molecule can be 12,000 Da (n is about 270).

In a specific embodiment of the disclosure an PD-L1 binding polypeptide is covalently linked to one poly(ethylene glycol) group of the formula: $-CO-(CH_2)_m-(OCH_2CH_2)_m-OR$, with the $-CO$ (i.e. carbonyl) of the poly(ethylene glycol) group forming an amide bond with one of the amino groups of the binding polypeptide; R being lower alkyl; x being 2 or 3; m being from about 450 to about 950; and n and m being chosen so that the molecular weight of the conjugate minus the binding polypeptide is from about 10 to 40 kDa. In one embodiment, a binding polypeptide's ε-amino group of a lysine is the available (free) amino group.

The above conjugates may be more specifically presented by formula (II): $P-NHCO-(CH_2)_x-(OCH_2CH_2)_m-OR$ (II), wherein P is the group of a binding polypeptide as described herein, (i.e. without the amino group or amino groups which form an amide linkage with the carbonyl shown in formula (II); and wherein R is lower alkyl; x is 2 or 3; m is from about 450 to about 950 and is chosen so that the molecular weight of the conjugate minus the binding polypeptide is from about 10 to about 40 kDa. As used herein, the given ranges of "m" have an orientational meaning. The ranges of "m" are determined in any case, and exactly, by the molecular weight of the PEG group.

One skilled in the art can select a suitable molecular mass for PEG, e.g., based on how the pegylated binding polypeptide will be used therapeutically, the desired dosage, circulation time, resistance to proteolysis, immunogenicity, and other considerations. For a discussion of PEG and its use to enhance the properties of proteins, see Katre, *Advanced Drug Delivery Reviews* 10: 91-114 (1993).

In one embodiment, PEG molecules may be activated to react with amino groups on a binding polypeptide, such as with lysines (Bencham et al., *Anal. Biochem.*, 131, 25 (1983); Veronese et al., *Appl. Biochem.*, 11, 141 (1985); Zalipsky et al., *Polymeric Drugs and Drug Delivery Systems*, adrs 9-110 ACS Symposium Series 469 (1999); Zalipsky et al., *Europ. Polym. J.*, 19, 1177-1183 (1983); Delgado et al., *Biotechnology and Applied Biochemistry*, 12, 119-128 (1990)).

In one specific embodiment, carbonate esters of PEG are used to form the PEG-binding polypeptide conjugates. N,N'-disuccinimidylcarbonate (DSC) may be used in the reaction with PEG to form active mixed PEG-succinimidyl carbonate that may be subsequently reacted with a nucleophilic group of a linker or an amino group of a binding polypeptide (see U.S. Pat. Nos. 5,281,698 and 5,932,462). In a similar type of reaction, 1,1'-(dibenzotriazolyl)carbonate and di-(2-pyridyl) carbonate may be reacted with PEG to form PEG-benzotriazolyl and PEG-pyridyl mixed carbonate (U.S. Pat. No. 5,382,657), respectively.

Pegylation of a $^{10F}n3$ polypeptide can be performed according to the methods of the state of the art, for example by reaction of the binding polypeptide with electrophilically active PEGs (supplier: Shearwater Corp., USA, www.shearwatercorp.com). Preferred PEG reagents of the present invention are, e.g., N-hydroxysuccinimidyl propionates (PEG-SPA), butanoates (PEG-SBA), PEG-succinimidyl propionate or branched N-hydroxysuccinimides such as mPEG2-NHS (Monfardini et al., *Bioconjugate Chem.* 6 (1995) 62-69). Such methods may used to pegylated at an f-amino group of a binding polypeptide lysine or the N-terminal amino group of the binding polypeptide.

In another embodiment, PEG molecules may be coupled to sulfhydryl groups on a binding polypeptide (Sartore et al., *Appl. Biochem. Biotechnol.*, 27, 45 (1991); Morpurgo et al., *Biocon. Chem.*, 7, 363-368 (1996); Goodson et al., *Bio/Technology* (1990) 8, 343; U.S. Pat. No. 5,766,897). U.S. Pat. Nos. 6,610,281 and 5,766,897 describes exemplary reactive PEG species that may be coupled to sulfhydryl groups.

In some embodiments where PEG molecules are conjugated to cysteine residues on a binding polypeptide, the cysteine residues are native to the binding polypeptide, whereas in other embodiments, one or more cysteine residues are engineered into the binding polypeptide. Mutations may be introduced into a binding polypeptide coding sequence to generate cysteine residues. This might be achieved, for example, by mutating one or more amino acid residues to cysteine. Preferred amino acids for mutating to a cysteine residue include serine, threonine, alanine and other hydrophilic residues. Preferably, the residue to be mutated to cysteine is a surface-exposed residue. Algorithms are well-known in the art for predicting surface accessibility of residues based on primary sequence or a protein. Alternatively, surface residues may be predicted by comparing the amino acid sequences of binding polypeptides, given that the crystal structure of the framework based on which binding polypeptides are designed and evolved has been solved (see Himanen et al., *Nature*. (2001) 20-27; 414(6866):933-8) and thus the surface-exposed residues identified. In one embodiment, cysteine residues are introduced into binding polypeptides at or near the N- and/or C-terminus, or within loop regions.

In some embodiments, the pegylated binding polypeptide comprises a PEG molecule covalently attached to the alpha amino group of the N-terminal amino acid. Site specific N-terminal reductive amination is described in Pepinsky et al., (2001) *JPET,* 297, 1059, and U.S. Pat. No. 5,824,784. The use of a PEG-aldehyde for the reductive amination of a protein utilizing other available nucleophilic amino groups is described in U.S. Pat. No. 4,002,531, in Wieder et al., (1979) *J. Biol. Chem.* 254, 12579, and in Chamow et al., (1994) *Bioconjugate Chem.* 5, 133.

In another embodiment, pegylated binding polypeptide comprises one or more PEG molecules covalently attached to a linker, which in turn is attached to the alpha amino group of the amino acid residue at the N-terminus of the binding polypeptide. Such an approach is disclosed in U.S. Patent Publication 2002/0044921 and in WO094/01451.

In one embodiment, a binding polypeptide is pegylated at the C-terminus. In a specific embodiment, a protein is pegylated at the C-terminus by the introduction of C-terminal azido-methionine and the subsequent conjugation of a methyl-PEG-triarylphosphine compound via the Staudinger reaction. This C-terminal conjugation method is described in Cazalis et al., *Bioconjug. Chem.* 2004; 15(5):1005-1009.

Monopegylation of a binding polypeptide can also be produced according to the general methods described in WO 94/01451. WO 94/01451 describes a method for preparing a recombinant polypeptide with a modified terminal amino acid alpha-carbon reactive group. The steps of the method involve forming the recombinant polypeptide and protecting it with one or more biologically added protecting groups at the N-terminal alpha-amine and C-terminal alpha-carboxyl. The polypeptide can then be reacted with chemical protecting agents to selectively protect reactive side chain groups and thereby prevent side chain groups from being modified. The polypeptide is then cleaved with a cleavage reagent specific for the biological protecting group to form an unprotected terminal amino acid alpha-carbon reactive group. The unprotected terminal amino acid alpha-carbon reactive group is modified with a chemical modifying agent. The side chain protected terminally modified single copy polypeptide is then deprotected at the side chain groups to form a terminally modified recombinant single copy polypeptide. The number and sequence of steps in the method can be varied to achieve selective modification at the N- and/or C-terminal amino acid of the polypeptide.

The ratio of a binding polypeptide to activated PEG in the conjugation reaction can be from about 1:0.5 to 1:50, between from about 1:1 to 1:30, or from about 1:5 to 1:15. Various aqueous buffers can be used in the present method to catalyze the covalent addition of PEG to the binding polypeptide. In one embodiment, the pH of a buffer used is from about 7.0 to 9.0. In another embodiment, the pH is in a slightly basic range, e.g., from about 7.5 to 8.5. Buffers having a pKa close to neutral pH range may be used, e.g., phosphate buffer.

Conventional separation and purification techniques known in the art can be used to purify PEGylated binding polypeptide, such as size exclusion (e.g. gel filtration) and ion exchange chromatography. Products may also be separated using SDS-PAGE. Products that may be separated include mono-, di-, tri- poly- and un-pegylated binding polypeptide, as well as free PEG. The percentage of mono-PEG conjugates can be controlled by pooling broader fractions around the elution peak to increase the percentage of mono-PEG in the composition. About ninety percent mono-PEG conjugates represents a good balance of yield and activity. Compositions in which, for example, at least ninety-two percent or at least ninety-six percent of the conjugates are mono-PEG species may be desired. In an embodiment of this invention the percentage of mono-PEG conjugates is from ninety percent to ninety-six percent.

In one embodiment, PEGylated binding polypeptide of the invention contain one, two or more PEG moieties. In one embodiment, the PEG moiety(ies) are bound to an amino acid residue which is on the surface of the protein and/or away from the surface that contacts the target ligand. In one embodiment, the combined or total molecular mass of PEG in PEG-binding polypeptide is from about 3,000 Da to 60,000 Da, optionally from about 10,000 Da to 36,000 Da. In a one embodiment, the PEG in pegylated binding polypeptide is a substantially linear, straight-chain PEG.

In one embodiment of the invention, the PEG in pegylated binding polypeptide is not hydrolyzed from the pegylated amino acid residue using a hydroxylamine assay, e.g., 450 mM hydroxylamine (pH 6.5) over 8 to 16 hours at room temperature, and is thus stable. In one embodiment, greater than 80% of the composition is stable mono-PEG-binding polypeptide, more preferably at least 90%, and most preferably at least 95%.

In another embodiment, the pegylated binding polypeptides of the invention will preferably retain at least 25%, 50%, 60%, 70%, 80%, 85%, 90%, 95% or 100% of the biological activity associated with the unmodified protein. In one embodiment, biological activity refers to its ability to bind to PD-L1, as assessed by KD, $k_{on}$ or $k_{off}$. In one specific embodiment, the pegylated binding polypeptide protein shows an increase in binding to PD-L1 relative to unpegylated binding polypeptide.

The serum clearance rate of PEG-modified polypeptide may be decreased by about 10%, 20%, 30%, 40%, 50%, 60%, 70%, 80%, or even 90%, relative to the clearance rate of the unmodified binding polypeptide. The PEG-modified polypeptide may have a half-life ($t_{1/2}$) which is enhanced relative to the half-life of the unmodified protein. The half-life of PEG-binding polypeptide may be enhanced by at least 10%, 20%, 30%, 40%, 50%, 60%, 70%, 80%, 90%, 100%, 125%, 150%, 175%, 200%, 250%, 300%, 400% or 500%, or even by 1000% relative to the half-life of the unmodified binding polypeptide. In some embodiments, the protein half-life is determined in vitro, such as in a buffered saline solution or in serum. In other embodiments, the protein half-life is an in vivo half life, such as the half-life of the protein in the serum or other bodily fluid of an animal.

Therapeutic Formulations and Modes of Administration

The present disclosure features methods for treating conditions or preventing pre-conditions which respond to an inhibition of PD-L1 biological activity. Preferred examples are conditions that are characterized by inflammation or cellular hyperproliferation. Techniques and dosages for administration vary depending on the type of specific polypeptide and the specific condition being treated but can be readily determined by the skilled artisan. In general, regulatory agencies require that a protein reagent to be used as a therapeutic is formulated so as to have acceptably low levels of pyrogens. Accordingly, therapeutic formulations will generally be distinguished from other formulations in that they are substantially pyrogen free, or at least contain no more than acceptable levels of pyrogen as determined by the appropriate regulatory agency (e.g., FDA).

Therapeutic compositions of the present disclosure may be administered with a pharmaceutically acceptable diluent, carrier, or excipient, in unit dosage form. Administration may be parenteral (e.g., intravenous, subcutaneous), oral, or topical, as non-limiting examples. In addition, any gene therapy technique, using nucleic acids encoding the polypeptides of the invention, may be employed, such as naked DNA delivery, recombinant genes and vectors, cell-based delivery, including ex vivo manipulation of patients' cells, and the like.

The composition can be in the form of a pill, tablet, capsule, liquid, or sustained release tablet for oral administration; or a liquid for intravenous, subcutaneous or parenteral administration; gel, lotion, ointment, cream, or a polymer or other sustained release vehicle for local administration.

Methods well known in the art for making formulations are found, for example, in "Remington: The Science and Practice of Pharmacy" (20th ed., ed. A. R. Gennaro A R., 2000, Lippincott Williams & Wilkins, Philadelphia, Pa.). Formulations for parenteral administration may, for example, contain excipients, sterile water, saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Nanoparticulate formulations (e.g., biodegradable nanoparticles, solid lipid nanoparticles, liposomes) may be used to control the biodistribution of the compounds. Other potentially useful parenteral delivery systems include ethylene-vinyl acetate copolymer particles, osmotic pumps, implantable infusion systems, and liposomes. The concentration of the compound in the formulation varies depending upon a number of factors, including the dosage of the drug to be administered, and the route of administration.

The polypeptide may be optionally administered as a pharmaceutically acceptable salt, such as non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acid such as hydrochloric acid, hydrobromic acid, sulfuric acid phosphoric acid, or the like. Metal complexes include zinc, iron, and the like. In one example, the polypeptide is formulated in the presence of sodium acetate to increase thermal stability.

Formulations for oral use include tablets containing the active ingredient(s) in a mixture with non-toxic pharmaceutically acceptable excipients. These excipients may be, for example, inert diluents or fillers (e.g., sucrose and sorbitol), lubricating agents, glidants, and anti-adhesives (e.g., magnesium stearate, zinc stearate, stearic acid, silicas, hydrogenated vegetable oils, or talc).

Formulations for oral use may also be provided as chewable tablets, or as hard gelatin capsules wherein the active ingredient is mixed with an inert solid diluent, or as soft gelatin capsules wherein the active ingredient is mixed with water or an oil medium.

A therapeutically effective dose refers to a dose that produces the therapeutic effects for which it is administered. The exact dose will depend on the disorder to be treated, and may be ascertained by one skilled in the art using known techniques. In general, the polypeptide is administered at about 0.01 µg/kg to about 50 mg/kg per day, preferably 0.01 mg/kg to about 30 mg/kg per day, most preferably 0.1 mg/kg to about 20 mg/kg per day. The polypeptide may be given daily (e.g., once, twice, three times, or four times daily) or preferably less frequently (e.g., weekly, every two weeks, every three weeks, monthly, or quarterly). In addition, as is known in the art, adjustments for age as well as the body weight, general health, sex, diet, time of administration, drug interaction, and the severity of the disease may be necessary, and will be ascertainable with routine experimentation by those skilled in the art.

Pharmaceutical Formulations of Disclosed Antibodies with Tumor Vaccines

A combined therapeutic product or formulation of a disclosed anti-PD-L1 antibody with a therapeutic vaccine provides synergistic oncologic therapeutic benefit. For example, the present disclosure provides a combination of a disclosed anti-PD-L1 antibody with "Neuvax" which is a E75-derived 9 mer synthetic peptide isolated from HER2/neu combined with GM-CSF as an adjuvant as described in U.S. Pat. No. 8,222,214, the disclosure of which is incorporated by reference herein. In addition, the present disclosure provides a combination of a disclosed anti-PD-L1 antibody with ALVAC-CEA vaccine, which is a canary pox virus combined with carcinoembryonic antigen.

Exemplary Uses

The PD-L1 binding proteins described herein and their related variants are useful in a number of therapeutic and diagnostic applications. These include the inhibition of the biological activity of PD-L1 by competing for or blocking the binding to a PD-L1 as well as the delivery of cytotoxic or imaging moieties to cells, preferably cells expressing PD-L1. The small size and stable structure of these molecules can be particularly valuable with respect to manufacturing of the drug, rapid clearance from the body for certain applications where rapid clearance is desired or formulation into novel delivery systems that are suitable or improved using a molecule with such characteristics.

On the basis of their efficacy as inhibitors of PD-L1 biological activity, the polypeptides of this disclosure are effective against a number of cancer conditions as well as complications arising from cancer, such as pleural effusion and ascites. Preferably, the PD-L1-binding polypeptides of the disclosure can be used for the treatment of prevention of hyperproliferative diseases or cancer and the metastatic spread of cancers. Preferred indications for the disclosed anti-PD-L1 antibodies include colorectal cancers, head and neck cancers, small cell lung cancer, non-small cell lung cancer (NSCLC) and pancreatic cancer. Non-limiting examples of cancers include bladder, blood, bone, brain, breast, cartilage, colon kidney, liver, lung, lymph node, nervous tissue, ovary, pancreatic, prostate, skeletal muscle, skin, spinal cord, spleen, stomach, testes, thymus, thyroid, trachea, urogenital tract, ureter, urethra, uterus, or vaginal cancer.

In addition, various inflammatory disorders can be treated with the disclosed anti-PD-L1 binding polypeptides disclosed herein. Such inflammatory disorders include, for example, intestinal mucosa inflammation wasting diseases associated with colitis, multiple sclerosis, systemic lupus erythematosus, viral infections, rheumatoid arthritis, osteoarthritis, psoriasis, and Crohn's disease.

A PD-L1 binding polypeptide can be administered alone or in combination with one or more additional therapies such as chemotherapy radiotherapy, immunotherapy, surgical intervention, or any combination of these. Long-term therapy is equally possible as is adjuvant therapy in the context of other treatment strategies, as described above.

In certain embodiments of such methods, one or more polypeptide therapeutic agents can be administered, together (simultaneously) or at different times (sequentially). In addition, polypeptide therapeutic agents can be administered with another type of compounds for treating cancer or for inhibiting angiogenesis.

In certain embodiments, the subject anti-PD-L1 antibodies agents of the invention can be used alone. Alternatively, the subject agents may be used in combination with other conventional anti-cancer therapeutic approaches directed to treatment or prevention of proliferative disorders (e.g., tumor). For example, such methods can be used in prophylactic cancer prevention, prevention of cancer recurrence and metastases after surgery, and as an adjuvant of other conventional cancer therapy. The present disclosure recognizes that the effectiveness of conventional cancer therapies (e.g., chemotherapy, radiation therapy, phototherapy, immunotherapy, and surgery) can be enhanced through the use of a subject polypeptide therapeutic agent.

A wide array of conventional compounds have been shown to have anti-neoplastic activities. These compounds have been used as pharmaceutical agents in chemotherapy to shrink solid tumors, prevent metastases and further growth, or decrease the number of malignant cells in leukemic or bone marrow malignancies. Although chemotherapy has been effective in treating various types of malignancies, many anti-neoplastic compounds induce undesirable side effects. It has been shown that when two or more different treatments are combined, the treatments may work synergistically and allow reduction of dosage of each of the treatments, thereby reducing the detrimental side effects exerted by each compound at higher dosages. In other instances, malignancies that are refractory to a treatment may respond to a combination therapy of two or more different treatments.

When a polypeptide therapeutic agent of the present invention is administered in combination with another conventional anti-neoplastic agent, either concomitantly or sequentially, such therapeutic agent may be found to enhance the therapeutic effect of the anti-neoplastic agent or overcome cellular resistance to such anti-neoplastic agent. This allows decrease of dosage of an anti-neoplastic agent, thereby reducing the undesirable side effects, or restores the effectiveness of an anti-neoplastic agent in resistant cells.

Pharmaceutical compounds that may be used for combinatory anti-tumor therapy include, merely to illustrate: aminoglutethimide, amsacrine, anastrozole, asparaginase, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

Certain chemotherapeutic anti-tumor compounds may be categorized by their mechanism of action into, for example, following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethylmelamineoxaliplatin, iphosphamide, melphalan, merchlorehtamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP-470, genistein) and growth factor inhibitors (e.g., VEGF inhibitors, fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers and caspase activators; and chromatin disruptors.

Depending on the nature of the combinatory therapy, administration of the polypeptide therapeutic agents may be continued while the other therapy is being administered and/or thereafter. Administration of the polypeptide therapeutic agents may be made in a single dose, or in multiple doses. In some instances, administration of the polypeptide therapeutic agents is commenced at least several days prior to the conventional therapy, while in other instances, administration is begun either immediately before or at the time of the administration of the conventional therapy.

In one example of a diagnostic application, a biological sample, such as serum or a tissue biopsy, from a patient suspected of having a condition characterized by inappropriate angiogenesis is contacted with a detectably labeled polypeptide of the disclosure to detect levels of PD-L1. The levels of PD-L1 detected are then compared to levels of PD-L1 detected in a normal sample also contacted with the labeled polypeptide. An increase of at least 10%, 20%, 30%, 40%, 50%, 60%, 70%, 80%, or 90% in the levels of the PD-L1 may be considered a diagnostic indicator.

In certain embodiments, the PD-L1 binding polypeptides are further attached to a label that is able to be detected (e.g., the label can be a radioisotope, fluorescent compound, enzyme or enzyme co-factor). The active moiety may be a radioactive agent, such as: radioactive heavy metals such as iron chelates, radioactive chelates of gadolinium or manganese, positron emitters of oxygen, nitrogen, iron, carbon, or gallium, $^{43}$K, $^{52}$Fe, $^{57}$Co, $^{67}$Cu, $^{67}$Ga, $^{68}$Ga, $^{123}$I, $^{125}$I, $^{131}$I, $^{132}$I, or $^{99}$Tc. A binding agent affixed to such a moiety may be used as an imaging agent and is administered in an amount effective for diagnostic use in a mammal such as a human and the localization and accumulation of the imaging agent is then detected. The localization and accumulation of the imaging agent may be detected by radioscintigraphy, nuclear magnetic resonance imaging, computed tomography or positron emission tomography. Immunoscintigraphy using PD-L1 binding polypeptides directed at PD-L1 may be used to detect and/or diagnose cancers and vasculature. For example, any of the binding polypeptide against a PD-L1 marker labeled with $^{99}$Technetium, $^{111}$Indium, or $^{125}$Iodine may be effectively used for such imaging. As will be evident to the skilled artisan, the amount of radioisotope to be administered is dependent upon the radioisotope. Those having ordinary skill in the art can readily formulate the amount of the imaging agent to be administered based upon the specific activity and energy of a given radionuclide used as the active moiety. Typically 0.1-100 millicuries per dose of imaging agent, preferably 1-10 millicuries, most often 2-5 millicuries are administered. Thus, compositions according to the present invention useful as imaging agents comprising a targeting moiety conjugated to a radioactive moiety comprise 0.1-100 millicuries, in some embodiments preferably 1-10 millicuries, in some embodiments preferably 2-5 millicuries, in some embodiments more preferably 1-5 millicuries.

The PD-L1 binding polypeptides can also be used to deliver additional therapeutic agents (including but not limited to drug compounds, chemotherapeutic compounds, and radiotherapeutic compounds) to a cell or tissue expressing PD-L1. In one example, the PD-L1 binding polypeptide is fused to a chemotherapeutic agent for targeted delivery of the chemotherapeutic agent to a tumor cell or tissue expressing PD-L1.

The PD-L1 binding polypeptides are useful in a variety of applications, including research, diagnostic and therapeutic applications. For instance, they can be used to isolate and/or purify receptor or portions thereof, and to study receptor structure (e.g., conformation) and function.

In certain aspects, the various binding polypeptides can be used to detect or measure the expression of PD-L1, for example, on endothelial cells (e.g., venous endothelial cells), or on cells transfected with a PD-L1 gene. Thus, they also have utility in applications such as cell sorting and imaging (e.g., flow cytometry, and fluorescence activated cell sorting), for diagnostic or research purposes.

In certain embodiments, the binding polypeptides of fragments thereof can be labeled or unlabeled for diagnostic purposes. Typically, diagnostic assays entail detecting the formation of a complex resulting from the binding of a binding polypeptide to PD-L1. The binding polypeptides or fragments can be directly labeled, similar to antibodies. A variety of labels can be employed, including, but not limited to, radionuclides, fluorescers, enzymes, enzyme substrates, enzyme cofactors, enzyme inhibitors and ligands (e.g., biotin, haptens). Numerous appropriate immunoassays are known to the skilled artisan (U.S. Pat. Nos. 3,817,827; 3,850,752; 3,901,654; and 4,098,876). When unlabeled, the binding polypeptides can be used in assays, such as agglutination assays. Unlabeled binding polypeptides can also be used in combination with another (one or more) suitable reagent which can be used to detect the binding polypeptide, such as a labeled antibody reactive with the binding polypeptide or other suitable reagent (e.g., labeled protein A).

In one embodiment, the binding polypeptides of the present invention can be utilized in enzyme immunoassays, wherein the subject polypeptides are conjugated to an enzyme. When a biological sample comprising a PD-L1 protein is combined with the subject binding polypeptides, binding occurs between the binding polypeptides and the PD-L1 protein. In one embodiment, a sample containing cells expressing a PD-L1 protein (e.g., endothelial cells) is combined with the subject antibodies, and binding occurs between the binding polypeptides and cells bearing a PD-L1 protein recognized by the binding polypeptide. These bound cells can be separated from unbound reagents and the presence of the binding polypeptide-enzyme conjugate specifically bound to the cells can be determined, for example, by contacting the sample with a substrate of the enzyme which produces a color or other detectable change when acted on by the enzyme. In another embodiment, the subject binding polypeptides can be unlabeled, and a second, labeled polypeptide (e.g., an antibody) can be added which recognizes the subject binding polypeptide.

In certain aspects, kits for use in detecting the presence of a PD-L1 protein in a biological sample can also be prepared. Such kits will include a PD-L1 binding polypeptide which binds to a PD-L1 protein or portion of said receptor, as well as one or more ancillary reagents suitable for detecting the presence of a complex between the binding polypeptide and the receptor protein or portions thereof. The polypeptide compositions of the present invention can be provided in lyophilized form, either alone or in combination with additional antibodies specific for other epitopes. The binding polypeptides and/or antibodies, which can be labeled or unlabeled, can be included in the kits with adjunct ingredients (e.g., buffers, such as Tris, phosphate and carbonate, stabilizers, excipients, biocides and/or inert proteins, e.g., bovine serum albumin). For example, the binding polypeptides and/or antibodies can be provided as a lyophilized mixture with the adjunct ingredients, or the adjunct ingredients can be separately provided for combination by the user. Generally these adjunct materials will be present in less than about 5% weight based on the amount of active binding polypeptide or antibody, and usually will be present in a total amount of at least about 0.001% weight based on polypeptide or antibody concentration. Where a second antibody capable of binding to the binding polypeptide is employed, such antibody can be provided in the kit, for instance in a separate vial or container. The second antibody, if present, is typically labeled, and can be formulated in an analogous manner with the antibody formulations described above.

Similarly, the present disclosure also provides a method of detecting and/or quantitating expression of PD-L1, wherein a composition comprising a cell or fraction thereof (e.g., membrane fraction) is contacted with a binding polypeptide which binds to a PD-L1 or portion of the receptor under conditions appropriate for binding thereto, and the binding is monitored. Detection of the binding polypeptide, indicative of the formation of a complex between binding polypeptide and PD-L1 or a portion thereof, indicates the presence of the receptor. Binding of a polypeptide to the cell can be determined by standard methods, such as those described in the working examples. The method can be used to detect expression of PD-L1 on cells from an individual. Optionally, a quantitative expression of PD-L1 on the surface of endothelial cells can be evaluated, for instance, by flow cytometry, and the staining intensity can be correlated with disease susceptibility, progression or risk.

The present disclosure also provides a method of detecting the susceptibility of a mammal to certain diseases. To illustrate, the method can be used to detect the susceptibility of a mammal to diseases which progress based on the amount of PD-L1 present on cells and/or the number of PD-L1-positive cells in a mammal.

Polypeptide sequences are indicated using standard one- or three-letter abbreviations. Unless otherwise indicated, each polypeptide sequence has amino termini at the left and a carboxy termini at the right; each single-stranded nucleic acid sequence, and the top strand of each double-stranded nucleic acid sequence, has a 5' termini at the left and a 3' termini at the right. A particular polypeptide sequence also can be described by explaining how it differs from a reference sequence.

The terms "PD-L1 inhibitor" and "PD-L1 antagonist" are used interchangeably. Each is a molecule that detectably inhibits at least one function of PD-L1. Conversely, a "PD-L1 agonist" is a molecule that detectably increases at least one function of PD-L1. The inhibition caused by a PD-L1 inhibitor need not be complete so long as it is detectable using an assay. Any assay of a function of PD-L1 can be used, examples of which are provided herein. Examples of functions of PD-L1 that can be inhibited by a PD-L1 inhibitor, or increased by a PD-L1 agonist, include cancer cell growth or apoptosis (programmed cell death), and so on. Examples of types of PD-L1 inhibitors and PD-L1 agonists include, but are not limited to, PD-L1 binding polypeptides such as antigen binding proteins (e.g., PD-L1 inhibiting antigen binding proteins), antibodies, antibody fragments, and antibody derivatives.

The terms "peptide," "polypeptide" and "protein" each refers to a molecule comprising two or more amino acid residues joined to each other by peptide bonds. These terms encompass, e.g., native and artificial proteins, protein fragments and polypeptide analogs (such as muteins, variants, and fusion proteins) of a protein sequence as well as post-translationally, or otherwise covalently or non-covalently, modified proteins. A peptide, polypeptide, or protein may be monomeric or polymeric.

A "variant" of a polypeptide (for example, an antibody) comprises an amino acid sequence wherein one or more amino acid residues are inserted into, deleted from and/or substituted into the amino acid sequence relative to another polypeptide sequence. Disclosed variants include, for example, fusion proteins.

A "derivative" of a polypeptide is a polypeptide (e.g., an antibody) that has been chemically modified, e.g., via conjugation to another chemical moiety (such as, for example, polyethylene glycol or albumin, e.g., human serum albumin), phosphorylation, and glycosylation. Unless otherwise indicated, the term "antibody" includes, in addition to antibodies comprising two full-length heavy chains and two full-length light chains, derivatives, variants, fragments, and muteins thereof, examples of which are described below.

An "antigen binding protein" is a protein comprising a portion that binds to an antigen and, optionally, a scaffold or framework portion that allows the antigen binding portion to adopt a conformation that promotes binding of the antigen binding protein to the antigen. Examples of antigen binding proteins include antibodies, antibody fragments (e.g., an antigen binding portion of an antibody), antibody derivatives, and antibody analogs. The antigen binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the antigen binding protein as well as wholly synthetic scaffolds comprising, for example, a biocompatible polymer. See, for example, Korndorfer et al., 2003, *Proteins: Structure, Function, and Bioinformatics*, Volume 53, Issue 1:121-129; Roque et al., 2004, *Biotechnol. Prog.* 20:639-654. In addition, peptide antibody mimetics ("PAMs") can be used, as well as scaffolds based on antibody mimetics utilizing fibronection components as a scaffold.

An antigen binding protein can have, for example, the structure of a naturally occurring immunoglobulin. An "immunoglobulin" is a tetrameric molecule. In a naturally occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa or lambda light chains. Heavy chains are classified as mu, delta, gamma, alpha, or epsilon, and define the antibody's isotype as IgM, IgD, IgG, IgA, and IgE, respectively. Preferably, the anti-PD-L1 antibodies disclosed herein are characterized by their variable domain region sequences in the heavy $V_H$ and light $V_L$ amino acid sequences. The preferred antibody is A6 which is a kappa IgG antibody. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)). The variable regions of each light/heavy chain pair form the antibody binding site such that an intact immunoglobulin has two binding sites.

A "multi-specific antibody" is an antibody that recognizes more than one epitope on one or more antigens. A subclass of this type of antibody is a "bi-specific antibody" which recognizes two distinct epitopes on the same or different antigens.

An antigen binding protein "specifically binds" to an antigen (e.g., human PD-L1) if it binds to the antigen with a dissociation constant of 1 nanomolar or less.

An "antigen binding domain, "antigen binding region," or "antigen binding site" is a portion of an antigen binding protein that contains amino acid residues (or other moieties) that interact with an antigen and contribute to the antigen binding protein's specificity and affinity for the antigen. For an antibody that specifically binds to its antigen, this will include at least part of at least one of its CDR domains.

An "epitope" is the portion of a molecule that is bound by an antigen binding protein (e.g., by an antibody). An epitope can comprise non-contiguous portions of the molecule (e.g., in a polypeptide, amino acid residues that are not contiguous in the polypeptide's primary sequence but that, in the context of the polypeptide's tertiary and quaternary structure, are near enough to each other to be bound by an antigen binding protein).

The "percent homology" of two polynucleotide or two polypeptide sequences is determined by comparing the sequences using the GAP computer program (a part of the GCG Wisconsin Package, version 10.3 (Accelrys, San Diego, Calif.)) using its default parameters.

A "host cell" is a cell that can be used to express a nucleic acid. A host cell can be a prokaryote, for example, *E. coli*, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Examples of host cells include the COS-7 line of monkey kidney cells (ATCC CRL 1651) (Gluzman et al., 1981, *Cell* 23:175), L cells, C127 cells, 3T3 cells (ATCC CCL 163), Chinese hamster ovary (CHO) cells or their derivatives such as Veggie CHO and related cell lines which grow in serum-free media (Rasmussen et al., 1998, *Cytotechnology* 28:31) or CHO strain DX-B11, which is deficient in DHFR (Urlaub et al., 1980, *Proc. Natl. Acad. Sci. USA* 77:4216-20), HeLa cells, BHK (ATCC CRL 10) cell lines, the CV1/EBNA cell line derived from the African green monkey kidney cell line CV1 (ATCC CCL 70) (McMahan et al., 1991, *EMBO J.* 10:2821), human embryonic kidney cells such as 293,293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Typically, a host cell is a cultured cell that can be transformed or transfected with a polypeptide-encoding nucleic acid, which can then be expressed in the host cell. The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but also to the progeny or potential progeny of such a cell. Because certain modifications may occur in succeeding generations due to, e.g., mutation or environmental influence, such progeny may not, in fact, be identical to the parent cell, but are still included within the scope of the term as used herein.

Antigen Binding Proteins

Antigen binding proteins (e.g., antibodies, antibody fragments, antibody derivatives, antibody muteins, and antibody variants) are polypeptides that bind to PD-L1, (preferably, human PD-L1). Antigen binding proteins include antigen binding proteins that inhibit a biological activity of PD-L1.

Oligomers that contain one or more antigen binding proteins may be employed as PD-L1 antagonists. Oligomers may be in the form of covalently-linked or non-covalently-linked dimers, trimers, or higher oligomers. Oligomers comprising two or more antigen binding protein are contemplated for use, with one example being a homodimer. Other oligomers include heterodimers, homotrimers, heterotrimers, homotetramers, heterotetramers, etc.

One embodiment is directed to oligomers comprising multiple antigen binding proteins joined via covalent or non-covalent interactions between peptide moieties fused to the antigen binding proteins. Such peptides may be peptide linkers (spacers), or peptides that have the property of promoting oligomerization. Leucine zippers and certain polypeptides derived from antibodies are among the peptides that can promote oligomerization of antigen binding proteins attached thereto, as described in more detail below.

In particular embodiments, the oligomers comprise from two to four antigen binding proteins. The antigen binding proteins of the oligomer may be in any form, such as any of the forms described above, e.g., variants or fragments. Preferably, the oligomers comprise antigen binding proteins that have PD-L1 binding activity.

In one embodiment, an oligomer is prepared using polypeptides derived from immunoglobulins. Preparation of Fusion Proteins Comprising Certain Heterologous Polypeptides Fused to Various Portions of antibody-derived polypeptides (including the Fc domain) has been described, e.g., by Ashkenazi et al., 1991, *Proc. Natl. Acad. Sci. USA* 88:10535; Byrn et al., 1990, *Nature* 344:677; and Hollenbaugh et al., 1992 "Construction of Immunoglobulin Fusion Proteins", in *Current Protocols in Immunology*, Suppl. 4, pages 10.19.1-10.19.11.

One embodiment is directed to a dimer comprising two fusion proteins created by fusing a PD-L1 binding fragment of an anti-PD-L1 antibody to the Fc region of an antibody. The dimer can be made by, for example, inserting a gene fusion encoding the fusion protein into an appropriate expression vector, expressing the gene fusion in host cells transformed with the recombinant expression vector, and allowing the expressed fusion protein to assemble much like antibody molecules, whereupon interchain disulfide bonds form between the Fc moieties to yield the dimer.

The term "Fc polypeptide" includes native and mutein forms of polypeptides derived from the Fc region of an antibody. Truncated forms of such polypeptides containing the hinge region that promotes dimerization also are included. Fusion proteins comprising Fc moieties (and oligomers formed therefrom) offer the advantage of facile purification by affinity chromatography over Protein A or Protein G columns.

Another method for preparing oligomeric antigen binding proteins involves use of a leucine zipper. Leucine zipper domains are peptides that promote oligomerization of the proteins in which they are found. Leucine zippers were originally identified in several DNA-binding proteins (Landschulz et al., 1988, *Science* 240:1759), and have since been found in a variety of different proteins. Among the known leucine zippers are naturally occurring peptides and derivatives thereof that dimerize or trimerize. Examples of leucine zipper domains suitable for producing soluble oligomeric proteins are described in WO 94/10308, and the leucine zipper derived from lung surfactant protein D (SPD) described in Hoppe et al., 1994, *FEBS Letters* 344:191. The use of a modified leucine zipper that allows for stable trimerization of a heterologous protein fused thereto is described in Fanslow et al., 1994, *Semin. Immunol.* 6:267-78. In one approach, recombinant fusion proteins comprising an anti-PD-L1 antibody fragment or derivative fused to a leucine zipper peptide are expressed in suitable host cells, and the soluble oligomeric anti-PD-L1 antibody fragments or derivatives that form are recovered from the culture supernatant.

Antigen-binding fragments of antigen binding proteins of the invention may be produced by conventional techniques. Examples of such fragments include, but are not limited to, Fab and F(ab')$_2$ fragments.

The present disclosure provides monoclonal antibodies that bind to PD-L1. Monoclonal antibodies may be produced using any technique known in the art, e.g., by immortalizing spleen cells harvested from the transgenic animal after completion of the immunization schedule. The spleen cells can be immortalized using any technique known in the art, e.g., by fusing them with myeloma cells to produce hybridomas. Myeloma cells for use in hybridoma-producing fusion procedures preferably are non-antibody-producing, have high fusion efficiency, and enzyme deficiencies that render them incapable of growing in certain selective media which support the growth of only the desired fused cells (hybridomas). Examples of suitable cell lines for use in mouse fusions include Sp-20, P3-X63/Ag8, P3-X63-Ag8.653, NS1/1.Ag 4 1, Sp210-Ag14, FO, NSO/U, MPC-11, MPC11-X45-GTG 1.7 and S194/5XX0 Bul; examples of cell lines used in rat fusions include R210.RCY3, Y3-Ag 1.2.3, IR983F and 48210. Other cell lines useful for cell fusions are U-266, GM1500-GRG2, LICR-LON-HMy2 and UC729-6.

Antigen binding proteins directed against PD-L1 can be used, for example, in assays to detect the presence of PD-L1 polypeptides, either in vitro or in vivo. The antigen binding proteins also may be employed in purifying PD-L1 proteins by immunoaffinity chromatography. Blocking antigen binding proteins can be used in the methods disclosed herein. Such antigen binding proteins that function as PD-L1 antagonists may be employed in treating any PD-L1-induced condition, including but not limited to various cancers.

Antigen binding proteins may be employed in an in vitro procedure, or administered in vivo to inhibit PD-L1-induced biological activity. Disorders caused or exacerbated (directly or indirectly) by the proteolytic activation of PD-L1, examples of which are provided herein, thus may be treated.

In one embodiment, the present invention provides a therapeutic method comprising in vivo administration of a PD-L1 blocking antigen binding protein to a mammal in need thereof in an amount effective for reducing an PD-L1-induced biological activity.

Antigen binding proteins include fully human monoclonal antibodies that inhibit a biological activity of PD-L1.

Antigen binding proteins may be prepared by any of a number of conventional techniques. For example, they may be purified from cells that naturally express them (e.g., an antibody can be purified from a hybridoma that produces it), or produced in recombinant expression systems, using any technique known in the art. See, for example, Monoclonal Antibodies, Hybridomas: A New Dimension in Biological Analyses, Kennet et al. (eds.), Plenum Press, New York (1980); and Antibodies: A Laboratory Manual, Harlow and Land (eds.), Cold Spring Harbor Laboratory Press, Cold Spring Harbor, N.Y., (1988).

Any expression system known in the art can be used to make the recombinant polypeptides of the invention. In general, host cells are transformed with a recombinant expression vector that comprises DNA encoding a desired polypeptide. Among the host cells that may be employed are prokaryotes, yeast or higher eukaryotic cells. Prokaryotes include gram negative or gram positive organisms, for example E. coli or bacilli. Higher eukaryotic cells include insect cells and established cell lines of mammalian origin. Examples of suitable mammalian host cell lines include the COS-7 line of monkey kidney cells (ATCC CRL 1651) (Gluzman et al., 1981, Cell 23:175), L cells, 293 cells, C127 cells, 3T3 cells (ATCC CCL 163), Chinese hamster ovary (CHO) cells, HeLa cells, BHK (ATCC CRL 10) cell lines, and the CV1/EBNA cell line derived from the African green monkey kidney cell line CV1 (ATCC CCL 70) as described by McMahan et al., 1991, EMBO J. 10: 2821. Appropriate cloning and expression vectors for use with bacterial, fungal, yeast, and mammalian cellular hosts are described by Pouwels et al. (Cloning Vectors: A Laboratory Manual, Elsevier, N.Y., 1985).

The transformed cells can be cultured under conditions that promote expression of the polypeptide, and the polypeptide recovered by conventional protein purification procedures. One such purification procedure includes the use of affinity chromatography, e.g., over a matrix having all or a portion (e.g., the extracellular domain) of PD-L1 bound thereto. Polypeptides contemplated for use herein include substantially homogeneous recombinant mammalian anti-PD-L1 antibody polypeptides substantially free of contaminating endogenous materials.

Antigen binding proteins may be prepared, and screened for desired properties, by any of a number of known techniques. Certain of the techniques involve isolating a nucleic acid encoding a polypeptide chain (or portion thereof) of an antigen binding protein of interest (e.g., an anti-PD-L1 antibody), and manipulating the nucleic acid through recombinant DNA technology. The nucleic acid may be fused to another nucleic acid of interest, or altered (e.g., by mutagenesis or other conventional techniques) to add, delete, or substitute one or more amino acid residues, for example.

Single chain antibodies may be formed by linking heavy and light chain variable domain (Fv region) fragments via an amino acid bridge (short peptide linker), resulting in a single polypeptide chain. Such single-chain Fvs (scFvs) have been prepared by fusing DNA encoding a peptide linker between DNAs encoding the two variable domain polypeptides ($V_L$ and $V_H$). The resulting polypeptides can fold back on themselves to form antigen-binding monomers, or they can form multimers (e.g., dimers, trimers, or tetramers), depending on the length of a flexible linker between the two variable domains (Kortt et al., 1997, Prot. Eng. 10:423; Kortt et al., 2001, Biomol. Eng. 18:95-108). By combining different $V_L$ and $V_H$-comprising polypeptides, one can form multimeric scFvs that bind to different epitopes (Kriangkum et al., 2001, Biomol. Eng. 18:31-40). Techniques developed for the production of single chain antibodies include those described in U.S. Pat. No. 4,946,778; Bird, 1988, Science 242:423; Huston et al., 1988, Proc. Natl. Acad. Sci. USA 85:5879; Ward et al., 1989, Nature 334:544, de Graaf et al., 2002, Methods Mol. Biol. 178:379-87.

Techniques are known for deriving an antibody of a different subclass or isotype from an antibody of interest, i.e., subclass switching. Thus, IgG antibodies may be derived from an IgM antibody, for example, and vice versa. Such techniques allow the preparation of new antibodies that possess the antigen-binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g., DNA encoding the constant domain of an antibody of the desired isotype (Lantto et al., 2002, Methods Mol. Biol. 178:303-16). Moreover, if an IgG4 is desired, it may also be desired to introduce a point mutation (CPSCP->CPPCP) in the hinge region (Bloom et al., 1997, Protein Science 6:407) to alleviate a tendency to form intra-H chain disulfide bonds that can lead to heterogeneity in the IgG4 antibodies.

In particular embodiments, antigen binding proteins of the present invention have a binding affinity ($K_a$) for PD-L1 of at least $10^6$. In other embodiments, the antigen binding proteins exhibit a $K_a$ of at least $10^7$, at least $10^8$, at least $10^9$, or at least $10^{10}$. In another embodiment, the antigen binding protein exhibits a $K_a$ substantially the same as that of an antibody described herein in the Examples.

In another embodiment, the present disclosure provides an antigen binding protein that has a low dissociation rate from PD-L1. In one embodiment, the antigen binding protein has a $K_{off}$ of $1\times10^{-4}$ to $^{-1}$ or lower. In another embodiment, the $K_{off}$ is $5\times10^{-5}$ to $^{-1}$ or lower. In another embodiment, the $K_{off}$ is substantially the same as an antibody described herein. In another embodiment, the antigen binding protein binds to PD-L1 with substantially the same $K_{off}$ as an antibody described herein.

In another aspect, the present disclosure provides an antigen binding protein that inhibits an activity of PD-L1. In one embodiment, the antigen binding protein has an $IC_{50}$ of 1000 nM or lower. In another embodiment, the $IC_{50}$ is 100 nM or lower; in another embodiment, the $IC_{50}$ is 10 nM or lower. In another embodiment, the $IC_{50}$ is substantially the same as that of an antibody described herein in the Examples. In another embodiment, the antigen binding protein inhibits an activity of PD-L1 with substantially the same $IC_{50}$ as an antibody described herein.

In another aspect, the present disclosure provides an antigen binding protein that binds to human PD-L1 expressed on the surface of a cell and, when so bound, inhibits PD-L1 signaling activity in the cell without causing a significant reduction in the amount of PD-L1 on the surface of the cell. Any method for determining or estimating the amount of PD-L1 on the surface and/or in the interior of the cell can be used. In other embodiments, binding of the antigen binding protein to the PD-L1-expressing cell causes less than about 75%, 50%, 40%, 30%, 20%, 15%, 10%, 5%, 1%, or 0.1% of the cell-surface PD-L1 to be internalized.

In another aspect, the present disclosure provides an antigen binding protein having a half-life of at least one day in vitro or in vivo (e.g., when administered to a human subject). In one embodiment, the antigen binding protein has a half-life of at least three days. In another embodiment, the antigen binding protein has a half-life of four days or longer. In another embodiment, the antigen binding protein has a half-life of eight days or longer. In another embodiment, the antigen binding protein is derivatized or modified such that it has a longer half-life as compared to the underivatized or unmodified antigen binding protein. In another embodiment, the antigen binding protein contains one or more point mutations to increase serum half life, such as described in WO00/09560, incorporated by reference herein.

The present disclosure further provides multi-specific antigen binding proteins, for example, bispecific antigen binding protein, e.g., antigen binding protein that bind to two different epitopes of PD-L1, or to an epitope of PD-L1 and an epitope of another molecule, via two different antigen binding sites or regions. Moreover, bispecific antigen binding protein as disclosed herein can comprise a PD-L1 binding site from one of the herein-described antibodies and a second PD-L1 binding region from another of the herein-described antibodies, including those described herein by reference to other publications. Alternatively, a bispecific antigen binding protein may comprise an antigen binding site from one of the herein described antibodies and a second antigen binding site from another PD-L1 antibody that is known in the art, or from an antibody that is prepared by known methods or the methods described herein.

Numerous methods of preparing bispecific antibodies are known in the art. Such methods include the use of hybrid-hybridomas as described by Milstein et al., 1983, *Nature* 305:537, and chemical coupling of antibody fragments (Brennan et al., 1985, *Science* 229:81; Glennie et al., 1987, *J. Immunol.* 139:2367; U.S. Pat. No. 6,010,902). Moreover, bispecific antibodies can be produced via recombinant means, for example by using leucine zipper moieties (i.e., from the Fos and Jun proteins, which preferentially form heterodimers; Kostelny et al., 1992, *J. Immunol.* 148:1547) or other lock and key interactive domain structures as described in U.S. Pat. No. 5,582,996. Additional useful techniques include those described in U.S. Pat. Nos. 5,959,083; and 5,807,706.

In another aspect, the antigen binding protein comprises a derivative of an antibody. The derivatized antibody can comprise any molecule or substance that imparts a desired property to the antibody, such as increased half-life in a particular use. The derivatized antibody can comprise, for example, a detectable (or labeling) moiety (e.g., a radioactive, colorimetric, antigenic or enzymatic molecule, a detectable bead (such as a magnetic or electrodense (e.g., gold bead), or a molecule that binds to another molecule (e.g., biotin or streptavidin), a therapeutic or diagnostic moiety (e.g., a radioactive, cytotoxic, or pharmaceutically active moiety), or a molecule that increases the suitability of the antibody for a particular use (e.g., administration to a subject, such as a human subject, or other in vivo or in vitro uses). Examples of molecules that can be used to derivatize an antibody include albumin (e.g., human serum albumin) and polyethylene glycol (PEG). Albumin-linked and PEGylated derivatives of antibodies can be prepared using techniques well known in the art. In one embodiment, the antibody is conjugated or otherwise linked to transthyretin (TTR) or a TTR variant. The TTR or TTR variant can be chemically modified with, for example, a chemical selected from the group consisting of dextran, poly (n-vinyl pyurrolidone), polyethylene glycols, proprylene glycol homopolymers, polypropylene oxide/ethylene oxide co-polymers, polyoxyethylated polyols and polyvinyl alcohols.

Indications

In one aspect, the present disclosure provides methods of treating a subject. The method can, for example, have a generally salubrious effect on the subject, e.g., it can increase the subject's expected longevity. Alternatively, the method can, for example, treat, prevent, cure, relieve, or ameliorate ("treat") a disease, disorder, condition, or illness ("a condition"). Among the conditions to be treated are conditions characterized by inappropriate expression or activity of PD-L1. In some such conditions, the expression or activity level is too high, and the treatment comprises administering a PD-L1 antagonist as described herein. The disorders or conditions are cancer-related. In particular, those cancers include, but are not limited to, lung, ovarian and colon carcinoma and various myelomas.

Specific medical conditions and diseases that are treatable or preventable with the antigen binding proteins of this disclosure include various cancers.

Therapeutic Methods and Administration of Antigen Binding Proteins

Certain methods provided herein comprise administering a PD-L1 binding antigen binding protein to a subject, thereby reducing a PD-L1-induced biological response that plays a role in a particular condition. In particular embodiments, methods of the invention involve contacting endogenous PD-L1 with a PD-L1 binding antigen binding protein, e.g., via administration to a subject or in an ex vivo procedure.

The term "treatment" encompasses alleviation or prevention of at least one symptom or other aspect of a disorder, or reduction of disease severity, and the like. An antigen binding protein need not effect a complete cure, or eradicate every symptom or manifestation of a disease, to constitute a viable therapeutic agent. As is recognized in the pertinent field, drugs employed as therapeutic agents may reduce the severity of a given disease state, but need not abolish every manifestation of the disease to be regarded as useful therapeutic agents. Similarly, a prophylactically administered treatment need not be completely effective in preventing the onset of a condition in order to constitute a viable prophylactic agent. Simply reducing the impact of a disease (for example, by reducing the number or severity of its symptoms, or by increasing the effectiveness of another treatment, or by producing another beneficial effect), or reducing the likelihood that the disease will occur or worsen in a subject, is sufficient. One embodiment of the invention is directed to a method comprising administering to a patient a PD-L1 antagonist in an amount and for a time sufficient to induce a sustained improvement over baseline of an indicator that reflects the severity of the particular disorder.

As is understood in the pertinent field, pharmaceutical compositions comprising the antibodies and fragments thereof of the disclosure are administered to a subject in a manner appropriate to the indication. Pharmaceutical compositions may be administered by any suitable technique, including but not limited to, parenterally, topically, or by inhalation. If injected, the pharmaceutical composition can be administered, for example, via intra-articular, intravenous, intramuscular, intralesional, intraperitoneal or subcutaneous routes, by bolus injection, or continuous infusion. Localized administration, e.g. at a site of disease or injury is contemplated, as are transdermal delivery and sustained release from implants. Delivery by inhalation includes, for example, nasal or oral inhalation, use of a nebulizer, inhalation of the antagonist in aerosol form, and the like. Other alternatives include eyedrops; oral preparations including pills, syrups, lozenges or chewing gum; and topical preparations such as lotions, gels, sprays, and ointments.

Use of antigen binding proteins in ex vivo procedures also is contemplated. For example, a patient's blood or other bodily fluid may be contacted with an antigen binding protein that binds PD-L1 ex vivo. The antigen binding protein may be bound to a suitable insoluble matrix or solid support material.

Advantageously, antigen binding proteins are administered in the form of a composition comprising one or more additional components such as a physiologically acceptable carrier, excipient or diluent. Optionally, the composition additionally comprises one or more physiologically active agents, for example, a second inflammation- or immune-inhibiting substance, an anti-angiogenic substance, an analgesic substance, etc., non-exclusive examples of which are provided herein. In various particular embodiments, the composition comprises one, two, three, four, five, or six physiologically active agents in addition to a PD-L1 binding antigen binding protein Combination Therapy In another aspect, the present disclosure provides a method of treating a subject with a PD-L1 inhibiting antigen binding protein and one or more other treatments. In one embodiment, such a combination therapy achieves synergy or an additive effect by, for example, attacking multiple sites or molecular targets in a tumor. Types of combination therapies that can be used in connection with the present invention include inhibiting or activating (as appropriate) multiple nodes in a single disease-related pathway, multiple pathways in a target cell, and multiple cell types within a target tissue.

In another embodiment, a combination therapy method comprises administering to the subject two, three, four, five, six, or more of the PD-L1 agonists or antagonists described herein. In another embodiment, the method comprises administering to the subject two or more treatments that together inhibit or activate (directly or indirectly) PD-L1-mediated signal transduction. Examples of such methods include using combinations of two or more PD-L1 inhibiting antigen binding proteins, of a PD-L1 inhibiting antigen binding protein and one or more other therapeutic moiety having anti-cancer properties (for example, cytotoxic agents, and/or immunomodulators), or of a PD-L1 inhibiting antigen binding protein and one or more other treatments (e.g., surgery, or radiation). Furthermore, one or more anti-PD-L1 antibodies or antibody derivatives can be used in combination with one or more molecules or other treatments, wherein the other molecule(s) and/or treatment(s) do not directly bind to or affect PD-L1, but which combination is effective for treating or preventing the condition being treated. In one embodiment, one or more of the molecule(s) and/or treatment(s) treats or prevents a condition that is caused by one or more of the other molecule(s) or treatment(s) in the course of therapy, e.g., nausea, fatigue, alopecia, cachexia, insomnia, etc. In every case where a combination of molecules and/or other treatments is used, the individual molecule(s) and/or treatment(s) can be administered in any order, over any length of time, which is effective, e.g., simultaneously, consecutively, or alternately. In one embodiment, the method of treatment comprises completing a first course of treatment with one molecule or other treatment before beginning a second course of treatment. The length of time between the end of the first course of treatment and beginning of the second course of treatment can be any length of time that allows the total course of therapy to be effective, e.g., seconds, minutes, hours, days, weeks, months, or even years.

In another embodiment, the method comprises administering one or more of the PD-L1 antagonists described herein and one or more other treatments (e.g., a therapeutic or palliative treatment). Where a method comprises administering more than one treatment to a subject, it is to be understood that the order, timing, number, concentration, and volume of the administrations is limited only by the medical requirements and limitations of the treatment, i.e., two treatments can be administered to the subject, e.g., simultaneously, consecutively, alternately, or according to any other regimen.

Example 1

This example provides a characterization of the disclosed anti-PD-L1 antibodies binding to human PD-L1 expressed on human lymphocytes. Human peripheral blood mononuclear cells were activated by culture with anti-CD3 for three days to promote expression of PD-L1. Binding was assessed by adding serial dilutions of the antibody to the activated lymphocytes. After washing, binding was detected by staining with a phycoerythrin labeled anti-human Ig reagent followed by analysis using a FACS Aria (Becton Dickinson, San Jose, Calif.). Since the anti-human Ig reagent reacts with immunoglobulin on B lymphocytes the cells were co-staining with an anti-human CD19 APC-Cy5 reagent. Data were obtained by gating on the CD19 negative lymphocytes and the results are shown in FIG. 1. Both H6 and H10 antibodies show potent binding activity with an $EC_{50}$ in the 100 µM range.

Example 2

Figure 2:
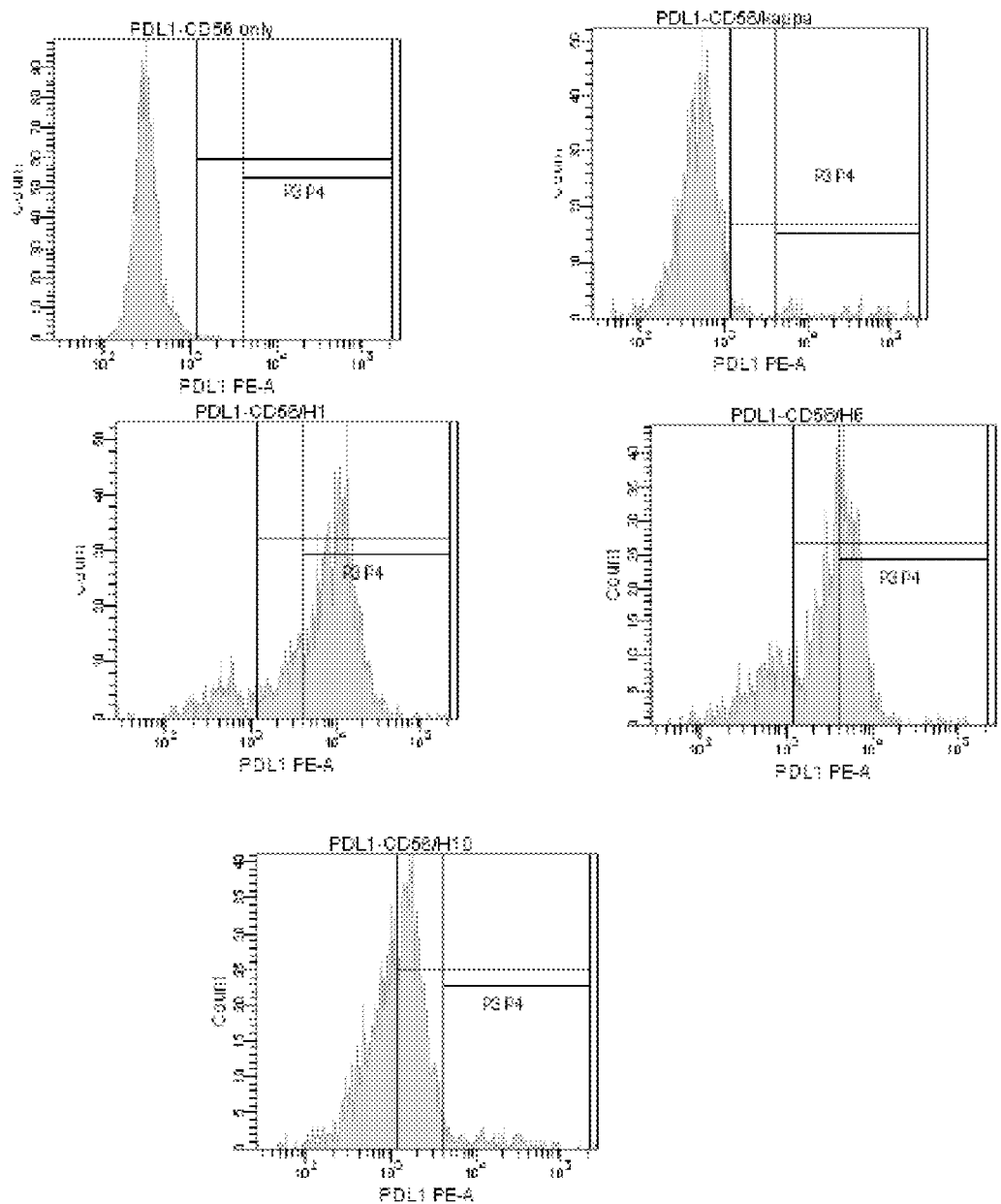
FIG. 2 shows disclosed anti-PD-L1 antibodies binding to human lymphocytes by FACSAria analysis.
Figure 2:
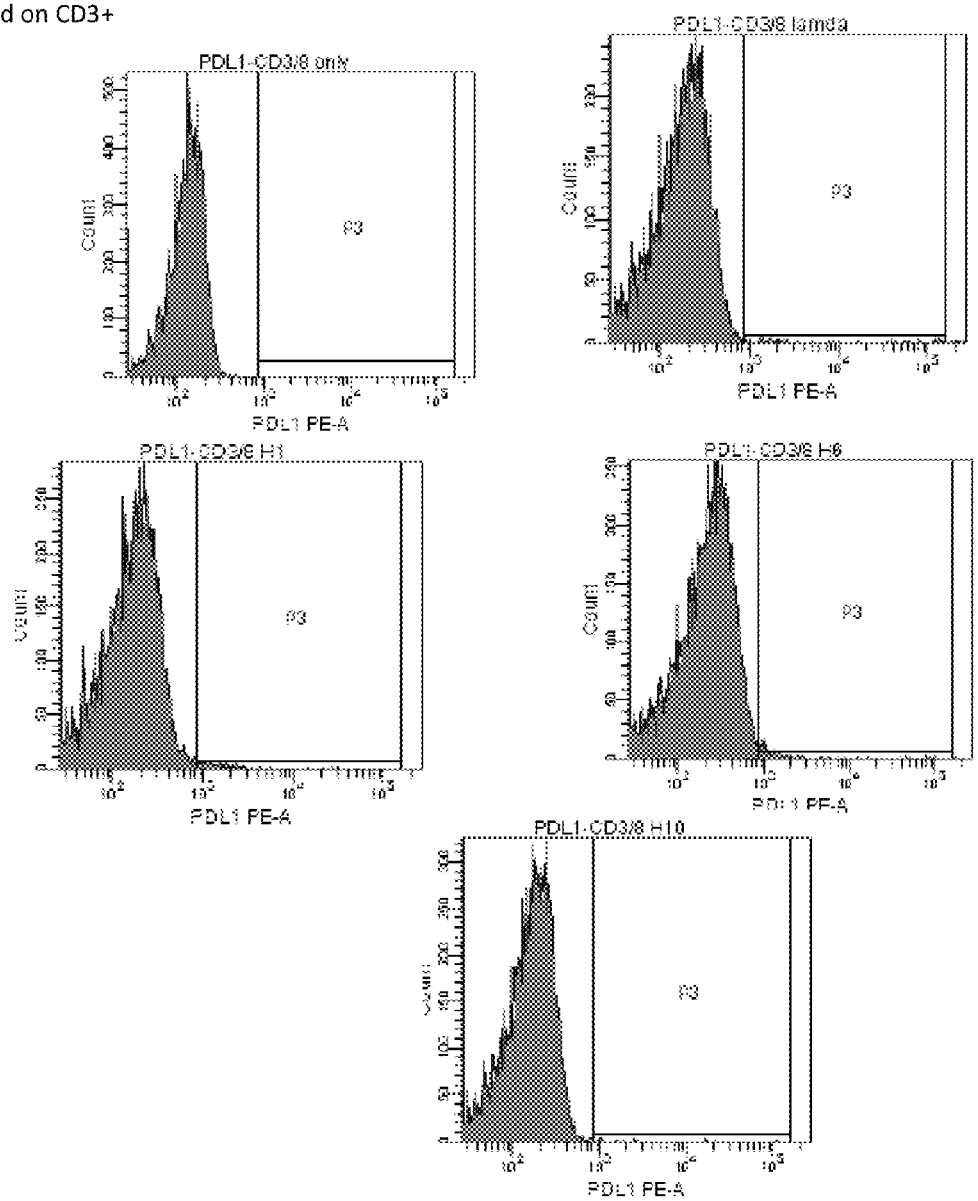

This example provides the results from binding the disclosed anti-PD-L1 antibodies to human lymphocytes. Anti-PD-L1 antibodies were assayed for binding to non-activated lymphocytes. Peripheral blood mononuclear cells were incubated with anti-PD-L1 antibodies (1 µg/ml) followed by washing. Binding of the anti-PD-L1 antibody was detected by staining with a phycoerythrin conjugated and human Ig reagent. To identify the stained populations the cells were co-stained with an anti-CD3 FITC or an anti-CD56 APC reagent. Since the anti-human Ig reagent reacts with immunoglobulin on B lymphocytes the cells were also stained with an anti-human CD19 APC-Cy5 reagent. The data in FIG. 2 were derived from the CD19 negative lymphocytes following analysis using a FACSAria (Becton Dickinson, San Jose, Calif.). The results show that CD56 positive NK cells, but not CD3+ T cells, react with the anti-PD-L1 antibodies.

Example 3

Figure 3:
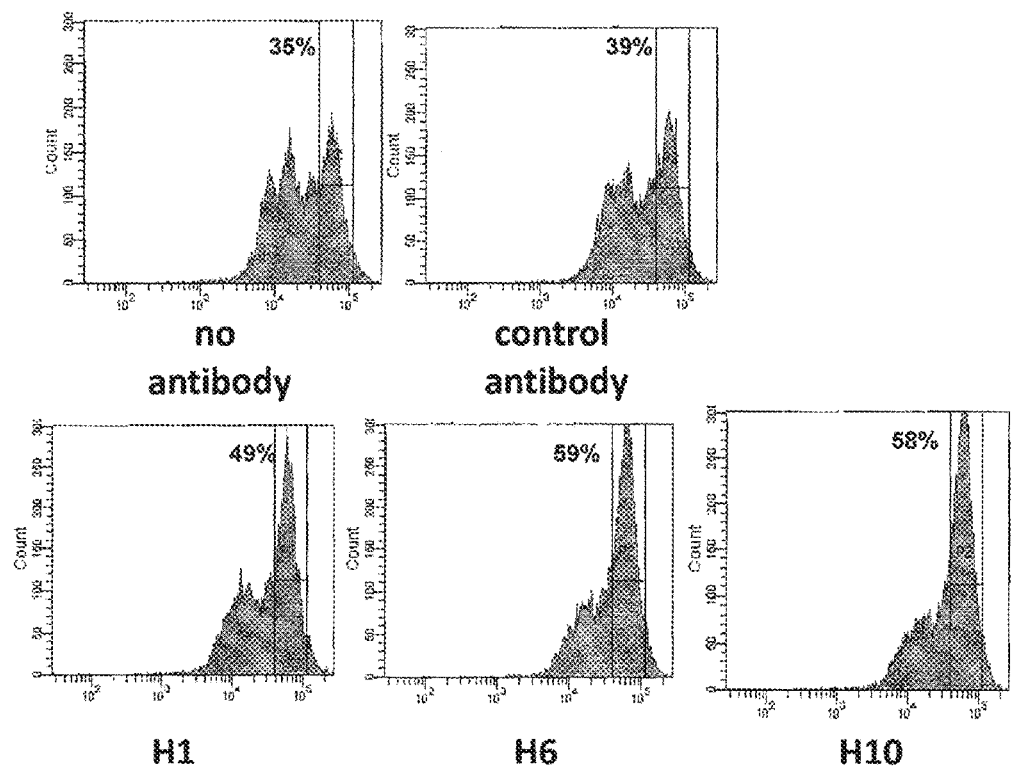
FIG. 3 shows disclosed anti-PD-L1 antibodies H1, H6 and H10 inhibit lymphocyte proliferation.

This example provides a showing of the effect of disclosed anti-PD-L1 antibodies on lymphocyte proliferation. Anti-PD-L1 antibodies were assayed for their ability to modulate the response of lymphocytes to stimulation. The anti-PD-L1 antibodies H1, H6 and H10 were added at 10 µg/ml to cultures of peripheral blood mononuclear cells labeled with the fluorescent dye carboxyfluorescein (CFSE) and stimulated with anti-CD3 (1 ng/ml). After three days of culture, the cells were assayed for proliferative activity by flow cytometry using a FACS Aria (Becton Dickinson, San Jose, Calif.). The results, shown in FIG. 3, show that the anti-PD-L1 antibodies inhibited lymphocyte proliferation.

Example 4

Figure 4:
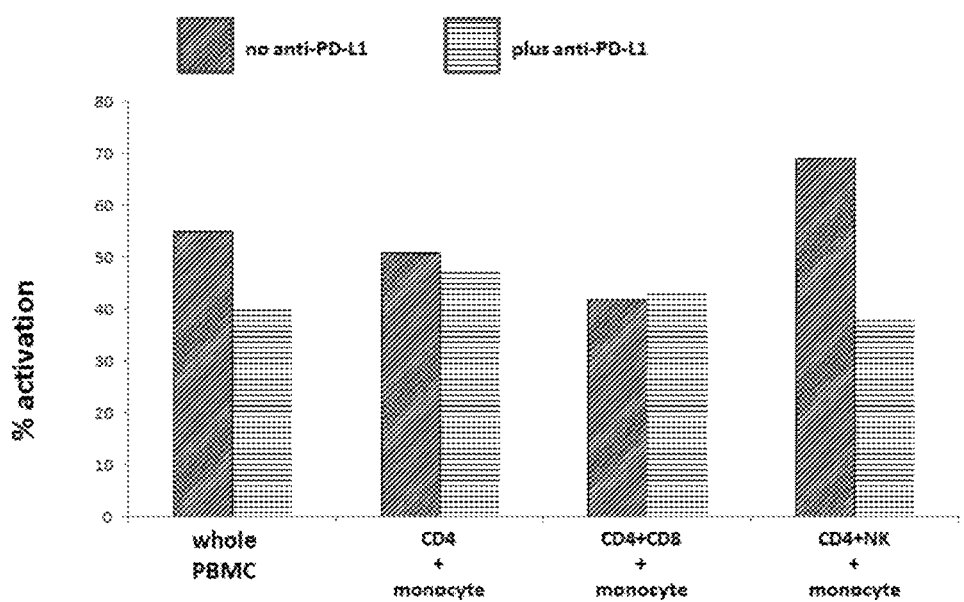
FIG. 4 shows disclosed anti-PD-L1 antibody H10 inhibit NK cell proliferation.

This example provides a showing of the effect of NK cells on the disclosed anti-PD-L1 antibodies on mediated inhibition of proliferation. With the anti-PD-L1 antibodies showing a preferential binding to NK cells, the significance of this in the inhibition of proliferation was tested. By cell sorting using a FACS Aria (Becton Dickinson, Dan Jose, Calif.) purified population of CD4+, CD8+, CD56+ (NK) and monocytes were obtained. As a base culture, $1.5 \times 10^5$ CD4+ cells and $3 \times 10^4$ monocytes were stimulated with anti-CD3 (1 ng/ml) with or without H10 anti-PD-L1 antibody (10 µg/ml). In separate cultures, either CD8+ cells or NK cells (both at $3 \times 10^4$) were added to this base culture. After three days of culture, cells were stained for expression of CD25 as a measure of lymphocyte activation as measured by flow cytometry. The results shown in FIG. 4 were compared to those obtained using whole, unfractionated PBMC ($1.5 \times 10^5$). The anti-PD-L1 antibody inhibited the activation of lymphocytes in the cultures containing whole PBMC and those where NK cells were added, but not in the absence of NK cells.

Example 5

Figure 5:
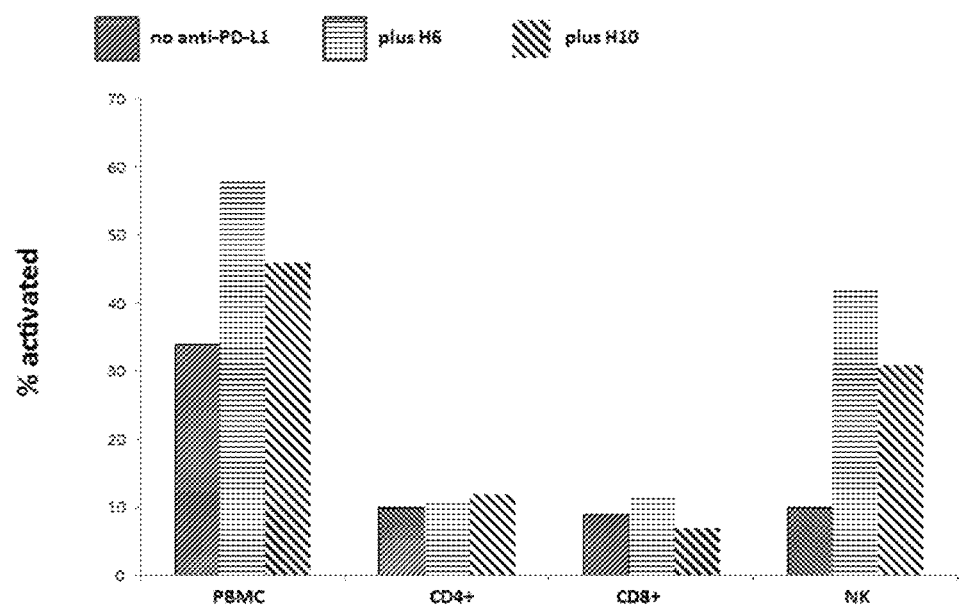
FIG. 5 shows disclosed anti-PD-L1 antibodies H6 and H10 enhance cell activation and that the responsive lymphocyte population is the NK cell.

This example provides a showing of an effect of anti-PD-L1 on NK cell activation. Disclosed anti-PD-L1 antibodies were assayed for their ability to promote the activation of lymphocytes. Peripheral blood mononuclear cells or purified populations of lymphocyte subsets isolated by cell sorting were cultured with IL-2 (100 U/ml) in the presence or absence of added anti-PD-L1 antibodies (10 µg/ml). After five days of culture, cells were stained for expression of CD25 as a measure of cell activation and analyzed by flow cytometry. The results shown in FIG. 5 reveal that H6 and H10 enhance cell activation and that the responsive lymphocyte population is the NK cell.

Example 6

Figure 6:
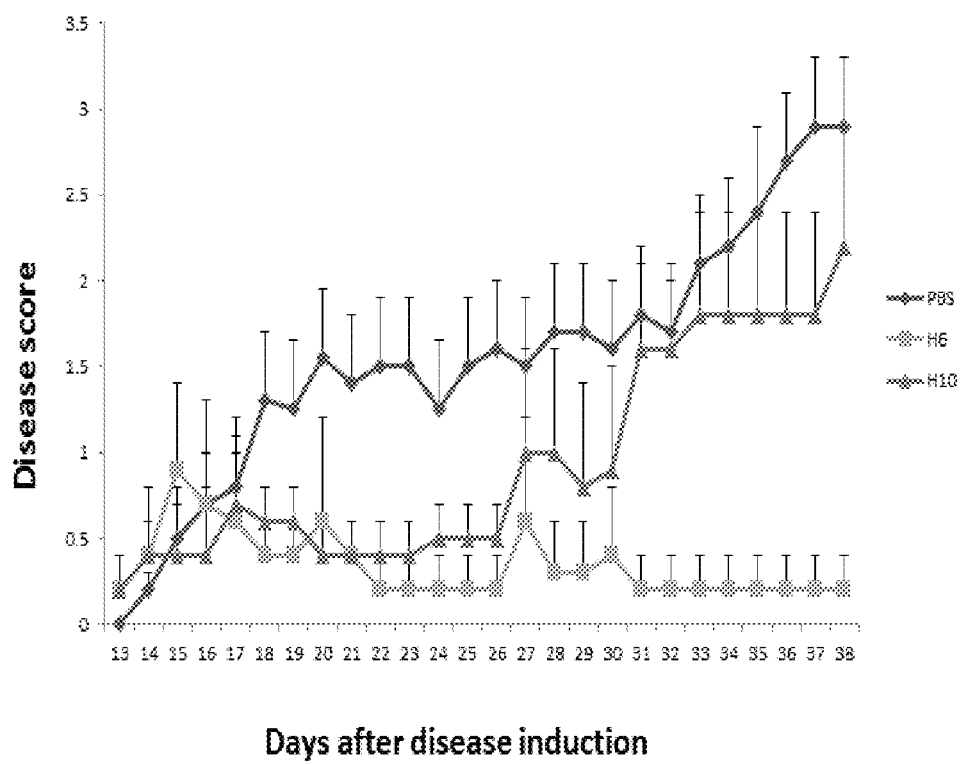
FIG. 6 shows effect of anti-PD-L1 antibodies H6 and H10 on the progression of disease in a murine model of multiple sclerosis (MS)

This example provides a showing of an effect of disclosed anti-PD-L1 antibodies on the progression of disease in a murine model of multiple sclerosis (MS). Anti-PD-L1 antibodies were assayed for their ability to modulate the course of disease in mice induced to develop experimental autoimmune encephalitis (EAE) as a model of MS. Disease was induced in C57Bl/6 mice following injection of myelin oligodendrocyte glycoprotein (MOG) peptide and pertussis toxin. Once symptoms of disease developed, the mice were treated every second day with an intraperitoneal injection of anti-PD-L1 antibody (0.1 mg). The results shown in FIG. 6 provide that both anti-PD-L1 antibodies H6 and H10 impacted the course of disease development with H6 greatly reducing disease severity.

Example 7

This example provides a characterization of the disclosed G12 anti-PD-L1 antibody. rhPD-L1 was immobilized on CM5 sensor chip using standard NHS/EDC coupling methodology. All measurements were conducted in HBS-EP buffer with a flow rate of 30 µL/min. Antibody was diluted so as to obtain a series of concentrations. A 1:1 (Langmuir) binding model was used to fit the data.

Table 1 provides the binding data for G12.

|  |  | G12 |
|---|---|---|
| Biacore | $k_{on}$ (M$^{-1}$ s$^{-1}$) | 1.31E+07 |
|  | $k_{off}$ (s$^{-1}$) | 4.90E−04 |
|  | Kd (M) | 3.74E−11 |

Example 8

This example provides the results from an experiment showing that G12 blocks the interaction between rhPD-1 and rhPD-L1. A 96-well ELISA plate was coated with 1 ng/µL PD1/His at 4° C. overnight, then blocked with casein in PBS. Pre-mixed 20 µl serial 2-fold diluted IgGs (started from 20 µg/ml) and 20 µl 0.25 µl/ml PD-L1/Fc and incubated the mixtures 30 min. washed the plate with PBS-Tween (PBST) 3 times. Transferred 25 µl the mixtures to the ELISA plate and incubated 30 min with shaking. Washed 3 times with PBST. Added HRP conjugated Goat anti-human Fc (1:500 in casein), used TMB as substrate and developed 30 min. 2M $H_2SO_4$ was added to stop the reaction. Read the OD at 450 nm.

TABLE 2

|  |  | G12 |
|---|---|---|
| Blocking PD-1/PD-L1 interaction (M) | $IC_{50}$ | 7.288E−11 |

Example 9

This example illustrates in vitro $EC_{50}$ data for the binding of G12 to human PD-L1 expressed on the surface of CHO cells. This example shows the binding characteristic for this antibody in terms of the maximal cell binding and the concentration at which 50% binding saturation ($EC_{50}$) is reached. In this example, the experimental procedure is as follows: 50,000 CHO-PD-L1 cells were aliquoted into the wells of a 96-well, v-bottom plate in 100 µl FACS Buffer (PBS+2% FBS). A dilution curve of the antibody was made in FACS Buffer encompassing the concentrations shown in FIG. 7. Cells were spun down, washed 1× with FACS Buffer, and then resuspended in 25 µl of antibody solution in triplicate. After 0.5 hr incubation, cells were washed 1× with FACS Buffer and resuspended in 50 µl PE-conjugated, goat anti-human IgG (γ-chain specific) secondary antibody (Southern Biotech Cat #2040-09). Cells were further incubated for 0.5 hr and then washed 1× with FACS Buffer. Cells were resuspended in 25 µl FACS Buffer and the median fluorescence intensity in the FL2-H channel was determined using the Intellicyt HTFC flow cytometer.

Figure 7:
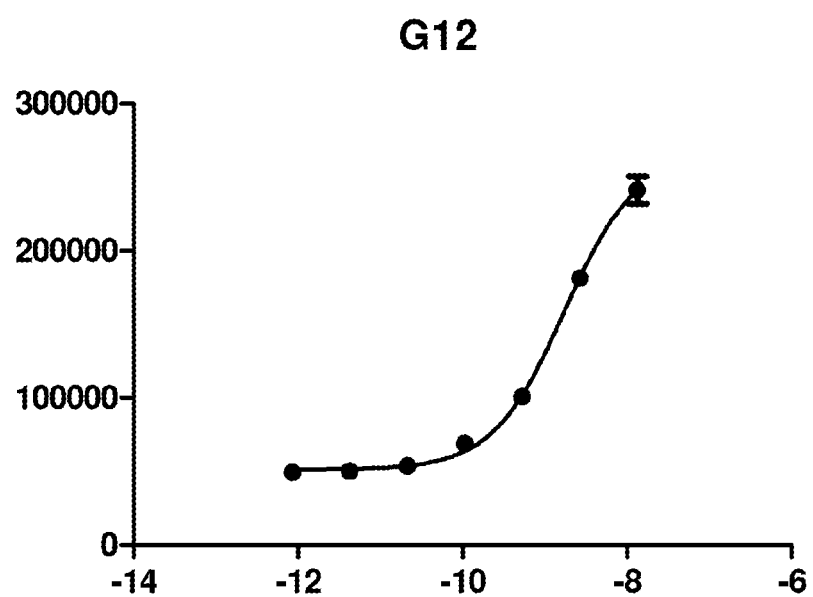
FIG. 7 shows the results of EC50 cell binding flow cytometry experiments, demonstrating that anti-PD-L1 antibody G12 binds the cell surface of CHO cells transfected with full length PD-L1 in a concentration dependent manner.

Results: As shown in FIG. 7 and Table 3, the cell binding $EC_{50}$ for the G12 anti-PD-L1 antibody on CHO-PD-L1 cells was 1.71E-09 M. Data was collected on the Intellicyt HTFC flow cytometer, processed using FlowJo software, and analyzed and plotted in GraphPad Prizm using non-linear regression fit. Data points are shown as the median fluorescence intensity (MFI) of positively labeled cells +/− Std Error.

TABLE 3

| | G12 | |
|---|---|---|
| Cell Binding EC50 (M) | CHO-PD-L1 | 1.71E−09 |

Example 10

This example provides in vitro $IC_{50}$ data for the blocking of the interaction between recombinant human PD-1 (PD-1-Fc Chimera; Sino Biologics) and human PD-L1 expressed CHO cells by anti-PD-L1 antibody G12. Here, CHO cells expressing PD-L1 were pre-incubated with G12 prior to the addition of rhPD-1-Fc chimeric protein. After incubation and washing, PD-1 binding to cell surface expressed PD-L1 was detected using an Alexa-Fluor 647 tagged anti-PD-1 antibody by flow cytometry (Intellicyt HTFC; FL-4H). This example shows that anti-PD-L1 monoclonal antibody G12 was able to inhibit efficiently the binding of PD-1 to PD-L1 expressed on the surface of CHO cells.

Figure 8:
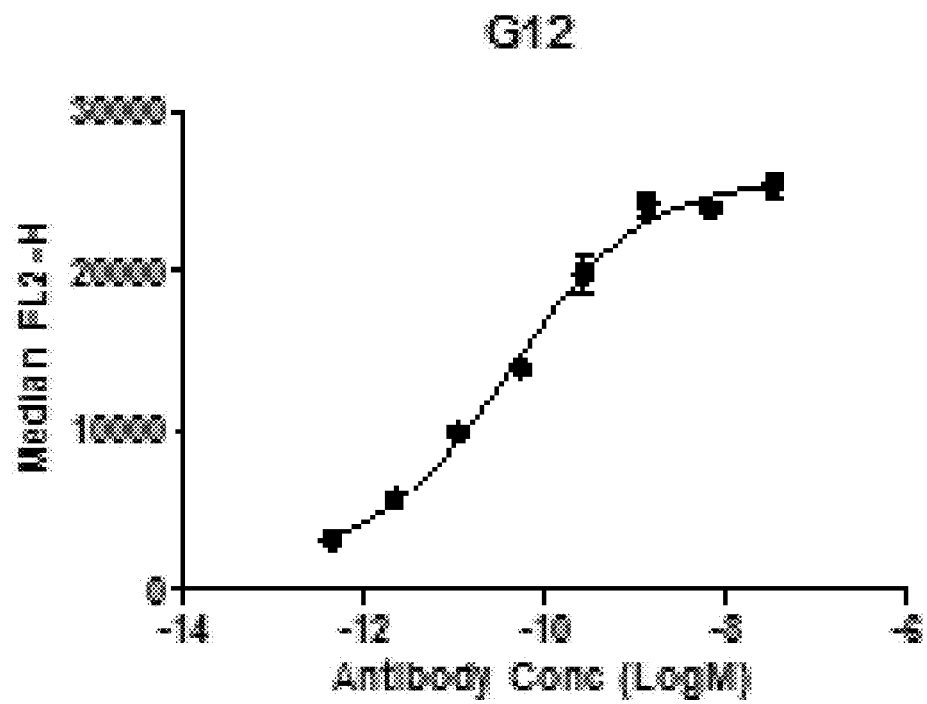
FIG. 8 shows the results of EC50 cell binding flow cytometry experiments, demonstrating that anti-PD-L1 antibody G12 binds in a concentration dependent manner to the cell surface of ES-2 ovarian carcinoma cells induced with IFNγ to increase the level of PD-L1 expression on these cells.

Results: As shown in FIG. 8 and Table 4, the $IC_{50}$ for blocking of the PD-1/PD-L1 cellular interaction by G12 is 1.76E-09 M. Data was collected on the Intellicyt HTFC flow cytometer, processed using FlowJo software, and analyzed and plotted in Graph Pad Prizm using non-linear regression fit. Data points are shown as the median fluorescence detected in the FL-4H channel +/− Std Error.

TABLE 4

| | G12 | |
|---|---|---|
| Inhibition of PD-1/PD-L1 Interaction IC50 (M) | CHO-PD-L1/ rhPD-1-Fc | 1.76E−09 |

Example 11

This example illustrates in vitro $EC_{50}$ data for the binding of G12 to PD-L1 expressed on the surface of ES-2 human ovarian carcinoma cells. This example shows the binding characteristic for this antibody in terms of the maximal cell binding and the concentration at which 50% binding saturation ($EC_{50}$) is reached. In this example, the experimental procedure is as follows: ES-2 cells were treated with 5001 U/ml IFNγ for 18 hours to increase PD-L1 levels above basal expression. After induction, 50,000 ES-2 cells were aliquoted into the wells of a 96-well, v-bottom plate in 100 μl FACS Buffer (PBS+2% FBS). A dilution curve of the antibody was made in FACS Buffer encompassing the concentrations shown in FIG. 9. Cells were spun down, washed 1× with FACS Buffer, and then resuspended in 25 μl of antibody solution in triplicate. After 0.5 hr incubation, cells were washed 1× with FACS Buffer and resuspended in 50 μl PE-conjugated, goat anti-human IgG (γ-chain specific) secondary antibody (Southern Biotech Cat #2040-09). Cells were further incubated for 0.5 hr and then washed 1× with FACS Buffer. Cells were resuspended in 25 μl FACS Buffer and the median fluorescence intensity in the FL2-H channel was determined using the Intellicyt HTFC flow cytometer.

Figure 9:
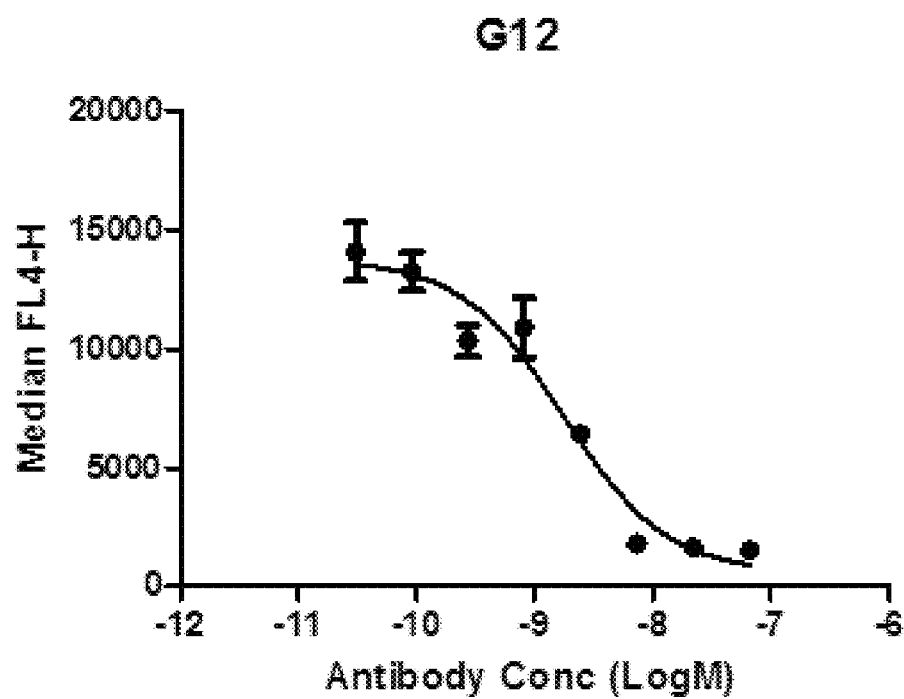
FIG. 9 shows IC50 data for the blocking of the interaction between recombinant human PD-1 and human PD-L1 expressed on CHO cells by anti-PD-L1 antibody G12.

Results: As shown in FIG. 9 and Table 5, the cell binding $EC_{50}$ for the G12 anti-PD-L1 antibody on ES-2 ovarian carcinoma cells was 4.58E-11 M. Data was collected on the Intellicyt HTFC flow cytometer, processed using FlowJo software, and analyzed and plotted in Graph Pad Prizm using non-linear regression fit. Data points are shown as the median fluorescence detected in the FL-2H channel +/− Std Error.

Cell binding $EC_{50}$ for anti-PD-L1 mAb G12 against human PD-L1 expressed on ES-2 ovarian cancer cells after treatment with 500 IU/ml recombinant hIFNγ for 18 hr is shown in Table 5.

TABLE 5

| | G12 | |
|---|---|---|
| Cell Binding EC50 (M) | ES-2 | 4.58E−11 |

Example 12

Figure 10:
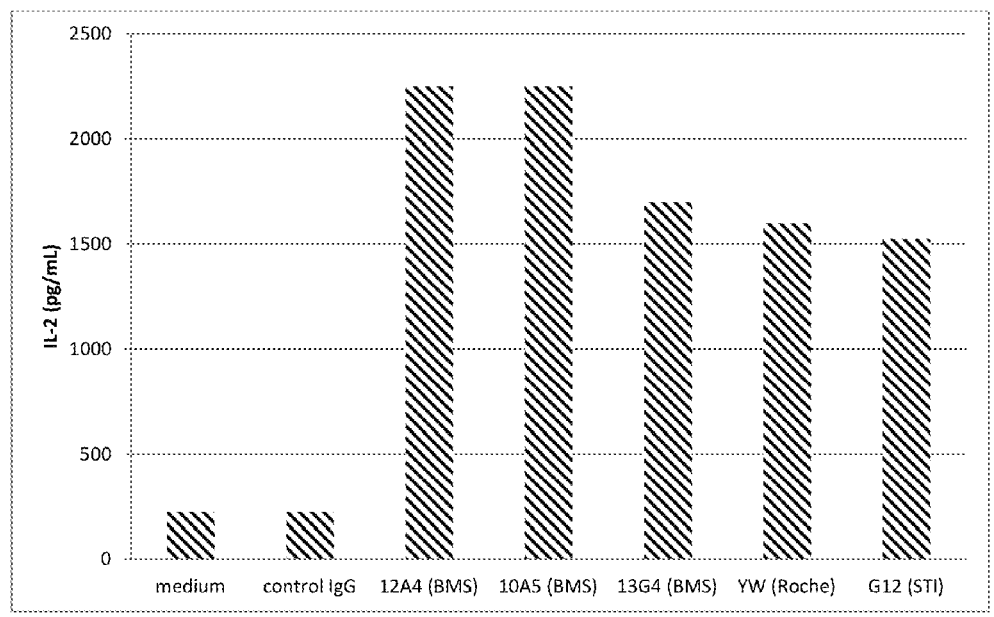
FIG. 10 shows a mixed lymphocyte reaction (MLR) to evaluate the effect of the antibodies on lymphocyte activity in lymphocyte effector cells. IL-2 secretion was measured in the presence or absence of the anti-PD-L1 human monoclonal antibody. The antibodies used were the disclosed G12 antibody as compared to prior disclosed antibodies 10A5 and 12A4 (Bristol-Myers/Medarex) that were obtained via in-house production from prior-disclosed antibody sequences (U.S. Patent Application 2009/0055944 the disclosure of which is incorporated by reference herein).

This example provides a mixed lymphocyte reaction (MLR) to evaluate the effect of the antibodies on lymphocyte activity in lymphocyte effector cells. IL-2 secretion was measured in the presence or absence of an anti-PD-L1 human monoclonal antibody (FIG. 10). The functional activity of the antibodies was assessed in an allogeneic mixed lymphocyte reaction (MLR) consisting of purified CD4+ T lymphocytes and allogeneic dendritic cells. The antibodies used were the disclosed G12 antibody as compared to prior disclosed antibodies 10A5 and 12A4 (Bristol-Myers/Medarex) that were obtained via in-house production from prior-disclosed antibody sequences (U.S. Patent Application 2009/0055944 the disclosure of which is incorporated by reference herein). To prepare the dendritic cells, monocytes, purified using a discontinuous Percoll gradient, were cultured with GM-CSF (1,000 U/ml) plus IL-4 (500 U/ml) for seven days. The CD4+ cells were prepared by negative selection using biotinylated antibodies reactive with CD8, CD16, CD19 and CD20. Removal of the reactive cells was achieved using biotin binding magnetic beads. The antibodies were added at the indicated concentrations to wells containing $10^5$ CD4+ cells labeled with carboxyfluorecein (CFSE) and $10^4$ dendritic cells. After five days of culture, supernatants were harvested for cytokine determination.

Example 13

Figure 12:
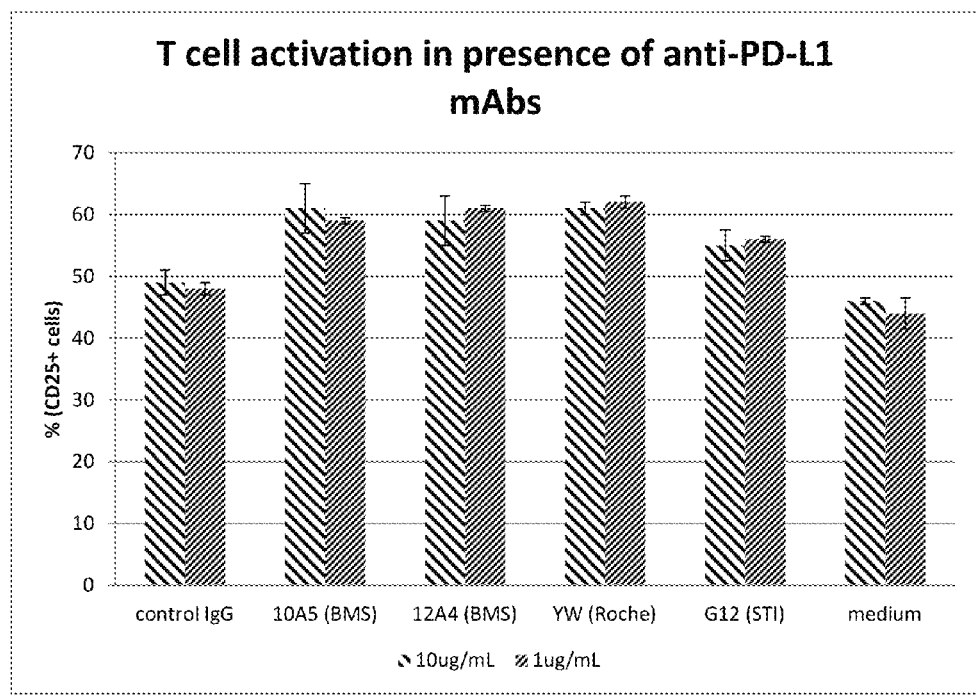
FIG. 12 shows a mixed lymphocyte reaction (MLR) was employed to evaluate the effect of the antibodies on lymphocyte activity by the anti-PD-L1 antibodies on lymphocyte effector cells. T cell activation was measured in the presence or absence of the anti-PD-L1 human monoclonal antibody. The antibodies used were the disclosed G12 antibody as compared to prior disclosed antibodies 10A5 and 12A4 (Bristol-Myers/Medarex) that were obtained via in-house production from prior-disclosed antibody sequences (U.S. Patent Application 2009/0055944 the disclosure of which is incorporated by reference herein).

This example provides a mixed lymphocyte reaction (MLR) was employed to demonstrate the effect of blocking the PD-L1/PD-1 pathway by the anti-PD-L1 antibodies on lymphocyte effector cells. T cell activation was measured in the presence or absence of the anti-PD-L1 human monoclonal antibody (FIG. 12). The functional activity of the antibodies was assessed in an allogeneic mixed lymphocyte reaction (MLR) consisting of purified CD4+ T lymphocytes and allogeneic dendritic cells. The antibodies used were the disclosed H6B1L, RSA1, RA3, RC5, SH1E2, SH1E4, SH1B11, and SH1C8 as compared to prior disclosed antibodies 10A5 (Bristol-Myers-Squibb/Medarex) and YW243.55S70 (Roche/Genentech) that were obtained via in-house production from prior-disclosed antibody sequences (U.S. Patent Application 2009/0055944 and U.S. Patent Application US 2010/0203056; the disclosure of which are incorporated by reference herein). To prepare the dendritic cells, monocytes, purified using a discontinuous Percoll gradient, were cultured with GM-CSF (1,000 U/ml) plus IL-4 (500 U/ml) for seven days. The CD4+ cells were prepared by negative selection using biotinylated antibodies reactive with CD8, CD16, CD19 and CD20. Removal of the reactive cells was achieved using biotin binding magnetic beads. The antibodies were added at the indicated concentrations to wells containing $10^5$ CD4+ cells labeled with carboxyfluorecein (CFSE) and $10^4$ dendritic cells. After five days of culture, the cells were collected and stained for CD25 expression as a measure of cell activation. Cell activation was measured by flow cytometry.

Figure 13:
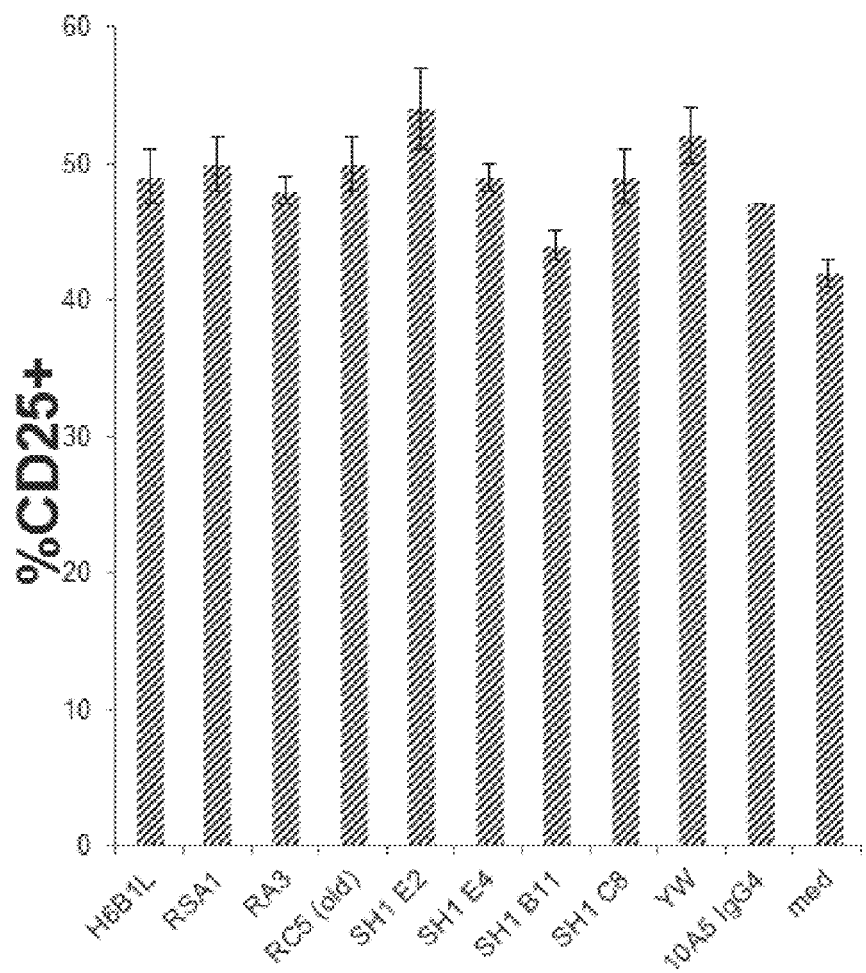
FIG. 13 shows a mixed lymphocyte reaction (MLR) was employed to evaluate the effect of the antibodies on lymphocyte activity by the anti-PD-L1 antibodies on lymphocyte effector cells. T cell activation was measured in the presence or absence of the anti-PD-L1 human monoclonal antibody. The antibodies used were the disclosed H6B1L, RSA1, RA3, RC5, SH1E2, SH1E4, SH1B11, and SH1C8 as compared to prior disclosed antibodies 10A5 (Bristol-Myers-Squibb/Medarex) and YW243.55S70 (Roche/Genentech) that were obtained via in-house production from prior-disclosed antibody sequences (U.S. Patent Application 2009/0055944 and U.S. Patent Application US 2010/0203056; the disclosure of which are incorporated by reference herein).
Figure 14:
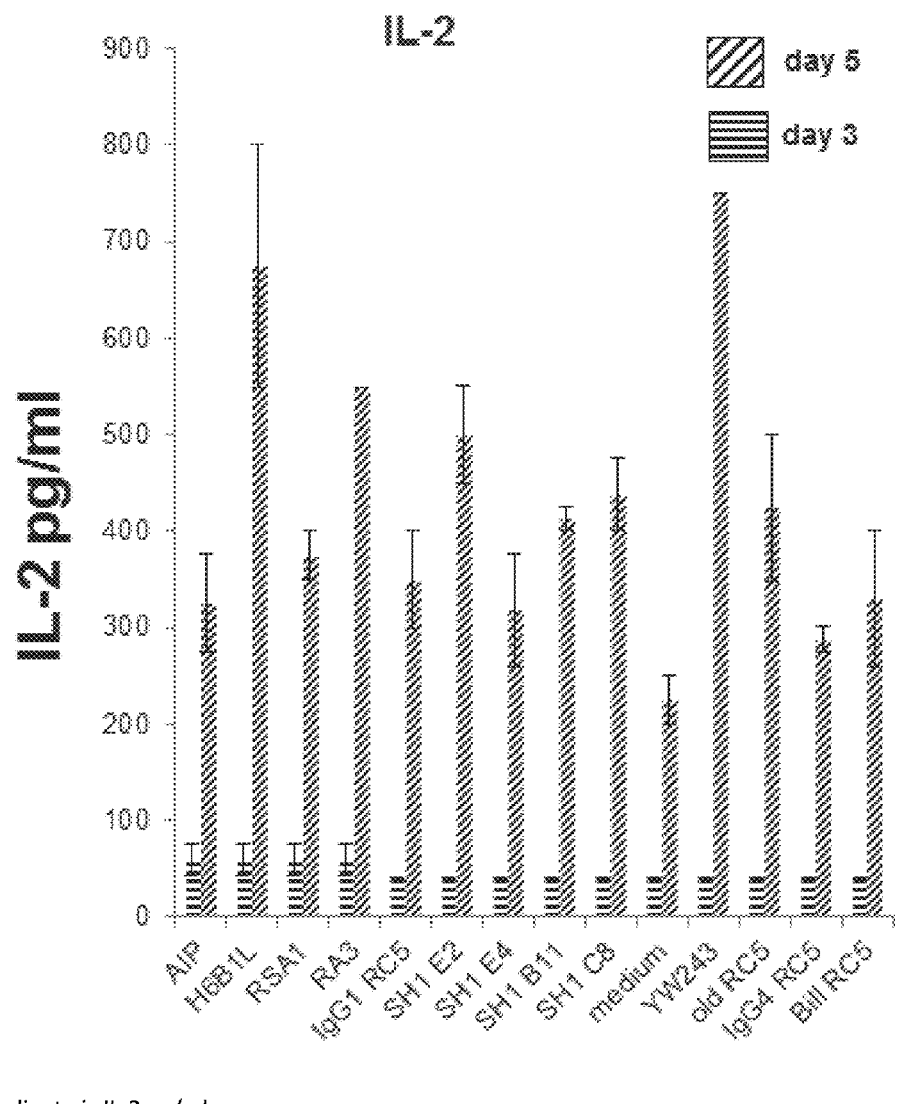
FIG. 14 shows a mixed lymphocyte reaction (MLR) to evaluate the effect of the antibodies on lymphocyte activity in lymphocyte effector cells. IL-2 secretion was measured in the presence or absence of the anti-PD-L1 human monoclonal antibody. The antibodies used were the disclosed H6B1L, RSA1, RA3, RC5, SH1E2, SH1E4, SH1B11, and SH1C8 as compared to prior disclosed antibodies 10A5 (Bristol-Myers-Squibb/Medarex) and YW243.55S70 (Roche/Genentech) that were obtained via in-house production from prior-disclosed antibody sequences (U.S. Patent Application 2009/0055944 and U.S. Patent Application US 2010/0203056; the disclosure of which are incorporated by reference herein).
Figure 15:
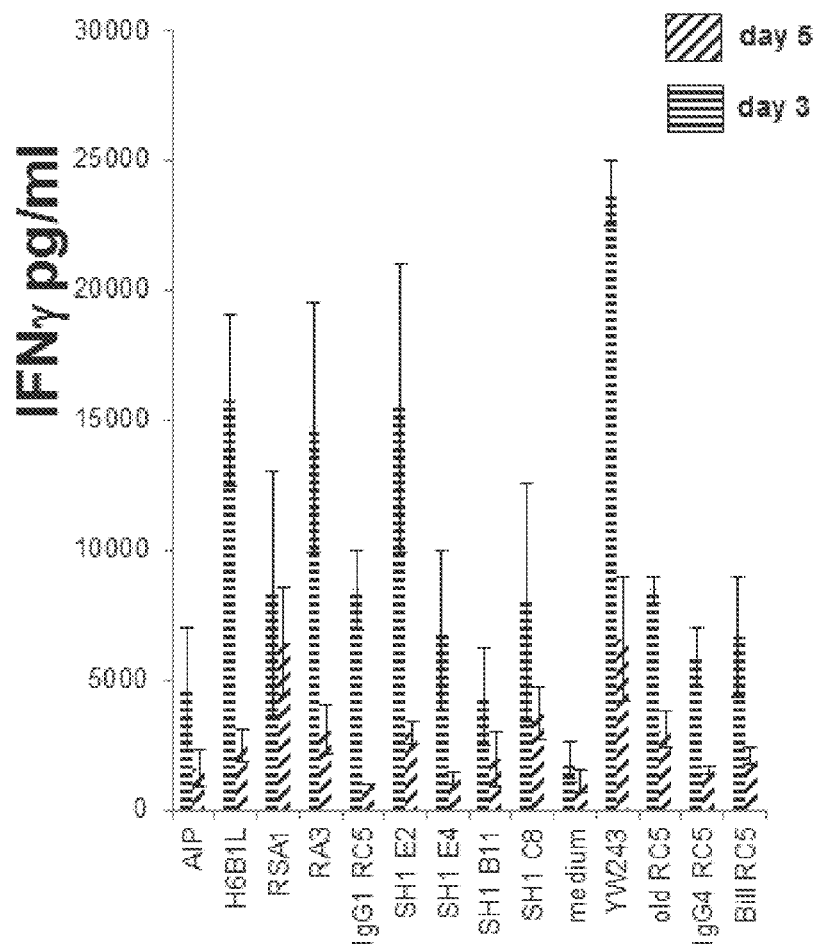
FIG. 15 shows a mixed lymphocyte reaction (MLR) was employed to demonstrate the effect of blocking the PD-L1/PD-1 pathway by the listed anti-PD-L1 antibodies on lymphocyte effector cells. IFN-γ secretion was measured in the presence or absence of the anti-PD-L1 human monoclonal antibody. The antibodies used were the disclosed H6B1L, RSA1, RA3, RC5, SH1E2, SH1E4, SH1B11, and SH1C8 as compared to prior disclosed antibodies 10A5 (Bristol-Myers-Squibb/Medarex) and YW243.55S70 (Roche/Genentech) that were obtained via in-house production from prior-disclosed antibody sequences (U.S. Patent Application 2009/0055944 and U.S. Patent Application US 2010/0203056; the disclosure of which are incorporated by reference herein).

The results for cell activation are shown in FIG. 13. With all anti-PD-L1 antibodies there was an increase in cell activation. In FIG. 13, the data are expressed as a percentage of test value with of the respect to that obtained in the absence of any added antibody. In this way, the percent increase in cell activation was realized.

Example 14

The ability of anti-PD-L1 antibodies to modulate immune responsiveness was assessed using a mixed lymphocyte reaction (MLR). With this assay, the effects anti-PD-L1 antibodies on cell activation and the production of IL-2 were measured. The MLR was performed by culturing $10^5$ purified human CD4+ cells from one donor with $10^4$ monocyte derived dendritic cells prepared from another donor. To prepare the dendritic cells, purified monocytes were cultured with GM-CSF (1,000 U/ml) and IL-4 (500 U/ml) for seven days. Anti-PD-L1 or control antibodies were added to the allogeneic MLR cultures at 10 μg/ml unless stated otherwise. Parallel plates were set up to allow collection of supernatants at day 3 and at day 5 to measure IL-2 using a commercial ELISA kit (Biolegend). The antibodies used were the disclosed H6B1L, RSA1, RA3, RC5, SH1E2, SH1E4, SH1B11, and SH1C8 as compared to prior disclosed antibodies 10A5 (Bristol-Myers-Squibb/Medarex) and YW243.55S70 (Roche/Genentech) that were obtained via in-house production from prior-disclosed antibody sequences (U.S. Patent Application 2009/0055944 and U.S. Patent Application US 2010/0203056; the disclosure of which are incorporated by reference herein).

Production of IL-2 was enhanced by the addition of the anti-PD-L1 antibodies.

Example 15

Figure 11:
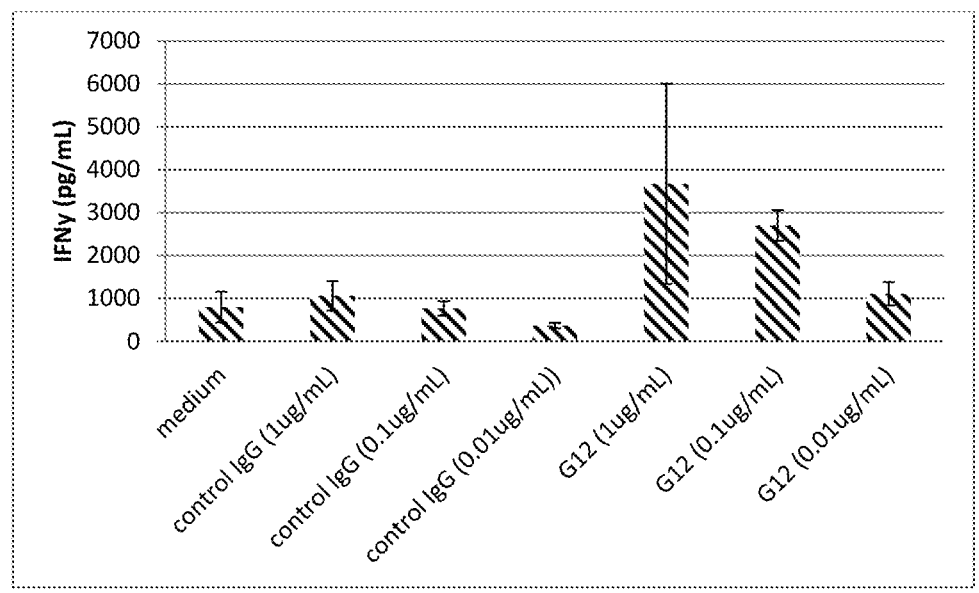
FIG. 11 shows a mixed lymphocyte reaction (MLR) was employed to demonstrate the effect of blocking the PD-L1/PD-1 pathway by the listed anti-PD-L1 antibodies on lymphocyte effector cells. IFN-γ secretion was measured in the presence or absence of the anti-PD-L1 human monoclonal antibody. The antibodies used were the disclosed G12 antibody as compared to prior disclosed antibody 10A5 (Bristol-Myers/Medarex) that was obtained via in-house production from prior-disclosed antibody sequences (see U.S. Patent Application 2009/0055944, the disclosure of which is incorporated by reference herein).

This example provides a mixed lymphocyte reaction (MLR) was employed to demonstrate the effect of blocking the PD-L1/PD-1 pathway by the anti-PD-L1 antibodies on lymphocyte effector cells. IFN-γ secretion was measured in the presence or absence of the anti-PD-L1 human monoclonal antibody (FIG. 11). The functional activity of the antibodies was assessed in an allogeneic mixed lymphocyte reaction (MLR) consisting of purified CD4+ T lymphocytes and allogeneic dendritic cells. The antibodies used were the disclosed H6B1L, RSA1, RA3, RC5, SH1E2, SH1E4, SH1B11, and SH1C8 as compared to prior disclosed antibodies 10A5 (Bristol-Myers-Squibb/Medarex) and YW243.55S70 (Roche/Genentech) that were obtained via in-house production from prior-disclosed antibody sequences (U.S. Patent Application 2009/0055944 and U.S. Patent Application US 2010/0203056; the disclosure of which are incorporated by reference herein).

To prepare the dendritic cells, monocytes, purified using a discontinuous Percoll gradient, were cultured with GM-CSF (1,000 U/ml) plus IL-4 (500 U/ml) for seven days. The CD4+ cells were prepared by negative selection using biotinylated antibodies reactive with CD8, CD16, CD19 and CD20. Removal of the reactive cells was achieved using biotin binding magnetic beads. The antibodies were added at the indicated concentrations to wells containing $10^5$ CD4+ cells labeled with carboxyfluorecein (CFSE) and $10^4$ dendritic cells. After five days of culture, supernatants were harvested for cytokine determination.

Production of IFN-γ was enhanced by the addition of the anti-PD-L1 antibodies.

Sequence Listing

| | Heavy chain variable domain region | Light chain variable domain region |
|---|---|---|
| E6 | QMQLVQSGAEVKKPGSSVKVSC KASGGTFNTYAIS WVRQAPGQGLEWMGGIIPLFGKADYAQKFQDRVTIT ADESTSTAYMELSSLRSEDTAVYYCARDKGREELGG NYYYAVDVWGPGTTVTVSS SEQ ID NO. 1 | DIVMTQTPYSVSASVGDRVTITCRASQEVSR WVAWYQQKPGQAPKSLIYASSRLQSGVPSRF TASGSGTDFTLVISSLQPEDFATYYCQQYSR FPLTFGGGTKVEIK SEQ ID NO. 2 |
| E7 | QVQLQQLGPGLVKPSQTLSLTCAISGDSVSSNSAAW NWIRQSPSRGLEWLGRTYYRSKWYTNYAVSMRSRIT INPDTSKNQFSLQLNSVTPEDTAVYFCAGGNSSSHD DYWGQGTLVTVSS SEQ ID NO. 3 | QPVLTQPASVSGSPGQSITISCTGTSSDVGG YNYVSWYQQHPGKAPKLMVYDVSKRPSGVSN RFSGSKSGNTASLTISGLQTEDEADYYCSSY TSSNTRVFGTGTKLTVL SEQ ID NO. 4 |
| E9 | EVQLVQSGAEVKKPGASVKVSCKASGYTFTSYGISW VRQAPGQGLEWMGWISAYNGNTNYAQKLQGRVTMTT DTSTSTAYMELRSLRSDDTAVYYCARDLFPTIFWEG GAFDIWGQGTMVTVSS SEQ ID NO. 5 | DIVMTQSPSTLSASVGDRVTITCRASQSFTT YLAWYQQKPGKAPKLLIYQTSNLESGVPSRF SGSGSGTEFTLTISSLQPDDFATYYCQQYSR YWWSFGQGTRLEIK SEQ ID NO. 6 |
| E11 | EVQLVQSGAEVKKPGASLKVSCKASGYTFNSYDINW VRQAPGQGLEWMGWINPNSGGTNYAQKFQGRVTMTR DTSTSTVYMELSSLTSEDTAVYYCARDLFPHIYGNY YGMDIWGQGTTVTVSS SEQ ID NO. 7 | AIQMTQSPSSLSASVGDRVTITCRASQSISS YLNWYQQKPGKAPKLLIYAASSLQSGVPSRF SGSGSGTDFTLTISSLQPEDFATYYCQQSSS TPLTFGQGTKVEIK SEQ ID NO. 8 |
| F1 | QVQLVESGGGVVQPGRSLRLSCAASGFTFSSYAMHW VRQAPGKGLEWVAVISFDGSNKYYADSVRGRFTISR DNSKNTLYLQMNSLRTEDTAVYYCARGWLDRDIDYW GQGTLVTVSS SEQ ID NO. 9 | QAVLTQPRSVSGSPGQSVTISCTGTSSDVGG YNYVSWYQQHPGKAPKLMIYDVRTRPSGVSD RFSGSKSGNTASLSISGLQAEDEADYYCSSH SSSTTVIFGGGTKLTVL SEQ ID NO. 10 |
| F4 | EVQLVQSGAEVKKPGASVKVSCKASGYTFTGYYMHW VRQAPGQGLEWMGWINPNSDNTGSAQKFQGRVFMTK | DIVMTQSPSSLSASVGDRVTITCRASQSISS YLNWYQQKPGKAPKLLIYAASSLQSGVPSRF |

| | Heavy chain variable domain region | Light chain variable domain region |
|---|---|---|
| | TTSLNTAYMELSGLRSEDTAIYYCARERSSGYFDFW GQGTLVTVSS SEQ ID NO. 11 | SGSGSGTDFTLTISSLQPEDFATYYCQQSYS TPITFGQGTRLEIK SEQ ID NO. 12 |
| F7 | EVQLVESGGGVVQPGRSLRLSCAASGFTFSSYWMSW VRQAPGKGLEWVANIKQDGSEKYYVDSVKGRFTISR DNAKNSLYLQMNSLRAEDTAVYYCAREGEHDAFDIW GQGTMVTVSS SEQ ID NO. 13 | QAVLTQPPSVSAAPGQRVTISCSGSNSNIAD TYVSWYQQLPGTAPRLLIYDNDQRPSGIPDR FSGSKSGTSATLGITGLQTGDEADYYCGTWD SSLSGVFGTGTKVTVL SEQ ID NO. 14 |
| F8 | QVQLVQSGGGVVQPGRSPRLSCAASGFTFNTYGMHW VRQAPGKGLEWVAVISDGGNNKKYADSVKGRFTISR DNAKNSLYLQMNSLRAEDTALYYCAKDIGESYYYM DVWGKGTTVTVSS SEQ ID NO. 15 | QSVLTQPASVSGSPGQSVTISCTGTSSDVGG FNSVSWYQQHPGKAPKLMIYDVSKRPSEISD RFSGSKSGNTASLTISGLQPEDEADYYCSSY TSSSTLVFGGGTKLTVL SEQ ID NO. 16 |
| F11 | QVQLQQSGPGLVKPSQSLSLTCAISGDSLSSNSAAW NWIRQSPSGGLEWLGRTYYRSKWYNEYVESLKSRIT INSDISRNQFSLHLNSVTPEDTAVYYCASGTGARGM DVWGQGTTVTVSS SEQ ID NO. 17 | SYVLTQPPSVSVSPGQTASISCSGYKLENKY VSWYQQRAGQSPVLVIYQDNKRPSGIPERFS GSNSGNTASLTITGLQPEDEADYYCSAWDSS LRAWVFGGGTQLTVL SEQ ID NO. 18 |
| G4 | QVQLQQSGPGLVKPSETLSLTCAISGDSVSENSAAW NWIRQSPSGGLEWLGRTYYRSKWYNEYVESLKSRIT INSDISRNQFSLHLNSVTPEDTAVYYCASGTGARGM DVWGQGTTVTVSS SEQ ID NO. 19 | QPVLTQPPSVSVSPGQTASITCSGDELGNKY VYWYQQKPGRSPVLVIYQDSKRPSGFPARFS GANSGNTATLTISGTQAMDEADYFCQAWDSS TAWVFGGGTKLTVL SEQ ID NO. 20 |
| G9 | EVQLVQSGAEVKKPGASVKVSCKASGYTFTGYYMHW VRQAPGQGLEWMGWINPNSDNTGSAQKFQGRVFMTK TTSLNTAYMELSGLRSEDTAIYYCARERSSGYFDFW GQGTLVTVSS SEQ ID NO. 21 | DIVMTQSPSSLSASVGDRVTITCRASQSISS YLNWYQQKPGKAPKLLIYAASSLQSGVPSRF SGSGSGTDFTLTISSLQPEDFATYYCQQSYS TPITFGQGTRLEIK SEQ ID NO. 22 |
| G11 | QVQLVQSGAEVKKPGSSVKVSCKASGGTFSRYGVHW VRQAPGQGLEWMGRLIPIVSMTNYAQKFQDRVSITT DKSTGTAYMELRSLTSEDTALYYCASVGQQLPWVFF AWGQGTLVTVSS SEQ ID NO. 23 | LPVLTQPASVSGSPGQSVTISCTGTSSDVGG HNYVSWYQQHPGKAPKLMIYEVNKRPSGVPD RFSGSKSDYTASLTISGLQPDDEADYFCSSY TATTTGVVFGTGTKVTVL SEQ ID NO. 24 |
| G12 | EVQLVQSGAEVKKPGASVKVSCKASGYTFTGYYMHW VRQAPGQGLEWMGWINPNSDNTGSAQKFQGRVFMTK TTSLNTAYMELSGLRSEDTAIYYCARERSSGYFDFW GQGTLVTVSS SEQ ID NO. 25 | DIVMTQSPSSLSASVGDRVTITCRASQSISS YLNWYQQKPGKAPKLLIYAASSLQSGVPSRF SGSGSGTDFTLTISSLQPEDFATYYCQQSYS TPITFGQGTRLEIK SEQ ID NO. 26 |
| H1 | QVQLVQSGAEVKKPGASVKVSCKTSGNTFTNYYMHW VRQAPGQGLEWMGIMNPSGGSTSYAQKFQGRVTMTR DKSTSTVYMELSSLTSEDTAVYYCARDLFPHIYGNY YGMDIWGQGTTVTVSS SEQ ID NO. 27 | DIVMTQSPPSLSASVGDRVTITCRASQSISS YLNWYQQKPGKAPKLLIYAASSLQSGVPSRF SGSGSGTDFTLTISSLQPEDFATYYCQQSYS TPYTFGQGTKVEIK SEQ ID NO. 28 |
| H3 | QVQLVQSGAEVKKPGSSVKVSCKASGGTFSSYAISW VRQAPGQGLEWMGGIIPIFGTASYAQKFQGRVTITA DESTTTAYMELSSLRSEDTAVYYCAREGPEYCSGGT CYSADAFDIWGQGTMVTVSS SEQ ID NO. 29 | QSVVTQPPSVSAAPGQKVTISCSGSTSNIEN YSVSWYQQLPGTAPKLLIYDNNKRPSGIPDR FSGSKSGTSATLGITGLQTGDEADYYCGTWD NRLSSVVFGGGTKVTVL SEQ ID NO. 30 |
| H4 | QVQLVQSGAEVKKPGSSVKVSCKASGGTFSSYAISW VRQAPGQGLEWMGRIIPILGIANYAQKFQGRVTITA DKSTSTAYMELSSLRSEDTAVYYCARSESGSYSHDY WGQGTTVTVSS SEQ ID NO. 31 | QPVLTQPPSVSAAPGQKVTISCSGSSSNIGN SHVSWFQQLPGTAPKLVIYDNDKRPSGIADR FSGSKSGTSATLGITGLQTGDEADYYCGTWD SSLSAGVFGGGTKLTVL SEQ ID NO. 32 |
| H5 | QVQLVESGAEVKKPGASVKVSCKASGYTFTSYYIHW VRQAPGQGLEWMGIINPSGGSTTYAQKFQGRVSMTR DTSTRTVYMELSGLISDDTAIYYCARDDDFYSGYPG DYWGQGTLVTVSS SEQ ID NO. 33 | QAVVTQPPSASGTPGQRVTISCSGSSSNVGV NHVFWYQHLPGMAPKLLIHRTNQWPSGVPDR FSGSKSGTSATLGITGLQTGDEADYYCGTWD SSLSAVFGGGTKLTVL SEQ ID NO. 34 |
| H6 | QMQLVQSGAEVKKPGSSVKVSCKASGGTFSSYAISW VRQAPGQGLEWMGGIIPIFGTANYAQKFQGRVTITA DESTSTAYMELSSLRSEDTAVYYCARGNIVATITPL DYWGQGTLVTVSS SEQ ID NO. 35 | SYELMQPPSVSVAPGKTATIACGGENIGRKT VHWYQQKPGQAPVLVIYYDSDRPSGIPERFS GSNSGNTATLTISRVEAGDEADYYCQVWDSS SDHRIFGGGTKLTVL SEQ ID NO. 36 |

Sequence Listing

| | Heavy chain variable domain region | Light chain variable domain region |
|---|---|---|
| H10 | EVQLVQSGGGLVQPGGSLRLSCAASGFTFSSYSMNW VRQAPGKGLEWVSYISSSSSTIYYADSVKGRFTISR DNAKNSLYLQMNSLRDEDTAVYYCARGDYYYGMDVW GQGTTVTVSS<br>SEQ ID NO. 37 | EIVLTQSPSSLSASIGDRVTLTCRASQSIRR FLNWYQQKPGKAPELLIYTASSLQSGVPSRF SGSGSGTDFTLTINSLQPEDFATYYCQQSYA VSPYTFGQGTKVEIR<br>SEQ ID NO. 38 |
| H12 | QMQLVQSGAEVKKPGSSVKVSCKASGGTFSSYAISW VRQAPGQGLEWMGGIIPIFGTANYAQKFQGRVTITA DESTSTAYMELSSLRSEDTAVYYCARGDFWSGYRTY YYYYGMDVWGQGTMVTVSS<br>SEQ ID NO. 39 | QSVVTQPPSVSAAPGQKVTISCSGSSSNIGN NYVSWYQQLPGTAPKLLIYDNNKRPSGIPDR FSGSKSGTSATLGITGLQTGDEADYYCGTWD SSLSAVVFGGGTKLTVL<br>SEQ ID NO. 40 |
| PDL-D2 | QVQLVQSGAEVKKPGASVKVSCKTSGYTFTSNAIGW VRQAPGQGLEWMGWISAYNGNTNYAQNLQGRVTMTT DTSTSTAYMELRSLRSDDTAVFYCARKGTGLHFDYW GQGTLVTVSS<br>SEQ ID NO. 41 | ALTQPASVSGSLGQSITISCTGSSSDVGGYK YVSWYQQHPGKAPKLMIYDVINRPSGVSSRF SGSKSANTASLTISGLQAEDEADYYCFSYSS RSTRIFGSGTKVTVL<br>SEQ ID NO. 42 |
| PDL-D11 | QVQLQQSGPGLVKPSQTLSLTCAISGDSVSSNSAAW NWIRQSPSRGLEWLGRTYYRSKWYNDYAVSVKSRIT INPDTSKNQFSLQLNSVTPEDTAVYYCARGAAGRAF DIWGQGTMVTVSS<br>SEQ ID NO. 43 | QTVVTQPPSVSKDLGQTATLTCTGNNNNVGN HGAAWLQQHQGHPPKLLSYRNNNRPSGISER LSASRSGNTASLTITGLQPEDEADYYCSAWD RSLSAWVFGGGTKLTVL<br>SEQ ID NO. 44 |
| PDL-H1 | EVQLVQSGGGLVQPGGSLRLSCAASGFTFSSYSMNW VRQAPGKGLEWVSYISSSSSTIYYADSVKGRFTISR DNAKNSLYLQMNSLRDEDTAVYYCARGDYYYGMDVW GQGTTVTVSS<br>SEQ ID NO. 45 | EIVLTQSPSSLSASIGDRVTLTCRASQSIRR FLNWYQQKPGKAPELLIYTASSLQSGVPSRF SGSGSGTDFTLTINSLQPEDFATYYCQQSYA VSPYTFGQGTKVEIK<br>SEQ ID NO. 46 |
| RB4 | EVQLVESGGGLVQPGGSLRLSCAASGFYLGSYWMAW VRQAPGKGLEWVAAIRQDGSETIYVDSVKGRFIISR DNGGNSVTLQMTTLRAGDTAVYYCARAHYFGFDNWG QGTLVTVSS<br>SEQ ID NO. 47 | QSVLTQPASVSGSPGQSISVSCTGTSSDVGR YNFVSWYQQHPGKAPKLMVFDVSNRPSGISN RFSGSKSGNTASLTISGLQAEDEADYYCSSY TTNSTYVFGSGTKVTVL<br>SEQ ID NO. 48 |
| RB11 | QMQLVQSGAEVKKPGASVKISCKASGYPFRNYYIHW VRQAPGQGLEWVGIINPDGGTITYAGKFQGRVSMTR DTSTSTVYMELSSLTSEDTAVYYCARDLFPHIYGNY YGMDIWGQGTTVTVSS<br>SEQ ID NO. 49 | QPVLTQPPSVSAAPGQKVTISCSGSSSNIAN NYVSWYQQLPGTAPKLLIFANNKRPSGIPDR FSGSKSGTSAALDITGLQTGDEADYYCGTWD SDLRAGVFGGGTKLTVL<br>SEQ ID NO. 50 |
| RC5 | EVQLLESGGGVVQPGGSLRLSCAASGFTFSSYWMSW VRQAPGKGLEWVANIKQDGSEKYYVDSVKGRFTISR DNSKNTVSLQMNSLRAEDTAVYYCAKDRYYNFPLGM DVWGQGTTVTVSS<br>SEQ ID NO. 51 | AIRMTQSPSSLSASVGDRVTITCRASQSISS YLNWYQQKPGKAPLLIYTTSSLKSGVPSRF SGSGSGTDFTLTISRLQPEDFATYYCQQSYS STWTFGRGTKVEIK<br>SEQ ID NO. 52 |
| RF5 | EVQLLESGAEVKKPGSSVKVSCKSSGDTFTNFAINW IRQAPGQGLEWMGRIIPLFGTTNYAQKFQGRVTITA DESTSTAFMDLNSLTSEDTAVYYCARTLGGDYYDSR GYYNWGQGTLVTVSS<br>SEQ ID NO. 53 | QSVLTQPASVSGSPGQSITISCTGTSSDVGS YNLVSWYQQYPGKAPKLMIYEVSERPSGVPD RFSGSKSGNTASLTVSGLQAEDEADYYCSSY TDSNNFRVFGGGTKLTVL<br>SEQ ID NO. 54 |
| RG9 | QVQLQQSGPGLVKPSQTLSLTCAISGDSVSSNSVVW NWFRQSPSRGLEWLGRAYYRSKWYNDYAVSVKSRIT INPDTSKNQLSLQLNSVTPEDTAVYYCAKGLDVWGQ GTTVTVSS<br>SEQ ID NO. 55 | EIVMTQSPSSLYASVGDRVTITCRASQSISS YLNWYQQKPGKVPKLLIYAASSLQSGVPSRF SGSGSGTDFTLTISGLQPEDFATYYCQQSYT PAWTFGQGTKLEIK<br>SEQ ID NO. 56 |
| RD1 | QVQLVQSGAEVKKPGSSVKVSCKASGGTFSSYAISW VRQAPGQGLEWMGGIIPIFGTANYAQKFQGRVTITA DESTSTAYMELSSLRSEDTAVYYCARDGIVADFQHW GQGTLVTVSS<br>SEQ ID NO. 57 | QSVVTQPPSVSAAPGQKVTISCSGSSSNIGN NYVSWYQQVPGTAPKLLIYDNDKRPSGIPDR FSGSKSGTSATLAITGLQTGDEADYYCGTWD SSLNAWVFGGGTKLTVL<br>SEQ ID NO. 58 |
| RF11 | QVQLVQSGAEVKKPGASVRVSCKASGGTFSSYAISW VRQAPGQGLEWMGGIIPIFGTANYAQKFQGRVTITA DESTSTAYMELSSLRSEDTAVYYCARDGIVADFQHW GQGTLVTVSS<br>SEQ ID NO. 59 | QSVLTQPPSVSAAPGQKVTISCSGSSSNIEN NYVSWYQHLPGTAPKLLIYDDFKRPSGIPDR FSGSKSGTSATLGITGLQTGDEADYYCGTWD SSLSAVVFGGGTKLTVL<br>SEQ ID NO. 60 |
| RH11 | QMQLVQSGAEVKKPGSSVKVSCKASGGTFNSYPISW VRQAPGQGLEWMGGIIPIFGTANYAQKFQGRVTITA | QSVLTQPPSASGSPGQSVTISCTGTSSDVGG YNYVSWYQQHPGKAPKLMIYEVSKRPSGVPD |

| | Heavy chain variable domain region | Light chain variable domain region |
|---|---|---|
| | DESTSTAYMELSSLRSEDTAMYYCAKNHPTATLDYW GQGTLVTVSS SEQ ID NO. 61 | RFSGSKSGNTASLTVSGLQAEDEADYYCSSY AGSNNLGVFGGGTKLTVL SEQ ID NO. 62 |
| RD9 | QVQLVQSGGNLVKPGGSLRLSCAASGFSFSSYDMNW VRQAPGRGLEWVSSISGTGRYEYYSPSVKGRFTISR DNANTSLYLQMNSLTADDTAVYFCTRGDILTGASAM DVWGQGTTVTVSS SEQ ID NO. 63 | DIQLTQSPSSLSASVGDRVTITCRASQGISS WLAWYQQKPGKAPKLLIYAASSLQSGVPSRF SGSGSGTDFTLTISSLQPEDFATYYCQQANS FPLTFGGGTKVEIK SEQ ID NO. 64 |
| RE10 | EVQLLESGGNLVKPGGSLRLSCAASGFSFSSYDMNW VRQAPGRGLEWVSSISGTGRYEYYSPSVKGRFTISR DNANTSLYLQMNSLTADDTAVYFCTRGDILTGASAM DVWGQGTTVTVSS SEQ ID NO. 65 | DVVMTQSPSTLSASVGDRVTITCRASQSIGT WLAWYQQKPGKAPNLLIYKASSLESGVPSRF SGSGSGTEFTLTISSLQPDDFATYYCQQANS FPLTFGGGTKVEIK SEQ ID NO. 66 |
| RA3 | QMQLVQSGAEVKKPGSSVKVSCKASGGTFSRYGVHW VRQAPGQGLEWMGRLIPIVSMTNYAQKFQDRVSITT DKSTGTAYMELRSLTSEDTALYYCASVGQQLPWVFF AWGQGTLVTVSS SEQ ID NO. 67 | DIQMTQSPSSLSASVGDRVTITCQASQDISN YLNWYQQKPGKAPKLLIYDASTLQSGVPSRF SGSGSGTDFTLTISSLQPEDFATYYCQQSYS SHWTFGQGTKVEIK SEQ ID NO. 68 |
| RG1 | EVQLVQSGAEVKKPGSSVKVSCKASGGTFSRYGVHW VRQAPGQGLEWMGRLIPIVSMTNYAQKFQDRVSITT DKSTGTAYMELRSLTSEDTALYYCASVGQQLPWVFF AWGQGTLVTVSS SEQ ID NO. 69 | QSVVTQPPSVSGAPGQRVTISCTGSSSNIGA GYGVHWYQHLPGSAPKLLIYGNSNRPSGVTD RISGSKSGTSASLAITGLQAEDEAVYYCQSY DSSLSTSVVFGGGTKLTVL SEQ ID NO. 70 |
| RB1 | QMQLVQSGGGLIQPGGSLRLSCAASGFTFSSYAMHW VRQAPGKGLEWVAVISFDGSNKYYADSVRGRFTISR DNSKNTLYLQMNSLRTEDTAVYYCARGWLDRDIDYW GQGTLVTVSS SEQ ID NO. 71 | QAGLTQPASVSGSPGQSITISCTGTSSDVGG YNYVSWYQQHPGKAPKLMIYDVTKRPSGVSN RFSGSKSGNTASLTISGLQAEDEANYYCSSY TSRSTSVLFGGGTKLTVL SEQ ID NO. 72 |
| RG7 | EVQLVESGGGVVLPGRSLRLSCAASGFTFSSYAMHW VRQAPGKGLEWVAVISFDGSNKYYADSVRGRFTISR DNSKNTLYLQMNSLRTEDTAVYYCARGWLDRDIDYW GQGTLVTVSS SEQ ID NO. 73 | QPVLTQPPSVSEAPRQRVTISCSGSSSNIGH NAVTWYQQVPGKAPKLLIYYDDLLPSGVSDR FSGSKSGTSASLAISGLQSEDEADYYCAAWD DSLNGWVFGGGTKLTVL SEQ ID NO. 74 |
| RA6 | QVQLVESGGGVVQPGRSLRLSCAASGFTFSSYAMHW VRQAPGKGLEWVAVISFDGSNKYYADSVRGRFTISR DNSKNTLYLQMNSLRTEDTAVYYCARGWLDRDIDYW GQGTLVTVSS SEQ ID NO. 75 | QAGLTQPASVSGSPGQSITISCTGTSSDVGG YNYVSWYQQHPGKAPKLMIYDVSNRPSGVPD RFSGSKSGNTASLTISGLQAEDDADYYCASY TSTSTLGVVFGGGTKLTVL SEQ ID NO. 76 |
| RA8 | QVQLVESGGGVVQPGRSLRLSCAASGFTFSSYAMHW VRQAPGKGLEWVAVISFDGSNKYYADSVRGRFTISR DNSKNTLYLQMNSLRTEDTAVYYCARGWLDRDIDYW GQGTLVTVSS SEQ ID NO. 77 | QPVLTQPASVSGSPGQSITISCTGTSSDVGG YNYVSWYQHHPGKAPKLMIFDVNKRPSGVSN RFSGSKSGNTASLTISGLQAEDEADYYCNSY TTSSTYVVFGGGTKLTVL SEQ ID NO. 78 |
| RA9 | QVQLVESGGGVVQPGRSLRLSCAASGFTFSSYAMHW VRQAPGKGLEWVAVISFDGSNKYYADSVRGRFTISR DNSKNTLYLQMNSLRTEDTAVYYCARGWLDRDIDYW GQGTLVTVSS SEQ ID NO. 79 | QSVLTQPPSASGTPGQRVTISCSGSSSNIGS NTVHWYQQLPGTAPKVLIYTNNQRPSGVPDR FSGSKSGTSASLAISGLQSEDEADYYCAAWD GRLQGWVFGGGTKLTVL SEQ ID NO. 80 |
| RB5 | QVQLVESGGGVVQPGRSLRLSCAASGFTFSSYAMHW VRQAPGKGLEWVAVISFDGSNKYYADSVRGRFTISR DNSKNTLYLQMNSLRTEDTAVYYCARGWLDRDIDYW GQGTLVTVSS SEQ ID NO. 81 | QSVVTQPPSVSAAPGQKVTISCSGSNSNIAN NYVSWYQQLPGTAPKLLIYDSNKRPSGIPDR FSGSKSGTSATLGITGLQTGDEADYYCGSWD SSLSVWMFGGGTKLTVL SEQ ID NO. 82 |
| RB8 | QVQLVESGGGVVQPGRSLRLSCAASGFTFSSYAMHW VRQAPGKGLEWVAVISFDGSNKYYADSVRGRFTISR DNSKNTLYLQMNSLRTEDTAVYYCARGWLDRDIDYW GQGTLVTVSS SEQ ID NO. 83 | LPVLTQPRSVSGSPGQSVTISCTGTSSDVGG YNYVSWYQQHPGKAPKLMIYDVTKRPSGVPD RFSGSKSGNTASLTISGLQAEDEADYYCSSY TGSSTLGPVFGGGTKLTVL SEQ ID NO. 84 |
| RC8 | EVQLVESGGGVVQPGRSLRLSCAASGFTFSSYAMHW VRQAPGKGLEWVAVISFDGSNKYYADSVRGRFTISR DNSKNTLYLQMNSLRTEDTAVYYCARGWLDRDIDYW GQGTLVTVSS SEQ ID NO. 85 | QSVLTQPPSVSAAPGQKVTISCSGNSSIGN NYVSWYQQLPGTAPKLLIYDNKRPSGIPDR FSGSKSGTSASLAISELRFEDEADYYCAAWD DTLSGHVFGPGTKLTVL SEQ ID NO. 86 |

| | Heavy chain variable domain region | Light chain variable domain region |
|---|---|---|
| RC10 | EVQLVESGGGVVQPGRSLRLSCAASGFTFSSYAMHW VRQAPGKGLEWVAVISFDGSNKYYADSVRGRFTISR DNSKNTLYLQMNSLRTEDTAVYYCARGWLDRDIDYW GQGTLVTVSS<br>SEQ ID NO. 87 | SYELMQPPSVSVPPGETARITCGGNNIGNKN VHWYQQKPGQAPVLVVREDSARPAGIPERFS GSNSGNSATLTISRVEAGDEADYYCQVWDNT SDHVVFGGGTKLTVL<br>SEQ ID NO. 88 |
| RD2 | QVQLVESGGGVVQPGRSLRLSCAASGFTFSSYAMHW VRQAPGKGLEWVAVISFDGSNKYYADSVRGRFTISR DNSKNTLYLQMNSLRTEDTAVYYCARGWLDRDIDYW GQGTLVTVSS<br>SEQ ID NO. 89 | SYELMQPPSVSEVPGQRVTISCSGSSSNIGN NAVNWFQQLPGKAPKLLVYYDDWVPSGISGR FSASKSGTSASLAISGLQSGDEGDYYCAVWD DRLSGVVFGGGTKLTVL<br>SEQ ID NO. 90 |
| RE8 | QVQLVESGGGVVQPGRSLRLSCAASGFTFSSYAMHW VRQAPGKGLEWVAVISFDGSNKYYADSVRGRFTISR DNSKNTLYLQMNSLRTEDTAVYYCARGWLDRDIDYW GQGTLVTVSS<br>SEQ ID NO. 91 | QSVVTQPPSVSAAPGQKVTISCSGSSSNIGN NYVSWYQQLPGTAPTLLIYDSNKRPSVIPDR FSGSKSGTSATLGITGLQTGDEADYYCGTWD DSLNGWVFGGGTKLTVL<br>SEQ ID NO. 92 |
| RE9 | EVQLVESGGGVVQPGRSLRLSCAASGFTFSSYAMHW VRQAPGKGLEWVAVISFDGSNKYYADSVRGRFTISR DNSKNTLYLQMNSLRTEDTAVYYCARGWLDRDIDYW GQGTMVTVSS<br>SEQ ID NO. 93 | QSALTQPASVSGSPGQSITISCTGTSSDVGG YNYVSWYQQHPGKAPKLMIYDVSNRPSGVSN RFSGSKSGNTASLTISGLQAEDEADYYCSSY RSSTLGPVFGGGTKLTVL<br>SEQ ID NO. 94 |
| RG12 | QVQLVESGGGVVQPGRSLRLSCAASGFTFSSYAMHW VRQAPGKGLEWVAVISFDGSNKYYADSVRGRFTISR DNSKNTLYLQMNSLRTEDTAVYYCARGWLDRDIDYW GQGTLVTVSS<br>SEQ ID NO. 95 | QAGLTQPPSASGSPGQSVTISCTGTSSDVGG YNYVSWYQQHPGKAPKLMIYDVSNRPSGVPD RFSGSKSGNTASLTISGLQAEDEADYYCSSY TSSSTLVVFGGGTKLTVL<br>SEQ ID NO. 96 |
| RSA1 | EVQLVQGGGGLVQPGGSLRLSCAASGFTFSSYSMNW VRQAPGKGLEWVSYISSSSSTIYYADSVKGRFTISR DNAKNSLYLQMNSLRDEDTAVYYCARGDYYYGMDVW GQGTTVTVSS<br>SEQ ID NO. 97 | NIQMTQSPSSVSASVGDRVTITCRASQDISR WLAWYQQKPGKAPKLLIYAASSLQSGVPSRF SGSGSGTDFALTISSLQPEDFATYYCQQADS FFSITFGQGTRLEIK<br>SEQ ID NO. 98 |
| R2A7 | QVQLVQSGSEVKKPGASVKVSCRASGYLFTNYGISW VRQAPGQGLEWMGWVSAHGEFTKYAPSLQDRVTMTS DISTTTAYMELRSLRSDDAGVYYCARDRGADHFDTW GQGTLVTVSS<br>SEQ ID NO. 99 | AIQLTQSPATLSLSPGERATLSCRASQSVGV YLAWYQQKPGQSPRLLIYDTSKRATGIPDRF SASGSGTDFTLTISRLEPEDFAVYYCHQRHS WPTTFGQGTRLEIK<br>SEQ ID NO. 100 |
| R2B12 | EVQLVQSGAEVKKPGASVKVSCKASGYTFTSYYMHW VRQAPGQGLEWMGMINPSSATTTYTQKFQGRVSMTR DTSTSTVYMELSSLTSEDTAVYYCARDLFPHIYGNY YGMDIWGQGTTVTVSS<br>SEQ ID NO. 101 | NIQMTQSPSSLSASVGDRVTITCRASQSISS YLNWYQQKPGKAPKLLIYAASSLQSGVPSRF SGSGSGTDFTLTISSLQPEDFATYYCQQSYS TLTFGGGTKVEIK<br>SEQ ID NO. 102 |
| R2C9 | EVQLVQSGAEVKKPGSSVKVSCKASGGTFSSHVISW VRQAPGQGLEWMGGIIPIFGTANYAQKFQGRVTITA DESTSTAYMELSSMRSEDTAVYYCATSGVVAATHFG YWGQGTLVTVSS<br>SEQ ID NO. 103 | QSVLTQPASVSGSPGQSITISCTGTSSDVGD YNLVSWYQQHPGKAPKLIIYEVNKRPSGVSN RFSGSKSGNTASLTISGLQAEDEADYYCSSY AGYNNLYVFGTGTKVTVL<br>SEQ ID NO. 104 |
| R2D5 | QVQLVQSGAEVKKPGSSVKVSCKASGGTFSSYAISW VRQAPGQGLEWMGGIIPIFGTANYAQKFQGRVTITA DESTSTAYMELSSLRSEDTAVYYCARGASGSYFITT YVDYWGQGTLVTVSS<br>SEQ ID NO. 105 | QSALTQPPSASGSPGQSVTISCTGTSSDVGG YNYVSWYQQHPGKAPKLIIYDVNMRPSGVPD RFSGSKSGNTASLTISGLQAEDEADYYCSSY AGLYFPLFGGGTQLTVL<br>SEQ ID NO. 106 |
| R2D7 | EVQLVESGGGLVQPGGPLRLSCAASGFTLSSYWMSW VRQAPGKGLEWVANIKYDGSETYYADSVKGRFTISR DNAKNSLYLQMNRLRLEDTAVYYCAREVSSAATSPL DRWGRGTLVTVSS<br>SEQ ID NO. 107 | DIVMTQSPSSLSASVGDRVTITCRASQSISS YLNWYQQKPGKAPKLLIYAASSLQSGVPSRF SGSGSGTDFTLTISSLQPEDFATYYCQQSHS SRYTFGQGTKLEIK<br>SEQ ID NO. 108 |
| R2F4 | EVQLVQSGAEVKKPGSSVKVSCKASGGTFSRYGVHW VRQAPGQGLEWMGRLIPIVSMTNYAQKFQDRVSITT DKSTSTAYMELRSLSEDTALYYCASVGQQLPWVFF AWGQGTLVTVSS<br>SEQ ID NO. 109 | QSVVTQPPSVSGAPGQRVTISCTGSSSNIGA GYGVHWYQHLPGSAPKLLIYGNSNRPSGVTD RISGSKSGTSASLAITGLQDEAVYYCQSY DSSLSTSVVFGGGTKLTVL<br>SEQ ID NO. 110 |
| R2A10 | EVQLVESGGGVVQPGGSLRLSCAASGFTFSSYAMHW VRQAPGKGLEWVAVISFDGSNKYYADSVRGRFTISR | QSVLTQPPSASGTPGQRVTISCSGSSSNIGS NTVHWYQQLPGTAPKVLIYTNNQRPSGVPDR |

| | Heavy chain variable domain region | Light chain variable domain region |
|---|---|---|
| | DNSKNTLYLQMNSLRTEDTAVYYCARGWLDRDIDYW GQGTLVTVSS SEQ ID NO. 111 | FSGSKSGTSASLAISGLQSEDEADYYCAAWD GRLQGWVFGGGTQLTVL SEQ ID NO. 112 |
| R2E2 | EVQLVESGGGVVQPGRSLRLSCAASGFTFSSYAMHW VRQAPGKGLEWVAVISFDGSNKYYADSVRGRFTISR DNSKNTLYLQMNSLRTEDTAVYYCARGWLDRDIDYW GQGTLVTVSS SEQ ID NO. 113 | QAGLTQPPSASGTPGQRVTISCFGSSSDIGS NTVNWYQQVSGRAPKLLLYTNGQRPSGVPDR FSGSKSGSSASLAISGLQSEDEADYYCASWD DSLKGYVFGTGTKVTVL SEQ ID NO. 114 |
| R3B8 | EVQLVQSGAEVKKPGSSVKVSCKASGGTFSSYAISW VRQAPGQGLEWMGRIIPILGIANYAQKFQGRVTITA DKSTSTAYMELSSLRSEDTAVYYCARVGGGAQTPFD YWGQGTLVTVSS SEQ ID NO. 115 | QSVLTQPPSVSAAPGQKVTISCSGSSSNIGN SYVSWYQHLPGTAPKLLIYDNNKRPSGIPDR FSGSKSATSATLGITGLQTADEADYYCGTWD SSLGVVFGGGTKLTVL SEQ ID NO. 116 |
| R3C3 | QVQLVQSGSEVKRPGASVRVSCKASGYIFSQYTIHW VRQAPGERLEWLGWINAVTGNTKYAQKFQGRVTITM DSSASTAFMEMSSLRSEDAGVYFCARDMVPFGGEIK YGFDFWGQGTMITVSS SEQ ID NO. 117 | QSALTQPASVSGSPGQSITISCTGTSSDVGG YNYVSWYQQHPGKAPKLMIYNVSKRPSGVSN RFSGSKSGNTASLTISGLQAEDEADYYCSSY TSSSTFVFGTGTKVTVL SEQ ID NO. 118 |
| R3E9 | QVQLVESGGGVVQPGRSLRLSCAASGFTFSSYGMHW VRQAPGKGLEWVALISYDGSNKYYADSMKGRFTISR DNSKNTLFLQMNSLRAEDTAVYYCAKTLMPASIMGY FTHWGQGTLVTVSS SEQ ID NO. 119 | SYELMQPPSVSVAPGETARITCGGNNIGSKS VHWYQQKPGQAPILVIYYDSRPSGIPERFS GSNSGNTATLTISRAEAGDEADYYCHVWDSY TDHVVFGGGTKLTVL SEQ ID NO. 120 |
| R3E10 | QVQLVQSGAEVKKPGASVKVSCKASGYTFTSYYMHW VRQAPGQGLEWMGIINPSDGSTSYAQKFQGRVTMTR DTSTSTVYMELSSLRSEDTAVYYCARGYYGSGIAMD VWGQGTTVTVSS SEQ ID NO. 121 | QPVLTQPPSLSVAPGKTASIACGGNNIGSKR VHWYQQKPGQAPVLVIYYESDRPSGIPERFS GTISQNTATLSISRVEAGDEADYYCQVWDRS SAHVVFGGGTKVTVL SEQ ID NO. 122 |
| R3F7 | QVQLVQSGAEVKKPGSSVKVSCKASGGTFSSYAISW VRQAPGQGLEWMGGIIPIFGTANYAQKFQGRVTITA DESTSTAYMELSSLRPEDTAVYYCARDNGDLGFDYW GQGTLVTVSS SEQ ID NO. 123 | AIQMTQSPSSLSASVGDRVTITCRASQSIST YLNWYQQKPGKAPKLLIYAASSLQNGVPSRF SGSGSGTDFTLTISSLQPEDFATYYCQQSYS TPRTFGPGTKVDIK SEQ ID NO. 124 |
| R3F10 | EVQLVESGGGLIQPGGSLRLSCAASGFTVSSNYMSW VRQAPGKGLEWVSVIYSGGTIYYADSVKGRFTISRD SSKNTLYLHMNSLRAEDTGVYYCAKGVGSWSIFDYW GQGTLVTVSS SEQ ID NO. 125 | DIQMTQSPSSLSASVGDRVTITCQASQDISN YLNWYQQKPGKAPKLLIFAGSNLQSGVPSRF SGSGSGTDFTLTITSLQPEDFATYYCQQSYT TPTFGQGTKVEIK SEQ ID NO. 126 |
| R4B10 | EVQLVESGAELKKPGSSMKVSCKASGGTFSSYAISW VRQAPGQGLEYIGRIIPIFGVTYYAQKFQGRVTISA DKSTSTVYLDLRSLRSEDTAVYYCARDLGGGDGDWG QGTLVTVSS SEQ ID NO. 127 | QSVVTQPASVSGSPGQSITISCTGTSSDVGS YNLVSWYQQHPGKAPKLMIYEGSKRPSGVST RFSGSKSGNTASLTISGLQAEDESDYYCSSY TGSAWVFGGGTKLTVL SEQ ID NO. 128 |
| R4H1 | EVQLVQSGAEVKKPGSSVKVSCKASGYTFTGYYMHW VRQAPGQGLEWMGRIIPIFGTANYAQKFQGRVTITA DESTSTAYMELSSLRSEDTAVYFCVTSAWSDWGQGT LVTVSS SEQ ID NO. 129 | QSVVTQPPSVSATPGQKVTISCSGSDSNIGN NYVSWFLQLPGTAPKLLIHNNDQRPSGVPDR FSGSKSGTSASLAITGLQAEDEADYYCQSFD DSLRGYLFGTGTKVTVL SEQ ID NO. 130 |
| R4A11 | EVQLVESGGGLVQPGGSLRLSCAASGFTFSSYWMSW VRQAPGKGLEWVANIKQDGSEKYYVDSVKGRFTISR DNSKNTLYLQMNSLGAEDTAVYYCAKGFYYPDHWGQ GTLVTVSS SEQ ID NO. 131 | QAVLTQPPSVSAAPGQKVTISCSGGSSNIAN NYVSWYQHLPGTAPKLLIYDDNKRPSGIPDR FSGSKSGTSATLGITGLQTGDGADYYCGTWD NSLNSDWVFGGGTKL SEQ ID NO. 132 |
| R3D2 | EVQLVESGGGVVQPGGSLRLSCEVSGFIFSDYGMHW VRQAPGKGLEWVSSISSSSYIYYADSVKGRFTISR DNAKNSLYLQMNSLRAEDTAMYYCARSWNYGRFFDY WDQGTLVTVSS SEQ ID NO. 133 | QSVLTQPPSVSVAPGKTARITCGGNNIGSKS VHWYQQKPGQAPVLVIYYDSRPSGIPERFS GSNSGNTATLTISRVEAGDEADYYCQVWDSS SDHYVFGTGTKLTVL SEQ ID NO. 134 |
| R5B8 | EVQLVESGGGLVQPGGSLRLSCAASGFTSSRNWMHW VRLAPGKGLVWVSLIAPDGSLTTYADSVKGRFTISR DTAKNSVQLLLNSLRAEDTGLYFCAREAGVSGGLDV WGQGTLVTVSS SEQ ID NO. 135 | VIWMTQSPSSLSASVGDRVTITCRASQTISS YLNWYQQKPGKAPKLLIYAASSLQSGVPSRF SGSGSGTDFTLTISSLQPEDFATYYCQQANS FPLTFGGGTKVEIK SEQ ID NO. 136 |

-continued

Sequence Listing

| | Heavy chain variable domain region | Light chain variable domain region |
|---|---|---|
| SH1A1Q | EVQLVQSGAEVKKPGSSVKVSCKASGGTFSSYAISW VRQAPGQGLEWMGGIIPIFGTANYAQKFQGRVTITA DKSTSTAYMELSSLRSEDTAVYYCAREGTIYDSSGY SFDYWGQGTLVTVSS<br>SEQ ID NO. 137 | QSVLTQPPSVSAAPGQKVTISCSGNNSNIAN NYVSWYQQLPGTAPKLLIYDNNYRPSGIPDR FSGSKSGTSATLDITGLQTGDEADYYCGVWD GSLTTGVFGGGTKLTVL<br>SEQ ID NO. 138 |
| SH1B7B(K) | EVQLVQSGAEVKKPGSSVKVSCKASGGTFSSYAISW VRQAPGQGLEWMGIINPSGGSTSYAQKFQGRVSMTR DTSTSTVYMELSSLTSEDTAVYYCARDLFPHIYGNY YGMDIWGQGTTVTVSS<br>SEQ ID NO. 139 | AIQMTQSPSSLSASVGDRVTITCRASQGISN YLAWYQQKPGKVPKLLIYAASTLESGVPSRF SGSGSGTDFTLTISSLQPEDLATYYCQQLHT FPLTFGGGTKVEIK<br>SEQ ID NO. 140 |
| SH1C1 | QVQLVQSGAEVKKPGSSVKVSCKASGGTFSSYAISW VRQAPGQGLEWMGGIIPIFGTANYAQKFQGRVTITA DKSTSTAYMELSSLRSEDTAVYYCARLAVPGAFDIW GQGTMVTVSS<br>SEQ ID NO. 141 | QPVLTQPPSASGSPGQSVTISCTGTSSDVGA YNFVSWYRQHPGKAPKLMIYEVNKRPSGVPD RFSGSKSGNTASLTVSGLQAEDEADYYCSSY AGTNSLGIFGTGTKLTVL<br>SEQ ID NO. 142 |
| SH1C8 | EVQLVESGGGVVQPGRSLRLSCAASGFTFSSYAMHW VRQAPGKGLEWVAVISYDGSNKYYADSVKGRFTISR DNSKNTLYLQMNSLRAEDTAVYYCARGQWLVTELDY WGQGTLVTVSS<br>SEQ ID NO. 143 | QSVVTQPPSVSAAPGQKVTISCSGSSSDIGN HYVSWYQQLPGTAPKLLIYDNNQRPSGIPDR FSGSKSGTSATLAITGLQTGDEADYYCGTWD NSLSPHLLFGGGTKLTVL<br>SEQ ID NO. 144 |
| SH1E10 | EVQLVESGSEVEKPGSSVKVSCKASGGTFSDSGISW VRQAPGQGLEWMGGIIPMFATPYYAQKFQDRVTITA DESTSTVYMELSGLRSDDTAVYYCARDRGRGHLPWY FDLWGRGTLVTVSS<br>SEQ ID NO. 145 | QSVLTQPPSVSAAPGQKVTISCSGSSSNMGN NYVSWYKQVPGTAPKLLIYENDKRPSGIPDR FSGSKSGTSATLGITGLQTGDEADYYCGTWD NSLSGFVFASGTKVTVL<br>SEQ ID NO. 146 |
| SH1E2 | EVQLVESGAEVKKPGSSVKVSCKASGGTFSSYAISW VRQAPGQGLEWMGGIIPIFGTANYAQKFQGRVTITA DESTSTAYMELSSLRSEDTAVYYCARAPYYYYYMDV WGQGTTVTVSS<br>SEQ ID NO. 147 | QSALTQPASVSGSLGQSVTISCTGSSSDVGS YNLVSWYQQHPGKAPNLMIYDVSKRSGVSNR FSGSKSGNTASLTISGLQAEDEADYYCSSYT GISTVVFGGGTKLTVL<br>SEQ ID NO. 148 |
| SH1A9 | EVQLLESGAEVKKPGSSVKVSCKASGGTLSRYALSW VRQAPGQGPEWVGAIIPIFGTPHYSKKFQDRVIITV DTSTNTAFMELSSLRFEDTALYFCARGHDEYDISGY HRLDYWGQGTLVTVSS<br>SEQ ID NO. 149 | QSVLTQPASVSGSPGQSITISCTGTSSDVGS YNLVSWYQQHPGKAPKLMIYEVSKRPSGVSN RFSGSKSGNTASLTISGLQAEDEADYYCSSY GGFNNLLFGGGTKLTVL<br>SEQ ID NO. 150 |
| SH1B11 | QVQLVQSGSELKKPGSSVKVSCKASGYSFSGYYIHW VRQAPGQGLEWMGWIDPNSGVTNYVRRFQGRVTMTR DTSLSTAYMELSGLTADDTAVYYCARDENLWQFGYL DYWGQGTLVTVSS<br>SEQ ID NO. 151 | DIVMTQSPSSLSASIGDRVTITCRASQRISA YVNWYQQKPGKAPKVLIYAASSLRSGVPSRF SGSGSGTDFTLTISSLQPEDFATYYCQQTYS SPWTFGQGTKVEIK<br>SEQ ID NO. 152 |
| SH1E4 | QVQLVQSGAEVKKPGSSVKVSCKASGGTFSRYGVHW VRQAPGQGLEWMGRLIPIVSMTNYAQKFQDRVSITT DKSTGTAYMELRSLTSEDTALYYCASVGQQLPWVFF AWGQGTLVTVSS<br>SEQ ID NO. 153 | QSVLTQPPSASGSPGQSVTISCTGTSSDIGG YDSVSWYQQHPGKAPKLMIYDVSKRPSGVSN RFSGSKSGNTASLTISGLQAEDEADYYCSSY TSSSIFFYVFGTGTKVTVL<br>SEQ ID NO. 154 |
| SH1B3 | QVQLVESGGGVVQPGRSLRLSCAASGFTFSSYAMHW VRQAPGKGLEWVAVISFDGSNKYYADSVRGRFTISR DNSKNTLYLQMNSLRTEDTAVYYCARGWLDRDIDYW GQGTLVTVSS<br>SEQ ID NO. 155 | LPVLTQPASVSGSPGQSITISCTGTTSDIGG YDYVSWYQQHPGKAPKLMIYDVSKRPSGVSN RFSGSKSGNTASLTISGLQAEDEADYYCSSY TSSSTHVFGTGTKLTVL<br>SEQ ID NO. 156 |
| SH1D1 | EVQLVESGGGVVQPGRSLRLSCAASGFTFSSYAMHW VRQAPGKGLEWVAVISFDGSNKYYADSVRGRFTISR DNSKNTLYLQMNSLRTEDTAVYYCARGWLDRDIDYW GQGTLVTVSS<br>SEQ ID NO. 157 | QSALTQPASVSGSPGQSITISCTGTSSDVGG YNYVSWYQQHPGKAPKLMIYDVSNRPSGVSN RFSGSKSGNTASLTISGLQAEDEADYYCSSY RSSTLGPVFGGGTKLTVL<br>SEQ ID NO. 158 |
| SH1D2 | QVQLVESGGGVVQPGRSLRLSCAASGFTFSSYAMHW VRQAPGKGLEWVAVISFDGSNKYYADSVRGRFTISR DNSKNTLYLQMNSLRTEDTAVYYCARGWLDRDIDYW GQGTLVTVSS<br>SEQ ID NO. 159 | QAGLTQPPSVSEAPRQRVTISCSGSSSNIGN NAVNWYQQLPGKAPKLLIYYDDLLPSGVSDR FSGSKSGTSASLAISGLQSEDEADYYCAAWD DSLNGYVFGTGTKLTVL<br>SEQ ID NO. 160 |
| SH1D12 | EVQLVESGGGVVQPGRSLRLSCAASGFTFSSYAMHW VRQAPGKGLEWVAVISFDGSNKYYADSVRGRFTISR | QSALTQPRSVSGSPGQSVTISCTGTSSDVGG YNYVSWYQQHPGKAPKLMIYDVSKRPSGVPD |

Sequence Listing

| | Heavy chain variable domain region | Light chain variable domain region |
|---|---|---|
| | DNSKNTLYLQMNSLRTEDTAVYYCARGWLDRDIDYW<br>GQGTLVTVSS<br>SEQ ID NO. 161 | RFSGSKSGNTASLTISGLQAEDEADYYCSSY<br>TSSTTHVFGTGTKVTVL<br>SEQ ID NO. 162 |
| SH1E1 | EVQLVESGGGVVQPGRSLRLSCAASGFTFSSYAMHW<br>VRQAPGKGLEWVAVISFDGSNKYYADSVRGRFTISR<br>DNSKNTLYLQMNSLRTEDTAVYYCARGWLDRDIDYW<br>GQGTLVTVSS<br>SEQ ID NO. 163 | QSVVTQPPSVSAAPGQKVTISCSGSSSNIGN<br>NYVSWYQQLPGTAPKLLIYDNNKRPSGIPDR<br>FSGSKSGTSATLGITGLQTGDEADYYCGTWD<br>SSLSVWVFGGGTQLTVL<br>SEQ ID NO. 164 |
| SH1G9 | QVQLVESGGGVVQPGRSLRLSCAASGFTFSSYAMHW<br>VRQAPGKGLEWVAVISFDGSNKYYADSVRGRFTISR<br>DNSKNTLYLQMNSLRTEDTAVYYCARGWLDRDIDYW<br>GQGTLVTVSS<br>SEQ ID NO. 165 | QSVLTQPASVSGSPGQSITISCTGTSSDVGG<br>YNYVSWYQQHPGRAPRLMIYDVSNRPSGVSN<br>RFSGSKSGNTASLTISGLQAEDEGDYYCSSY<br>TSGGTLGPVFGGGTKLTVL<br>SEQ ID NO. 166 |
| SH1A11 | EVQLVQSGGGLVQPGGSLRLSCAASGFTFSDYGMHW<br>VRQPPGKGLEWLAVISYDGSYKIHADSVQGRFTISR<br>DNAKNSVFLQMNSLKTEDTAVYYCTTDRKWLAWHGM<br>DVWGQGTTVTVSS<br>SEQ ID NO. 167 | QAGLTQPPSASGTPGQRVTISCSGSSSNIGS<br>NTVNWYQQLPGTAPKLLIYSNNQRPSGVPDR<br>FSGSKSGTSASLAISGLQSEDEADYYCAAWD<br>DSLNGWVFGGGTKLTVL<br>SEQ ID NO. 168 |
| SH1C2 | EVQLVQSGAEVKKPGSSVKVSCKASGGTFSSYAISW<br>VRQAPGQGLEWMGGIIPIFGTANYAQKFQGRVTITA<br>DESTSTAYMELSSLRSEDTAVYYCARDGIVADFQHW<br>GQGTLVTVSS<br>SEQ ID NO. 169 | AIRMTQSPSSLSASVGDRVTITCRASQSISN<br>YLNWYQQRPGKAPNLLIYAASSLQSGVPSRF<br>SGSGSGTDFTLTISSLQPEDFATYYCQQTYS<br>TPYTFGQGTKLEIK<br>SEQ ID NO. 170 |
| SH1G8 | EVQLVESGAEVKKPGASVKVSCKASGDTFSRYGITW<br>VRQAPGQGLEWMGNIVPFFGATNYAQKFQGRLTITA<br>DKSSYTSYMDLSSLRSDDTAVYYCARDHFYGSGGYF<br>DYWGQGTLVTVSS<br>SEQ ID NO. 171 | QSVLTQPASVSGSPGQSITISCTGTSSDVGG<br>YNYVSWYRQHPGKAPKLMIYDVSYRPSGVSN<br>RFSGSKSGNTASLTISGLQAEDEADYYCSSY<br>TDSSTRYVFGTGTKLTVL<br>SEQ ID NO. 172 |
| SH1H2 | EVQLLESGAEVKKPGASVKVSCKASGYTFNSYDINW<br>VRQAPGQGLEWMGGIIPVFGTANYAESFQGRVTMTA<br>DHSTSTAYMELNNLRSEDTAVYYCARDRWHYESRPM<br>DVWGQGTTVTVSS<br>SEQ ID NO. 173 | QPVLTQPPSASGTPGQRVAISCSGSRSNIEI<br>NSVNWYQQLPGTAPKLLIYDNNKRPSGIPDR<br>FSGSKSGTSATLGITGLQTGDEADYYCGSWD<br>SSLSADVFGTGTKLTVL<br>SEQ ID NO. 174 |
| SH1B10 | EVQLVESGGGLVRPGGSLRLACAASGFSFSDYYMTW<br>IRQAPGRGLEWIAYISDSGQTVHYADSVKGRFTISR<br>DNTKNSLFLQVNTLRAEDTAVYYCAREDLLGYYLQS<br>WGQGTLVTVSS<br>SEQ ID NO. 175 | QSVLTQPPSVSAAPGKKVTISCSGSSSNIGN<br>NYVSWYQQLPGTAPKLLIYRNNQRPSGVPDR<br>FSGSKSGTSASLAISGLQSEDEADYYCATWD<br>DSLNGWVFGGGTKLTVL<br>SEQ ID NO. 176 |
| SH1B7A(L) | QVQLQQSGPGLVKPSQTLSLTCAISGDSVSSNSAAW<br>NWIRQSPSRGLEWLGRTYYRSKWYNDYAVSVKSRIT<br>INPDTSKNQFSLQLNSVTPEDTAVYYCARDEPRAVA<br>GSQAYYYYGMDVWGQGTTVTVSS<br>SEQ ID NO. 177 | QSVVTQPPSVSGAPGQRVTISCTGSSSNIGA<br>GYDVHWYQQLPGTAPKLLIYGNNNRHSGVPD<br>RFSGSKSGTSASLAITGLQAEDEAEFFCGTW<br>DSRLTTYVFGSGTKLTVL<br>SEQ ID NO. 178 |
| SH1E6 | QVQLVQSGAEVKKPGSSVKVSCKASGGTFSRYGVHW<br>VRQAPGQGLEWMGRLIPIVSMTNYAQKFQDRVSITT<br>DKSTGTAYMELRSLTSEDTALYYCASVGQQLPWVFF<br>AWGQGTLVTVSS<br>SEQ ID NO. 179 | QSVVTQPPSVSAAPGQKVTISCSGSSSNIGN<br>NYVSWYQQLPGTAPKLLIYDNNKRPSGIPDR<br>FSGSKSGTSATLGITGLQTGDEADYYCGTWD<br>SSLSAVVFGGGTKLTVL<br>SEQ ID NO. 180 |
| SH1C11 | EVQLVQSGAEVKKPGASVKVSCKASGYTFTSYYMHW<br>VRQAPGQGLEWMGIINPSDGSTSYAQKFQGRVTMTR<br>DTSTSTVHMELSSLRSEDTAVYYCARDLFPHIYGNY<br>YGMDIWGQGTTVTVSS<br>SEQ ID NO. 181 | VIWMTQSPSSLSASVGDRVTITCRASQSISS<br>YLNWYQQKPGKAPKLLIYEASTLESGVPSRF<br>SGSGSGTEFTLTISSLQPEDFATYYCQQSYS<br>TPYTFGQGTKLEIK<br>SEQ ID NO. 182 |
| SH1A2 | QMQLVQSGGGVVQPGRSLRLSCAASGFTFSSYAMHW<br>VRQAPGKGLEWVAVISFDGSNKYYADSVRGRFTISR<br>DNSKNTLYLQMNSLRTEDTAVYYCARGWLDRDIDYW<br>GQGTLVTVSS<br>SEQ ID NO. 183 | QSVVTQPPSVSAAPGQKVTISCSGSSSNIGN<br>NYVSWYQQVPGTAPKLLIYDNNKRPSGIPDR<br>FSGSNSDTSATLGITGLQTGDEADYYCGTWD<br>SSLSAWVFGGGTKLTVL<br>SEQ ID NO. 184 |
| SH1B1 | QVQLVQSGGGVVQPGRSLRLSCAASGFTFSSYAMHW<br>VRQAPGKGLEWVAVISFDGSNKYYADSVRGRFTISR<br>DNSKNTLYLQMNSLRTEDTAVYYCARGWLDRDIDYW<br>GQGTLVTVSS<br>SEQ ID NO. 185 | QSVVTQPPSVSAAPGQKVTISCSGSSSNIGN<br>NYVSWYQQLPGTAPKLLIYDNNKRPSGIPDR<br>FSGSKSGTSATLGITGLQTGDEADYYCGTWD<br>SSLSAGSVVFGGGTKLTVL<br>SEQ ID NO. 186 |

-continued

| | Heavy chain variable domain region | Light chain variable domain region |
|---|---|---|
| R6B2 | EVQLVQSGAEVKKPGSSVKVSCKASGGTFSSYAISW VRQAPGQGLEWMGGIIPIFGTANYAQKFQGRVTITA DESTSTAYMELSSLRSEDTAVYYCARDGIVADFQHW GQGTLVTVSS SEQ ID NO. 187 | QPVLTQPRSVSGSPGQSVTISCTGTSSDVGG YNFVSWYQQNPGKAPKLMIYDVSKRPSGVPD RFSGSKSGNTASLTVSGLRAEDEADYYCASY AGGRTFVFGGGTKVTVL SEQ ID NO. 188 |
| R6B7 | QMQLVQSGAEVKKPGSSVKVSC KASGGTFNSYPIS WVRQAPGQGLEWMGGIIPIFGTANYAQKFQGRVTIT ADESTSTAYMELSSLRSEDTAMYYCAKNHPTATLDY WGQGTLVTVSS SEQ ID NO. 189 | QSVLTQSPSSFSASTGDRVTITCRASQGISS YLAWYQQKPGKAPKLLIYAASTLQSGVPSRF SGSGSGTDFTLTISCLQSEDFATYYCQQYYS YPLTFGGGTKVTVL SEQ ID NO. 190 |
| R6B11 | QVQLVQSGGGVVQPGRSLRLSCAASGFPFRSYDMHW VRQAPGEGLEWVALISSDGSNKYYLDSVKGRFTISR DNSKNTLYLQMNSLRAEDTAVYYCAKDLLPYSSSWD YYYYYGMDVWGQGTTVTVSS SEQ ID NO. 191 | LPVLTQPASVSASAGQSIAISCTGISSDIGD YNSVSWYQRHPGKAPKLIIYDVSSRPSGVAD RFSGSKSGSTASLSISGLQAEDEADYYCASY TASDNPVFGGGTKLTVL SEQ ID NO. 192 |
| R6D1 | EVQLVESGGGLVQPGGSLRLSCAASGFNIKDTYIHW VRQAPGKGLEWVARIYPTNGYTRYADSVKGRFTISA DTSKNTAYLQMNSLRAEDTAVYYCSRWGGDGFYAMD YWGQGTLVTVSS SEQ ID NO. 193 | SYELMQPPSVSVAPGKTATIACGGENIGRKT VHWYQQKPGQAPVLVIYYDSDRPSGIPERFS GSNSGNTATLTISRVEAGDEADYYCQVWDSS SDHRIFGGGTKLTVL SEQ ID NO. 194 |
| R6C8 | EVQLVESGGGLVKPGGSRKLSCAASGFTFSNYGMHW VRQAPEKGLEWVAYISSGSSTIYYADTVKGRFTISR DNAKNTLFLQMTSLRSEDTAMYYCARRGLLLDYWGQ GTTLTVSS SEQ ID NO. 195 | QSVLTQPPSVSAAPGQEVTISCSGSNSNIGN NYVSWYQQLPGTAPKLLIYDNNERPSGIPDR FSGSKSGTSATLGITGLQTGDEADYYCGTWD SSLSAGVFGGGTKLTVL SEQ ID NO. 196 |
| R9G8 | EVQLVQSGAEVKKPGASVKVSCKASGYTFTSYGISW VRQAPGQGLEWMGWISAYNGNTNYAQKLQGRVTMTT DTSTSTAYMELRSLRSDDTAVYYCARDLFPTIFWEG GAFDIWGQGTMVTVSS SEQ ID NO. 197 | QSVLTQPPSVSAAPGQEVTISCSGSNSNIGN NYVSWYQQLPGTAPKLLIYDNNERPSGIPDR FSGSKSGTSATLGITGLQTGDEADYYCGTWD SSLSAGVFGGGTKLTVL SEQ ID NO. 198 |
| R7D1 | QVQLVQSGSEVEKPGSSVKVSCKASGGTFSDSGISW VRQAPGQGLEWMGGIIPMFATPYYAQKFQDRVTITA DESTSTVYMELSGLRSDDTAVFYCARDRGRGHLPWY FDLWGRGTLVTVSS SEQ ID NO. 199 | QSVLTQPPSVSAAPGQEVTISCSGSNSNIGN NYVSWYQQLPGTAPKLLIYDNNERPSGIPDR FSGSKSGTSATLGITGLQTGDEADYYCGTWD SSLSAGVFGGGTKLTVL SEQ ID NO. 200 |
| R7D2 | QVQLVQSGAEVKKPGSSVKVSCKASGGTFSSYAISW VRQAPGQGLEWMGGIIPIFGTANYAQKFQGRVTITA DESTSTAYMELSSLRSEDTAVYYCARDGIVADFQHW GQGTLVTVSS SEQ ID NO. 201 | AIRMTQSPSSLSASVGDRVTITCRASQSISN YLNWYQQRPGKAPNLLIYAASSLQSGVPSRF SGSGSGTDFTLTISSLQPEDFATYYCQQTYS PTYTFGQGTKLEIK SEQ ID NO. 202 |
| R7E7 | EVQLLESGAEVKKPGSSVKVSCKASGGTFSSYAISW VRQAPGQGLEWMGRIIPILGIADYAQKFQGRVTITA DKFTSTAYMELSSLRSEDTAVYYCATVEGWGAVTTF DYWGQGTLVTVSS SEQ ID NO. 203 | QSVLTQPPSVSAAPGQEVTISCSGSNSNIGN NYVSWYQQLPGTAPKLLIYDNNERPSGIPDR FSGSKSGTSATLGITGLQTGDEADYYCGTWD SSLSAGVFGGGTKLTVL SEQ ID NO. 204 |
| R7F2 | QVQLVQSGAEVKKPGSSVKVSCKASGGTLSSYAISW VRQVPGHGLEWMGRIISMLGVSNYAQNFQGRVTITA DKSTSTAYMELRSLTSDDTAVYYCATVTIFDGDYYA MDVWGQGTTVTVSS SEQ ID NO. 205 | QSVLTQPPSVSGAPGQRVTISCTGSSSNIGA GYDVYWYQHLLGKAPKLLIYGNSNRPSGVSD RFSASKSGTSVSLAITGLQAEDEADYYCQSY DSSLSGYVFGTGTKLTVL SEQ ID NO. 206 |
| R7F7 | EVQLVQSGAEVKKPGSSVKVSCKASGGTFSSHVISW VRQAPGQGLEWMGIILPSFGKTNYAQKFQGRVTMTG DTSTSTVYMELSSLTSEDTAVYYCVREFSGGYFDYW GQGTLVTVSS SEQ ID NO. 207 | QPVLTQPASVSGSPGQSITISCTGTSSDVGS YNLVSWYQQHPGKAPKLMIYEVSKRPSGVSN RFSGSKSGNTASLTISGLQAEDEADYYCNTY TSSGTYVIGTGTKVTVL SEQ ID NO. 208 |
| R9H2 | QVQLVQSGAEVKKPGASVKVSCKASGYTFTSYVIHW VRQAPGQRLEWMGWIHAGNGHTKYAQNFQGRVTITR DTSATTAYVEVSSLGSEDTALYYCAREGSDIGLDLH YWGQGTLVTVSS SEQ ID NO. 209 | QPVLTQPASVSGSPGQSITISCTGTSSDIGR YNYVSWYQQHPGKAPKVMIYDVSNRPSGVSN RFSGSKSGNTASLTISGLQAEDEADYYCSSY TSSSTWVFGGGTKLTVL SEQ ID NO. 210 |
| R9H6 | EVQLVQSGGGVVQPGRSLRLSCEASGFTFRNFAMHW VRQAPGKGLEWAAVISVDGSREHYADSVKGRFTISR | QSVVTQPPSVSAAPGQKVTISCSGSSSNIGN NYVSWYQQLPGTAPKILIYDNDKRPSGIPDR |

| | Heavy chain variable domain region | Light chain variable domain region |
|---|---|---|
| | DNSQNTVYLQMNGLRPEDTAEYYCAREGEGSTWSSF<br>DYWGQGTLVTVSS<br>SEQ ID NO. 211 | FSGSKSGTSATLGITGLQTGDEADYYCGTWD<br>RSLSGYVFGTGTKVTVL<br>SEQ ID NO. 212 |
| H6B1L | QMQLVQSGAEVKKPGSSVKVSCKASGGTFSSYAYSW<br>VRQAPGQGLEWMGGIIPSFGTANYAQKFQGRVTITA<br>DESTSTAYMELSSLRSEDTAVYYCARGPIVATITPL<br>DYWGQGTLVTVSS<br>SEQ ID NO. 213 | SYELMQPPSVSVAPGKTATIACGGENIGRKT<br>VHWYQQKPGQAPVLVIYYDSDRPSGIPERFS<br>GSNSGNTATLTISRVEAGDEADYYCLVWDSS<br>SDHRIFGGGTKLTVL<br>SEQ ID NO. 214 |
| H6A1 | QMQLVQSGAEVKKPGSSVKVSCKASGGTFSSYAYSW<br>VRQAPGQGLEWMGGIIPIFGTANYAQKFQGRVTITA<br>DESTSTAYMELSSLRSEDTAVYYCARGPIVATITPL<br>DYWGQGTLVTVSS<br>SEQ ID NO. 215 | SYELMQPPSVSVAPGKTATIACGGENIGRKT<br>VHWYQQKPGQAPVLVIYYDSDRPSGIPERFS<br>GSNSGNTATLTISRVEAGDEADYYCQVWDSS<br>SDHRIFGGGTKLTVL<br>SEQ ID NO. 216 |
| H6B1 | QMQLVQSGAEVKKPGSSVKVSCKASGGTFSSYAYSW<br>VRQAPGQGLEWMGGIIPSFGTANYAQKFQGRVTITA<br>DESTSTAYMELSSLRSEDTAVYYCARGPIVATITPL<br>DYWGQGTLVTVSS<br>SEQ ID NO. 217 | SYELMQPPSVSVAPGKTATIACGGENIGRKT<br>VHWYQQKPGQAPVLVIYYDSDRPSGIPERFS<br>GSNSGNTATLTISRVEAGDEADYYCQVWDSS<br>SDHRIFGGGTKLTVL<br>SEQ ID NO. 218 |
| H6B2 | QMQLVQSGAEVKKPGSSVKVSCKASGGTFSSYAISW<br>VRQAPGQGLEWMGGIIPAFGTANYAQKFQGRVTITA<br>DESTSTAYMELSSLRSEDTAVYYCARGPIVATITPL<br>DYWGQGTLVTVSS<br>SEQ ID NO. 219 | SYELMQPPSVSVAPGKTATIACGGENIGRKT<br>VHWYQQKPGQAPVLVIYYDSDRPSGIPERFS<br>GSNSGNTATLTISRVEAGDEADYYCQVWDSS<br>SDHRIFGGGTKLTVL<br>SEQ ID NO. 220 |
| H19C | QVQLVQSGAEVKKPGASVKVSCKTSGNTFTNYALHW<br>VRQAPGQGLEWMGGMKPSGGSTSIAQKFQGRVTMTR<br>DKSTSTVYMELSSLTSEDTAVYYCARDLFPHIFGNY<br>YGMDIWGQGTTVTVSS<br>SEQ ID NO. 221 | DIVMTQSPPSLSASVGDRVTITCRASQSISS<br>YLNWYQQKPGKAPKLLIYATSSLQYGVPSRF<br>SGSGSGTDFTLTISSLQPEDFATYYCQGSYS<br>TPYTFGQGTKVEIK<br>SEQ ID NO. 222 |
| H110D | QVQLVQSGAEVKKPGASVKVSCKTSGNTFTNYYMHW<br>VRQAPGQGLEWMGSMQPSGGSTSLAQKFQGRVTMTR<br>DKSTSTVYMELSSLTSEDTAVYYCARDLFPHILGNY<br>YGMDIWGQGTTVTVSS<br>SEQ ID NO. 223 | DIVMTQSPPSLSASVGDRVTITCRASQSISS<br>YLNWYQQKPGKAPKLLIYAASSLQSGVPSRF<br>SGSGSGTDFTLTISSLQPEDFATYYCQGSYS<br>TPYTFGQGTKVEIK<br>SEQ ID NO. 224 |
| H11F | QVQLVQSGAEVKKPGASVKVSCKTSGNTFTNYPMHW<br>VRQAPGQGLEWMGSMKPSGGSTSLAPKFQGRVTMTR<br>DKSTSTVYMELSSLTSEDTAVYYCARDLFPHIIGNY<br>YGMDIWGQGTTVTVSS<br>SEQ ID NO. 225 | DIVMTQSPPSLSASVGDRVTITCRASQSISS<br>YLNWYQQKPGKAPKLLIYAASSLQYGVPSRF<br>SGSGSGTDFTLTISSLQPEDFATYYCQGSYS<br>TPYTFGQGTKVEIK<br>SEQ ID NO. 226 |
| H1C1 | QVQLVQSGAEVKKPGASVKVSCKTSGNTFTNYSMHW<br>VRQAPGQGLEWMGIMNPSGGSTSYAQKFQGRVTMTR<br>DKSTSTVYMELSSLTSEDTAVYYCARDLFPHIYGNY<br>YGMDIWGQGTTVTVSS<br>SEQ ID NO. 227 | DIVMTQSPPSLSASVGDRVTITCRASQSISS<br>YLNWYQQKPGKAPKLLIYAASSLQSGVPSRF<br>SGSGSGTDFTLTISSLQPEDFATYYCQQSYS<br>TPYTFGQGTKVEIK<br>SEQ ID NO. 228 |
| GPG1A2 | EVQLVQSGAEVKKPGASVKVSCKASGYTFTGYYMHW<br>VRQAPGQGLEWMGWINPNSDNTGSAQKFQGRVFMTK<br>TTSLNTAYMELSGLRSEDTAIYYCARERSSGYFDFW<br>GQGTLVTVSS<br>SEQ ID NO. 229 | DIVMTQSPSSLSASVGDRVTITCRASQSISS<br>FLNWYQQKPGKAPKLLIYAASSLQSGVPSRF<br>SGSGSGTDFTLTISSLQPEDFATYYCQQSYS<br>TPITFGQGTKVEIK<br>SEQ ID NO. 230 |
| GPGG8 | QVQLVQSGAEVKKLGASVKVSCKASGYPFTGYYMHW<br>VRQAPGQGLEWMGWINPNGDNTGLAQKFQGRVFMTK<br>TTSLNTAYMELSGLRSEDTAIYYCARERSSGYFDFW<br>GQGTLVTVSS<br>SEQ ID NO. 231 | DIVMTQSPSSLSASVGDRVTITCRATPSTSS<br>YLNWYQQKPGKAPKLLIYAASSLQSGVPSRF<br>SGSGSGTDFTLTISSLQPEDFATYYCQQSYS<br>TPITFGQGTKLEIK<br>SEQ ID NO. 232 |
| GPGG10 | QVQLVQSGAEVKKPGASVKVSCKTSGYPFTGYYMHW<br>VRQAPGQGLEWMGWINPLSDTTGSAQKFQGRVFMTK<br>TTSLNTAYMELSGLRSEDTAIYYCARERSSGYFDFW<br>GQGTLVTVSS<br>SEQ ID NO. 233 | DIVMTQSPSSLSASVGDRVTITCRASQSISS<br>YLNWYQQKPGKAPKLLIYAASSLQSGVPSRF<br>SGSGSGTDFTLTISSLQPEDFATYYCQQSYS<br>TPITFGQGTKLEIK<br>SEQ ID NO. 234 |
| GPGH7 | QVQLVQSGAEVKKPGASVKVSCKASGYTFTGYYMHW<br>VRQAPGQGLEWMGWINPLSDNTGSAQKFQGRVFMTK<br>TTSLNTAYMELSGLRSEDTAIYYCARERSSGYFDFW<br>GQGTLVTVSS<br>SEQ ID NO. 235 | DIVMTQSPSSLSASVGDRVTITCRASQSISS<br>FLNWYQQKPGKAPKLLIYLASSLQSGVPSRF<br>SGSGSGTDFTLTISSLQPEDFATYYCQQSYS<br>TPITFGQGTKVEIK<br>SEQ ID NO. 236 |

-continued

Sequence Listing

| | Heavy chain variable domain region | Light chain variable domain region |
|---|---|---|
| GPGH10 | QVQLVQSGAEVKKPGASVKVSCKTSGYTFTGYYMHW VRQAPGQGLEWMGWINPNSDNTGYAQKFQGRVFMTK TTSLNTAYMELSGLRSEDTAIYYCARERSSGYFDFW GQGTLVTVSS<br>SEQ ID NO. 237 | DIVMTQSPSSLSASVGDRVTITCRASQSISS FLNWYQQKPGKAPKLLIYAASSLQSGVPSRF SGSGSGTDFTLTISSLQPEDFATYYCQQAYS TPITFGQGTKVEIK<br>SEQ ID NO. 238 |
| GPGH11 | QVQLVQSGAEVKKPGASVKVSCKASGYPFTGYYMHW VRQAPGQGLEWMGWINPLSDSTGSAQKFQGRVFMTK TTSLNTAYMELSGLRSEDTAIYYCARERSSGYFDFW GQGTLVTVSS<br>SEQ ID NO. 2<br>SEQ ID NO. 239 | DIVMTQSPSSLSASVGDRVTITCRASQSISS YLNWYQQKPGKAPKLLIYAASSLQSGVPSRF SGSGSGTDFTLTISSLQPEDFATYYCQQSYS TPITFGQGTKLEIK<br>SEQ ID NO. 240 |
| GPGH10P | QVQLVQSGAEVKKPGASVKVSCKTSGYTFTGYYMHW VRQAPGQGLEWMGWINPNSDNTGYAQKFQGRVFMTK TTSLNTAYMELSGLRSEDTAIYYCARERSSGYFDFW GQGTLVTVSS<br>SEQ ID NO. 241 | DIVMTQSPSSLSASVGDRVTITCRASQSISS FLNWYQQKPGKAPKLLIYAASSLQSGVPSRF SGSGSGTDFTLTISSLQPEDFATYYCQQPYS TPITFGQGTKVEIK<br>SEQ ID NO. 242 |

We claim:

1. A fully human antibody of an IgG class that binds to a PD-L1 epitope, that has a heavy chain variable domain sequence that is at least 95% identical to the amino acid sequences selected from the group consisting of SEQ ID NO. 35, SEQ ID NO. 51, SEQ ID NO. 137, SEQ ID NO. 155, SEQ ID NO. 157, SEQ ID NO. 159, SEQ ID NO. 161, SEQ ID NO. 163, SEQ ID NO. 165, SEQ ID NO. 179, SEQ ID NO. 183, SEQ ID NO. 185, SEQ ID NO. 213, SEQ ID NO. 215, SEQ ID NO. 217, and SEQ ID NO. 219, and that has a light chain variable domain sequence that is at least 95% identical to the amino acid sequences selected from the group consisting of SEQ ID NO. 36, SEQ ID NO. 52, SEQ ID NO. 138, SEQ ID NO. 156, SEQ ID NO. 158, SEQ ID NO. 160, SEQ ID NO. 162, SEQ ID NO. 164, SEQ ID NO. 166, SEQ ID NO. 180, SEQ ID NO. 184, SEQ ID NO. 186, SEQ ID NO. 214, SEQ ID NO. 216, SEQ ID NO. 218, and SEQ ID NO. 220, and wherein the antibody has a heavy chain/light chain variable domain sequence selected from the group consisting of SEQ ID NO. 35/SEQ ID NO. 36 (called H6 herein), SEQ ID NO. 51/SEQ ID NO. 52 (called RC5 herein), SEQ ID NO. 137/SEQ ID NO. 138 (called SH1A1Q herein), SEQ ID NO. 155/SEQ ID NO. 156 (called SH1B3 herein), SEQ ID NO. 157/SEQ ID NO. 158 (called SH1D1 herein), SEQ ID NO. 159/SEQ ID NO. 160 (called SH1D2 herein), SEQ ID NO. 161/SEQ ID NO. 162 (called SH1D12 herein), SEQ ID NO. 163/SEQ ID NO. 164 (called SH1E1 herein), SEQ ID NO. 165/SEQ ID NO. 166 (called SH1G9 herein SEQ ID NO. 179/SEQ ID NO. 180 (called SH1E6 herein), SEQ ID NO. 183/SEQ ID NO. 184 (called SH1A2 herein), SEQ ID NO. 185/SEQ ID NO. 186 (called SH1B1 herein), SEQ ID NO. 213/SEQ ID NO. 214 (called H6B1L herein), SEQ ID NO. 215/SEQ ID NO. 216 (called H6A1 herein), SEQ ID NO. 217/SEQ ID NO. 218 (called H6B1 herein), and SEQ ID NO. 219/SEQ ID NO. 220 (called H6B2 herein).

2. A Fab fully human antibody fragment that binds to a PD-L1 epitope, having a variable domain region from a heavy chain and a variable domain region from a light chain, wherein the heavy chain variable domain sequence that is at least 95% identical to the amino acid sequences selected from the group consisting of SEQ ID NO. 35, SEQ ID NO. 51, SEQ ID NO. 137, SEQ ID NO. 155, SEQ ID NO. 157, SEQ ID NO. 159, SEQ ID NO. 161, SEQ ID NO. 163, SEQ ID NO. 165, SEQ ID NO. 179, SEQ ID NO. 183, SEQ ID NO. 185, SEQ ID NO. 213, SEQ ID NO. 215, SEQ ID NO. 217, and SEQ ID NO. 219, and that has a light chain variable domain sequence that is at least 95% identical to the amino acid sequences selected from the group consisting of SEQ ID NO. 36, SEQ ID NO. 52, SEQ ID NO. 138, SEQ ID NO. 156, SEQ ID NO. 158, SEQ ID NO. 160, SEQ ID NO. 162, SEQ ID NO. 164, SEQ ID NO. 166, SEQ ID NO. 180, SEQ ID NO. 184, SEQ ID NO. 186, SEQ ID NO. 214, SEQ ID NO. 216, SEQ ID NO. 218, and SEQ ID NO. 220, and wherein the antibody has a heavy chain/light chain variable domain sequence selected from the group consisting of SEQ ID NO. 35/SEQ ID NO. 36, SEQ ID NO. 51/SEQ ID NO. 52, SEQ ID NO. 137/SEQ ID NO. 138, SEQ ID NO. 155/SEQ ID NO. 156, SEQ ID NO. 157/SEQ ID NO. 158, SEQ ID NO. 159/SEQ ID NO. 160, SEQ ID NO. 161/SEQ ID NO. 162, SEQ ID NO. 163/SEQ ID NO. 164, SEQ ID NO. 165/SEQ ID NO. 166, SEQ ID NO. 179/SEQ ID NO. 180, SEQ ID NO. 183/SEQ ID NO. 184, SEQ ID NO. 185/SEQ ID NO. 186, SEQ ID NO. 213/SEQ ID NO. 214, SEQ ID NO. 215/SEQ ID NO. 216, SEQ ID NO. 217/SEQ ID NO. 218, and SEQ ID NO. 219/SEQ ID NO. 220.

3. A single chain human antibody that binds to a PD-L1 epitope, having a variable domain region from a heavy chain and a variable domain region from a light chain and a peptide linker connection the heavy chain and light chain variable domain regions, wherein the heavy chain variable domain sequence that is at least 95% identical to the amino acid sequences selected from the group consisting of SEQ ID NO. 35, SEQ ID NO. 51, SEQ ID NO. 137, SEQ ID NO. 155, SEQ ID NO. 157, SEQ ID NO. 159, SEQ ID NO. 161, SEQ ID NO. 163, SEQ ID NO. 165, SEQ ID NO. 179, SEQ ID NO. 183, SEQ ID NO. 185, SEQ ID NO. 213, SEQ ID NO. 215, SEQ ID NO. 217, and SEQ ID NO. 219, and that has a light chain variable domain sequence that is at least 95% identical to the amino acid sequences selected from the group consisting of SEQ ID NO. 36, SEQ ID NO. 52, SEQ ID NO. 138, SEQ ID NO. 156, SEQ ID NO. 158, SEQ ID NO. 160, SEQ ID NO. 162, SEQ ID NO. 164, SEQ ID NO. 166, SEQ ID NO. 180, SEQ ID NO. 184, SEQ ID NO. 186, SEQ ID NO. 214, SEQ ID NO. 216, SEQ ID NO. 218, and SEQ ID NO. 220, and wherein the single chain fully human antibody has a heavy chain/light chain variable domain sequence selected from the group consisting of SEQ ID NO. 35/SEQ ID NO. 36, SEQ ID NO. 51/SEQ ID NO. 52, SEQ ID NO. 137/SEQ ID NO. 138, SEQ ID NO. 155/SEQ ID NO. 156, SEQ ID NO. 157/SEQ ID NO. 158, SEQ ID NO. 159/SEQ ID NO. 160, SEQ ID NO. 161/SEQ ID NO. 162, SEQ ID NO. 163/SEQ ID NO. 164, SEQ ID NO. 165/SEQ ID NO. 166, SEQ ID NO. 183/SEQ ID NO. 184, SEQ ID NO. 185/SEQ ID NO. 186, SEQ ID NO. 213/SEQ ID NO. 214, SEQ ID NO. 215/SEQ ID NO. 216, SEQ ID NO. 217/SEQ ID NO. 218, and SEQ ID NO. 219/SEQ ID NO. 220.

4. A method for treating a broad spectrum of mammalian cancers, comprising administering an effective amount of an anti-PD-L1 polypeptide, wherein the anti-PD-L1 polypeptide is selected from the group consisting of a fully human antibody of an IgG class that binds to a PD-L1 epitope a Fab fully human antibody fragment, having a variable domain region from a heavy chain and a variable domain region from a light chain, a single chain human antibody, having a variable domain region from a heavy chain and a variable domain region from a light chain and a peptide linker connection the heavy chain and light chain variable domain regions, and combinations thereof;

wherein the fully human antibody has a heavy chain variable domain sequence that is at least 95% identical to the amino acid sequences selected from the group consisting of SEQ ID NO. 35, SEQ ID NO. 51, SEQ ID NO. 137, SEQ ID NO. 155, SEQ ID NO. 157, SEQ ID NO. 159, SEQ ID NO. 161, SEQ ID NO. 163, SEQ ID NO. 165, SEQ ID NO. 179, SEQ ID NO. 183, SEQ ID NO. 185, SEQ ID NO. 213, SEQ ID NO. 215, SEQ ID NO. 217, and SEQ ID NO. 219, and that has a light chain variable domain sequence that is at least 95% identical to the amino acid sequences selected from the group consisting of SEQ ID NO. 36, SEQ ID NO. 52, SEQ ID NO. 138, SEQ ID NO. 156, SEQ ID NO. 158, SEQ ID NO. 160, SEQ ID NO. 162, SEQ ID NO. 164, SEQ ID NO. 166, SEQ ID NO. 180, SEQ ID NO. 184, SEQ ID NO. 186, SEQ ID NO. 214, SEQ ID NO. 216, SEQ ID NO. 218, and SEQ ID NO. 220, and wherein the fully human antibody has a heavy chain/light chain variable domain sequence selected from the group consisting of SEQ ID NO. 35/SEQ ID NO. 36, SEQ ID NO. 51/SEQ ID NO. 52, SEQ ID NO. 137/SEQ ID NO. 138, SEQ ID NO. 155/SEQ ID NO. 156, SEQ ID NO. 157/SEQ ID NO. 158, SEQ ID NO. 159/SEQ ID NO. 160, SEQ ID NO. 161/SEQ ID NO. 162, SEQ ID NO. 163/SEQ ID NO. 164, SEQ ID NO. 165/SEQ ID NO. 166, SEQ ID NO. 179/SEQ ID NO. 180, SEQ ID NO. 183/SEQ ID NO.

184, SEQ ID NO. 185/SEQ ID NO. 186, SEQ ID NO. 213/SEQ ID NO. 214, SEQ ID NO. 215/SEQ ID NO. 216, SEQ ID NO. 217/SEQ ID NO. 218, and SEQ ID NO. 219/SEQ ID NO. 220;

wherein the Fab fully human antibody fragment has the heavy chain variable domain sequence that is at least 95% identical to the amino acid sequences selected from the group consisting of SEQ ID NO. 35, SEQ ID NO. 51, SEQ ID NO. 137, SEQ ID NO. 155, SEQ ID NO. 157, SEQ ID NO. 159, SEQ ID NO. 161, SEQ ID NO. 163, SEQ ID NO. 165, SEQ ID NO. 179, SEQ ID NO. 183, SEQ ID NO. 185, SEQ ID NO. 213, SEQ ID NO. 215, SEQ ID NO. 217, and SEQ ID NO. 219, and that has the light chain variable domain sequence that is at least 95% identical to the amino acid sequences selected from the group consisting of SEQ ID NO. 36, SEQ ID NO. 52, SEQ ID NO. 138, SEQ ID NO. 156, SEQ ID NO. 158, SEQ ID NO. 160, SEQ ID NO. 162, SEQ ID NO. 164, SEQ ID NO. 166, SEQ ID NO. 180, SEQ ID NO. 184, SEQ ID NO. 186, SEQ ID NO. 214, SEQ ID NO. 216, SEQ ID NO. 218, and SEQ ID NO. 220, and wherein the fully human antibody Fab fragment has a heavy chain/light chain variable domain sequence selected from the group consisting of SEQ ID NO. 35/SEQ ID NO. 36, SEQ ID NO. 51/SEQ ID NO. 52, SEQ ID NO. 137/SEQ ID NO. 138, SEQ ID NO. 155/SEQ ID NO. 156, SEQ ID NO. 157/SEQ ID NO. 158, SEQ ID NO. 159/SEQ ID NO. 160, SEQ ID NO. 161/SEQ ID NO. 162, SEQ ID NO. 163/SEQ ID NO. 164, SEQ ID NO. 165/SEQ ID NO. 166, SEQ ID NO. 179/SEQ ID NO. 180, SEQ ID NO. 183/SEQ ID NO. 184, SEQ ID NO. 185/SEQ ID NO. 186, SEQ ID NO. 213/SEQ ID NO. 214, SEQ ID NO. 215/SEQ ID NO. 216, SEQ ID NO. 217/SEQ ID NO. 218, and SEQ ID NO. 219/SEQ ID NO. 220; and wherein the single chain human antibody has the heavy chain variable domain sequence that is at least 95% identical to the amino acid sequences selected from the group consisting of SEQ ID NO. 35, SEQ ID NO. 51, SEQ ID NO. 137, SEQ ID NO. 155, SEQ ID NO. 157, SEQ ID NO. 159, SEQ ID NO. 161, SEQ ID NO. 163, SEQ ID NO. 165, SEQ ID NO. 179, SEQ ID NO. 183, SEQ ID NO. 185, SEQ ID NO. 213, SEQ ID NO. 215, SEQ ID NO. 217, and SEQ ID NO. 219, and that has the light chain variable domain sequence that is at least 95% identical to the amino acid sequences selected from the group consisting of SEQ ID NO. 36, SEQ ID NO. 52, SEQ ID NO. 138, SEQ ID NO. 156, SEQ ID NO. 158, SEQ ID NO. 160, SEQ ID NO. 162, SEQ ID NO. 164, SEQ ID NO. 166, SEQ ID NO. 180, SEQ ID NO. 184, SEQ ID NO. 186, SEQ ID NO. 214, SEQ ID NO. 216, SEQ ID NO. 218, and SEQ ID NO. 220, and wherein the single chain human antibody has a heavy chain/light chain variable domain sequence selected from the group consisting of SEQ ID NO. 35/SEQ ID NO. 36, SEQ ID NO. 51/SEQ ID NO. 52, SEQ ID NO. 137/SEQ ID NO. 138, SEQ ID NO. 155/SEQ ID NO. 156, SEQ ID NO. 157/SEQ ID NO. 158, SEQ ID NO. 159/SEQ ID NO. 160, SEQ ID NO. 161/SEQ ID NO. 162, SEQ ID NO. 163/SEQ ID NO. 164, SEQ ID NO. 165/SEQ ID NO. 166, SEQ ID NO. 179/SEQ ID NO. 180, SEQ ID NO. 183/SEQ ID NO. 184, SEQ ID NO. 185/SEQ ID NO. 186, SEQ ID NO. 213/SEQ ID NO. 214, SEQ ID NO. 215/SEQ ID NO. 216, SEQ ID NO. 217/SEQ ID NO. 218, and SEQ ID NO. 219/SEQ ID NO. 220.

5. The method for treating a broad spectrum of mammalian cancers of claim 4, wherein the broad spectrum of mammalian cancers to be treated is selected from the group consisting of ovarian, colon, breast, lung cancers, myelomas, neuroblastic-derived CNS tumors, monocytic leukemias, B-cell derived leukemias, T-cell derived leukemias, B-cell derived lymphomas, T-cell derived lymphomas, mast cell derived tumors, and combinations thereof.

* * * * *